United States Patent
Fujita et al.

(10) Patent No.: US 6,596,751 B2
(45) Date of Patent: Jul. 22, 2003

(54) α-SUBSTITUTED CARBOXYLIC ACID DERIVATIVES

(75) Inventors: Takashi Fujita, Kashiwa (JP); Kunio Wada, Asaka (JP); Minoru Oguchi, Tokyo (JP); Hidehito Honma, Tokyo (JP); Toshihiko Fujiwara, Ebina (JP); Haruo Iwabuchi, Urawa (JP)

(73) Assignee: Sankyo Company Limited, Tokyo (JP)

( * ) Notice: Subject to any disclaimer, the term of this patent is extended or adjusted under 35 U.S.C. 154(b) by 0 days.

(21) Appl. No.: 09/972,206

(22) Filed: Oct. 5, 2001

(65) Prior Publication Data
US 2003/0069294 A1 Apr. 10, 2003

Related U.S. Application Data

(63) Continuation of application No. PCT/JP00/02215, filed on Apr. 6, 2000.

(30) Foreign Application Priority Data

Apr. 6, 1999 (JP) .............................. 11-099286
Jul. 29, 1999 (JP) .......................... 11-215141

(51) Int. Cl.$^7$ .................. A61K 31/4184; C07D 235/16
(52) U.S. Cl. .................. 514/394; 548/309.7; 548/310.1
(58) Field of Search ............ 548/309.7, 310.1; 514/394

(56) References Cited

U.S. PATENT DOCUMENTS

| 4,942,245 A | 7/1990 | Masuzawa et al. |
| 2002/0128254 A1 | 9/2002 | Kawamoto et al. |

FOREIGN PATENT DOCUMENTS

| HU | 204796 B A | 10/1989 |
| JP | 8-504194 A | 5/1996 |
| JP | 9-295970 A | 11/1997 |
| JP | 10-501222 A | 2/1998 |
| JP | 10-114751 A | 5/1998 |
| JP | 10-504808 A | 5/1998 |
| WO | WO 94/12181 A | 6/1994 |
| WO | WO 95/32710 A | 12/1995 |
| WO | WO 96/00730 A | 1/1996 |
| WO | WO 97/31907 A | 9/1997 |
| WO | WO 98/31359 A | 7/1998 |
| WO | WO 99/08501 A | 2/1999 |
| WO | WO 99/29640 A | 6/1999 |

OTHER PUBLICATIONS

U.S. patent application Ser. No. 09/971,634, Fujita et al., filed Oct. 5, 2001.
\* English language Abstract only.
\*\* Patent family member of WO 94/12181 A.
\*\*\* Patent family member of WO 95/32710 A.
\*\*\*\* Patent family member of WO 96/00730 A.

*Primary Examiner*—Laura L. Stockton
(74) *Attorney, Agent, or Firm*—Frishauf, Holtz, Goodman & Chick, P.C.

(57) ABSTRACT

The α-substituted carboxylic acid derivatives having the formula (I):

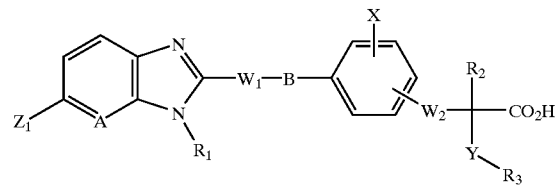

wherein $R_1$ is an alkyl group, etc., $R_2$ is a hydrogen atom, etc., $R_3$ is a hydrogen atom, etc., A is =CH-group, etc., B is an oxygen atom, etc., $W_1$ is a $C_1$–$C_8$ alkylene group, $W_2$ is a single bond or a $C_1$–$C_8$ alkylene group, X is a hydrogen atom, etc., Y is an oxygen atom, etc., and $Z_1$ is an alkoxy group, etc., and pharmacologically acceptable salts, esters and amides thereof are useful for treatment and/or prevention of diabetes mellitus, impaired glucose tolerance, gestational diabetes mellitus, or the like. Some of the derivatives of the formula (I) are novel compounds.

14 Claims, No Drawings

α-SUBSTITUTED CARBOXYLIC ACID DERIVATIVES

This application is a continuation-in-part application of International Application PCT/JP00/02215 filed Apr. 6, 2000 (not published in English) which is incorporated herein by this reference.

TECHNICAL FIELD

The present invention relates to α-substituted carboxylic acid derivatives having excellent insulin resistance improving activity, hypoglycemic activity, anti-inflammatory activity, immunoregulatory activity, aldose reductase inhibiting activity, 5-lipoxygenase inhibiting activity, peroxidized lipid production suppressing activity, PPAR activating activity, anti-osteoporosis activity, leukotrienes antagonistic activity, adipose cell formation promoting activity, cancer cell proliferation suppressing activity or calcium antagonistic activity, to their pharmacologically acceptable esters, to their pharmacologically acceptable amides and to their pharmacologically acceptable salts.

Further, the present invention is directed to preventives and/or therapeutic agents for diseases such as diabetes mellitus, hyperlipemia, obesity, glucose tolerance insufficiency, hypertension, fatty liver, diabetic complications (e.g. retinopathy, nephropathy, neurosis, cataract, coronary artery diseases, etc.), arteriosclerosis, gestational diabetes mellitus, polycystic ovary syndrome, cardiovascular diseases (e.g. ischemic heart disease, etc.), cell injury lesion (e.g. cerebral injury induced by stroke, etc.) caused by atherosclerosis or ischemic heart disease, gout, inflammatory diseases (e.g. arthrosteitis, pain, fervescence, rheumatic arthritis, inflammatory enteritis, acne, sunburn, psoriasis, eczema, allergic diseases, asthma, GI ulcer, cachexia, autoimmune disease, pancreatitis, etc.), cancer, osteoporosis, cataract, and so on containing said α-substituted carboxylic acid derivatives, their pharmacologically acceptable esters, their pharmacologically acceptable amides or their pharmacologically acceptable salts as an active ingredient.

Furthermore, this invention concerns a pharmaceutical composition (particularly, preventives and/or therapeutic agents for diabetes mellitus or diabetic complications) containing at least one of sulfonylureas, α-glucosidase inhibitors, aldose reductase inhibitors, biguanides, statin type compounds, squalene synthesis inhibitors, fibrate type compounds, LDL disassimilation promoters, angiotensin II antagonists, angiotensin converting enzyme inhibitors, anticancer agents, and RXR activators (RXR agonists) together with said α-substituted carboxylic acid derivatives, their pharmacologically acceptable esters, their pharmacologically acceptable amides or their pharmacologically acceptable salts.

BACKGROUND TECHNOLOGY

Some of the α-substituted carboxylic acid derivatives of the present application are disclosed in (1) JP Unexamined Pub. H8 (1996)-504194 Gazette, (2) JP Unexamined Pub. H10 (1998)-501222 Gazette, (3) JP Unexamined Pub. H10 (1998)-504808 Gazette, (4) JP Unexamined Pub. H10 (1998)-114751 Gazette, (5) WO 98/31359 Gazette. However, the activities of the compounds described in these Gazettes are as therapeutic agents for anti-platelet aggregation, osteoclast mediating bone resorption suppression, osteoporosis and the like, which are different from those of the present invention.

Further, compounds showing an effect in treating diabetes mellitus or hypoglycemic activity are disclosed in (6) WO 97/31907 Gazette. However, the compounds described in said Gazette may have a benzimidazole ring, one of the structural features of the compounds in the present application also have the same group, but on the benzene ring of said benzimidazole ring in said Gazette there is no substituent or, if any substituent is present there, said substituent is only a lower alkyl group. On the other hand, the compounds of the present invention have comparatively bulky substituent(s) on the benzene ring of the benzimidazole ring, so they are different from the compounds of said Gazette.

Moreover, compounds having an effect in treating diabetes mellitus are disclosed in (7) WO 99/29640 Gazette. However, the compounds described in said Gazette may be α-carboxylic acids having a benzimidazole structure similar to the compounds of the present application, but they are different from the compounds of the present application, because in this case the α-substituent is an amino group or a protecting group thereof such as an alkoxycarbonyl group or an alkoxycarbonyl group which is comparatively easily removable. In addition, the compounds described in said Gazette are different from those of the present application in the nature of their fibroblast proliferation factor antagonism effects.

DISCLOSURE OF THE INVENTION

As the result of investigations for a long time on the search of synthesis and pharmacology of a series of said α-substituted carboxylic acid derivatives, their pharmacologically acceptable esters, their pharmacologically acceptable amides and their pharmacologically acceptable salts, the present inventors have found the features that said α-substituted carboxylic acid derivatives have excellent insulin resistance improving activity, hypoglycemic activity, anti-inflammatory activity, immunoregulatory activity, aldose reductase inhibiting activity, 5-lipoxygenase inhibiting activity, peroxidized lipid production suppressing activity, PPAR activating activity, anti-osteoporosis activity, leukotrienes antagonistic activity, adipose cell formation promoting activity, cancer cell proliferation suppressing activity or calcium antagonistic activity, with less side effects and high lipophilic solubility. Thus, the present invention has been established.

The other object of the present invention is to provide preventives and/or therapeutic agents against diseases such as diabetes mellitus, hyperlipemia, obesity, glucose tolerance insufficiency, hypertension, fatty liver, diabetic complications (e.g. retinopathy, nephropathy, neurosis, cataract, coronary artery diseases, etc.), arteriosclerosis, gestational diabetes mellitus, polycystic ovary syndrome, cardiovascular diseases (e.g. ischemic heart disease, etc.), cell injury lesion (e.g. cerebral injury induced by stroke, etc.) caused by aterosclerosis or ischemic heart disease, gout, inflammatory diseases (e.g. arthrosteitis, pain, fervescence, rheumatic arthritis, inflammatory enteritis, acne, sunburn, psoriasis, eczema, allergic diseases, asthma, GI ulcer, cachexia, autoimmune disease, pancreatitis, etc.), cancer, osteoporosis, cataract, and so on containing said α-substituted carboxylic acid derivatives, their pharmacologically acceptable esters, their pharmacologically acceptable amides or their pharmacologically acceptable salts as an active ingredient. Further, another object of the present invention is to provide a pharmaceutical composition (particularly, preventives and/or therapeutic agents for diabetes mellitus or diabetic complications) containing at least one of sulfonylureas, α-glucosidase inhibitors, aldose reductase inhibitors, biguanides, statins type compounds, squalene synthesis inhibitors, fibrate type compounds, LDL disassimilation promotors, angiotensin II antagonists, angiotensin converting enzyme inhibitors, anti-cancer agents, and RXR activators (RXR agonists) together with said α-substituted carboxylic acid derivatives, their pharmacologically acceptable esters, their pharmacologically acceptable amides or their pharmacologically acceptable salts. The present invention relates to α-substituted carboxylic acid derivatives having the general formula (I):

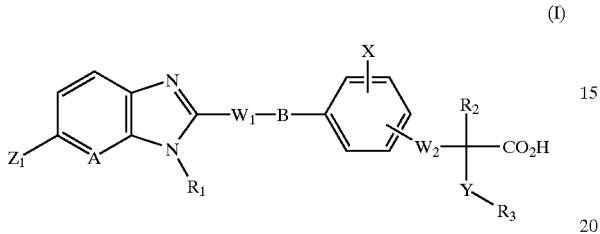

(I)

[wherein $R_1$, $R_2$ and $R_3$ are the same or different, and each is a (i) hydrogen atom, (ii) $C_1$–$C_6$ alkyl group, (iii) $C_6$–$C_{10}$ aryl group (optionally having 1–5 substituting moieties $\alpha_1$ hereafter described), (iv) $C_7$–$C_{16}$ aralkyl group (optionally having 1–5 substituting moieties $\alpha_1$ hereafter described on the aryl moiety thereof), (v) $C_1$–$C_6$ alkylsulfonyl group, (vi) $C_1$–$C_6$ halogenoalkylsulfonyl group, (vii) $C_6$–$C_{10}$ arylsulfonyl group (optionally having 1–5 substituting moieties $\alpha_1$ hereafter described) or (viii) $C_7$–$C_{16}$ aralkylsulfonyl group (optionally having 1–5 substituting moieties $\alpha_1$ hereafter described on the aryl moiety thereof), A is a nitrogen atom or =CH-group, B is an oxygen atom or a sulfur atom, $W_1$ is a $C_1$–$C_8$ alkylene group, $W_2$ is a single bond or a $C_1$–$C_8$ alkylene group, X is a (i) hydrogen atom, (ii) $C_1$–$C_6$ alkyl group, (iii) $C_1$–$C_6$ halogenoalkyl group, (iv) $C_1$–$C_6$ alkoxy group, (v) halogen atom, (vi) hydroxy group, (vii) cyano group, (viii) nitro group, (ix) $C_3$–$C_{10}$ cycloalkyl group, (x) $C_6$–$C_{10}$ aryl group (optionally having 1–5 substituting moieties β hereafter described), (xi) $C_7$–$C_{16}$ aralkyl group (optionally having 1–5 substituting moieties β hereafter described on the aryl moiety thereof), (xii) $C_1$–$C_7$ aliphatic acyl group, (xiii) $C_4$–$C_{11}$ cycloalkylcarbonyl group, (xiv) $C_7$–$C_{11}$ arylcarbonyl group (optionally having 1–5 substituting moieties β hereafter described), (xv) $C_8$–$C_{17}$ aralkylcarbonyl group (optionally having 1–5 substituting moieties β hereafter described on the aryl moiety thereof), (xvi) monocyclic type heteroaromatic ring-carbonyl group (optionally having 1–5 substituting moieties β hereafter described), (xvii) carbamoyl group, (xviii) $C_7$–$C_{11}$ arylaminocarbonyl group (optionally having 1–5 substituting moieties β hereafter described on the aryl moiety thereof) or (xix) amino group (optionally having 1 to 2 substituting moieties β described hereafter), Y is an oxygen atom or S(O)p (wherein p is an integer from 0 to 2), $Z_1$ is a (i) hydrogen atom, (ii) $C_1$–$C_6$ alkyl group, (iii) $C_1$–$C_6$ alkoxy group, (iv) $C_1$–$C_6$ alkylthio group, (v) halogen atom, (vi) $C_6$–$C_{10}$ aryl group (optionally having 1–5 substituting moieties $\alpha_1$ hereafter described), (vii) $C_7$–$C_{16}$ aralkyl group (optionally having 1–5 substituting moieties $\alpha_1$ hereafter described on the aryl moiety thereof), (viii) $C_6$–$C_{10}$ aryloxy group (optionally having 1–5 substituting moieties $\alpha_1$ hereafter described), (ix) $C_7$–$C_{16}$ aralkyloxy group (optionally having 1–5 substituting moieties $\alpha_1$ hereafter described on the aryl moiety thereof), (x) $C_3$–$C_{10}$ cycloalkyloxy group, (xi) $C_3$–$C_{10}$ cycloalkylthio group, (xii) saturated heterocyclic ring-oxy group (optionally having 1–5 substituting moieties $\alpha_1$ hereafter described), (xiii) monocyclic type heteroaromatic ring-oxy group (optionally having 1–5 substituting moieties $\alpha_1$ hereafter described), (xiv) $C_6$–$C_{10}$ arylthio group (optionally having 1–5 substituting moieties $\alpha_1$ hereafter described on the aryl moiety thereof), (xv) $C_7$–$C_{16}$ aralkylthio group (optionally having 1–5 substituting moieties $\alpha_1$ hereafter described on the aryl moiety thereof), (xvi) saturated heterocyclic ring-thio group (optionally having 1–5 substituting moieties $\alpha_1$ hereafter described), (xvii) monocyclic type heteroaromatic ring-thio group (optionally having 1–5 substituting moieties $\alpha_1$ hereafter described), (xviii) amino group (optionally having 1–2 substituting moieties $\alpha_1$ hereafter described) or (xix) hydroxy group, said substituting moiety $\alpha_1$ is a (i) $C_1$–$C_6$ alkyl group, (ii) $C_1$–$C_6$ halogenoalkyl group, (iii) $C_1$–$C_6$ alkoxy group, (iv) halogen atom, (v) hydroxy group, (vi) cyano group, (vii) nitro group, (viii) $C_3$–$C_{10}$ cycloalkyl group, (ix) $C_6$–$C_{10}$ aryl group (optionally having 1–5 substituting moieties β hereafter described), (x) $C_7$–$C_{16}$ aralkyl group (optionally having 1–5 substituting moieties β hereafter described on the aryl moiety thereof), (xi) $C_1$–$C_7$ aliphatic acyl group, (xii) $C_4$–$C_{11}$ cycloalkylcarbonyl group, (xiii) $C_7$–$C_{11}$ arylcarbonyl group (optionally having 1–5 substituting moieties β hereafter described), (xiv) $C_8$–$C_{17}$ aralkylcarbonyl group (optionally having 1–5 substituting moieties β hereafter described on the aryl moiety thereof), (xv) monocyclic type heteroaromatic ring-carbonyl group (optionally having 1–5 substituting moieties β hereafter described), (xvi) carbamoyl group, (xvii) $C_7$–$C_{11}$ arylaminocarbonyl group (optionally having 1–5 substituting moieties β hereafter described on the aryl moiety thereof), (xviii) amino group (optionally having 1 to 2 substituting moieties β described hereafter) or (xix) carboxyl group, said substituting moiety β is a (i) $C_1$–$C_{10}$ to alkyl group, (ii) halogen atom, (iii) $C_6$–$C_{10}$ aryl group (optionally having 1–5 substituting moieties γ hereafter described), (iv) $C_7$–$C_{16}$ aralkyl group (optionally having 1–5 substituting moieties γ hereafter described on the aryl moiety thereof), (v) $C_1$–$C_7$ aliphatic acyl group, (vi) $C_7$–$C_{11}$ arylcarbonyl group (optionally having 1–5 substituting moieties γ hereafter described), (vii) $C_8$–$C_{17}$ aralkylcarbonyl group (optionally having 1–5 substituting moieties γ hereafter described on the aryl moiety thereof), (viii) $C_4$–$C_{11}$ cycloalkylcarbonyl group, (ix) monocyclic type heteroaromatic ring-carbonyl group (optionally having 1–5 substituting moieties γ hereafter described), (x) carbamoyl group or (xi) $C_7$–$C_{11}$ arylaminocarbonyl group (optionally having 1–5 substituting moieties γ hereafter described on the aryl moiety thereof), and said substituting moiety γ is a $C_1$–$C_6$ alkyl group, $C_1$–$C_6$ halogenoalkyl group, halogen atom or hydroxy group], the general formula (II)

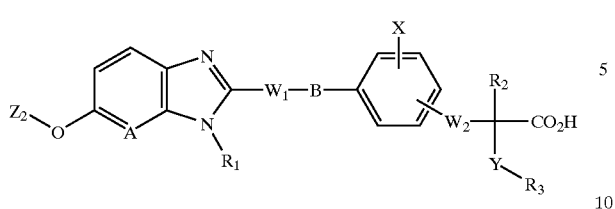

(II)

[wherein $R_1$, $R_2$ and $R_3$ are the same or different, and each is a (i) hydrogen atom, (ii) $C_1$–$C_6$ alkyl group, (iii) $C_6$–$C_{10}$ aryl group (optionally having 1–5 substituting moieties $\alpha_1$ hereafter described), (iv) $C_7$–$C_{16}$ aralkyl group (optionally having 1–5 substituting moieties $\alpha_1$ hereafter described on the aryl moiety thereof), (v) $C_1$–$C_6$ alkylsulfonyl group, (vi) $C_1$–$C_6$ halogenoalkylsulfonyl group, (vii) $C_6$–$C_{10}$ arylsulfonyl group (optionally having 1–5 substituting moieties $\alpha_1$ hereafter described) or (viii) $C_7$–$C_{16}$ aralkylsulfonyl group (optionally having 1–5 substituting moieties $\alpha_1$ hereafter described on the aryl moiety thereof), A is a nitrogen atom or =CH-group, B is an oxygen atom or a sulfur atom, $W_1$ is a $C_1$–$C_8$ alkylene group, $W_2$ is a single bond or a $C_1$–$C_8$ alkylene group, X is a (i) hydrogen atom, (ii) $C_1$–$C_6$ alkylene group, (iii) $C_1$–$C_6$ halogenoalkyl group, (iv) $C_1$–$C_6$ alkoxy group, (v) halogen atom, (vi) hydroxy group, (vii) cyano group, (viii) nitro group, (ix) $C_3$–$C_{10}$ cycloalkyl group, (x) $C_6$–$C_{10}$ aryl group (optionally having 1–5 substituting moieties $\beta$ hereafter described), (xi) $C_7$–$C_{16}$ aralkyl group (optionally having 1–5 substituting moieties $\beta$ hereafter described on the aryl moiety thereof), (xii) $C_1$–$C_7$ aliphatic acyl group, (xiii) $C_4$–$C_{11}$ cycloalkylcarbonyl group, (xiv) $C_7$–$C_{11}$ arylcarbonyl group (optionally having 1–5 substituting moieties $\beta$ hereafter described), (xv) $C_8$–$C_{17}$ aralkylcarbonyl group (optionally having 1–5 substituting moieties $\beta$ hereafter described on the aryl moiety thereof), (xvi) monocyclic type heteroaromatic ring-carbonyl group (optionally having 1–5 substituting moieties $\beta$ described hereafter), (xvii) carbamoyl group, (xviii) $C_7$–$C_{11}$ arylaminocarbonyl group (optionally having 1–5 substituting moieties $\beta$ hereafter described on the aryl moiety thereof) or (xix) amino group (optionally having 1 to 2 substituting moieties $\beta$ described hereafter), Y is an oxygen atom or S(O)p group (wherein p is an integer from 0 to 2)

$Z_2$ is a saturated heterocyclic ring (optionally having 1–5 substituting moieties $\alpha_1$ hereafter described), or $C_6$–$C_{10}$ aryl group (optionally having 1–5 substituting moieties $\alpha_2$ hereafter described), said substituting moiety $\alpha_1$ is a (i) $C_1$–$C_6$ alkyl group, (ii) $C_1$–$C_6$ halogenoalkyl group, (iii) $C_1$–$C_6$ alkoxy group, (iv) halogen atom, (v) hydroxy group, (vi) cyano group, (vii) nitro group, (viii) $C_3$–$C_{10}$ cycloalkyl group, (ix) $C_6$–$C_{10}$ aryl group (optionally having 1–5 substituting moieties $\beta$ hereafter described), (x) $C_7$–$C_{16}$ aralkyl group (optionally having 1–5 substituting moieties $\beta$ hereafter described on the aryl moiety thereof), (xi) $C_1$–$C_7$ aliphatic-acyl group, (xii) $C_4$–$C_{11}$ cycloalkylcarbonyl group, (xiii) $C_7$–$C_{11}$ arylcarbonyl group (optionally having 1–5 substituting moieties $\beta$ hereafter described), (xiv) $C_8$–$C_{17}$ aralkylcarbonyl group (optionally having 1–5 substituting moieties $\beta$ hereafter described on the aryl moiety thereof), (xv) monocyclic type heteroaromatic ring-carbonyl group (optionally having 1–5 substituting moieties $\beta$ hereafter described), (xvi) carbamoyl group, (xvii) $C_7$–$C_{11}$ arylaminocarbonyl group (optionally having 1–5 substituting moieties $\beta$ hereafter described on the aryl moiety thereof), (xviii) amino group (optionally having 1 to 2 substituting moieties $\beta$ described hereafter) or (xix) carboxyl group, said substituting moiety $\alpha_2$ is a (i) $C_3$–$C_{10}$ cycloalkyl group, (ii) $C_6$–$C_{10}$ aryl group (optionally having 1–5 substituting moieties $\beta$ hereafter described), (iii) $C_7$–$C_{16}$ aralkyl group (optionally having 1–5 substituting moieties $\beta$ hereafter described on the aryl moiety thereof), (iv) $C_1$–$C_7$ aliphatic acyl group, (v) $C_4$–$C_{11}$ cycloalkylcarbonyl group, (vi) $C_7$–$C_{11}$ arylcarbonyl group (optionally having 1–5 substituting moieties $\beta$ hereafter described), (vii) $C_8$–$C_{17}$ aralkylcarbonyl group (optionally having 1–5 substituting moieties $\beta$ hereafter described on the aryl moiety thereof), (viii) monocyclic type heteroaromatic ring-carbonyl group (optionally having 1–5 substituting moieties $\beta$ hereafter described), or (ix) $C_7$–$C_{11}$ arylaminocarbonyl group (optionally having 1–5 substituting moieties $\beta$ hereafter described on the aryl moiety thereof), said substituting moiety $\beta$ is a (i) $C_1$–$C_{10}$ alkyl group, (ii) halogen atom, (iii) $C_6$–$C_{10}$ aryl group (optionally having 1–5 substituting moieties $\gamma$ hereafter described), (iv) $C_7$–$C_{16}$ aralkyl group (optionally having 1–5 substituting moieties $\gamma$ hereafter described on the aryl moiety thereof), (v) $C_1$–$C_7$ aliphatic acyl group, (vi) $C_7$–$C_{11}$ arylcarbonyl group (optionally having 1–5 substituting moieties $\gamma$ hereafter described), (vii) $C_8$–$C_{17}$ aralkylcarbonyl group (optionally having 1–5 substituting moieties $\gamma$ hereafter described on the aryl moiety thereof), (viii) $C_4$–$C_{11}$ cycloalkylcarbonyl group, (ix) monocyclic type heteroaromatic ring-carbonyl group (optionally having 1–5 substituting moieties $\gamma$ hereafter described), (x) carbamoyl group or (xi) $C_7$–$C_{11}$ arylaminocarbonyl group (optionally having 1–5 substituting moieties $\gamma$ hereafter described on the aryl moiety thereof), and said substituting moiety $\gamma$ is a $C_1$–$C_6$ alkyl group, $C_1$–$C_6$ halogenoalkyl group, halogen group or hydroxy group], the general formula (III)

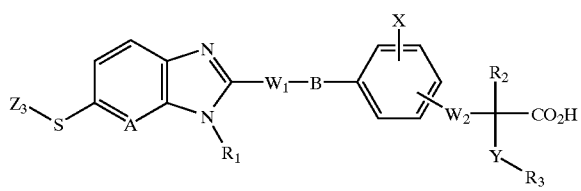

(III)

[wherein $R_1$, $R_2$ and $R_3$ are the same or different, and each is a (i) hydrogen atom, (ii) $C_1$–$C_6$ alkyl group, (iii) $C_6$–$C_{10}$ aryl group (optionally having 1–5 substituting moieties $\alpha_1$ hereafter described), (iv) $C_7$–$C_{16}$ aralkyl group (optionally having 1–5 substituting moieties $\alpha_1$ hereafter described on the aryl moiety thereof), (v) $C_1$–$C_6$ alkylsulfonyl group, (vi) $C_1$–$C_6$ halogenoalkylsulfonyl group, (vii) $C_6$–$C_{10}$ arylsulfonyl group (optionally having 1–5 substituting moieties $\alpha_1$ hereafter described) or (viii) $C_7$–$C_{16}$ aralkylsulfonyl group (optionally having 1–5 substituting moieties $\alpha_1$ hereafter described on the aryl moiety thereof), A is a nitrogen atom or =CH-group, B is an oxygen atom or a sulfur atom, $W_1$ is a $C_1$–$C_8$ alkylene group, $W_2$ is a single bond or a $C_1$–$C_8$ alkylene group, X is a (i) hydrogen atom, (ii) $C_1$–$C_6$ alkyl group, (iii) $C_1$–$C_6$ halogenoalkyl group, (iv) $C_1$–$C_6$ alkoxy group, (v) halogen atom, (vi) hydroxy group, (vii) cyano group, (viii) nitro group, (ix) $C_3$–$C_{10}$ cycloalkyl group, (x) $C_6$–$C_{10}$ aryl group (optionally having 1–5 substituting moieties β hereafter described), (xi) $C_7$–$C_{16}$ aralkyl group (optionally having 1–5 substituting moieties β hereafter described on the aryl moiety thereof), (xii) $C_1$–$C_7$ aliphatic acyl group, (xiii) $C_4$–$C_{11}$ cycloalkylcarbonyl group, (xiv) $C_7$–$C_{11}$ arylcarbonyl group (optionally having 1–5 substituting moieties β hereafter described), (xv) $C_8$–$C_{17}$ aralkylcarbonyl group (optionally having 1–5 substituting moieties β hereafter described on the aryl moiety thereof), (xvi) monocyclic type heteroaromatic ring-carbonyl group (optionally having 1–5 substituting moieties β hereafter described), (xvii) carbamoyl group, (xviii) $C_7$–$C_{11}$ arylaminocarbonyl group (optionally having 1–5 substituting moieties β hereafter described on the aryl moiety thereof) or (xix) amino group (optionally having 1 to 2 substituting moieties β described hereafter), Y is an oxygen atom or S(O)p group (wherein p is an integer from 0 to 2), $Z_3$ is a (i) $C_1$–$C_6$ alkyl group, (ii) $C_6$–$C_{10}$ aryl group (optionally containing 1–5 substituting moieties $\alpha_1$ hereafter described), (iii) $C_7$–$C_{16}$ aralkyl group (optionally containing 1–5 substituting moieties $\alpha_1$ hereafter described on the aryl moiety thereof), (iv) $C_3$–$C_{10}$ cycloalkyl group or (v) saturated heterocyclic ring group (optionally containing 1–5 substituting moieties $\alpha_1$ hereafter described), said substituting moiety $\alpha_1$ is a (i) $C_1$–$C_6$ alkyl group, (ii) $C_1$–$C_6$ halogenoalkyl group, (iii) $C_1$–$C_6$ alkoxy group, (iv) halogen atom, (v) hydroxy group, (vi) cyano group, (vii) nitro group, (viii) $C_3$–$C_{10}$ cycloalkyl group, (ix) $C_6$–$C_{10}$ aryl group (optionally having 1–5 substituting moieties β hereafter described), (x) $C_7$–$C_{16}$ aralkyl group (optionally having 1–5 substituting moieties β hereafter described on the aryl moiety thereof), (xi) $C_1$–$C_7$ aliphatic acyl group, (xii) $C_4$–$C_{11}$ cycloalkylcarbonyl group, (xiii) $C_7$–$C_{11}$ arylcarbonyl group (optionally having 1–5 substituting moieties β hereafter described), (xiv) $C_8$–$C_{17}$ aralkylcarbonyl group (optionally having 1–5 substituting moieties β hereafter described on the aryl moiety thereof), (xv) monocyclic type heteroaromatic ring-carbonyl group (optionally having 1–5 substituting moieties β hereafter described), (xvi) carbamoyl group, (xvii) $C_7$–$C_{11}$ arylaminocarbonyl group (optionally having 1–5 substituting moieties β hereafter described on the aryl moiety thereof), (xviii) amino group (optionally having 1 to 2 substituting moieties β described hereafter) or (xix) carboxyl group, said substituting moiety β is a (i) $C_1$–$C_{10}$ alkyl group, (ii) halogen atom, (iii) $C_6$–$C_{10}$ aryl group (optionally having 1–5 substituting moieties γ hereafter described), (iv) $C_7$–$C_{16}$ aralkyl group (optionally having 1–5 substituting moieties γ hereafter described on the aryl moiety thereof), (v) $C_1$–$C_7$ aliphatic acyl group, (vi) $C_7$–$C_{11}$ arylcarbonyl group (optionally having 1–5 substituting moieties γ hereafter described), (vii) $C_8$–$C_{17}$ aralkylcarbonyl group (optionally having 1–5 substituting moieties γ hereafter described on the aryl moiety thereof), (viii) $C_4$–$C_{11}$ cycloalkylcarbonyl group, (ix) monocyclic type heteroaromatic ring-carbonyl group (optionally having 1–5 substituting moieties γ hereafter described), (x) carbamoyl group or (xi) $C_7$–$C_{11}$ arylaminocarbonyl group (optionally having 1–5 substituting moieties γ hereafter described on the aryl moiety thereof), and said substituting moiety γ is a $C_1$–$C_6$ alkyl group, $C_1$–$C_6$ halogenoalkyl group, halogen atom or hydroxy group], or the general formula (IV)

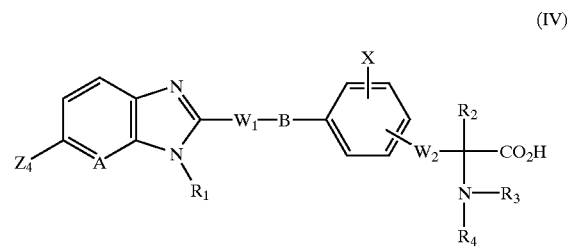

(IV)

[wherein $R_1$, $R_2$ and $R_3$ are the same or different, and each is a (i) hydrogen atom, (ii) $C_1$–$C_6$ alkyl group, (iii) $C_6$–$C_{10}$ aryl group (optionally having 1–5 substituting moieties $\alpha_1$ hereafter described), (iv) $C_7$–$C_{16}$ aralkyl group (optionally having 1–5 substituting moieties $\alpha_1$ hereafter described on the aryl moiety thereof), (v) $C_1$–$C_6$ alkylsulfonyl group, (vi) $C_1$–$C_6$ halogenoalkylsulfonyl group, (vii) $C_6$–$C_{10}$ arylsulfonyl group (optionally having 1–5 substituting moieties $\alpha_1$ hereafter described) or (viii) $C_7$–$C_{16}$ aralkylsulfonyl group (optionally having 1–5 substituting moieties $\alpha_1$ hereafter described on the aryl moiety thereof), $R_4$ is a (i) $C_1$–$C_6$ alkyl group, (ii) $C_6$–$C_{10}$ aryl group (optionally having 1–5 substituting moieties $\alpha_1$ hereafter described) or (iii) $C_7$–$C_{16}$ aralkyl group (optionally having 1–5 substituting moieties $\alpha_1$ hereafter described on the aryl moiety thereof), A is a nitrogen atom or =CH-group, B is an oxygen atom or a sulfur atom, $W_1$ is a $C_1$–$C_8$ alkylene group, $W_2$ is a single bond or a $C_1$–$C_8$ alkylene group, X is a (i) hydrogen atom, (ii) $C_1$–$C_6$ alkyl group, (iii) $C_1$–$C_6$ halogenoalkyl group, (iv) $C_1$–$C_6$ alkoxy group, (v) halogen atom, (vi) hydroxy group, (vii) cyano group, (viii) nitro group, (ix) $C_3$–$C_{10}$ cycloalkyl group, (x) $C_6$–$C_{10}$ aryl group (optionally having 1–5 substituting moieties β hereafter described), (xi) $C_7$–$C_{16}$ aralkyl group (optionally having 1–5 substituting moieties, hereafter described on the aryl moiety thereof), (xii) $C_1$–$C_7$ aliphatic acyl group, (xiii) $C_4$–$C_{11}$ cycloalkylcarbonyl group, (xiv) $C_7$–$C_{11}$ arylcarbonyl group (optionally having 1–5 substituting moieties β hereafter described), (xv) $C_8$–$C_{17}$ aralkylcarbonyl group (optionally having 1–5 substituting moieties β hereafter described on the aryl moiety thereof), (xvi) monocyclic type heteroaromatic ring-carbonyl group (optionally having 1–5 substituting moieties β hereafter described), (xvii) carbamoyl group, (xviii) $C_7$–$C_{11}$ arylaminocarbonyl group (optionally having 1–5 substituting moieties β hereafter described on the aryl moiety thereof) or (xix) amino group (optionally having 1 to 2 substituting moieties β described hereafter), Y is an oxygen atom or S(O)p (wherein p is an integer from 0 to 2), $Z_4$ is a (i) $C_1$–$C_6$ alkoxy group, (ii) $C_1$–$C_6$ alkylthio group, (iii) halogen atom, (iv) $C_6$–$C_{10}$ aryl group (optionally having 1–5 substituting moieties $\alpha_1$ hereafter described), (v) $C_7$–$C_{16}$ aralkyl group (optionally having 1–5 substituting moieties $\alpha_1$ hereafter described on the aryl moiety thereof), (vi) $C_6$–$C_{10}$ aryloxy group (optionally having 1–5 substituting moieties $\alpha_1$ hereafter described), (vii) $C_7$–$C_{16}$ aralkyloxy group (optionally having 1–5 substituting moieties $\alpha_1$ hereafter described on the aryl moiety thereof), (viii) $C_3$–$C_{10}$ cycloalkyloxy group, (ix) $C_3$–$C_{10}$ cycloalkylthio group, (x) saturated heterocyclic ring-oxy group (optionally having 1–5 substituting moieties $\alpha_1$ hereafter described), (xi) monocyclic type heteroaromatic ring-oxy group (optionally having 1–5 substituting moieties $\alpha_1$ hereafter described), (xii) $C_6$–$C_{10}$ arylthio group (optionally having 1–5 substituting moieties $\alpha_1$ hereafter described), (xiii) $C_7$–$C_{16}$ aralkylthio group (optionally having 1–5 substituting moieties $\alpha_1$ hereafter described on the aryl moiety thereof), (xiv) saturated heterocyclic ring-thio group (optionally having 1–5 substituting moieties $\alpha_1$ hereafter described), (xv) monocyclic type heteroaromatic ring-thio group (optionally having 1–5 substituting moieties $\alpha_1$ hereafter described), (xvi) amino group (optionally having 1 to 2 substituting moieties $\alpha_1$ hereafter described) or (xvii) hydroxy group, said substituting moiety $\alpha_1$ is a (i) $C_1$–$C_6$ alkyl group, (ii) $C_1$–$C_6$ halogenoalkyl group, (iii) $C_1$–$C_6$ alkoxy group, (iv) halogen atom, (v) hydroxy group, (vi) cyano group, (vii) nitro group, (viii) $C_3$–$C_{10}$ cycloalkyl group, (ix) $C_6$–$C_{10}$ aryl group (optionally having 1–5 substituting moieties β hereafter described), (x) $C_7$–$C_{16}$ aralkyl group (optionally having 1–5 substituting moieties β hereafter described on the aryl moiety thereof), (xi) $C_1$–$C_7$ aliphatic acyl group, (xii) $C_4$–$C_{11}$ cycloalkylcarbonyl group, (xiii) $C_7$–$C_{11}$ arylcarbonyl group (optionally having 1–5 substituting moieties β hereafter described), (xiv) $C_8$–$C_{17}$ aralkylcarbonyl group (optionally having 1–5 substituting moieties β hereafter described on the aryl moiety thereof), (xv) monocyclic type heteroaromatic ring-carbonyl group (optionally having 1–5 substituting moieties β hereafter described), (xvi) carbamoyl group, (xvii) $C_7$–$C_{11}$ arylaminocarbonyl group (optionally having 1–5 substituting moieties β hereafter described on the aryl moiety thereof), (xviii) amino group (optionally having 1 to 2 substituting moieties β described hereafter) or (xix) carboxyl group, said substituting moiety β is a (i) $C_1$–$C_{10}$ alkyl group, (ii) halogen atom, (iii) $C_6$–$C_{10}$ aryl group (optionally having 1–5 substituting moieties γ hereafter described), (iv) $C_7$–$C_{16}$ aralkyl group (optionally having 1–5 substituting moieties γ hereafter described on the aryl moiety thereof), (v) $C_1$–$C_7$ aliphatic acyl group, (vi) $C_7$–$C_{11}$ arylcarbonyl group (optionally having 1–5 substituting moieties γ hereafter described), (vii) $C_8$–$C_{17}$ aralkylcarbonyl group (optionally having 1–5 substituting moieties γ hereafter described on the aryl moiety thereof), (viii) $C_4$–$C_{11}$ cycloalkylcarbonyl group, (ix) monocyclic type heteroaromatic ring-carbonyl group (optionally having 1–5 substituting moieties γ hereafter described), (x) carbamoyl group or (xi) $C_7$–$C_{11}$ arylaminocarbonyl group (optionally having 1–5 substituting moieties γ hereafter described on the aryl moiety thereof), and said substituting moiety γ is a $C_1$–$C_6$ alkyl group, $C_1$–$C_6$ halogenoalkyl group, halogen atom or hydroxy group], their pharmacologically acceptable esters, their pharmacologically acceptable amides or their pharmacologically acceptable salts. Further, $Z_2$O-group in the general formula (II), $Z_3$S-group in the general formula (III) and $Z_4$ in the general formula (IV) is contained in the scope of $Z_1$ in the general formula (I).

When $R_1$, $R_2$, $R_3$, $R_4$, X, $Z_1$, $Z_3$, $\alpha_1$ and γ represent a "$C_1$–$C_6$ alkyl group", said group means a straight or branched alkyl group of 1 to 6 carbon atoms. Examples of said group are methyl, ethyl, propyl, isopropyl, butyl, isobutyl, s-butyl, t-butyl, pentyl, s-pentyl, isopentyl, 2-methylbutyl, neopentyl, 1-ethylpropyl, hexyl, 4-methylpentyl (isohexyl), 3-methylpentyl, 2-methylpentyl, 1-methylpentyl (s-hexyl), 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group. $C_1$–$C_4$ alkyl groups are preferable, and $C_1$–$C_2$ alkyl groups are more preferable.

When $R_1$, $R_2$, $R_3$, $R_4$, $Z_1$, $Z_3$ and $Z_4$ represent a "$C_6$–$C_{10}$ aryl group (optionally having 1–5 substituting moieties $\alpha_1$ described hereafter)", when X, $\alpha_1$ and $\alpha_2$ represent a "$C_6$–$C_{10}$ aryl group (optionally having 1–5 substituting moieties β hereafter described)", when β is a "$C_6$–$C_{10}$ aryl group (optionally having 1–5 substituting moieties γ hereafter described)", and when $Z_2$ is a "$C_6$–$C_{10}$ aryl group (optionally having 1–5 substituting moieties $\alpha_2$ described hereafter)", said $C_6$–$C_{10}$ aryl group illustratively includes phenyl, indenyl and naphthyl.

When $R_1$, $R_2$, $R_3$, $R_4$, $Z_1$ and $Z_3$ represent a "$C_7$–$C_{16}$ aralkyl group (optionally having 1–5 substituting moieties $\alpha_1$ hereafter described on the aryl moiety thereof)", when X, $\alpha_1$ and $\alpha_2$ represent a "$C_7$–$C_{16}$ aralkyl group (optionally having 1–5 substituting moieties β hereafter described on the aryl moiety thereof)" and when β is a "$C_7$–$C_{16}$ aralkyl group (optionally having 1–5 substituting moieties γ hereafter described on the aryl moiety thereof)", said $C_7$–$C_{16}$ aralkyl group means a $C_1$–$C_6$ alkyl group which is substituted by said $C_6$–$C_{10}$ aryl group. Examples of said aralkyl moiety are benzyl, naphthylmethyl, indenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 5-phenylpentyl, 5-naphthylpentyl, 6-phenylhexyl and 6-naphthylhexyl.

When $R_1$, $R_2$ and $R_3$ represent a "$C_1$–$C_6$ alkylsulfonyl group", said group means a group in which said $C_1$–$C_6$ alkyl group is bonded to the sulfonyl moiety. Examples of said group are methanesulfonyl, ethanesulfonyl, propanesulfonyl, isopropanesulfonyl, butanesulfonyl, isobutanesulfonyl, s-butanesulfonyl, t-butanesulfonyl, pentanesulfonyl, isopentanesulfonyl, 2-methylbutanesulfonyl, neopentanesulfonyl, 1-ethylpropanesulfonyl, hexanesulfonyl, 4-methylpentanesulfonyl, 3-methylpentanesulfonyl, 2-methylpentanesulfonyl, 3,3-dimethylpentanesulfonyl, 2,2-dimethylbutanesulfonyl, 1,1-dimethylbutanesulfonyl, 1,2-dimethylbutanesulfonyl, 1,3-dimethylbutanesulfonyl, 2,3-dimethylbutanesulfonyl and 2-ethylbutanesulfonyl. $C_1$–$C_4$ alkylsulfonyl groups are preferable, $C_1$–$C_2$ alkylsulfonyl groups are more preferable, and methanesulfonyl is the most preferable.

When $R_1$, $R_2$ and $R_3$ represent a "$C_1$–$C_6$ halogenoalkylsulfonyl group", said group means a group in which the alkyl moiety of said $C_1$–$C_6$ alkylsulfonyl group is substituted by one or more halogen atoms. Examples of said group are trifluoromethanesulfonyl, trichloromethanesulfonyl, difluoromethanesulfonyl, dichloro-methanesulfonyl, dibromomethanesulfonyl, fluoromethanesulfonyl, 2,2,2-trifluoroethanesulfonyl, 2,2,2-trichloroethanesulfonyl, 2-bromoethanesulfonyl, 2-chloroethanesulfonyl, 2-fluoroethanesulfonyl, 2-iodoethanesulfonyl, 3-chloropropanesulfonyl, 4-fluorobutanesulfonyl, 6-iodohexanesulfonyl and 2,2-dibromethanesulfonyl.

$C_1$–$C_4$ halogenoalkylsulfonyl groups are preferable, $C_1$–$C_2$ halogenoalkylsulfonyl groups are more preferable, and trifluoromethanesulfonyl is the most preferable.

When $R_1$, $R_2$ and $R_3$ represent a "$C_6$–$C_{10}$ arylsulfonyl group (optionally having 1–5 substituting moieties $\alpha_1$ hereafter described)", said $C_6$–$C_{10}$ arylsulfonyl moiety means a group in which said $C_6$–$C_{10}$ aryl group is bonded to a sulfonyl moiety. Examples of said $C_6$–$C_{10}$ arylsulfonyl moiety are phenylsulfonyl, indenylsulfonyl and naphthylsulfonyl.

When $R_1$, $R_2$ and $R_3$ represent a "$C_7$–$C_{16}$ aralkylsulfonyl group (optionally having 1–5 substituting moieties $\alpha_1$ hereafter described on the aryl moiety thereof)", said $C_7$–$C_{16}$ aralkylsulfonyl moiety free of the substituting moiety means a group in which said $C_7$–$C_{16}$ aralkyl is bonded to a sulfonyl moiety. Examples of said $C_7$–$C_{16}$ aralkylsulfonyl moiety are benzylsulfonyl, naphthylmethylsulfonyl, indenylmethylsulfonyl, 1-phenethylsulfonyl, 2-phenethylsulfonyl, 1-naphthylethylsulfonyl, 2-naphthylethylsulfonyl, 1-phenylpropylsulfonyl, 2-phenylpropylsulfonyl, 3-phenylpropylsulfonyl, 1-naphthylpropylsulfonyl, 2-naphthylpropylsulfonyl, 3-naphthylpropylsulfonyl, 1-phenylbutylsulfonyl, 2-phenylbutylsulfonyl, 3-phenylbutylsulfonyl, 4-phenylbutylsulfonyl, 1-naphthylbutylsulfonyl, 2-naphthylbutylsulfonyl, 3-naphthylbutylsulfonyl, 4-naphthylbutylsulfonyl, 5-phenylpentylsulfonyl, 5-naphthylpentylsulfonyl, 6-phenylhexylsulfonyl and 6-naphthylhexylsulfonyl.

When $W_1$ and $W_2$ represent a "$C_1$–$C_6$ alkylene group", said group means a straight or branched chain alkylene group containing 1 to 8 carbon atoms. Examples of said group are methylene, methylmethylene, ethylene, propylene, trimethylene, 1-methylethylene, tetramethylene, 1-methyltrimethylene, 2-methyltrimethylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene, 4,4-dimethyltetramethylene, heptamethylene, 1-methylhexamethylene, 2-methylhexamethylene, 5-methylhexamethylene, 3-ethylpentamethylene, octamethylene, 2-methylheptamethylene, 5-methylheptamethylene, 2-ethylhexamethylene, 2-ethyl-3-methylpentamethylene and 3-ethyl-2-methylpentamethylene. The straight chain type $C_1$–$C_6$ alkylene groups are preferable, the straight chain type $C_1$–$C_4$ alkylene groups are more preferable, and the straight chain type $C_1$–$C_2$ alkylene groups are the most preferable.

When X, $\alpha_1$ and $\gamma$ represent a "$C_1$–$C_6$ halogenoalkyl group", said group means a group in which said $C_1$–$C_6$ alkyl group is substituted by one or more halogen atoms. Examples of said group are trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl, and 2,2-dibromethyl. $C_1$–$C_4$ halogenoalkyl groups are preferable, $C_1$–$C_2$ halogenoalkyl groups are more preferable, and trifluoromethyl is the most preferable.

When X, $Z_1$, $Z_4$ and $\alpha_1$ represent a "$C_1$–$C_6$ alkoxy group", said group means a group in which said $C_1$–$C_6$ alkyl group is bonded to oxygen atom. Examples of said group are methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, and 2-ethylbutoxy. $C_1$–$C_4$ alkoxy groups are preferable, $C_1$–$C_2$ alkoxy groups are more preferable, and methoxy is the most preferable.

When X, $Z_1$, $Z_4$, $\alpha_1$, $\beta$ and $\gamma$ represent a "halogen atom", said group means illustratively a fluorine atom, chlorine atom, bromine atom and iodine atom. Fluorine atom, chlorine atom and bromine atom are preferable, and fluorine atom and chlorine atom are more preferable.

When X, $Z_3$, $\alpha_1$ and $\alpha_2$ represent a "$C_3$–$C_{10}$ cycloalkyl group", said group means a 3 to 10 member saturated cyclic ring type hydrocarbon. Examples of said group are cyclopropyl, cyclobutyl, cyclopentyl, cyclohexyl, cycloheptyl, norbornyl and adamantyl. Cyclopropyl, cyclohexyl and adamantyl are preferable, and adamantyl is more preferable.

When X, $\alpha_1$, $\alpha_2$ and $\beta$ represent a "$C_1$–$C_7$ aliphatic acyl group", said group involves illustratively formyl, acetyl, propionyl, butyryl, isobutyryl, valeryl, isovaleryl, pivaloyl, hexanoyl, acryloyl, methacryloyl and crotonoyl. $C_1$–$C_5$ aliphatic acyl groups are preferable, $C_1$–$C_3$ aliphatic acyl groups are more preferable, and acetyl is the most preferable.

When X, $\alpha_1$, $\alpha_2$ and $\beta$ represent a "$C_4$–$C_{11}$ cycloalkylcarbonyl group", said group means a group in which said $C_3$–$C_{10}$ cycloalkyl group is bonded to a carbonyl group. Examples of said group are cyclopropylcarbonyl, cyclobutylcarbonyl, cyclopentylcarbonyl, cyclohexylcarbonyl, cycloheptylcarbonyl, norbornylcarbonyl and adamantylcarbonyl. $C_4$–$C_7$ cycloalkylcarbonyl groups are preferable.

When X, $Z_2$, $\alpha_1$ and $\alpha_2$ represent a "$C_7$–$C_{11}$ arylcarbonyl group (optionally having 1–5 substituting moieties $\beta$ hereafter described)", and when $\beta$ represents "$C_7$–$C_{11}$ arylcarbonyl group (optionally having 1–5 substituting moieties $\gamma$ hereafter described)", said $C_7$–$C_{11}$ arylcarbonyl moiety means a group in which said $C_6$–$C_{10}$ aryl group is bonded to a carbonyl group. Examples of said $C_7$–$C_{11}$ arylcarbonyl moiety are benzoyl, 1-indanecarbonyl, 2-indanecarbonyl and 1- or 2-naphthoyl.

When X, $\alpha_1$ and $\alpha_2$ represent a "$C_8$–$C_{17}$ aralkylcarbonyl group (optionally having 1–5 substituting moieties $\beta$ hereafter described on the aryl moiety thereof)" and when $\beta$ represents "$C_8$–$C_{17}$ aralkylcarbonyl group (optionally having 1–5 substituting moieties $\gamma$ hereafter described on the aryl moiety thereof)", said $C_8$–$C_{17}$ aralkylcarbonyl moiety means a group in which said $C_7$–$C_{16}$ aralkyl group is bonded to carbonyl group. Examples of said $C_8$–$C_{17}$ aralkylcarbonyl moiety are phenylacetyl, 3-phenylpropionyl, 4-phenylbutyryl, 5-phenylpentanoyl, 6-phenylhexanoyl, naphthylacetyl, 4-naphthylbutyryl and 6-naphthylhexanoyl.

When X, $\alpha_1$ and $\alpha_2$ represent a "monocyclic type heteroaromatic ring-carbonyl group (optionally having 1–5 substituting moieties β hereafter described)" and when β represents a "monocyclic type heteroaromatic ring-carbonyl group (optionally having 1–5 substituting moieties γ hereafter described)", said monocyclic type heteroaromatic ring-carbonyl moiety means a group in which a 5–7 member heteroaromatic ring containing 1–3 heteroatoms selected from the group consisting of oxygen, nitrogen and sulfur atoms is bonded to a carbonyl group. Examples of said monocyclic type heteroaromatic ring-carbonyl moiety are 5-member heteroaromatic ring-carbonyl groups such as furylcarbonyl, thienylcarbonyl, pyrrolylcarbonyl, pyrazolylcarbonyl, imidazolylcarbonyl, oxazolylcarbonyl, isoxazolylcarbonyl, thiazolylcarbonyl, isothiazolylcarbonyl, 1,2,3-oxadiazolylcarbonyl, triazolylcarbonyl and thiadiazolylcarbonyl; 6-member heteroaromatic ring-carbonyl groups such as pyranylcarbonyl, nicotinoyl, isonicotinoyl, pyridazinylcarbonyl, pyrimidinylcarbonyl and pyrazinylcarbonyl; and 7-member heteroaromatic ring-carbonyl groups such as azepinylcarbonyl, etc.

When X, $\alpha_1$ and $\alpha_2$ represent a "$C_7$–$C_{11}$ arylaminocarbonyl group (optionally having 1–5 substituting moieties β hereafter described on the aryl moiety thereof)" and when β represents a "$C_7$–$C_{11}$ arylaminocarbonyl group (optionally having 1–5 substituting moieties γ hereafter described on the aryl moiety thereof)", said $C_7$–$C_{11}$ arylaminocarbonyl moiety means a group in which the amino group of the aminocarbonyl group is substituted by said $C_6$–$C_{10}$ aryl group. Examples of said $C_7$–$C_{11}$ arylaminocarbonyl moiety are phenylaminocarbonyl, indenylaminocarbonyl and naphthylaminocarbonyl.

When $Z_1$ and $Z_4$ represent a "$C_1$–$C_6$ alkylthio group", it means a group in which said $C_1$–$C_6$ alkyl group is bonded to a sulfur atom. Examples of said group are methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio. $C_1$–$C_4$ alkylthio groups are preferable, $C_1$–$C_2$ alkylthio groups are more preferable, and methylthio groups are the most preferable.

When $Z_1$ and $Z_4$ represent a "$C_6$–$C_{10}$ aryloxy group (optionally having 1–5 substituting moieties $\alpha_1$ hereafter described)", said $C_6$–$C_{10}$ aryloxy moiety means a group in which said $C_6$–$C_{10}$ aryl group is substituted by an oxygen atom. Examples thereof are phenoxy, indenyloxy and naphthyloxy.

When $Z_1$ and $Z_4$ represent a "$C_7$–$C_{16}$ aralkyloxy group (optionally having 1–5 substituting moieties $\alpha_1$ hereafter described on the aryl moiety thereof)", said $C_7$–$C_{16}$ aralkyloxy moiety means a group in which said $C_7$–$C_{16}$ aralkyloxy is substituted by an oxygen atom. Examples of said $C_7$–$C_{16}$ aralkyloxy moiety are benzyloxy, naphthylmethloxy, indenylmethyloxy, 1-phenethyloxy, 2-phenethyloxy, 1-naphthylethyloxy, 2-naphthylethyloxy, 1-phenylpropyloxy, 2-phenylpropyloxy, 1-phenylpropyloxy, 2-phenylpropyloxy, 3-phenylpropyloxy, 1-naphthylpropyloxy, 2-naphthylpropyloxy, 3-naphthylpropyloxy, 1-phenylbutyloxy, 2-phenylbutyloxy, 3-phenylbutyloxy, 4-phenylbutyloxy, 1-naphthylbutyloxy, 2-naphthylbutyloxy, 3-naphthylbutyloxy, 4-naphthylbutyloxy, 5-phenylpentyloxy, 5-naphthylpentyloxy, 6-phenylhexyloxy and 6-naphthylhexyloxy.

When $Z_1$ and $Z_4$ represent "$C_3$–$C_{10}$ cycloalkyloxy group", said group means a group in which said $C_3$–$C_{10}$ cycloalkyl group is substituted by an oxygen atom. Examples of said group are cyclopropyloxy, cyclobutyloxy, cyclopentyloxy, cyclohexyloxy, cycloheptyloxy, norbornyloxy and adamantyloxy. $C_3$–$C_6$ cycloalkyloxy groups are preferable, and $C_5$–$C_6$ cycloalkyloxy groups are more preferable.

When $Z_1$ and $Z_4$ represent a "$C_3$–$C_{10}$ cycloalkylthio group", said group means a group in which said $C_3$–$C_{10}$ cycloalkyl group is substituted by a sulfur atom. Examples of said group are cyclopropylthio, cyclobutylthio, cyclopentylthio, cyclohexylthio, cycloheptylthio, norbornylthio and admantylthio. $C_3$–$C_6$ cycloalkylthio groups are preferable, and $C_5$–$C_6$ cycloalkylthio groups are more preferable.

When $Z_2$ and $Z_3$ represent a "saturated heterocyclic ring group (optionally having 1–5 substituting moieties $\alpha_1$ hereafter described)", said saturated heterocyclic ring moiety means a group in which a 4–7 member saturated heterocyclic ring group contains at least one ring atom selected from nitrogen, oxygen and sulfur atoms. Examples of said saturated heterocyclic ring moiety are 4-member saturated heterocyclic rings such as azetidyl, etc.; 5-member saturated heterocyclic rings such as pyrrolidyl, tetrahydrofuranyl, tetrahydrothiophenyl, imidazolidyl, oxazolidyl, isoxazolidyl, thiazolidyl, isothiazolidyl, etc.; 6-member saturated heterocyclic rings such as piperidino, tetrahydropyranyl, tetrahydrothiopyranyl, piperazino, morpholino, thiomorpholino, etc.; and 7-member saturated heterocyclic ring groups such as homopiperazino, etc.

When $Z_1$ and $Z_4$ represent a "saturated heterocyclic ring-oxy group (optionally having 1–5 substituting moieties $\alpha_1$ hereafter described)", said saturated heterocyclic ring-oxy moiety means a group in which said saturated heterocyclic ring is bonded to oxygen atom. Examples of said saturated heterocyclic ring-oxy moiety are 4-member saturated heterocyclic ring-oxy groups such as azetidyloxy, etc.; 5-member saturated heterocyclic ring-oxy groups such as pyrrolidyloxy, tetrahydrofuranyloxy, tetrahydrothiophenyloxy, imidazolidyloxy, oxazolidyloxy, isoxazolidyloxy, thiazolidyloxy, isothiazolidyloxy, etc.; 6-member saturated heterocyclic ring-oxy groups such as piperidinoxy, tetrahydropyranyloxy, tetrahydrothiopyranyloxy, piperazinoxy, morpholinoxy, thiomorpholinoxy, etc.; and 7-member saturated heterocyclic ring-oxy groups such as homopiperazinoxy, etc.

When $Z_1$ and $Z_3$ represent a "monocyclic type heteroaromatic ring-oxy group (optionally having 1–5 substituting moieties $\alpha_1$ hereafter described)", said monocyclic heteroaromatic ring-oxy moiety means a group in which said 5–7 member heteroaromatic ring containing 1–3 heteroatom(s) selected from the group consisting of oxygen, nitrogen and sulfur atoms is bonded to an oxygen atom. Examples of said saturated heterocyclic ring-oxy moiety are 5-member heteroaromatic ring-oxy groups such as furyloxy, thienyloxy, pyrrolyloxy, pyrazolyloxy, imidazolyloxy, oxazolyloxy, isoxazolyloxy, thiazolyloxy, isothiazolyloxy, 1,2,3-oxadiazolyloxy, triazolyloxy, tetrazolyloxy, thiadiazolyloxy, etc.; 6-member heteroaromatic ring-oxy groups such as pyranyloxy, pyridyloxy, pyridazinyloxy, pyrimidinyloxy, pyrazinyloxy, etc.; and 7-member heterocyclic ring-oxy groups such as azepinyloxy, etc.

When $Z_1$ and $Z_4$ represent a "$C_6$–$C_{10}$ arylthio group (optionally having 1–5 substituting moieties $\alpha_1$ hereafter described on the aryl moiety thereof)", said $C_6$–$C_{10}$ arylthio moiety means a group in which said $C_6$–$C_{10}$ aryl group is substituted by a sulfur atom. Examples of said $C_6$–$C_{10}$ arylthio moiety are phenylthio, indenylthio and naphthylthio.

When $Z_1$ and $Z_4$ represent a "$C_7$–$C_{16}$ aralkylthio group (optionally having 1–5 substituting moieties $\alpha_1$ hereafter described)", said $C_7$–$C_{16}$ aralkylthio moiety means a group in which said $C_7$–$C_{16}$ aralkylthio group is substituted by a sulfur atom. Examples of said $C_7$–$C_{16}$ aralkylthio moiety are benzylthio, naphthylmethylthio, indenylmethylthio, 1-phenethylthio, 2-phenethylthio, 1-naphthylethylthio, 2-naphthylethylthio, 1-phenylpropylthio, 2-phenylpropylthio, 3-phenylpropylthio, 1-naphthylpropylthio, 2-naphthylpropylthio, 3-naphthylpropylthio, 1-phenylbutylthio, 2-phenylbutylthio, 3-phenylbutylthio, 4-phenylbutylthio, 1-naphthylbutylthio, 2-naphthylbutylthio, 3-naphthylbutylthio, 4-naphthylbutylthio, 5-phenylpentylthio, 5-naphthylpentylthio, 6-phenylhexylthio and 6-naphthylhexylthio.

When $Z_1$ and $Z_4$ represent a "saturated heterocyclic ring-thio group (optionally having 1–5 substituting moieties $\alpha_1$ hereafter described)", said saturated heterocyclic ring-thio moiety means a group in which said saturated heterocyclic ring is bonded to a sulfur atom. Examples of said saturated heterocyclic ring-thio moiety are 4-member saturated heterocyclic ring-oxy groups such as azetidylthio, etc.; 5-member saturated heterocyclic ring-thio groups such as pyrrolidylthio, tetrahydrofuranyl, imidazolidylthio, oxazolidylthio, isoxazolidylthio, thiazolidylthio, isothiazolidylthio, etc.; 6-member saturated heterocyclic ring-thio groups such as piperidinylthio, tetrahydropyranylthio, tetrahydrothiopyranylthio, piperazinylthio, morpholylthio, thiomorpholylthio, etc.; and 7-member saturated heterocyclic ring-thio groups such as homopiperazinothio, etc.

When $Z_1$ and $Z_4$ represent a "monocyclic type heteroaromatic ring-thio group (optionally having 1–5 substituting moieties $\alpha_1$ hereafter described)", said monocyclic heteroaromatic ring-thio moiety means a group in which said 5–7 member heteroaromatic ring containing 1–3 heteroatom(s) selected from the group consisting of oxygen, nitrogen and sulfur atoms is bonded to a sulfur atom. Examples of said saturated heterocyclic ring-thio moiety are 5-member heteroaromatic ring-thio groups such as furylthio, thienylthio, pyrrolylthio, pyrazolylthio, imidazolylthio, oxazolylthio, isoxazolylthio, thiazolylthio, isothiazolyltho, 1,2,3-oxadiazolylthio, triazolylthio, tetrazolylthio, thiadiazolylthio, etc.; 6-member heteroaromatic ring-thio groups such as pyranylthio, pyridylthio, pyridazinylthio, pyrimidinylthio, pyrazinylthio, etc.; and 7-member heterocyclic ring-thio groups such as azepinylthio, etc.

When β represents a "$C_1$–$C_{10}$ alkyl group", said group means a straight chain or branched chain alkyl group of 1–10 carbon atoms. Examples of said group are heptyl, 1-methylhexyl, 2-methylhexyl, nonyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl and 7,7-dimethyloctyl, in addition to those illustrated in the definition of said $C_1$–$C_6$ alkyl group. $C_1$–$C_6$ alkyl groups are preferable, $C_1$–$C_4$ alkyl groups are more preferable, and $C_1$–$C_2$ alkyl groups are the most preferable.

When the substituting moiety β represents a "$C_6$–$C_{10}$ aryl group (optionally having 1–5 substituting moieties γ), in view of the definition of said substituting moiety γ, examples of said group having the substituting moiety γ are 4-methylphenyl, 4-methylnaphthyl, 3,4-dimethylphenyl, 2,3,4-trimethylphenyl, 4-propylphenyl, 4-propylnaphthyl, 2-, 3- or 4-trifluoromethylphenyl, 2-, 3- or 4-trifluoromethylnaphthyl, 3,4-ditrifluoromethylphenyl, 2,3,4-tritrifluoromethylphenyl, 4-tetrafluoropropylnaphthyl, 4-fluorophenyl, 4-fluoronaphthyl, 3,4-difluorophenyl, 2,3,4-trifluorophenyl, 4-hydroxyphenyl, 4-hydroxynaphthyl, 3,4-dihydroxyphenyl and 2,3,4-trihydroxyphenyl. As to said group, $C_6$–$C_{10}$ aryl groups (optionally having 1–3 substituting moieties γ) are preferable, phenyl groups (optionally having 1–3 substituting moieties γ) are more preferable, and phenyl or 4-trifluoromethylphenyl are the most preferable.

When the substituting moiety β represents a "$C_7$–$C_{16}$ aralkyl group (optionally having 1–5 substituting moieties γ on the aryl moiety thereof)", examples of said group having such a substituting moiety are 4-methylbenzyl, 2,3,4-trimethylbenzyl, 4-methylphenethyl, 2,3,4-trimethylphenethyl, 4-(4-methylphenyl)butyl, 2-, 3- or 4-trifluoromethylbenzyl, 3,4-ditrifluoromethylbenzyl, 2,3,4-tritrifluoromethylbenzyl, 4-tetrafluoropropylbenzyl, 4-trifluoromethylphenethyl, 3,4-ditrifluoromethylphenethyl, 2,3,4-tritrifluoromethylphenethyl, 4-tetrafluoropropylphenethyl, 4-(4-trifluoromethylphenyl)butyl, 4-(4-tetrafluoropropyl)butyl, 6-(4-trifluoromethylphenyl)hexyl, 6-(4-tetrafluoropropylphenyl)hexyl, 2-, 3- or 4-trifluoromethylnaphthylmethyl, 4-tetrafluoropropylnaphthylmethyl, 4-(4-trifluoromethylnaphthyl)butyl, 4-(4-tetrafluoropropylnaphthyl)butyl, 4-fluorobenzyl, 2,3,4-trifluorobenzyl, 4-fluorophenethyl, 2,3,4-trifluorophenethyl, 4-(4-fluorophenyl)butyl, 4-hydroxybenzyl, 2,3,4-trihydroxybenzyl, 4-hydroxyphenethyl, 2,3,4-trihydroxyphenethyl and 4-(4-hydroxyphenyl)butyl. As to said group, $C_7$–$C_{16}$ aralkyl groups (optionally having 1–3 substituting moieties γ on the aryl moiety thereof) are preferable, phenyl-$C_1$–$C_6$ alkyl groups (optionally having 1–3 substituting moieties γ on the phenyl moiety) are more preferable, further phenyl-$C_1$–$C_6$ alkyl groups (optionally having one trifluoromethyl group on the phenyl moiety) are yet more preferable, and phenyl-$C_1$–$C_2$ alkyl groups (optionally having one trifluoromethyl group on the phenyl moiety) are the most preferable.

When the substituting moiety β represents a "$C_7$–$C_{11}$ arylcarbonyl group (optionally having 1–5 substituting moieties γ)", examples of said group having such a substituting moiety are 4-methylbenzoyl, 1- or 2-(5-methyl)naphthoyl, 4-trifluoromethylbenzoyl, 4-tetrafluoropropylbenzoyl, 1-(5-trifluoromethylindane)-carbonyl, 2-(5-trifluoromethylindane)carbonyl, 2-(6-trifluoromethylindane)carbonyl, 1- or 2-(5-trifluoromethyl)naphthoyl, 4-fluorobenzoyl, 1- or 2-(5-fluoro)naphthoyl, 4-hydroxybenzoyl and 1- or 2-(5-hydroxy)naphthoyl. As said group, $C_7$–$C_{11}$ arylcarbonyl groups (optionally having 1–3 substituting moieties γ) are preferable, benzoyl groups (optionally having 1–3 substituting moieties γ) are more preferable, further benzoyl groups (optionally having one substituting moiety γ) are yet more preferable, and benzoyl groups (optionally having one substituting moiety, trifluoromethyl) are the most preferable.

When the substituting moiety β represents a "$C_8$–$C_{17}$ aralkylcarbonyl group (optionally having 1–5 substituting moieties on the aryl moiety thereof", examples of said group having such a substituting moiety are 4-methylphenylacetyl, 4-(4-methyl)phenylbutyryl, 6-(methylnaphthyl)hexanoyl, 2-, 3- or 4-trifluoromethylphenylacetyl, 4-tetrafluoropropylphenylacetyl, 4-(4-trifluoromethyl)phenylbutyryl, 6-(4-trifluoromethyl)phenylhexanoyl, 4-trifluoromethylnaphthylacetyl, 6-(trifluoromethylnaphthyl)hexanoyl, 4-fluorophenylacetyl, 4-(4-fluoro)phenylbutyryl, 6-(fluoronaphthyl)hexanoyl, 4-hydroxyphenylacetyl, 4-(4-hydroxy)phenylbutyryl and 6-(hydroxynaphthyl)hexanoyl. As to said group, $C_8$–$C_{17}$ aralkylcarbonyl groups (optionally having 1–3 substituting moieties γ on the aryl moiety) are preferable, phenyl-$C_1$–$C_6$ alkylcarbonyl groups (optionally having 1–3 substituting moieties γ on the aryl moiety) are more preferable, further phenyl-$C_1$–$C_6$ alkylcarbonyl groups (optionally having one substituting moiety, $C_1$–$C_6$ halogenoalkyl on the aryl moiety) are still more preferable, furthermore phenyl-$C_1$–$C_6$ alkylcarbonyl groups (optionally having one substituting moiety, trifluoromethyl on the aryl moiety) are yet more preferable, and phenylacetyl or 4-trifluoromethylphenylacetyl are the most preferable.

When the substituting moiety β represents a "monocyclic type heteroaromatic ring-carbonyl group (optionally having 1–5 substituting moieties γ)", examples of the group having such a substituting moiety are methylfurylcarbonyl, methylthienylcarbonyl, methylpyrrolylcarbonyl, methylnicotinoyl, trifluoromethylfurylcarbonyl, trifluoromethylthienylcarbonyl, trifluoromethylpyrrolylcarbonyl, trifluoromethyloxazolylcarbonyl, trifluoromethylthiazolylcarbonyl, trifluoromethylnicotinoyl, tetrafluoropropylfurylcarbonyl, tetrafluoropropylthienylcarbonyl, tetrafluoropropylpyrrolylcarbonyl, fluorofurylcarbonyl, fluorothienylcarbonyl, fluoropyrrolylcarbonyl, fluoronicotinoyl, hydroxyfurylcarbonyl, hydroxythienylcarbonyl, hydroxypyrrolylcarbonyl and hydroxynicotinyol. As to said group, monocyclic type heteroaromatic ring-carbonyl groups (optionally having 1–3 substituting moieties γ) are preferable, monocyclic type heteroaromatic ring-carbonyl groups (optionally having one substituting moiety γ) are more preferable, further monocyclic type heteroaromatic ring-carbonyl groups (optionally having one substituting moiety, trifluoromethyl) are still more preferable, furthermore 5- or 6-member monocyclic type heteroaromatic ring-carbonyl groups (optionally having one substituting moiety, trifluoromethyl) are yet more preferable, and furylcarbonyl, thienylcarbonyl, pyrrolylcarbonyl or nicotinoyl are the most preferable. When the substituting moiety β represents a "$C_7$–$C_{11}$ arylaminocarbonyl group (optionally having 1–5 substituting moieties γ on the aryl moiety thereof)", examples of said group having such a substituting moiety are 4-methylphenylcarbamoyl, 2,3,4-trimethylphenylcarbamoyl, 1- or 2-(6- or 7-methylnaphthyl)carbamoyl, 2-, 3- or 4-trifluoromethylphenylcarbamoyl, 4-tetrafluoropropylphenylcarbamoyl, 3,4-difluoromethylphenylcarbamoyl, 2,3,4-tritrifluoromethylphenylcarbamoyl, 1- or 2-(6- or 7-trifluoromethylnaphthyl)carbamoyl, 2-(6-tetrafluoropropylnaphthyl)carbamoyl, 4-fluorophenylcarbamoyl, 2,3,4-trifluorophenylcarbamoyl, 1- or 2-(6- or 7-fluoronaphthyl)carbamoyl, 4-hydroxyphenylcarbamoyl, 2,3,4-trihydroxyphenylcarbamoyl and 1- or 2-(6- or 7-hydroxynaphthyl)carbamoyl. As to said group, $C_7$–$C_{11}$ arylaminocarbonyl groups (optionally having 1–3 substituting moieties γ on the aryl moiety) are preferable, phenylaminocarbonyl groups (optionally having 1–3 substituting moieties γ on the phenyl moiety) are more preferable, further phenylaminocarbonyl groups (optionally having 1–3 $C_1$–$C_6$ halogenoalkyl groups as the substituting moiety γ on the phenyl moiety) are more preferable, and furthermore phenylaminocarbonyl groups (optionally having one trifluoromethyl group as the substituting moiety) are the most preferable.

When X, $α_1$ and $α_2$ represent a "$C_6$–$C_{10}$ aryl group (optionally having 1–5 substituting moieties β) in view of the definition of said β, examples of said group having such a substituting moiety are methylphenyl, acetylphenyl, benzoylphenyl, biphenylyl, methylbiphenylyl, methylnaphthyl, acetylnaphthyl and benzoylnaphthyl. As to said group, $C_6$–$C_{10}$ aryl groups (optionally having 1–3 substituting moieties β) are preferable, phenyl groups (optionally having 1–3 substituting moieties β) are more preferable, further phenyl groups (optionally having 1 or 2 substituting moieties β) are yet more preferable, and furthermore phenyl groups (optionally having 1 substituting moiety β) are the most preferable.

When X, $α_1$ and $α_2$ represent a "$C_7$–$C_{16}$ aralkyl group (optionally having 1–5 substituting moieties β on the aryl moiety)", examples of said group having such a substituting moiety are methylbenzyl, acetylbenzyl, benzoylbenzyl, biphenylylmethyl, methylbiphenylylmethyl, methylnaphthylmethyl, acetylnaphthylmethyl, benzoylnaphthylmethyl, methylphenethyl, acetylphenethyl, methylnaphthylethyl, acetylnaphthylethyl, methylphenylbutyl, acetylphenylbutyl, methylnaphthylbutyl and acetylnaphthylbutyl. As to said group, $C_7$–$C_{16}$ aralkyl groups (optionally having 1–3 substituting moieties β on the aryl moiety) are preferable, phenyl-$C_1$–$C_6$ alkyl groups (optionally having 1–3 substituting moieties β on the phenyl moiety) are more preferable, further phenyl-$C_1$–$C_4$ alkyl groups (optionally having 1 or 2 substituting moieties β on the phenyl moiety) are yet more preferable, and furthermore benzyl or phenethyl groups (optionally having one substituting moiety β) are the most preferable.

When X, $α_1$ and $α_2$ represent a "$C_7$–$C_{11}$ arylcarbonyl group (optionally having 1–5 substituting moieties β)", examples of said group having such a substituting moiety are methylbenzoyl, biphenylylcarbonyl, acetylbenzoyl, carbamoylbenzoyl, 4-trifluoromethylphenylcarbamoylbenzoyl and trifluoronaphthylcarbonyl. As to said group, $C_7$–$C_{11}$ arylcarbonyl groups (optionally having 1–3 substituting moieties β) are preferable, benzoyl groups (optionally having 1–3 substituting moieties β) are more preferable, further benzoyl groups (optionally having 1 or 2 substituting moieties β) are yet more preferable, and furthermore benzoyl groups (optionally having one substituting moiety β) are the most preferable.

When X, $α_1$ and $α_2$ represent a "$C_8$–$C_{17}$ aralkylcarbonyl group (optionally having 1–5 substituting moieties β on the aryl moiety thereof), examples of said group having such a substituting moiety are methylphenylacetyl, acetylphenylacetyl, benzoylphenylacetyl, biphenylylacetyl, carbamoylphenylacetyl, (4-trifluoromethylphenylcarbamoyl)phenylacetyl, 4-(methylphenyl)butyryl, 4-[(4-trifluoromethylphenylcarbamoyl)phenyl]butyryl, methylnaphthylacetyl and carbamoylnaphthylacetyl. As to said group, $C_8$–$C_{17}$ aralkylcarbonyl groups (optionally having 1–3 substituting moieties β on the aryl moiety) are preferable, phenyl-$C_2$–$C_7$ alkylcarbonyl groups (optionally having 1–3 substituting moieties β on the phenyl moiety) are more preferable, further phenyl-$C_2$–$C_7$ alkylcarbonyl groups (optionally having one substituting moiety β on the phenyl moiety) are yet more preferable, and furthermore phenylacetyl groups (optionally having one substituting moiety β on the phenyl moiety) are the most preferable.

When X, $α_1$ and $α_2$ represent a "monocyclic type heteroaromatic ring-carbonyl group (optionally having 1–5 substituting moieties β hereafter described)", examples of said group are methylfurylcarbonyl, methylthienylcarbonyl, methylpyrrolylcarbonyl, methyloxazolylcarbonyl, methylthiazolylcarbonyl, methyltriazolylcarbonyl, methylpyranylcarbonyl, methylnicotinoyl, methylpyridazinylcarbonyl, methylpyrimidinylcarbonyl, acetylfurylcarbonyl, acetylthienylcarbonyl, acetylpyrrolylcarbonyl, acetyloxazolylcarbonyl, acetylthiazolylcarbonyl, acetylnicotinoyl, carbamoylfurylcarbonyl, carbamoylthienylcarbonyl, carbamoylpyrrolylcarbonyl, carbamoyloxazolylcarbonyl, carbamoylthiazolylcarbonyl and carbamoylnicotinoyl. As to said group, monocyclic type heteroaromatic ring-carbonyl groups (optionally having 1–3 substituting moieties β) are preferable, further monocyclic type heteroaromatic ring-carbonyl groups (optionally having 1 or 2 substituting moieties β) are more preferable, furthermore 5- or 6-member monocyclic type heteroaromatic ring-carbonyl groups (optionally having 1 or 2 substituting moieties β) are yet more preferable, and 5- or 6-member monocyclic type heteroaromatic ring-carbonyl groups (optionally having one substituting moiety β) are the most preferable.

When X, $α_1$ and $α_2$ represent a "$C_7$–$C_{11}$ arylaminocarbonyl group (optionally having 1–5 substituting moieties β hereafter described on the aryl moiety thereof)", examples of said group having such a substituting moiety are methylphenylcarbonyl, biphenylylcarbamoyl, acetylphenylcarbamoyl, methylnaphthylcarbamoyl, and acetylnaphthylcarbamoyl. As to said group, $C_7$–$C_{11}$ arylaminocarbonyl groups (optionally having 1–3 substituting moieties β on the aryl moiety) are preferable, further phenylaminocarbonyl groups (optionally having 1–3 substituting moieties β on the phenyl moiety) are more preferable, and phenylaminocarbonyl groups (optionally having one substituting moiety on the phenyl moiety) are the most preferable.

When X and $α_1$ represent an "amino group optionally having 1 or 2 substituting moieties β", examples of said group are amino, methylamino, ethylamino, propylamino, isopropylamino, butylamino, s-butylamino, t-butylamino, pentylamino, hexylamino, dimethylamino, diethylamino, N-ethyl-N-methylamino, dipropylamino, dibutylamino, dipentylamino, dihexylamino, phenylamino, 1- or 2-indenylamino, 1- or 2-naphthylamino, benzylamino, 1- or 2-naphthylmethylamino, 1-indenylmethylamino, 1- or 2-phenethylamino, 1-, 2- or 3-phenylpropylamino, 4-phenylbutylamino, 1-phenylbutylamino, 5-phenylpentylamino, 6-phenylhexylamino, dibenzylamino, formylamino, acetylamino, propionylamino, butyrylamino, isobutyrylamino, valerylamino, isovalerylamino, pivaloylamino, hexanoylamino, acryloylamino, methacryloylamino, crotonoylamino, benzoylamino, 1-indanecarbonylamino, 1- or 2-naphthoylamino, 1-indanecarbonylamino, 1- or 2-naphthoylamino, phenylacetylamino, 3-phenylpropionylamino, 4-phenylbutyrylamino, 5-phenylpentanoylamino, 6-phenylhexanoylamino, cyclopropionylamino, cyclobutyrylamino, cyclopentanoylamino, cyclohexanoylamino, pyrrolylcarbonylamino, imidazolylcarbonylamino, pyrazolylcarbonylamino, triazolylcarbonylamino, tetrazolylcarbonylamino, nicotinoylamino, isonicotinoylamino, pyrazinylcarbonylamino, pyrimidinylcarbonylamino, pyridazinylcarbonylamino, thiazolylcarbonylamino, oxazolylcarbonylamino, oxadiazolylcarbonylamino, thiadiazolylcarbonylamino, N,N-diacetylamino, N-formyl-N-hexylamino, N-acetyl-N-methylamino, N-acetyl-N-ethylamino, N-acetyl-N-propylamino, N-acetyl-N-butylamino, N-acetyl-N-pentylamino, N-acetyl-N-hexylamino, N-benzoyl-N-methylamino, N-benzoyl-N-ethylamino, N-benzoyl-N-propylamino, N-benzoyl-N-butylamino, N-benzoyl-N-pentylamino, N-benzoyl-N-hexylamino, N-benzoyl-N-phenylamino, N-benzyl-N-benzoylamino, N-hexyl-N-1-naphthoylamino, N-hexyl-N-2-naphthoylamino, N-hexyl-N-phenylacetylamino, N-isobutyl-N-cycloheptanoylamino, N-butyl-N-nicotinoylamino, N-hexyl-N-nicotinoylamino, N-isonicotinoyl-N-hexylamino and 4-trifluoromethylphenylcarbamoylamino. As said group, amino groups optionally having 1 or 2 substituting moieties selected from $C_1$–$C_{10}$ alkyl, $C_1$–$C_7$ aliphatic acyl and phenylaminocarbonyl group (optionally having 1–3 substituting moieties γ on the phenyl moiety) are preferable, further amino groups optionally having 1 or 2 substituting moieties selected from $C_1$–$C_6$ alkyl, $C_1$–$C_2$ aliphatic acyl and phenylaminocarbonyl group (optionally having one substituting moiety γ on the phenyl moiety) are more preferable, and furthermore amino groups optionally substituted with one phenylaminocarbonyl groups (optionally having one substituting moiety γ on the phenyl moiety) are the most preferable.

When $R_1$, $R_2$, $R_3$, $R_4$, $Z_1$, $Z_3$ and $Z_4$ represent a "$C_6$–$C_{10}$ aryl group (optionally having 1–5 substituting moieties $α_1$)", in view of the definition of X, $α_1$ and $α_2$ described above, examples of said group having such a substituting moiety are methylphenyl, trifluoromethylphenyl, hydroxyphenyl, 4-hydroxy-2,3,5-trimethylphenyl, 3,5-di-t-butyl-4-hydroxyphenyl, adamantylphenyl, 4-amino-3,5-dimethylphenyl, acetylphenyl, methoxyphenyl, benzoylphenyl, fluorophenyl, difluorophenyl, chlorophenyl, dichlorophenyl, bromophenyl, nitrophenyl, (dimethylamino)phenyl, biphenylyl, methylbiphenylyl, methylnaphthyl, trifluoronaphthyl, hydroxynaphthyl, methoxynaphthyl, fluoronaphthyl and chloronaphthyl. As to said group, $C_6$–$C_{10}$ aryl groups (optionally having 1–3 substituting moieties $α_1$) are preferable, further phenyl groups (optionally having 1–3 substituting moieties $α_1$) are more preferable, furthermore phenyl groups (optionally having 1 or 2 substituting moieties $α_1$) are yet more preferable, and phenyl groups (optionally having one substituting moiety $α_1$) are the most preferable.

When $Z_2$ represents a "$C_6$–$C_{10}$ aryl group (optionally having 1–5 substituting moieties $α_1$)", examples of said group are adamantylphenyl, biphenylyl, methylbiphenylyl, benzylphenyl, acetylphenyl, cyclohexylcarbonylphenyl, benzoylphenyl, benzylcarbonylphenyl, pyridinecarbonylphenyl and phenylaminocarbonyl. As to said group, $C_6$–$C_{10}$ aryl groups (optionally having 1–3 substituting moieties $α_2$) are preferable, further phenyl groups (optionally having 1–3 substituting moieties $α_2$) are more preferable, furthermore phenyl groups (optionally having 1 or 2 substituting moiety $α_2$) are yet more preferable, and phenyl groups (optionally having one substituting moiety $α_2$) are the most preferable.

When $R_1$, $R_2$, $R_3$, $R_4$, $Z_1$, $Z_3$ and $Z_4$ represents a "$C_7$–$C_{16}$ aralkyl group (optionally having 1–5 substituting moieties $α_1$ on the aryl moiety thereof)", examples of said group having such a substituting moiety are methylbenzyl, trifluoromethylbenzyl, hydroxybenzyl, 4-hydroxy-2,3,5-trimethylbenzyl, 3,5-di-t-butyl-4-hydroxybenzyl, adamantylbenzyl, 4-amino-3,5-dimethylbenzyl, acetylbenzyl, methoxybenzyl, benzoylbenzyl, fluorobenzyl, difluorobenzyl, chlorobenzyl, dichlorobenzyl, nitrobenzyl, (dimethylamino)benzyl, biphenylylmethyl, methylbiphenylylmethyl, methylphenethyl, trifluoromethylphenethyl, hydroxyphenethyl, 4-hydroxy-2,3,5-trimethylphenethyl, 3,5-di-t-butyl-4-hydroxyphenethyl, adamantylphenethyl, 4-amino-3,5-dimethylphenethyl, acetylphenethyl, methoxyphenethyl, benzoylphenethyl, fluorophenethyl, difluorophenethyl, chlorophenethyl, nitrophenethyl, (dimethylamino)phenethyl, biphenylylethyl, methylbiphenylyl, methylphenylbutyl, trifluoromethylphenylbutyl, hydroxyphenylbutyl, 4-hydroxy-2,3,5-trimethylphenylbutyl, 3,5-di-t-butyl-4-hydroxyphenylbutyl, adamantylphenylbutyl, 4-amino-3,5-dimethylphenylbutyl, acetylphenylbutyl, methoxyphenylbutyl, fluorophenylbutyl, chlorophenylbutyl, nitrophenylbutyl, (dimethyl)phenylbutyl, biphenylylbutyl, methylnaphthylmethyl, trifluoronaphthylmethyl, hydroxynaphthylmethyl, methoxynaphthylmethyl, fluoronaphthylmethyl and chloropnaphthylmethyl. As to said group, $C_7$–$C_{16}$ aralkyl groups (optionally having 1–3 substituting moieties $\alpha_1$ on the aryl moiety) are preferable, further phenyl-$C_1$–$C_6$ alkyl groups (optionally having 1–3 substituting moieties $\alpha_1$ on the phenyl moiety) are more preferable, further phenyl-$C_1$–$C6$ alkyl groups (optionally having one substituting moiety $\alpha_1$ on the phenyl moiety) are yet more preferable, phenyl-$C_1$–$C_4$ alkyl groups (optionally having one substituting moiety $\alpha_1$ on the phenyl moiety) are still further preferable, and further phenyl-$C_1$–$C_2$ alkyl groups (optionally having one substituting moiety $\alpha_1$ on the phenyl moiety) are the most preferable.

When $R_1$, $R_2$ and $R_3$ represent a "$C_6$–$C_{10}$ arylsulfonyl group (optionally having 1–5 substituting moieties $\alpha_1$)", examples of said group having such a substituting moiety are methylphenylsulfonyl, acetylphenylsulfonyl, benzoylphenylsulfonyl, biphenylylsulfonyl, methylbiphenylylsulfonyl, methylnaphthylsulfonyl, acetylnaphthylsulfonyl and benzoylnaphthylsulfonyl. As to said group, $C_6$–$C_{10}$ arylsulfonyl groups (optionally having 1–3 substituting moieties $\alpha_1$) are preferable, further phenylsulfonyl groups (optionally having 1–3 substituting moieties $\alpha_1$) are more preferable, and furthermore phenylsulfonyl groups (optionally having one substituting moiety $\alpha_1$) are the most preferable.

When $R_1$, $R_2$ and $R_3$ represent a "$C_7$–$C_{16}$ aralkylsulfonyl group (optionally having 1–5 substituting moieties $\alpha_1$ on the aryl moiety thereof)", examples of said group having such a substituting moiety are methylbenzylsulfonyl, acetylbenzylsulfonyl, benzoylbenzylsulfonyl, biphenylylmethylsulfonyl, methylbiphenylylmethylsulfonyl, methylnaphthylmethylsulfonyl, acetylnaphthylmethylsulfonyl, benzoylnaphthylmethylsulfonyl, methylphenethylsulfonyl, acetylphenethylsulfonyl, methylnaphthylethylsulfonyl, acetylnaphthylethylsulfonyl, methylphenylbutylsulfonyl, acetylphenylbutylsulfonyl, methylnaphthylbutylsulfonyl and acetylnaphthylbutylsulfonyl. As to said group, $C_7$–$C_{16}$ aralkylsulfonyl groups (optionally having 1–3 substituting moieties $\alpha_1$ on the aryl moiety) are preferable, further phenyl-$C_1$–$C_6$ alkylsulfonyl groups (optionally having 1–3 substituting moieties $\alpha_1$ on the phenyl moiety) are more preferable, furthermore phenyl-$C_1$–$C_4$ alkylsulfonyl groups (optionally having one substituting moiety $\alpha_1$ on the phenyl moiety) are yet more preferable, and benzylsulfonyl or phenethylsulfonyl groups (optionally having one substituting moiety $\alpha$ on the phenyl moiety) are the most preferable.

When $Z_1$ and $Z_4$ represent a "$C_6$–$C_{10}$ aryloxy groups (optionally having 1–5 substituting moieties $\alpha_1$)", examples of said group having such a substituting moiety are methylphenoxy, trifluoromethylphenoxy, hydroxyphenoxy, 4-hydroxy-2,3,5-trimethylphenoxy, 3,5-di-t-butyl-4-hydroxyphenoxy, cyclopropylphenoxy, adamantylphenoxy, cyanophenoxy, nitrophenoxy, 4-amino-3,5-dimethylphenoxy, acetylphenoxy, methoxyphenoxy, benzoylphenoxy, fluorophenoxy, difluorophenoxy, chlorophenoxy, dichlorophenoxy, nitrophenoxy, (dimethylamino)phenoxy, 4-(4-trifluoromethylphenylcarbamoylamino)-3,5-dimethylphenoxy, biphenylyloxy, methylbiphenylyloxy, dimethylaminophenoxy, methylnaphthyloxy, trifluoronaphthyloxy, hydroxynaphthyloxy, methoxynaphthyloxy, fluoronaphthyloxy and chloronaphthyloxy. As to said group, $C_6$–$C_{10}$ aryloxy groups (optionally having 1–3 substituting moieties $\alpha_1$) are preferable, further phenoxy groups (optionally having 1–5 substituting moieties $\alpha_1$) are more preferable, furthermore phenoxy groups (optionally having one or two substituting moieties $\alpha_1$) are yet more preferable, and phenoxy groups (optionally having one substituting moiety $\alpha_1$) are the most preferable.

When $Z_1$ and $Z_4$ represent a "$C_7$–$C_{16}$ aralkyloxy group (optionally having 1–5 substituting moieties $\alpha_1$ hereafter described on the aryl moiety thereof)", examples of said group having such a substituting moiety are methylbenzyloxy, trifluoromethylbenzyloxy, hydroxybenzyloxy, 4-hydroxy-2,3,5-trimethylbenzyloxy, 3,5-di-t-butyl-4-hydroxybenzyloxy, adamantylbenzyloxy, 4-amino-3,5-dimethylbenzyloxy, acetylbenzyloxy, methoxybenzyloxy, benzoylbenzyloxy, fluorobenzyloxy, difluorobenzyloxy, chlorobenzyloxy, dichlorobenzyloxy, nitrobenzyloxy, (dimethylamino)benzyloxy, biphenylylmethoxy, methylbiphenylylmethoxy, methylphenethyloxy, trifluoromethylphenethyloxy, hydroxyphenethyloxy, 4-hydroxy-2,3,5-trimethylphenethyloxy, 3,5-di-t-butyl-4-hydroxyphenethyloxy, adamantylphenethyloxy, 4-amino-3,5-dimethylphenethyloxy, acetylphenethyloxy, methoxyphenethyloxy, benzoylphenethyloxy, fluorophenethyloxy, difluorophenethyloxy, chlorophenethyloxy, nitrophenethyloxy, (dimethylamino)phenethyloxy, biphenylylethyloxy, methylbiphenylylethoxy, methylphenylbutoxy, trifluoromethylphenylbutoxy, hydroxyphenylbutoxy, 4-hydroxy-2,3,5-trimethylphenylbutoxy, 3,5-di-t-butyl-4-hydroxyphenylbutoxy, adamantylphenylbutoxy, 4-amino-3,5-dimethylphenylbutoxy, acetylphenylbutoxy, methoxyphenylbutoxy, fluorophenylbutoxy, chlorophenylbutoxy, nitrophenylbutoxy, (dimethylamino)phenylbutoxy, biphenylbutoxy, methylnaphthylmethoxy, trifluoronaphthylmethoxy, hydroxynaphthylmethoxy, methoxynaphthylmethoxy, fluoronaphthylmethoxy and chloronaphthylmethoxy. As to said group, $C_7$–$C_{16}$ aralkyloxy groups (optionally having 1–3 substituting moieties $\alpha_1$ on the aryl moiety thereof) are preferable, further phenyl-$C_1$–$C_6$ alkyloxy groups (optionally having 1–3 substituting moieties $\alpha_1$ on the phenyl moiety) are more preferable, furthermore phenyl-$C_1$–$C_6$ alkyloxy groups (optionally having one substituting moiety $\alpha_1$ on the phenyl moiety) are yet more preferable, moreover phenyl-$C_1$–$C_4$ alkyloxy groups (optionally having one substituting moiety $\alpha_1$ on the phenyl moiety) are still more preferable, and phenyl-$C_1$–$C_2$ alkyloxy groups (optionally having one substituting moiety $\alpha_1$ on the phenyl moiety) are the most preferable.

When $Z_1$ and $Z_4$ represent a "saturated heterocyclic ring-oxy group (optionally having 1–5 substituting moieties $\alpha_1$)", said group means a monovalent group mainly derived from a monosaccharide. Said monosaccharides illustratively include pentoses such as arabinose, xylose, ribose, etc., hexoses such as glucose, galactose, mannose, etc., aminosugars such as glucosamine, galactosamine, etc., uronic acids such as glucuronic acid, etc. As to said groups, monovalent groups derived from monosaccharides showing physiological activity in vivo of warm-blooded animals (particularly human beings) are preferable, further monovalent groups derived from an uronic acid are more preferable, and monovalent groups derived from glucuronic acid are particularly preferable.

When $Z_2$ and $Z_3$ represent a "saturated heterocyclic ring group (optionally having 1–5 substituting moieties $\alpha_1$)", said group means a monovalent group mainly derived by removing the hydroxy group from said monosaccharide. As to said group, monovalent groups derived from monosaccharides showing phyiological activity in vivo of warm-blooded animals (particularly human beings) are preferable, further monovalent groups derived from an uronic acid are more preferable, and monovalent groups derived from glucuronic acid are particularly preferable.

When $Z_1$ and $Z_4$ represent a "monocyclic type heteroaromatic ring-oxy group (optionally having 1–5 substituting moieties $\alpha_1$)", examples of said group are fluorofuryloxy, fluorothienyloxy, fluoropyrrolyloxy, fluorooxazolyloxy, fluorothiazolyloxy, fluorotriazolyloxy, fluoropyranyloxy, fluoropyridyloxy, fluoropyridazinyloxy, fluoropyrimidinyloxy, methylfuryloxy, methylthienyloxy, methylpyrrolyloxy, methyloxazolyloxy, methylthiazolyloxy, methylpyridyloxy, methoxyfuryl, methoxythienyl, methoxypyrrolyloxy, methoxyoxazolyloxy, methylthiazolyloxy, methoxypyridyloxy, dimethylaminofuryloxy, dimethylaminoethienyloxy, dimethylaminopyrrolyloxy, dimethylaminooxazolyloxy, dimethylaminothiazolyloxy, and dimethylaminopyridyloxy. As to said group, monocyclic type heteroaromatic ring-oxy groups (optionally having 1–3 substituting moieties $\alpha_1$) are preferable, further 5- or 6-member monocyclic type heteroaromatic ring-oxy groups (optionally having one or two substituting moieties $\alpha_1$) are more preferable, furthermore 5- or 6-member monocyclic type heteroaromatic ring-oxy groups (optionally having one or two substituting moieties $\alpha_1$) are yet more preferable, and 5- or 6-member monocyclic type heteroaromatic ring-oxy groups containing one or more hetero-atom(s) (optionally having one substituting moiety $\alpha_1$) are the most preferable.

When $Z_1$ and $Z_4$ represent a "$C_6$–$C_{10}$ arylthio group (optionally having 1–5 substituting moieties $\alpha_1$)", examples of said group are methylphenylthio, trifluoromethylphenylthio, hydroxyphenylthio, 4-hydroxy-2,3,5-trimethylphenylthio, 3,5-di-t-butyl-4-hydroxyphenylthio, adamantylphenylthio, 4-amino-3,5-dimethylphenylthio, acetylphenylthio, methoxyphenylthio, benzoylphenylthio, fluorophenylthio, difluorophenylthio, chlorophenylthio, dichlorophenylthio, nitrophenylthio, (dimethylamino)phenylthio, biphenylylthio, methylbiphenylylthio, methylnaphthylthio, trifluoronaphthylthio, hydroxynaphthylthio, methoxynaphthylthio, fluoronaphthylthio, and chloronaphthylthio. As to said group, $C_6$–$C_{10}$ arylthio groups (optionally having 1–3 substituting moieties $\alpha_1$) are preferable, further phenylthio groups (optionally having 1–3 substituting moieties $\alpha_1$) are more preferable, furthermore phenylthio groups (optionally having one or two substituting moieties $\alpha_1$) are yet more preferable, and phenylthio groups (optionally having one substituting moiety $\alpha_1$) are the most preferable.

When $Z_1$ and $Z_4$ represent a "$C_7$–$C_{16}$ aralkylthio group (optionally having 1–5 substituting moieties $\alpha_1$ on the aryl moiety thereof)", examples of said group having such a substituting moiety are methylbenzylthio, trifluoromethylbenzylthio, hydroxybenzylthio, 4-hydroxy-2,3,5-trimethylbenzylthio, 3,5-di-t-butyl-4-hydroxybenzylthio, adamantylbenzylthio, 4-amino-3,5-dimethylbenzylthio, acetylbenzylthio, methoxybenzylthio, benzoylbenzylthio, fluorobenzylthio, difluorobenzylthio, chlorobenzylthio, dichlorobenzylthio, nitrobenzylthio, (dimethylamino)benzylthio, biphenylylmethylthio, methylbiphenylylmethylthio, methylphenethylthio, trifluoromethylphenethylthio, hydroxyphenethylthio, 4-hydroxy-2,3,5-trifluoro-phenethylthio, 3,5-di-t-butyl 4hydroxyphenethylthio, adamantylphenethylthio, 4-amino-3,5-dimethylphenethylthio, acetylphenethylthio, methoxyphenethylthio, benzoylphenethylthio, fluorophenethylthio, difluorophenethylthio, chlorophenethylthio, nitrophenethylthio, (dimethylamino)phenethylthio, biphenylylethylthio, methylbiphenylylethylthio, methylphenylylbutylthio, trifluoromethylphenylbutylthio, hydroxyphenylbutylthio, 4-hydroxy-2,3,5-trimethylphenylbutylthio, 3,5-di-t-butyl-4-hydroxyphenylbutylthio, adamantyl-phenylbutylthio, 4-amino-3,5-dimethylphenylbutylthio, acetylphenylbutylthio, methoxyphenylbutylthio, fluorophenylbutylthio, chlorophenylbutylthio, nitrophenylbutylthio, (dimethylamino)phenylbutylthio, biphenylylbutylthio, methylnaphthylmethylthio, trifluoromethylnaphthylmethylthio, hydroxynaphthylmethylthio, methoxynaphthylmethylthio, fluoronaphthylmethylthio, and chloronaphthylmethylthio. As to said groups, $C_7$–$C_{16}$ aralkylthio groups (optionally having 1–3 substituting moieties $\alpha_1$ on the aryl moiety) are preferable, further phenyl-$C_1$–$C_6$ alkylthio groups (optionally having 1–3 substituting moieties $\alpha_1$ on the phenyl moiety) are more preferable, furthermore phenyl-$C_1$–$C_6$ alkylthio groups (optionally having one substituting moiety $\alpha_1$ on the phenyl moiety) are yet more preferable, then phenyl-$C_1$–$C_4$ alkylthio groups (optionally having one substituting moiety $\alpha_1$ on the phenyl moiety) are still more preferable, and phenyl-$C_1$–$C_2$ alkylthio groups (optionally having one substituting moiety $\alpha_1$ on the phenyl moiety) are the most preferable.

When $Z_1$ and $Z_4$ represent a "saturated heterocyclic ring-thio group (optionally having 1–5 substituting moieties $\alpha_1$)", examples of said group having such a substituting moiety are methylpyrrolidylthio, methoxypyrrolidylthio, methyltetrahydrofuranylthio, methoxytetrahydrofuranylthio, methylpiperidylthio, methoxypiperidylthio, methyltetrahydropyranylthio, methoxytetrahydropyranylthio, methyltetrahydrothiopyranylthio, methoxytetrahydrothiopyranylthio, methylpiperazinylthio, methoxypiperazinylthio, methylmorpholylthio, methoxymorpholylthio, methylthiomorpholylthio and methoxythiomorpholylthio. As to said group, 5- or 6-member saturated heterocyclic ring-thio groups (optionally having 1–5 substituting moieties $\alpha_1$) are preferable, further 5- or 6-member saturated heterocyclic ring-thio groups (optionally having 1–3 substituting moieties $\alpha_1$) are more preferable, and furthermore 5- or 6-member saturated heterocyclic ring-thio groups (optionally having one substituting moiety α₁) are the most preferable.

When $Z_1$ and $Z_4$ represent a "monocyclic type heteroaromatic ring-thio group (optionally having 1–5 substituting moieties $α_1$)", examples of said group having the substituting moiety are fluorofurylthio, fluorothienylthio, fluoropyrrolylthio, fluorooxazolylthio, fluorothiazolylthio, fluorotriazolylthio, fluoropyranylthio, fluoropyridylthio, fluoropyridazinylthio, fluoropyrimidinylthio, methylfurylthio, methylthienylthio, methylpyrrolylthio, methyloxazolylthio, methylthiazolylthio, methylpyridylthio, methoxyfurylthio, methoxythienylthio, methoxypyrrolylthio, methoxyoxazolylthio, methoxythiazolylthio, methoxypyridylthio, dimethylaminofurylthio, dimethylaminothienylthio, dimethylaminopyrrolylthio, dimethylaminooxazolylthio, dimethylaminothiazolylthio and dimethylaminopyridylthio. As to said group, 5–7 member monocyclic type heteroaromatic ring-thio groups (optionally having 1–3 subsituting moieties $α_1$) are preferable, further 5–6 member monocyclic type heteroaromatic ring-thio groups (optionally having one or two substituting moieties $α_1$) are more preferable, furthermore 5 or 6-member monocyclic type heteroaromatic ring-thio groups (optionally having one substituting moiety $α_1$) are yet more preferable, and 5- or 6-member monocyclic type heteroaromatic ring-thio groups containing one or two heteroatom(s) (optionally having one substituting moiety $α_1$) are the most preferable.

When $Z_1$ and $Z_4$ represent an "amino group (optionally having 1 or 2 substituting moieties $α_1$)", examples of said group are amino, methylamino, ethylamino, propylamino, isopropylamino, butylamino, s-butylamino, t-butylamino, pentylamino, hexylamino, dimethylamino, diethylamino, N-ethyl-N-methylamino, dipropylamino, dibutylamino, dipentylamino, dihexylamino, phenylamino, 1 - or 2-indenylamino, 1- or 2-naphthylamino, diphenylamino, formylamino, acetylamino, propionylamino, butyrylamino, isobutyrylamino, valerylamino, isovalerylamino, pivaloylamino, hexanoylamino, acryloylamino, methacryloylamino, crotonoylamino, benzoylamino, 1-indanecarbonylamino, 1- or 2-naphthoylamino, 2,6-diisopropylbenzoylamino, phenylacetylamino, 3-phenylpropionylamino, 4-phenylbutyrylamino, 5-phenylpentanoylamino, 6-phenylhexanoylamino, cyclopropanecarbonylamino, cyclobutanecarbonylamino, cyclopentanecarbonylamino, cyclohexanoylamino, pyrrolylcarbonylamino, imidazolylcarbonylamino, pyrazolylcarbonylamino, triazolylcarbonylamino, tetrazolylcarbonylamino, nicotinoylamino, isonicotinoylamino, pyrazinylcarbonyl-amino, pyrimidinylcarbonylamino, pyridazinylcarbonylamino, thiazolylcarbonylamino, oxazolylcarbonylamino, oxadiazolylcarbonylamino, thiadiazolylcarbonylamino, 4-trifluoromethylphenylcarbamoylamino, N,N-diacetylamino, N-formyl-N-hexylamino, N-acetyl-N-methylamino, N-acetyl-N-ethylamino, N-acetyl-N-propylamino, N-acetyl-N-butylamino, N-acetyl-N-pentylamino, N-acetyl-N-hexylamino, N-benzoyl-N-methylamino, N-benzoyl-N-ethylamino, N-benzoyl-N-propylamino, N-benzoyl-N-butylamino, N-benzoyl-N-pentylamino, N-benzoyl-N-hexylamino, N-benzoyl-N-phenylamino, N-benzyl-N-benzoylamino, N-hexyl-N-1-naphthoylamino, N-hexyl-N-2-naphthoylamino, N-hexyl-N-phenylacetylamino, N-isobutyl-N-cycloheptanecarbonylamino, N-butyl-N-nictonoylamino, N-hexyl-N-nicotinoylamino, and N-isonicotinoyl-N-hexylamino. As to said group, amino groups (optionally having one or two substituting moieties selected from $C_1$–$C_6$ alkyl, $C_1$–$C_7$ aliphatic acyl, $C_6$–$C_{10}$ aryl optionally having 1–3 substituting moieties β, $C_7$–$C_{16}$ aralkyl optionally having 1–3 substituting moieties on the aryl moiety thereof and $C_7$–$C_{11}$ arylcarbonyl optionally having 1–3 substituting moieties β on the aryl moiety thereof) are preferable, and further amino groups (optionally having one or two substituting moieties β selected from $C_1$–$C_4$ alkyl, $C_1$–$C_2$ aliphatic acyl, phenyl optionally having one substituting moiety β, phenyl-$C_1$–$C_4$ alkyl optionally having one substituting moiety β on the phenyl moiety thereof and benzoyl optionally having one substituting moiety β on the phenyl moiety thereof) are more preferable.

The α-substituted carboxylic acid derivatives of the compounds (I) to (IV) in the present invention having a carboxyl group can be converted into their salts in a conventional manner. Examples of such salts are alkali metal salts such as the sodium salt, potassium salt or lithium salt; alkaline earth metal salts such as the calcium salt or magnesium salt; metal salts such as the aluminum salt, iron salt, zinc salt, copper salt, nickel salt, cobalt salt, etc.; inorganic salts such as the ammonium salt; amine salts like organic salts such as the t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt; N-benzyl-N-phenethylamine salt, piperazine salt or tetramethylammonium salt; and tris (hydroxymethyl)aminomethane salt.

The α-substituted carboxylic acid derivatives of the compounds (I) to (IV) in the present invention can be converted into their salts even in the case of their having any basic moiety such as a pyridyl or quinolyl group and also in the case of having no bases. Examples of such salts are hydrohalogenic acid salts such as hydrofluoride, hydrochloride, hydrobromide, hydroiodide; inorganic acid salts such as nitrate, perchlorate, sulfate, phosphate; lower alkanesulfonic acid salts such as methanesulfonate, trifluoromethanesulfonate, ethanesulfonate; arylsulfonic acid salts such as benzenesulfonate, p-toluenesulfonate, etc.; amino acid salts such as glutamate, aspartate, etc.; organic carboxylic acid salts such as fumarate, succinate, citrate, tartrate, oxalate, maleate; amino acid salts such as ornithine, glutamate, aspartate and the like. Of these, hydrohalogenic acid salts and organic acid salts are preferable. The α-substituted carboxylic acid derivatives of the compounds (I) to (IV) in the present invention can be converted into their pharmacologically acceptable esters in a conventional manner. No special limitation is given to these pharmacologically acceptable esters of the α-substituted carboxylic acid derivatives of the compounds (I) to (IV) as long as they are medically useful and pharmacologically acceptable in the form of the α-substituted carboxylic acid derivatives of the compounds (I) to (IV). The esters of the α-substituted carboxylic acid derivatives of the compounds (I) to (IV) in the present invention illustratively include $C_1$–$C_6$ alkyl substituted by $C_1$–$C_6$ alkyl, $C_7$–$C_{19}$ aralkyl or $C_1$–$C_7$ aliphatic acyloxy, $C_1$–$C_6$ alkyl substituted by $C_1$–$C_7$ alkyloxycarbonyloxy, $C_1$–$C_6$ alkyl substituted by $C_5$–$C_7$ cycloalkylcarbonyloxy, $C_1$–$C_6$ alkyl substituted by $C_6$–$C_8$ cycloalkyloxycarbonyloxy, $C_1$–$C_6$ alkyl substituted by $C_7$–$C_{11}$ arylcarbonyloxy, $C_1$–$C_6$ alkyl substituted by $C_7$–$C_{11}$ aryloxycarbonyloxy and 2-oxo-1,3-dioxolene-4-ylmethyl group having $C_1$–$C_6$ alkyl as a substituent at the 5-position.

Concerning the ester group, $C_1$–$C_6$ alkyl groups include illustratively methyl, ethyl, propyl, isopropyl, butyl, isobutyl, s-butyl, t-butyl, pentyl, methylbutyl, dimethylpropyl, ethylpropyl, hexyl, methylpentyl, dimethylbutyl, ethylbutyl, and trimethylpropyl. $C_1$–$C_4$ alkyl groups are preferable, further methyl, ethyl, propyl, isopropyl, butyl or isobutyl are more preferable, and methyl or ethyl are the most preferable.

$C_7$–$C_{19}$ aralkyl groups includes benzyl, phenethyl, phenylpropyl, phenylbutyl, naphthylmethyl and benzyl. Benzyl is preferable.

$C_5$–$C_7$ cycloalkyl groups includes cyclopentyl, cyclohexyl and cycloheptyl. Cyclohexyl is preferable.

$C_6$–$C_{10}$ aryl groups includes phenyl and naphthyl, and phenyl is preferable.

Preferable examples of the ester residue are methyl, ethyl, propyl, isopropyl, butyl, isobutyl, t-butyl, benzyl, acetoxymethyl, 1-(acetoxy)ethyl, propionyloxymethyl, 1-propionyloxyethyl, butyryloxymethyl, 1-butyryloxyethyl, 1-isobutyryloxyethyl, valeryloxymethyl, 1-valeryloxyethyl, isovaleryloxymethyl, 1-isovaleryloxyethyl, pivaloyloxymethyl, 1-pivaloyloxyethyl, methoxycarbonyloxymethyl, 1-methoxycarbonyloxyethyl, ethoxycarbonyloxymethyl, 1-ethoxycarbonyloxyethyl, propoxycarbonyloxymethyl, 1-propoxycarbonyloxyethyl, isopropoxycarbonyloxymethyl, 1-isopropoxycarbonyloxyethyl, butoxycarbonyloxymethyl, 1-butoxycarbonyloxyethyl, isobutoxycarbonyloxymethyl, 1-isobutoxycarbonyloxyethyl, t-butoxycarbonyloxymethyl, 1-(t-butoxycarbonyloxy)ethyl, cyclopentanecarbonyloxymethyl, 1-cyclopentanecarbonyloxyethyl, cyclopentanecarbonyloxymethyl, 1-cyclopentanecarbonyloxyethyl, cyclohexanecarbonyloxymethyl, 1-cyclohexanecarbonyloxyethyl, cyclopentyloxycarbonyloxymethyl, 1-cyclopentyloxycarbonyloxyethyl, cyclohexyloxycarbonyloxymethyl, 1-cyclohexyloxycarbonyloxyethyl, benzoyloxymethyl, 1-benzoyloxyethyl, phenoxycarbonyloxymethyl, 1-phenoxycarbonyloxyethyl and 5-methyl-2-oxo-1,3-dioxolene-4-ylmethyl.

The amides of the α-substituted carboxylic acid derivatives of the compounds (I) to (IV) in the present invention mean the compounds in which the carboxyl group of the α-substituted carboxylic acid derivatives and ammonia are condensed with dehydration. Concretely, they are prepared by converting the carboxyl group into a —$CONH_2$ group.

The compounds of the present invention involve various isomers.

For example, the carbon atom at the 2-position of the α-substituted carboxylic acid derivatives of the compounds (I) to (IV) is asymmetrical, and any asymmetric carbon exists on the substituent. So, optical isomers may exist in the compounds of the invention.

Thus, the α-carbon atom is an asymmetric carbon to which $R_2$, Y and the nitrogen atom are bonded, as a result of which stereoisomers in R conformation and S conformation exist. The present invention involves each isomer or a mixture of isomers in free ratio. Such stereoisomers can be prepared by synthesizing α-substituted carboxylic acid derivatives (I)–(IV) from optically resolved starting compounds or by subjecting once synthesized α-substituted carboxylic acid derivatives (I)–(IV), if desired, to optical resolution by conventional optical resolution methods or separating methods, or by asymmetric synthesis.

Further, when Y represents a sulfoxide group, the sulfur atom becomes an asymmetric center to afford optical isomers. Also in this case, the respective isomers or a mixture in a free ratio are included in the scope of the present invention, and such stereoisomers can be optically resolved by conventional optical resolution methods or separating methods, or they can be also prepared by asymmetric synthesis.

Further, geometric isomers can exist also in the cases of those compounds having any double bond(s).

The present invention includes all these kinds of isomers.

In addition, the compounds (I) to (IV) in the present invention may absorb water, be attached to adsorbed water, be converted into a hydrate or form a solvate by allowing to leave in the atmosphere or by being recrystallized. They are to be included in the present invention.

Furthermore, compounds (I)–(IV) of the present invention may absorb another kind of solvent to give a solvate, which will be included in the present invention. Moreover, compounds which may be converted in vivo by metabolism into the α-substituted carboxylic acid derivatives (I)–(IV) or pharmacologically acceptable salts thereof of the present invention, namely so-called pro-drugs are included also in this invention.

Further, a pharmaceutical composition may be prepared by admixing one of sulfonylureas, α-glucosidase inhibitors, aldose reductase inhibitors, biguanides, statin type compounds, squalene synthesis inhibitors, fibrate type compounds, LDL disassimilation promotors, angiotensin II antagonists, angiotensin converting enzyme inhibitors, anti-cancer agents, and RXR activators together with said α-substituted carboxylic acid derivatives (I)–(IV), their pharmacologically acceptable esters, their pharmacologically acceptable amides and their pharmacologically acceptable salts. The sulfonylureas in the above-described definition mean a drug capable of accelerating insulin excretion and illustratively include tolbutamide, acetohexamide, tolazamide, chlorpropamide, etc.

The α-glucosidase inhibitors above-described mean a drug capable of inhibiting digestive enzymes such as amylase, maltase, α-dextrinase, sucrase, etc. so as to delay the digestion of starch and sucrose, and illustratively include acarbose, N-(1,3-dihydroxy-2-propyl)valiolamine (international non-proprietary name: voglibose), miglitol, and so on.

The aldose reductase inhibitors in the description above mean a drug capable of inhibiting diabetic complications by inhibiting the rate-determining enzyme at the first step of the polyol route and illustratively includes tolrestat, epalrestat, 2,7-difluoro-spiro (9H-fluoren-9,4'-imidazolindin)-2',5'-dione (international non-proprietary name: imirestat), 3-[(4-bromo-2-fluorophenyl)methyl]-7-chloro-3,4-dihydro-2,4-dioxo-1(2H)-quinazolin acetate (international non-proprietary name: zenarestat), 6-fluoro-2,3-dihydro-2',5'-dioxo-spiro[4H-1-benzopyran4,4'-imidazolidin]-2-carboxamide (SNK-860), zopolrestat, sorbinil, 1-[(3-bromo-2-benzofuranyl)sulfonyl]-2,4-imidazolidinedione (M-16209), and so on.

The biguanides in the description above mean a drug having anaerobic glycolysis promoting activity, peripheral insulin enhancing activity, glucose intestinal absorption suppression activity, hepatic glucose neogenesis suppression activity, aliphatic acid oxidation inhibition activity, and the like, and illustratively include phenformin, metformin, buformin, etc.

The statin type compounds in the description above mean a drug capable of lowering blood cholesterol by inhibiting hydroxymethylglutaryl CoA (HMG-CoA) reductase, and illustratively include pravastatin and its sodium salt, simvastatin, lovastatin, atorvastatin, celivastatin, fluvastatin, etc.

The squalene synthesis inhibitors in the description above mean a drug capable of lowering blood cholesterol by inhibiting squalene synthesis and illustratively include monopotassium (S)-α-[bis(2,2-dimethyl-1-oxopropoxy)methoxy]phosphinyl-3-phenoxybenzene-butanesulfonate (BMS-188494), and so on.

The fibrate type compounds in the description above mean a drug capable of lowering blood triglyceride levels by suppressing the synthesis and excretion of triglycerides in the liver and activating lipoprotein lipase, and illustratively include bezafibrate, beclofibrate, binifibrate, cyprofibrate, clinofibrate, clofibrate, clofibric acid, etofibrate, fenofibrate, gemfibrozil, nicofibrate, pirifibrate, ronifibrate, simfibrate, thefibrate, etc.

The LDL disassimilation promotors in the description above mean a drug capable of lowering blood cholesterol by enhancing LDL (low density lipoprotein) acceptor activity and illustratively include those compounds or salts thereof disclosed in JP Unexamined, Pub. H7 (1995)-316144 Gazette, concretely N-[2-[4-bis(4-fluorophenyl)methyl-1-piperazinyl]ethyl]-7,7-diphenyl-2,4,6-heptatrienoic acid amide, and so on.

The statin type compounds, squalene synthesis inhibitors, fibrate type compounds and LDL disassimilation promotors described above may be replaced by other drugs having blood cholesterol and triglyceride lowering activity. Examples of such drugs are nicotinic acid derivatives such as nicomol, niceritrol, etc.; anti-oxidants such as probucol, etc.; and ion exchange resin derivatives such as cholestylamine resin, etc. The angiotensin II antagonists in the description above mean a drug capable of lowering blood pressure by suppressing strongly hypertension due to angiotensin II.

Examples of such drugs are losartan potassium, candesartan cilexetil, valsartan, termisartan, ormesartan, etc.

The angiotensin converting enzyme inhibitors in the description above mean a drug capable of partially lowering blood sugar in diabetic patients by lowering blood pressure at a time by inhibiting angiotensin-converting enzyme, and illustratively include captopril, enarapril, alacepril, delapril, ramipril, lisinopril, imidapril, benazepril, ceronapril, cilazapril, enalaprilat, fosinopril, moveltiprl, perindopril, quinapril, spirapril, temocapril, trandolapril, etc.

Examples of preferable α-substituted carboxylic acid derivatives having the general formula (I) will be shown below.
(1) The α-substituted carboxylic acid derivatives (wherein $R_1$, $R_2$ and $R_3$ are the same or different, and each is a (i) hydrogen atom, (ii) $C_1$–$C_6$ alkyl group, (iii) $C_6$–$C_{10}$ aryl group (optionally having 1–3 substituting moieties $α_1$), (iv) $C_7$–$C_{16}$ aralkyl group (optionally having 1–3 substituting moieties $α_1$ on the aryl moiety thereof), (v) $C_1$–$C_4$ alkylsulfonyl group or (vi) $C_1$–$C_6$ halogenoalkylsulfonyl group), pharmacologically acceptable esters thereof, pharmacologically acceptable amides thereof or pharmacologically acceptable salts thereof.
(2) The α-substituted carboxylic acid derivatives (wherein $R_1$, $R_2$ and $R_3$ are the same or different, and each is a (i) hydrogen atom, (ii) $C_1$–$C_4$ alkyl group, (iii) phenyl group (optionally having one substituting moiety $α_1$), (iv) phenyl-$C_1$–$C_2$ alkyl group (optionally having 1–3 substituting moieties $α_1$ on the phenyl moiety) or (v) $C_1$–$C_2$ alkylsulfonyl group), pharmacologically acceptable esters thereof, pharmacologically acceptable amides thereof or pharmacologically acceptable salts thereof.
(3) The α-substituted carboxylic acid derivatives (wherein $R_1$, $R_2$ and $R_3$ are the same or different, and each is a (i) hydrogen atom, (ii) $C_1$–$C_4$ alkyl group or (iii) benzyl group (optionally having one substituting moiety $α_1$ on the phenyl moiety thereof)), pharmacologically acceptable esters thereof, pharmacologically acceptable amides thereof or pharmacologically acceptable salts thereof.
(4) The α-substituted carboxylic acid derivatives (wherein $R_1$ is a $C_1$–$C_2$ alkyl group, $R_2$ is a hydrogen atom, and $R_3$ is a $C_1$–$C_4$ alkyl group or phenyl-$C_1$–$C_4$ alkyl group (optionally having one substituting moiety $α_1$ on the phenyl moiety thereof)), pharmacologically acceptable esters thereof, pharmacologically acceptable amides thereof or pharmacologically acceptable salts thereof.
(5) The α-substituted carboxylic acid derivatives (wherein $R_1$ is a $C_1$–$C_2$ alkyl group, $R_2$ is a hydrogen atom and $R_3$ is a hydrogen atom), pharmacologically acceptable esters thereof, pharmacologically acceptable amides thereof or pharmacologically acceptable salts thereof.
(6) The α-substituted carboxylic acid derivatives (wherein $R_1$ is a $C_1$–$C_2$ alkyl group, $R_2$ is a hydrogen atom and $R_3$ is a phenyl group (optionally having one substituting moiety $α_1$), pharmacologically acceptable esters thereof, pharmacologically acceptable amides thereof or pharmacologically acceptable salts thereof.
(7) The α-substituted carboxylic acid derivatives (wherein $R_1$ is a $C_1$–$C_2$ alkyl group, $R_2$ is a hydrogen atom and $R_3$ is a phenyl group (optionally having one substituting moiety $α_1$), pharmacologically acceptable esters thereof, pharmacologically acceptable amides thereof or pharmacologically acceptable salts thereof.
(8) The α-substituted carboxylic acid derivatives (wherein $R_1$ is a $C_1$–$C_2$ alkyl group, $R_2$ is hydrogen atom and $R_3$ is a $C_1$–$C_2$ alkylsulfonyl group), pharmacologically acceptable esters thereof, pharmacologically acceptable amides thereof or pharmacologically acceptable salts thereof.
(9) The α-substituted carboxylic acid derivatives (wherein A is a nitrogen atom), pharmacologically acceptable esters thereof, pharmacologically acceptable amides thereof or pharmacologically acceptable salts thereof.
(10) The α-substituted carboxylic acid derivatives (wherein A is a =CH-group), pharmacologically acceptable esters thereof, pharmacologically acceptable amides thereof or pharmacologically acceptable salts thereof.
(11) The α-substituted carboxylic acid derivatives (wherein B is an oxygen atom), pharmacologically acceptable esters thereof, pharmacologically acceptable amides thereof or pharmacologically acceptable salts thereof.
(12) The α-substituted carboxylic acid derivatives (wherein B is a sulfur atom), pharmacologically acceptable esters thereof, pharmacologically acceptable amides thereof or pharmacologically acceptable salts thereof.
(13) The α-substituted carboxylic acid derivatives (wherein $W_1$ is a $C_1$–$C_6$ alkylene group), pharmacologically acceptable esters thereof, pharmacologically acceptable amides thereof or pharmacologically acceptable salts thereof.
(14) The α-substituted carboxylic acid derivatives (wherein $W_1$ is a $C_1$–$C_4$ alkylene group), pharmacologically acceptable esters thereof, pharmacologically acceptable amides thereof or pharmacologically acceptable salts thereof.
(15) The α-substituted carboxylic acid derivatives (wherein $W_1$ is a $C_1$–$C_2$ alkylene group), pharmacologically acceptable esters thereof, pharmacologically acceptable amides thereof or pharmacologically acceptable salts thereof.
(16) The α-substituted carboxylic acid derivatives (wherein $W_1$ is a methylene group), pharmacologically acceptable

(17) The α-substituted carboxylic acid derivatives (wherein $W_2$ is a single bond or a $C_1$–$C_6$ alkylene group), pharmacologically acceptable esters thereof, pharmacologically acceptable amides thereof or pharmacologically acceptable salts thereof.

(18) The α-substituted carboxylic acid derivatives (wherein $W_2$ is a $C_1$–$C_4$ alkylene group), pharmacologically acceptable esters thereof, pharmacologically acceptable amides thereof or pharmacologically acceptable salts thereof.

(19) The α-substituted carboxylic acid derivatives (wherein $W_2$ is a $C_1$–$C_2$ alkylene group), pharmacologically acceptable esters thereof, pharmacologically acceptable amides thereof or pharmacologically acceptable salts thereof.

(20) The α-substituted carboxylic acid derivatives (wherein $W_2$ is a methylene group), pharmacologically acceptable esters thereof, pharmacologically acceptable amides thereof or pharmacologically acceptable salts thereof.

(21) The α-substituted carboxylic acid derivatives (wherein X is a (i) hydrogen atom, (ii) $C_1$–$C_4$ alkyl group, (iii) $C_1$–$C_2$ halogenoalkyl group, (iv) $C_1$–$C_4$ alkoxy group, (v) halogen atom, (vi) hydroxy group, (vii) cyano group, (viii) nitro group, (ix) $C_1$–$C_5$ aliphatic acyl group or (x) amino group (optionally having one substituting moiety β)), pharmacologically acceptable esters thereof, pharmacologically acceptable amides thereof or pharmacologically acceptable salts thereof.

(22) The α-substituted carboxylic acid derivatives (wherein X is (i) a hydrogen atom, (ii) $C_1$–$C_2$ alkyl group, (iii) halogen atom, (iv) hydroxy group, (v) $C_1$–$C_2$ aliphatic acyl group or (vi) amino group), pharmacologically acceptable esters thereof, pharmacologically acceptable amides thereof or pharmacologically acceptable salts thereof.

(23) The α-substituted carboxylic acid derivatives (wherein X is a hydrogen atom), pharmacologically acceptable esters thereof, pharmacologically acceptable amides thereof or pharmacologically acceptable salts thereof.

(24) The α-substituted carboxylic acid derivatives (wherein $Z_1$ is a (i) $C_1$–$C_4$ alkoxy group, (ii) $C_1$–$C_4$ alkylthio group, (iii) halogen atom, (iv) $C_6$–$C_{10}$ aryloxy group (optionally having 1–5 substituting moieties $α_1$), (v) $C_7$–$C_{16}$ aralkyloxy group (optionally having 1–3 substituting moieties $α_1$ on the aryl moiety), (vi) $C_6$–$C_{10}$ cycloalkyloxy group, (vii) saturated heterocyclic ring-oxy group (optionally having 1–5 substituting moieties $α_1$), (viii) $C_6$–$C_{10}$ arylthio group (optionally having 1–3 substituting moieties $α_1$), (ix) saturated heterocyclic ring-thio group (optionally having 1–5 substituting moieties $α_1$), (x) amino group (optionally having one substituting moiety $α_1$) or (xi) hydroxy group), pharmacologically acceptable esters thereof, pharmacologically acceptable amides thereof or pharmacologically acceptable salts thereof.

(25) The α-substituted carboxylic acid derivatives (wherein $Z_1$ is a (i) $C_1$–$C_2$ alkoxy group, (ii) $C_1$–$C_2$ alkylthio group, (iii) halogen atom, (iv) phenoxy group (optionally having 1–5 substituting moieties $α_1$), (v) saturated heterocyclic ring-oxy group (optionally having 1–5 substituting moieties $α_1$), (vi) phenylthio group (optionally having 1–5 substituting moieties $α_1$), (vii) saturated heterocyclic ring-thio group (optionally having 1–5 substituting moieties $α_1$), (viii) amino group or (ix) hydroxy group), pharmacologically acceptable esters thereof, pharmacologically acceptable amides thereof or pharmacologically acceptable salts thereof.

(26) The α-substituted carboxylic acid derivatives (wherein $Z_1$ is a (i) $C_1$–$C_2$ alkoxy group, (ii) $C_1$–$C_2$ alkylthio group, (iii) phenoxy group (optionally having 1–5 substituting moieties $α_1$), (iv) saturated heterocyclic ring-oxy group (optionally having 1–5 substituting moieties $α_1$), (v) phenylthio group (optionally having 1–5 substituting moieties $α_1$) or (vi) hydroxy group), pharmacologically acceptable esters thereof, pharmacologically acceptable amides thereof or pharmacologically acceptable salts thereof.

(27) The α-substituted carboxylic acid derivatives (wherein $Z_1$ is a (i) $C_1$–$C_2$ alkoxy group, (ii) phenoxy group (optionally having 1–3 substituting moieties $α_1$) or (iii) phenylthio group (optionally having 1–3 substituting moieties $α_1$), pharmacologically acceptable esters thereof, pharmacologically acceptable amides thereof or pharmacologically acceptable salts thereof.

(28) The α-substituted carboxylic acid derivatives (wherein the substituting moiety $α_1$ is a (i) $C_1$–$C_6$ alkyl group, (ii) $C_1$–$C_2$ halogenoalkyl group, (iii) $C_1$–$C_4$ alkoxy group, (iv) halogen atom, (v) hydroxy group, (vi) cyano group, (vii) nitro group, (viii) $C_6$–$C_{10}$ cycloalkyl group, (ix) $C_1$–$C_2$ aliphatic acyl group, (x) $C_7$–$C_{11}$ arylcarbonyl group (optionally having 1–3 substituting moieties β), (xi) carbamoyl group, (xii) amino group (optionally having 1 to 2 substituting moieties β) or (xiii) carboxyl group), pharmacologically acceptable esters thereof, pharmacologically acceptable amides thereof or pharmacologically acceptable salts thereof.

(29) The α-substituted carboxylic acid derivatives (wherein the substituting moiety $α_1$ is a (i) $C_1$–$C_4$ alkyl group, (ii) $C_1$–$C_2$ halogenoalkyl group, (iii) $C_1$–$C_2$ alkoxy group, (iv) halogen atom, (v) hydroxy group, (vi) cyano group, (vii) nitro group, (viii) adamantyl group, (ix) benzoyl group (optionally having one substituting moiety β), (x) amino group (optionally having one substituting moiety β) or (xi) carboxyl group), pharmacologically acceptable esters thereof, pharmacologically acceptable amides thereof or pharmacologically acceptable salts thereof.

(30) The α-substituted carboxylic acid derivatives (wherein the substituting moiety $α_1$ is a (i) $C_1$–$C_4$ alkyl group, (ii) halogen atom, (iii) hydroxy group, (iv) adamantyl group, (v) benzoyl group, (vi) amino group (optionally having one substituting moiety β) or (vii) carboxyl group), pharmacologically acceptable esters thereof, pharmacologically acceptable amides thereof or pharmacologically acceptable salts thereof.

(31) The α-substituted carboxylic acid derivatives (wherein the substituting moiety $α_1$ is a (i) $C_1$–$C_4$ alkyl group, (ii) halogen atom, (iii) hydroxy group or (iv) adamantyl group), pharmacologically acceptable esters thereof, pharmacologically acceptable amides thereof or pharmacologically acceptable salts thereof.

(32) The α-substituted carboxylic acid derivatives (wherein the substituting moiety $α_1$ is a $C_1$–$C_4$ alkyl group or a hydroxy group), pharmacologically acceptable esters thereof, pharmacologically acceptable amides thereof or pharmacologically acceptable salts thereof.

(33) The α-substituted carboxylic acid derivatives (wherein the substituting moiety $α_1$ is a halogen atom or an adamantyl group), pharmacologically acceptable esters thereof, pharmacologically acceptable amides thereof or pharmacologically acceptable salts thereof.

(34) The α-substituted carboxylic acid derivatives (wherein the substituting moiety $α_1$ is a hydroxy group or a carboxyl group), pharmacologically acceptable esters thereof, pharmacologically acceptable amides thereof or pharmacologically acceptable salts thereof.

(35) The α-substituted carboxylic acid derivatives (wherein the substituting moiety $α_1$ is a $C_1$–$C_4$ alkyl group, benzoyl group or amino group (optionally having one substituting moiety β)), pharmacologically acceptable esters thereof, pharmacologically acceptable amides thereof or pharmacologically acceptable salts thereof.

(36) The α-substituted carboxylic acid derivatives (wherein the substituting moiety $α_1$ is a benzoyl group), pharmacologically acceptable esters thereof, pharmacologically acceptable amides thereof or pharmacologically acceptable salts thereof.

(37) The α-substituted carboxylic acid derivatives (wherein the substituting moiety β is a (i) $C_1$–$C_6$ alkyl group, (ii) halogen atom, (iii) phenyl group (optionally having 1–3 substituting moieties γ), (iv) phenyl-$C_1$–$C_4$ alkyl group (optionally having 1–3 substituting moieties γ on the phenyl moiety), (v) $C_1$–$C_5$ aliphatic acyl group or (vi) phenylaminocarbonyl group (optionally having 1–3 substituting moieties γ on the phenyl moiety), pharmacologically acceptable esters thereof, pharmacologically acceptable amides thereof or pharmacologically acceptable salts thereof.

(38) The α-substituted carboxylic acid derivatives (wherein the substituting moiety β is a (i) $C_1$–$C_4$ alkyl group, (ii) halogen atom or (iii) phenylaminocarbonyl group (optionally having 1–3 substituting moieties γ on the phenyl moiety)), pharmacologically acceptable esters thereof, pharmacologically acceptable amides thereof or pharmacologically acceptable salts thereof.

(39) The α-substituted carboxylic acid derivatives (wherein the substituting moiety β is a phenylaminocarbonyl group (optionally having one substituting moiety γ on the phenyl moiety)), pharmacologically acceptable esters thereof, pharmacologically acceptable amides thereof or pharmacologically acceptable salts thereof.

(40) The α-substituted carboxylic acid derivatives (wherein the substituting moiety γ is a (i) $C_1$–$C_2$ alkyl group, (ii) $C_1$–$C_2$ halogenoalkyl group, (iii) halogen atom or (iv) hydroxy group), pharmacologically acceptable esters thereof, pharmacologically acceptable amides thereof or pharmacologically acceptable salts thereof.

(41) The α-substituted carboxylic acid derivatives (wherein the substituting moiety γ is a trifluoromethyl group or a halogen atom), pharmacologically acceptable esters thereof, pharmacologically acceptable amides thereof or pharmacologically acceptable salts thereof.

(42) The α-substituted carboxylic acid derivatives (wherein the substituting moiety γ is a trifluoromethyl group), pharmacologically acceptable esters thereof, pharmacologically acceptable amides thereof or pharmacologically acceptable salts thereof.

Further, those compounds in which $R_1$, $R_2$ and $R_3$ are selected from (1)–(8) above, A is selected from (9)–(10) above, B is selected from (11)–(12), $W_1$ is selected from (13)–(16) above, $W_2$ is selected from (17)–(20) above, X is selected from (21)–(23) above, $Z_1$ is selected from (24)–(27) above, $α_1$ is selected from (28)–(36) above, β is selected from (37)–(39) above and γ is selected from (40)–(42) above in the α-substituted carboxylic acid derivatives of the general formula (I) are preferable.

For example, the following compounds are preferable in the α-substituted carboxylic acid derivatives of the general formula (I) above.

(43) The α-substituted carboxylic acid derivatives (wherein $R_1$, $R_2$ and $R_3$ are the same or different, and each is a (i) hydrogen atom, (ii) $C_1$–$C_6$ alkyl group, (iii) $C_6$–$C_{10}$ aryl group (optionally having 1–3 substituting moieties $α_1$), (iv) $C_7$–$C_{16}$ aralkyl group (optionally having 1–3 substituting moieties $α_1$ on the aryl moiety thereof), (v) $C_1$–$C_4$ alkylsulfonyl group or (vi) $C_1$–$C_6$ halogenoalkylsulfonyl group, A is a =CH-group, B is an oxygen atom, $W_1$ is a $C_1$–$C_4$ alkylene group, $W_2$ is a $C_1$–$C_4$ alkylene group, X is a (i) hydrogen atom, (ii) $C_1$–$C_4$ alkyl group, (iii) $C_1$–$C_2$ halogenoalkyl group, (iv) $C_1$–$C_4$ alkoxy group, (v) halogen atom, (vi) hydroxy group, (vii) cyano group, (viii) nitro group, (ix) $C_1$–$C_5$ aliphatic acyl group or (x) amino group (optionally having one substituting moiety β), Y is an oxygen atom or S(O)p (wherein p is an integer from 0 to 2), $Z_1$ is a (i) $C_1$–$C_4$ alkoxy group, (ii) $C_1$–$C_4$ alkylthio group, (iii) halogen atom, (iv) $C_6$–$C_{10}$ aryloxy group (optionally having 1–5 substituting moieties $α_1$), (v) $C_7$–$C_{16}$ aralkyloxy group (optionally having 1–3 substituting moieties $α_1$ on the aryl moiety thereof), (vi) $C_6$–$C_{10}$ cycloalkyloxy group, (vii) saturated heterocyclic ring-oxy group (optionally having 1–5 substituting moieties $α_1$), (viii) $C_6$–$C_{10}$ arylthio group (optionally having 1–5 substituting moieties $α_1$), (ix) saturated heterocyclic ring-thio group (optionally having 1–5 substituting moieties $α_1$), (x) amino group (optionally having one substituting moiety $α_1$ hereafter described) or (xi) hydroxy group, said substituting moiety $α_1$ is a (i) $C_1$–$C_6$ alkyl group, (ii) $C_1$–$C_2$ halogenoalkyl group, (iii) $C_1$–$C_4$ alkoxy group, (iv) halogen atom, (v) hydroxy group, (vi) cyano group, (vii) nitro group, (viii) $C_6$–$C_{10}$ cycloalkyl group, (ix) $C_1$–$C_2$ aliphatic acyl group (x) $C_7$–$C_{11}$ arylcarbonyl group (optionally having 1–3 substituting moieties γ), (xi) carbamoyl group, (xii) amino group (optionally having 1 to 2 substituting moieties β) or (xiii) carboxyl group, said substituting moiety β is a (i) $C_1$–$C_6$ alkyl group, (ii) halogen atom, (iii) phenyl group (optionally having 1–3 substituting moieties γ), (iv) phenyl-$C_1$–$C_4$ alkyl group (optionally having 1–3 substituting moieties γ on the phenyl moiety thereof), (v) $C_1$–$C_5$ aliphatic acyl group or (vi) phenylaminocarbonyl group (optionally having 1–3 substituting moieties γ on the phenyl moiety thereof), and said substituting moiety γ is a (i) $C_1$–$C_2$ alkyl group, (ii) $C_1$–$C_2$ halogenoalkyl group, (iii) halogen atom or (iv) hydroxy group), pharmacologically acceptable esters thereof, pharmacologically acceptable amides thereof or pharmacologically acceptable salts thereof

(44) The α-substituted carboxylic acid derivatives (wherein $R_1$, $R_2$ and $R_3$ are the same or different, and each is a (i) hydrogen atom, (ii) $C_1$–$C_4$ alkyl group, (iii) phenyl group (optionally having one substituting moiety $α_1$), (iv) phenyl-$C_1$–$C_2$ alkyl group (optionally having 1–3 substituting moieties $α_1$ on the phenyl moiety thereof) or (v) $C_1$–$C_2$ alkylsulfonyl group, A is a =CH-group, B is an oxygen atom, $W_1$ is a $C_1$–$C_2$ alkylene group, $W_2$ is a $C_1$–$C_2$ alkylene group, X is a (i) hydrogen atom, (ii) $C_1$–$C_2$ alkyl group, (iii) halogen atom, (iv) hydroxy group, (v) $C_1$–$C_2$ aliphatic acyl group or (vi) amino group, Y is an oxygen atom or S(O)p group (wherein p is an integer of 0–2), $Z_1$ is a (i) $C_1$–$C_2$ alkoxy group, (ii) $C_1$–$C_2$ alkylthio group, (iii) halogen atom, (iv) phenoxy group (optionally having 1–5 substituting moieties $\alpha_1$), (v) saturated heterocyclic ring-oxy group (optionally having 1–5 substituting moieties $\alpha_1$), (vi) phenylthio group (optionally having 1–5 substituting moieties $\alpha_1$), (vii) saturated heterocyclic ring-thio group (optionally having 1–5 substituting moieties $\alpha_1$), (viii) amino group or (ix) hydroxy group, the substituting moiety $\alpha_1$ is a (i) $C_1$–$C_4$ alkyl group, (ii) $C_1$–$C_2$ halogenoalkyl group, (iii) $C_1$–$C_2$ alkoxy group, (iv) halogen atom, (v) hydroxy group, (vi) cyano group, (vii) nitro group, (viii) adamantyl group, (ix) benzoyl group (optionally having one substituting moiety $\beta$), (x) amino group (optionally having one substituting moiety $\beta$) or (xi) carboxyl group, the substituting moiety $\beta$ is a (i) $C_1$–$C_4$ alkyl group, (ii) halogen atom or (iii) phenylaminocarbonyl group (optionally having 1–3 substituting moieties $\gamma$ on the phenyl moiety), and the substituting moiety $\gamma$ is a trifluoromethyl group or a halogen atom), pharmacologically acceptable esters thereof, pharmacologically acceptable amides thereof or pharmacologically acceptable salts thereof.

(45) The α-substituted carboxylic acid derivatives (wherein $R_1$, $R_2$ and $R_3$ are the same or different, and each is a (i) hydrogen atom, (ii) $C_1$–$C_4$ alkyl group or (iii) benzyl group (optionally having one substituting moiety $\alpha_1$ on the phenyl moiety thereof), A is a =CH-group, B is an oxygen atom, $W_1$ is a $C_1$–$C_2$ alkylene group, $W_2$ is a methylene group, X is a hydrogen atom, Y is an oxygen atom or S(O)p group (wherein p is an integer of 0–2), $Z_1$ is a (i) $C_1$–$C_2$ alkoxy group, (ii) $C_1$–$C_2$ alkylthio group, (iii) phenoxy group (optionally having 1–5 substituting moieties $\alpha_1$) (iv) saturated heterocyclic ring-oxy group (optionally having 1–5 substituting moieties $\alpha_1$), (v) phenylthio group (optionally having 1–5 substituting moieties $\alpha_1$) or (vi) hydroxy group), the substituting moiety $\alpha_1$ is a (i) $C_1$–$C_4$ alkyl group, (ii) halogen atom, (iii) hydroxy group, (iv) adamantyl group, (v) benzoyl group, (vi) amino group (optionally having one substituting moiety $\beta$) or (vii) carboxyl group, the substituting moiety $\beta$ is a phenylaminocarbonyl group (optionally having one substituting moiety $\gamma$ on the phenyl moiety thereof), and the substituting moiety $\gamma$ is a trifluoromethyl group, pharmacologically acceptable esters thereof, pharmacologically acceptable amides thereof or pharmacologically acceptable salts thereof.

Further, preferable embodiments of the α-substituted carboxylic acid derivatives of the general formula (II) above-described will be shown below.

(46) The α-substituted carboxylic acid derivatives (wherein $Z_2$ is a 5- or 6-member saturated heterocyclic ring group (optionally having 1–5 substituting moieties $\alpha_1$) or a phenyl group optionally having 1–3 substituting moieties $\alpha_2$), pharmacologically acceptable esters thereof, pharmacologically acceptable amides thereof or pharmacologically acceptable salts thereof.

(47) The α-substituted carboxylic acid derivatives (wherein $Z_2$ is a tetrahydropyranyl group (optionally having 1–5 substituting moieties $\alpha_1$)), pharmacologically acceptable esters thereof, pharmacologically acceptable amides thereof or pharmacologically acceptable salts thereof.

(48) The α-substituted carboxylic acid derivatives (wherein $Z_2$ is a phenyl group (optionally having one substituting moiety $\alpha_2$), pharmacologically acceptable esters thereof, pharmacologically acceptable amides thereof or pharmacologically acceptable salts thereof.

(49) The α-substituted carboxylic acid derivatives (wherein the substituting moiety $\alpha_2$ is a (i) $C_6$–$C_{10}$ cycloalkyl group, (ii) phenyl group (optionally having 1–3 substituting moieties $\beta$)), (iii) phenylcarbonyl group (optionally having 1–3 substituting moieties $\beta$), or (iv) monocyclic type heteroaromatic ring-carbonyl group (optionally having 1–3 substituting moieties $\beta$)), pharmacologically acceptable esters thereof, pharmacologically acceptable amides thereof or pharmacologically acceptable salts thereof.

(50) The α-substituted carboxylic acid derivatives (wherein the substituting moiety $\alpha_2$ is a $C_6$–$C_{10}$ cycloalkyl group), pharmacologically acceptable esters thereof, pharmacologically acceptable amides thereof or pharmacologically acceptable salts thereof.

(51) The α-substituted carboxylic acid derivatives (wherein the substituting moiety $\alpha_2$ is an adamantyl group), pharmacologically acceptable esters thereof, pharmacologically acceptable amides thereof or pharmacologically acceptable salts thereof.

Further, those compounds in which $R_1$, $R_2$ and $R_3$ are selected from (1)–(8) above, A is selected from (9) or (10) above, B is selected from (11) or (12) above, $W_1$ is selected from (13)–(16) above, $W_2$ is selected from (17)–(20) above, X is selected from (21)–(23) above, $Z_2$ is selected from (46)–(48) above, $\alpha_1$ is selected from (28)–(36) above, $\alpha_2$ is selected from (49)–(51) above, $\beta$ is selected from (37)–(39) above and $\gamma$ is selected from (40)–(42) above in the α-substituted carboxylic acid derivatives of the general formula (II) are preferable.

For example, the following compounds in the α-substituted carboxylic acid derivatives of the general formula (II) are also preferable.

(52) The α-substituted carboxylic acid derivatives (wherein $R_1$, $R_2$ and $R_3$ are the same or different, and each is a (i) hydrogen atom, (ii) $C_1$–$C_4$ alkyl group, (iii) phenyl group (optionally having one substituting moiety $\alpha_1$), (iv) phenyl-$C_1$–$C_2$ alkyl group (optionally having 1–3 substituting moieties $\alpha_1$ on the phenyl moiety thereof) or (v) $C_1$–$C_2$ alkylsulfonyl group, A is a =CH-group, B is an oxygen atom, $W_1$ is a $C_1$–$C_4$ alkylene group, $W_2$ is a $C_1$–$C_4$ alkylene group, X is a (i) hydrogen atom, (ii) $C_1$–$C_2$ alkyl group, (iii) halogen atom, (iv) hydroxy group, (v) $C_1$–$C_2$ aliphatic acyl group or (vi) amino group, Y is an oxygen atom or S(O)p group (wherein p is an integer of 0–2), $Z_2$ is a 5- or 6-member saturated heterocyclic ring group (optionally having 1–5 substituting moieties $\alpha_1$) or a phenyl group (optionally having 1–3 substituting moieties $\alpha_2$), the substituting moiety $\alpha_1$ is a (i) $C_1$–$C_4$ alkyl group, (ii) halogen atom, (iii) hydroxy group, (iv) adamantyl group, (v) benzoyl group, (vi) amino group (optionally having one substituting moiety $\beta$) or (vii) carboxyl group, the substituting moiety $\alpha_2$ is a $C_6$–$C_{10}$ cycloalkyl group, the substituting moiety $\beta$ is a (i) $C_1$–$C_4$ alkyl group, (ii) halogen atom or (iii) phenylaminocarbonyl group (optionally having 1–3 substituting moieties $\gamma$ on the phenyl moiety thereof), and the substituting moiety $\gamma$ is a trifluoromethyl group or a halogen atom, pharmacologically acceptable esters thereof, pharmacologically acceptable amides thereof or pharmacologically acceptable salts thereof.

(53) The $\alpha$-substituted carboxylic acid derivatives (wherein $R_1$, $R_2$ and $R_3$ are the same or different, and each is a (i) hydrogen atom, (ii) $C_1$–$C_4$ alkyl group or (iii) benzyl group (optionally having one substituting moiety $\alpha_1$ on the phenyl moiety thereof), A is a =CH-group, B is an oxygen atom, $W_1$ is a $C_1$–$C_2$ alkylene group, $W_2$ is a $C_1$–$C_2$ alkylene group, X is a hydrogen atom, Y is an oxygen atom or S(O)p group (wherein p is an integer of 0–2), $Z_2$ is a tetrahydropyranyl group (optionally having 1–5 substituting moieties $\alpha_1$), and the substituting moieties $\alpha_1$ is a hydroxy group or a carboxyl group, pharmacologically acceptable esters thereof, pharmacologically acceptable amides thereof or pharmacologically acceptable salts thereof.

(54) The $\alpha$-substituted carboxylic acid derivatives (wherein $R_1$, $R_2$ and $R_3$ are the same or different, and each is a (i) hydrogen atom, (ii) $C_1$–$C_4$ alkyl group or (iii) benzyl group (optionally having one substituting moiety $\alpha_1$ on the phenyl moiety thereof), A is a =CH-group, B is an oxygen atom, $W_1$ is a $C_1$–$C_2$ alkylene group, $W_2$ is a $C_1$–$C_2$ alkylene group, X is a hydrogen atom, Y is an oxygen atom or S(O)p group (wherein p is an integer of 0–2), $Z_2$ is a phenyl group (having one substituting moiety $\alpha_2$), the substituting moiety $\alpha_1$ is a halogen atom or an adamantyl group, and the substituting moiety $\alpha_2$ is adamantyl, pharmacologically acceptable esters thereof, pharmacologically acceptable amides thereof or pharmacologically acceptable salts thereof.

Further, preferable embodiments of the $\alpha$-substituted carboxylic acid derivatives of the general formula (III) will be shown below.

(55) The $\alpha$-substituted carboxylic acid derivatives (wherein $Z_3$ is a (i) $C_1$–$C_4$ alkyl group, (ii) $C_6$–$C_{10}$ aryl group (optionally having 1–3 substituting moieties $\alpha_1$) or (iii) $C_3$–$C_{10}$ cycloalkyl group), pharmacologically acceptable esters thereof, pharmacologically acceptable amides thereof or pharmacologically acceptable salts thereof.

(56) The $\alpha$-substituted carboxylic acid derivatives (wherein $Z_3$ is a $C_1$–$C_4$ alkyl group, phenyl group (optionally having 1–3 substituting moieties $\alpha_1$) or $C_3$–$C_{10}$ cycloalkyl group), pharmacologically acceptable esters thereof, pharmacologically acceptable amides thereof or pharmacologically acceptable salts thereof.

(57) The $\alpha$-substituted carboxylic acid derivatives (wherein $Z_3$ is a phenyl group (optionally having 1–3 substituting moieties $\alpha_1$)), pharmacologically acceptable esters thereof, pharmacologically acceptable amides thereof or pharmacologically acceptable salts thereof.

Furthermore, those compounds in the $\alpha$-substituted carboxylic acid derivatives of the general formula (III) in which $R_1$, $R_2$ and $R_3$ are selected from (1)–(8) above, A is selected from (9) or (10) above, B is selected from (11) or (12) above, $W_1$ is selected from (13)–(16) above, $W_2$ is selected from (17)–(20) above, X is selected from (21)–(23) above, $Z_3$ is selected from (55)–(57), $\alpha_1$ is selected from (28)–(36) above, $\beta$ is selected from (37)–(39) above, and $\gamma$ is selected from (40)–(42) above are preferable. For examples, the following compounds in the $\alpha$-substituted carboxylic acid derivatives of the general formula (III) are also preferable.

(58) The $\alpha$-substituted carboxylic acid derivatives (wherein $R_1$, $R_2$ and $R_3$ are the same or different, and each is a (i) hydrogen atom, (ii) $C_1$–$C_4$ alkyl group or (iii) benzyl group (optionally having one substituting moiety $\alpha_1$ on the phenyl moiety thereof)), A is a =CH-group, B is an oxygen atom, $W_1$ is a $C_1$–$C_2$ alkylene group, $W_2$ is a $C_1$–$C_2$ alkylene group, X is a hydrogen atom, Y is an oxygen atom or S(O)p (wherein p is an integer of 0–2), $Z_3$ is a (i) $C_1$–$C_4$ alkyl group, (ii) $C_6$–$C_{10}$ aryl group (optionally having 1–3 substituting moieties $\alpha_1$) or (iii) $C_3$–$C_{10}$ cycloalkyl group, and the substituting moiety $\alpha_1$ is a (i) $C_1$–$C_4$ alkyl group, (ii) halogen atom, (iii) hydroxy group or (iv) adamantyl group), pharmacologically acceptable esters thereof, pharmacologically acceptable amides thereof or pharmacologically acceptable salts thereof.

(59) The $\alpha$-substituted carboxylic acid derivatives (wherein $R_1$ is a $C_1$–$C_2$ alkyl group, $R_2$ is a hydrogen atom, $R_3$ is a $C_1$–$C_4$ alkyl group or a phenyl-$C_1$–$C_4$ alkyl group (optionally having one substituting moiety $\alpha_1$ on the phenyl moiety thereof), A is a =CH-group, B is an oxygen atom, $W_1$ is a methylene group, $W_2$ is a methylene group, X is a hydrogen atom, Y is an oxygen atom or S(O)p (wherein p is an integer of 0–2)

$Z_3$ is a phenyl group (optionally having 1–3 substituting moieties $\alpha_1$), and the substituting moiety $\alpha_1$ is a $C_1$–$C_4$ alkyl group or a hydroxy group), pharmacologically acceptable esters thereof, pharmacologically acceptable amides thereof or pharmacologically acceptable salts thereof.

Further, preferable embodiments in the $\alpha$-substituted carboxylic acid derivatives of the general formula (IV) above-described will be shown below.

(60) The $\alpha$-substituted carboxylic acid derivatives (wherein $R_4$ is a $C_1$–$C_4$ alkyl group or phenyl group (optionally having 1–3 substituting moieties $\alpha_1$)), pharmacologically acceptable esters thereof, pharmacologically acceptable amides thereof or pharmacologically acceptable salts thereof.

(61) The $\alpha$-substituted carboxylic acid derivatives (wherein $R_4$ is a phenyl group (optionally having one substituting moiety $\alpha_1$)), pharmacologically acceptable esters thereof, pharmacologically acceptable amides thereof or pharmacologically acceptable salts thereof.

(62) The $\alpha$-substituted carboxylic acid derivatives (wherein $Z_4$ is a (i) $C_1$–$C_4$ alkoxy group, (ii) $C_1$–$C_4$ alkylthio group (iii) $C_6$–$C_{10}$ aryloxy group (optionally having 1–3 substituting moieties $\alpha_1$), (iv) benzyloxy group (optionally having 1–3 substituting moieties $\alpha_1$ on the phenyl moiety thereof), (v) $C_6$–$C_{10}$ arylthio group (optionally having 1–3 substituting moieties $\alpha_1$) or (vi) benzylthio group (optionally having 1–5 substituting moieties $\alpha_1$ on the phenyl moiety thereof)), pharmacologically acceptable esters thereof, pharmacologically acceptable amides thereof or pharmacologically acceptable salts thereof.

(63) The $\alpha$-substituted carboxylic acid derivatives (wherein $Z_4$ is a (i) $C_1$–$C_4$ alkoxy group, (ii) $C_1$–$C_2$ alkylthio group, (iii) phenoxy group (optionally having 1–3 substituting moieties $\alpha_1$) (iv) phenylthio group (optionally having 1–3 substituting moieties $\alpha_1$)), pharmacologically acceptable esters thereof, pharmacologically acceptable amides thereof or pharmacologically acceptable salts thereof.

(64) The $\alpha$-substituted carboxylic acid derivatives (wherein $Z_4$ is a $C_1$–$C_2$ alkoxy group or a phenoxy group (optionally having 1–3 substituting moieties $\alpha_1$)), pharmacologically acceptable esters thereof, pharmacologically acceptable amides thereof or pharmacologically acceptable salts thereof.

(65) The $\alpha$-substituted carboxylic acid derivatives (wherein $Z_4$ is a $C_1$–$C_2$ alkoxy group), pharmacologically acceptable esters thereof, pharmacologically acceptable amides thereof or pharmacologically acceptable salts thereof.

(66) The $\alpha$-substituted carboxylic acid derivatives (wherein $Z_4$ is a phenoxy group (optionally having 1–3 substituting moieties $\alpha_1$)), pharmacologically acceptable esters thereof, pharmacologically acceptable amides thereof or pharmacologically acceptable salts thereof.

Furthermore, those compounds in the $\alpha$-substituted carboxylic acid derivatives of the general formula (IV) above-described in which $R_1$, $R_2$ and $R_3$ are selected from (1)–(8) above, $R_4$ is selected from (60) or (61) above, A is selected from (9) or (10) above, B is selected from (11) or (12) above, $W_1$ is selected from (13)–(16) above, $W_2$ is selected from (17)–(20) above, X is selected from (21)–(23) above, $Z_4$ is selected from (62)–(66) above, $\alpha_1$ is selected from (28)–(36), $\beta$ is selected from (37)–(39), and $\gamma$ is selected from (40)–(42) above are also preferable.

For example, the following compounds in the $\alpha$-substituted carboxylic acid derivatives of the general formula (IV) above are also preferable.

(67) The $\alpha$-substituted carboxylic acid derivatives (wherein $R_1$, $R_2$ and $R_3$ are the same or different, and each is a (i) hydrogen atom, (ii) $C_1$–$C_4$ alkyl group or (iii) benzyl group (optionally having one substituting moiety $\alpha_1$ on the phenyl moiety thereof)), $R_4$ is a $C_1$–$C_4$ alkyl group or a phenyl group (optionally having 1–3 substituting moieties $\alpha_1$), A is a =CH-group, B is an oxygen atom, $W_1$ is a $C_1$–$C_2$ alkylene group, $W_2$ is a $C_1$–$C_2$ alkylene group, X is a (i) hydrogen atom, (ii) $C_1$–$C_2$ alkyl group, (iii) halogen atom, (iv) hydroxy group, (v) $C_1$–$C_2$ aliphatic acyl group or (vi) amino group, $Z_4$ is a (i) $C_1$–$C_4$ alkoxy group, (ii) $C_1$–$C_2$ alkylthio group, (iii) phenoxy group (optionally having 1–3 substituting moieties $\alpha_1$) or (iv) phenylthio group (optionally having 1–3 substituting moieties $\alpha_1$), and the substituting moiety $\alpha_1$ is a (i) $C_1$–$C_4$ alkyl group, (ii) halogen atom, (iii) hydroxy group, (iv) adamantyl group, (v) benzoyl group, (vi) amino group (optionally having one substituting moiety $\beta$) or (vii) carboxyl group, the substituting moiety $\beta$ is a (i) $C_1$–$C_4$ alkyl group, (ii) halogen atom or (iii) phenylaminocarbonyl group (optionally having 1–3 substituting moieties $\gamma$ on the phenyl moiety thereof), and the substituting moiety $\gamma$ is a trifluoromethyl group or a halogen atom), pharmacologically acceptable esters thereof, pharmacologically acceptable amides thereof or pharmacologically acceptable salts thereof.

(68) The $\alpha$-substituted carboxylic acid derivatives (wherein $R_1$ is a $C_1$–$C_2$ alkyl group, $R_2$ is a hydrogen atom, $R_3$ is a hydrogen atom, $R_4$ is a phenyl group (optionally having one substituting moiety $\alpha_1$), A is a =CH-group, B is an oxygen atom, $W_1$ is a methylene group, $W_2$ is methylene group, X is a hydrogen atom, $Z_4$ is a $C_1$–$C_2$ alkoxy group, and the substituting moiety $\alpha_1$ is a benzoyl group), pharmacologically acceptable esters thereof, pharmacologically acceptable amides thereof or pharmacologically acceptable salts thereof.

(69) The $\alpha$-substituted carboxylic acid derivatives (wherein $R_1$ is a $C_1$–$C_2$ alkyl group, $R_2$ is a hydrogen atom, $R_3$ is a hydrogen atom, $R_4$ is a phenyl group (optionally having one substituting moiety $\alpha_1$), A is a =CH-group, B is an oxygen atom, $W_1$ is a methylene group, $W_2$ is a methylene group, X is a hydrogen atom, $Z_4$ is a phenoxy group (optionally having 1–3 substituting moieties $\alpha_1$), the substituting moiety $\alpha_1$ is a $C_1$–$C_4$ alkyl group, a benzoyl group or an amino group (optionally having one substituting moiety $\beta$), the substituting moiety $\beta$ is a phenylaminocarbonyl group (optionally having one substituting moiety $\gamma$ on the phenyl moiety thereof), and the substituting moiety $\gamma$ is a trifluoromethyl group), pharmacologically acceptable esters thereof, pharmacologically acceptable amides thereof or pharmacologically acceptable salts thereof.

Examples of the $\alpha$-substituted carboxylic acid derivatives of the present invention can be shown in Tables 1–5, but the scope of the invention should not be limited by those compounds. Further, the compounds in Tables 1–5 have each the chemical structure (I-1) to (I-5). The abbreviations in the tables have the following significance.

Ac: acetyl
Ada: adamantyl
Boz: benzoyl
Bu: butyl
iBu: isobutyl,
sBu: s-butyl
tBu: t-butyl,
Bz: benzyl
Byr: butyryl
iByr: isobutyryl
Car: carbamoyl
Et: ethyl
GlcA: $\beta$-D-glucopyranuranosyloxy Hx: hexyl,
iHx: isohexyl
sHx: s-hexyl
cHx: cyclohexyl
Hynyl: hexanoyl
Imid: imidazolyl
Me: methyl
Mor: morpholinyl
Nic: nicotinoyl
iNic: isonicotinoyl
Np: naphthyl
Ph: phenyl
Pip: 1-piperidinyl
Pipra: piperazinyl Pn: pentyl
cPn: cyclopentyl
cPnc: cyclopentylcarbonyl
Pr: propyl
cPr: cyclopropyl
iPr: isopropyl
Prn: propionyl
Pyr: pyridyl
Pyrd: pyrrolidinyl
TioMor: thiomorpholinylcarbonyl
Tos: p-toluenesulfonyl
Va: valeryl group
E.C.No.: exemplification compound number.

TABLE 1

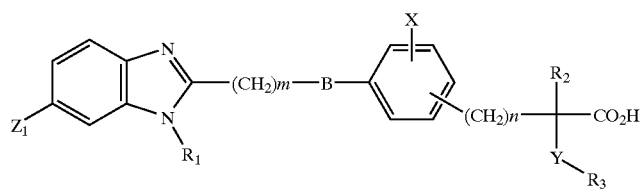

(I-1)

| E.C.No. | B | X | Y | $Z_1$ | $R_1$ | $R_2$ | $R_3$ | m | n |
|---|---|---|---|---|---|---|---|---|---|
| 1-1 | O | H | O | 4-AdaPhO | Me | H | 4-FBz | 1 | 1 |
| 1-2 | O | H | O | 4-AdaPhO | Me | H | 4-FBz | 1 | 0 |
| 1-3 | O | H | O | 4-AdaPhO | Me | H | 4-FBz | 1 | 2 |
| 1-4 | O | H | O | 4-AdaPhO | Me | H | 4-FBz | 1 | 3 |
| 1-5 | O | H | O | 4-AdaPhO | Me | H | 4-FBz | 1 | 4 |
| 1-6 | O | H | O | 4-AdaPhO | Me | H | 4-FBz | 1 | 5 |
| 1-7 | O | H | O | 4-AdaPhO | Me | H | 4-FBz | 1 | 6 |
| 1-8 | O | H | O | 4-AdaPhO | Me | H | 4-FBz | 1 | 7 |
| 1-9 | O | H | O | 4-AdaPhO | Me | H | 4-FBz | 1 | 8 |
| 1-10 | O | H | O | 4-AdaPhO | Me | H | 4-FBz | 2 | 1 |
| 1-11 | O | H | O | 4-AdaPhO | Me | H | 4-FBz | 3 | 1 |
| 1-12 | O | H | O | 4-AdaPhO | Me | H | 4-FBz | 4 | 1 |
| 1-13 | O | H | O | 4-AdaPhO | Me | H | 4-FBz | 5 | 1 |
| 1-14 | O | H | O | 4-AdaPhO | Me | H | 4-FBz | 6 | 1 |
| 1-15 | O | H | O | 4-AdaPhO | Me | H | 4-FBz | 7 | 1 |
| 1-16 | O | H | O | 4-AdaPhO | Me | H | 4-FBz | 8 | 1 |
| 1-17 | O | H | S | 4-AdaPhO | Me | H | H | 1 | 1 |
| 1-18 | O | H | S | 4-AdaPhO | Me | H | Me | 1 | 1 |
| 1-19 | O | H | S | 4-AdaPhO | Me | H | Et | 1 | 1 |
| 1-20 | O | H | S | 4-AdaPhO | Me | H | Bu | 1 | 1 |
| 1-21 | O | H | S | 4-AdaPhO | Me | H | Ph | 1 | 1 |
| 1-22 | O | H | S | 4-AdaPhO | Me | H | Bz | 1 | 1 |
| 1-23 | O | H | S | 4-AdaPhO | Me | H | 4-ClBz | 1 | 1 |
| 1-24 | S | H | S | 4-AdaPhO | Me | H | 4-FBz | 1 | 1 |
| 1-25 | O | H | O | 4-AdaPhO | Me | H | 4-FBz | 1 | 1 |
| 1-26 | O | H | S | 4-AdaPhO | 4-FBz | H | 4-FBz | 1 | 1 |
| 1-27 | O | H | S | 4-AdaPhO | Et | H | 4-FBz | 1 | 1 |
| 1-28 | O | H | S | 4-AdaPhO | Pr | H | 4-FBz | 1 | 1 |
| 1-29 | O | H | S | 4-AdaPhO | iPr | H | 4-FBz | 1 | 1 |
| 1-30 | O | H | S | 4-AdaPhO | Bu | H | 4-FBz | 1 | 1 |
| 1-31 | O | H | S | 4-AdaPhO | iBu | H | 4-FBz | 1 | 1 |
| 1-32 | O | H | S | 4-AdaPhO | sBu | H | 4-FBz | 1 | 1 |
| 1-33 | O | H | S | 4-AdaPhO | Pn | H | 4-FBz | 1 | 1 |
| 1-34 | O | H | S | 4-AdaPhO | Hx | H | 4-FBz | 1 | 1 |
| 1-35 | O | H | S | 4-AdaPhO | Ph | H | 4-FBz | 1 | 1 |
| 1-36 | O | H | S | 4-AdaPhO | Bz | H | 4-FBz | 1 | 1 |
| 1-37 | O | H | S | 4-AdaPhO | Me | Me | 4-FBz | 1 | 1 |
| 1-38 | O | H | S | 4-AdaPhO | Me | Et | 4-FBz | 1 | 1 |
| 1-39 | O | H | S | 4-AdaPhO | Me | Pr | 4-FBz | 1 | 1 |
| 1-40 | O | H | S | 4-AdaPhO | Me | iPr | 4-FBz | 1 | 1 |
| 1-41 | O | H | S | 4-AdaPhO | Me | Bu | 4-FBz | 1 | 1 |
| 1-42 | O | H | S | 4-AdaPhO | Me | iBu | 4-FBz | 1 | 1 |
| 1-43 | O | H | S | 4-AdaPhO | Me | SBu | 4-FBz | 1 | 1 |
| 1-44 | O | H | S | 4-AdaPhO | Me | Pn | 4-FBz | 1 | 1 |
| 1-45 | O | H | S | 4-AdaPhO | Me | Hx | 4-FBz | 1 | 1 |
| 1-46 | O | H | S | 4-AdaPhO | Me | Ph | 4-FBz | 1 | 1 |
| 1-47 | O | H | S | 4-AdaPhO | Me | 4-FPh | 4-FBz | 1 | 1 |
| 1-48 | O | H | S | 4-AdaPhO | Me | 3-$CF_3$Ph | 4-FBz | 1 | 1 |

TABLE 1-continued (I-1)

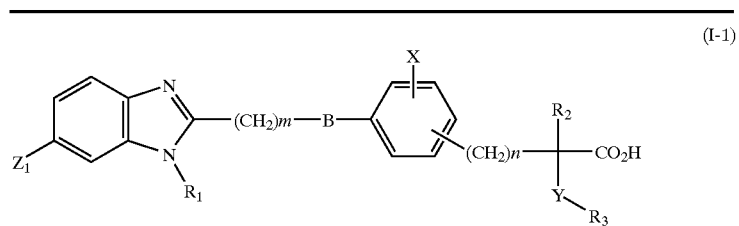

| E.C.No. | B | X | Y | Z₁ | R₁ | R₂ | R₃ | m | n |
|---|---|---|---|---|---|---|---|---|---|
| 1-49 | O | H | S | 4-AdaPhO | Me | 3-MeOPh | 4-FBz | 1 | 1 |
| 1-50 | O | H | S | 4-AdaPhO | Me | 2-MePh | 4-FBz | 1 | 1 |
| 1-51 | O | H | S | 4-AdaPhO | Me | 4-CNPh | 4-FBz | 1 | 1 |
| 1-52 | O | H | S | 4-AdaPhO | Me | Bz | 4-FBz | 1 | 1 |
| 1-53 | O | H | S | 4-AdaPhO | Me | 3-FBz | 4-FBz | 1 | 1 |
| 1-54 | O | H | S | 4-AdaPhO | Me | 2-CF₃Bz | 4-FBz | 1 | 1 |
| 1-55 | O | H | S | 4-AdaPhO | Me | 3,5-diMeOBz | 4-FBz | 1 | 1 |
| 1-56 | O | H | S | 4-AdaPhO | Me | 4-ClBz | 4-FBz | 1 | 1 |
| 1-57 | O | Cl | S | 4-AdaPhO | Me | H | 4-FBz | 1 | 1 |
| 1-58 | O | F | S | 4-AdaPhO | Me | H | 4-FBz | 1 | 1 |
| 1-59 | O | Br | S | 4-AdaPhO | Me | H | 4-FBz | 1 | 1 |
| 1-60 | O | Me | S | 4-AdaPhO | Me | H | 4-FBz | 1 | 1 |
| 1-61 | O | MeO | S | 4-AdaPhO | Me | H | 4-FBz | 1 | 1 |
| 1-62 | O | EtO | S | 4-AdaPhO | Me | H | 4-FBz | 1 | 1 |
| 1-63 | O | iPr | S | 4-AdaPhO | Me | H | 4-FBz | 1 | 1 |
| 1-64 | O | CF₃ | S | 4-AdaPhO | Me | H | 4-FBz | 1 | 1 |
| 1-65 | O | HO | S | 4-AdaPhO | Me | H | 4-FBz | 1 | 1 |
| 1-66 | O | EtO | S | 4-AdaPhO | Me | H | 4-FBz | 1 | 1 |
| 1-67 | O | tBu | S | 4-AdaPhO | Me | H | 4-FBz | 1 | 1 |
| 1-68 | O | Ac | S | 4-AdaPhO | Me | H | 4-FBz | 1 | 1 |
| 1-69 | O | Boz | S | 4-AdaPhO | Me | H | 4-FBz | 1 | 1 |
| 1-70 | O | PhAc | S | 4-AdaPhO | Me | H | 4-FBz | 1 | 1 |
| 1-71 | O | cPnc | S | 4-AdaPhO | Me | H | 4-FBz | 1 | 1 |
| 1-72 | O | NH₂ | S | 4-AdaPhO | Me | H | 4-FBz | 1 | 1 |
| 1-73 | O | NHAc | S | 4-AdaPhO | Me | H | 4-FBz | 1 | 1 |
| 1-74 | O | NHBoz | S | 4-AdaPhO | Me | H | 4-FBz | 1 | 1 |
| 1-75 | O | NHMe | S | 4-AdaPhO | Me | H | 4-FBz | 1 | 1 |
| 1-76 | O | NHiPr | S | 4-AdaPhO | Me | H | 4-FBz | 1 | 1 |
| 1-77 | O | NHPh | S | 4-AdaPhO | Me | H | 4-FBz | 1 | 1 |
| 1-78 | O | NHBz | S | 4-AdaPhO | Me | H | 4-FBz | 1 | 1 |
| 1-79 | O | NMeEt | S | 4-AdaPhO | Me | H | 4-FBz | 1 | 1 |
| 1-80 | O | NEtPh | S | 4-AdaPhO | Me | H | 4-FBz | 1 | 1 |
| 1-81 | O | NPhBz | S | 4-AdaPhO | Me | H | 4-FBz | 1 | 1 |
| 1-82 | O | Ph | S | 4-AdaPhO | Me | H | 4-FBz | 1 | 1 |
| 1-83 | O | Np | S | 4-AdaPhO | Me | H | 4-FBz | 1 | 1 |
| 1-84 | O | CN | S | 4-AdaPhO | Me | H | 4-FBz | 1 | 1 |
| 1-85 | O | NO₂ | S | 4-AdaPhO | Me | H | 4-FBz | 1 | 1 |
| 1-86 | O | H | O | 4-HO-3,5-di-tBuPhS | Me | H | 4-FBz | 1 | 1 |
| 1-87 | O | H | O | 4-HO-3,5-di-tBuPhS | Me | H | H | 1 | 1 |
| 1-88 | O | H | S | 4-HO-3,5-di-tBuPhS | Me | H | Me | 1 | 1 |
| 1-89 | O | H | S | 4-HO-3,5-di-tBuPhS | Me | H | Et | 1 | 1 |
| 1-90 | O | H | S | 4-HO-3,5-di-tBuPhS | Me | H | Hx | 1 | 1 |
| 1-91 | O | H | S | 4-HO-3,5-di-tBuPhS | Me | H | Bz | 1 | 1 |
| 1-92 | O | H | O | 4-HO-3,5-di-tBuPhS | Me | H | Ph | 1 | 1 |
| 1-93 | O | H | O | 4-HO-3,5-di-tBuPhS | Me | H | 4-FBz | 1 | 0 |
| 1-94 | O | H | O | 4-HO-3,5-di-tBuPhS | Me | H | 4-FBz | 1 | 2 |
| 1-95 | O | H | O | 4-HO-3,5-di-tBuPhS | Me | H | 4-FBz | 1 | 3 |
| 1-96 | O | H | O | 4-HO-3,5-di-tBuPhS | Me | H | 4-FBz | 1 | 4 |
| 1-97 | O | H | O | 4-HO-3,5-di-tBuPhS | Me | H | 4-FBz | 1 | 5 |
| 1-98 | O | H | O | 4-HO-3,5-di-tBuPhS | Me | H | 4-FBz | 1 | 6 |
| 1-99 | O | H | O | 4-HO-3,5-di-tBuPhS | Me | H | 4-FBz | 1 | 7 |

TABLE 1-continued (I-1)

| E.C.No. | B | X | Y | Z$_1$ | R$_1$ | R$_2$ | R$_3$ | m | n |
|---|---|---|---|---|---|---|---|---|---|
| 1-100 | O | H | O | 4-HO-3,5-di-tBuPhS | Me | H | 4-FBz | 1 | 8 |
| 1-101 | O | H | O | 4-HO-3,5-di-tBuPhS | Me | H | 4-FBz | 2 | 1 |
| 1-102 | O | H | O | 4-HO-3,5-di-tBuPhS | Me | H | 4-FBz | 3 | 1 |
| 1-103 | O | H | O | 4-HO-3,5-di-tBuPhS | Me | H | 4-FBz | 4 | 1 |
| 1-104 | O | H | O | 4-HO-3,5-di-tBuPhS | Me | H | 4-FBz | 5 | 1 |
| 1-105 | O | H | O | 4-HO-3,5-di-tBuPhS | Me | H | 4-FBz | 6 | 1 |
| 1-106 | O | H | O | 4-HO-3,5-di-tBuPhS | Me | H | 4-FBz | 7 | 1 |
| 1-107 | O | H | O | 4-HO-3,5-di-tBuPhS | Me | H | 4-FBz | 8 | 1 |
| 1-108 | S | H | S | 4-HO-3,5-di-tBuPhS | Me | H | 4-FBz | 1 | 1 |
| 1-109 | O | H | O | 4-HO-3,5-di-BuPhS | Me | H | 4-FBz | 1 | 1 |
| 1-110 | O | H | S | 4-HO-3,5-di-tBuPhO | Me | H | 4-FBz | 1 | 1 |
| 1-111 | O | H | S | 4-HO-3,5-di-tBuPhS | Et | H | 4-FBz | 1 | 1 |
| 1-112 | O | H | S | 4-HO-3,5-di-tBuPhS | Pr | H | 4-FBz | 1 | 1 |
| 1-113 | O | H | S | 4-HO-3,5-di-tBuPhS | iPr | H | 4-FBz | 1 | 1 |
| 1-114 | O | H | S | 4-HO-3,5-di-tBuPhS | Bu | H | 4-FBz | 1 | 1 |
| 1-115 | O | H | S | 4-HO-3,5-di-tBuPhS | iBu | H | 4-FBz | 1 | 1 |
| 1-116 | O | H | S | 4-HO-3,5-di-tBuPhS | sBu | H | 4-FBz | 1 | 1 |
| 1-117 | O | H | S | 4-HO-3,5-di-tBuPhS | Hx | H | 4-FBz | 1 | 1 |
| 1-118 | O | H | S | 4-HO-3,5-di-tBuPhS | Hx | H | 4-FBz | 1 | 1 |
| 1-119 | O | H | S | 4-HO-3,5-di-tBuPhS | Ph | H | 4-FBz | 1 | 1 |
| 1-120 | O | H | S | 4-HO-3,5-di-tBuPhS | Bz | H | 4-FBz | 1 | 1 |
| 1-121 | O | H | S | 4-HO-3,5-di-tBuPhS | Me | Me | 4-FBz | 1 | 1 |
| 1-122 | O | H | S | 4-HO-3,5-di-tBuPhS | Me | Et | 4-FBz | 1 | 1 |
| 1-123 | O | H | S | 4-HO-3,5-di-tBuPhS | Me | Pr | 4-FBz | 1 | 1 |
| 1-124 | O | H | S | 4-HO-3,5-di-tBuPhS | Me | iPr | 4-FBz | 1 | 1 |
| 1-125 | O | H | S | 4-HO-3,5-di-tBuPhS | Me | Bu | 4-FBz | 1 | 1 |
| 1-126 | O | H | S | 4-HO-3,5-di-tBuPhS | Me | iBu | 4-FBz | 1 | 1 |
| 1-127 | O | H | S | 4-HO-3,5-di-tBuPhS | Me | sBu | 4-FBz | 1 | 1 |
| 1-128 | O | H | S | 4-HO-3,5-di-tBuPhS | Me | Pn | 4-FBz | 1 | 1 |
| 1-129 | O | H | S | 4-HO-3,5-di-tBuPhS | Me | Hx | 4-FBz | 1 | 1 |
| 1-130 | O | H | S | 4-HO-3,5-di-tBuPhS | Me | Ph | 4-FBz | 1 | 1 |
| 1-131 | O | H | S | 4-HO-3,5-di-tBuPhS | Me | 4-FPh | 4-FBz | 1 | 1 |
| 1-132 | O | H | S | 4-HO-3,5-di-tBuPhS | Me | 3-CF$_3$Ph | 4-FBz | 1 | 1 |

TABLE 1-continued (I-1)

| E.C.No. | B | X | Y | Z₁ | R₁ | R₂ | R₃ | m | n |
|---|---|---|---|---|---|---|---|---|---|
| 1-133 | O | H | S | 4-HO-3,5-di-tBuPhS | Me | 3-MeOPh | 4-FBz | 1 | 1 |
| 1-134 | O | H | S | 4-HO-3,5-di-tBuPhS | Me | 2-MePh | 4-FBz | 1 | 1 |
| 1-135 | O | H | S | 4-HO-3,5-di-tBuPhS | Me | 4-CNPh | 4-FBz | 1 | 1 |
| 1-136 | O | H | S | 4-HO-3,5-di-tBuPhS | Me | Bz | 4-FBz | 1 | 1 |
| 1-137 | O | H | S | 4-HO-3,5-di-tBuPhS | Me | 3-FBz | 4-FBz | 1 | 1 |
| 1-138 | O | H | S | 4-HO-3,5-di-tBuPhS | Me | 2-CF₃Bz | 4-FBz | 1 | 1 |
| 1-139 | O | H | S | 4-HO-3,5-di-tBuPhS | Me | 3,5-diMeOBz | 4-FBz | 1 | 1 |
| 1-140 | O | H | S | 4-HO-3,5-di-tBuPhS | Me | 4-ClBz | 4-FBz | 1 | 1 |
| 1-141 | O | Cl | S | 4-HO-3,5-di-tBuPhS | Me | H | 4-FBz | 1 | 1 |
| 1-142 | O | F | S | 4-HO-3,5-di-tBuPhS | Me | H | 4-FBz | 1 | 1 |
| 1-143 | O | Br | S | 4-HO-3,5-di-tBuPhS | Me | H | 4-FBz | 1 | 1 |
| 1-144 | O | Me | S | 4-HO-3,5-di-tBuPhS | Me | H | 4-FBz | 1 | 1 |
| 1-145 | O | MeO | S | 4-HO-3,5-di-tBuPhS | Me | H | 4-FBz | 1 | 1 |
| 1-146 | O | EtO | S | 4-HO-3,5-di-tBuPhS | Me | H | 4-FBz | 1 | 1 |
| 1-147 | O | iPr | S | 4-HO-3,5-di-tBuPhS | Me | H | 4-FBz | 1 | 1 |
| 1-148 | O | CF₃ | S | 4-HO-3,5-di-tBuPhS | Me | H | 4-FBz | 1 | 1 |
| 1-149 | O | HO | S | 4-HO-3,5-di-tBuPhS | Me | H | 4-FBz | 1 | 1 |
| 1-150 | O | EtO | S | 4-HO-3,5-di-tBuPhS | Me | H | 4-FBz | 1 | 1 |
| 1-151 | O | tBu | S | 4-HO-3,5-di-tBuPhS | Me | H | 4-FBz | 1 | 1 |
| 1-152 | O | Ac | S | 4-HO-3,5-di-tBuPhS | Me | H | 4-FBz | 1 | 1 |
| 1-153 | O | Boz | S | 4-HO-3,5-di-tBuPhS | Me | H | 4-FBz | 1 | 1 |
| 1-154 | O | PhAc | S | 4-HO-3,5-di-tBuPhS | Me | H | 4-FBz | 1 | 1 |
| 1-155 | O | cPnc | S | 4-HO-3,5-di-tBuPhS | Me | H | 4-FBz | 1 | 1 |
| 1-156 | O | NH₂ | S | 4-HO-3,5-di-tBuPhS | Me | H | 4-FBz | 1 | 1 |
| 1-157 | O | NHAc | S | 4-HO-3,5-di-tBuPhS | Me | H | 4-FBz | 1 | 1 |
| 1-158 | O | NHBoz | S | 4-HO-3,5-di-tBuPhS | Me | H | 4-FBz | 1 | 1 |
| 1-159 | O | NHMe | S | 4-HO-3,5-di-tBuPhS | Me | H | 4-FBz | 1 | 1 |
| 1-160 | O | NHiPr | S | 4-HO-3,5-di-tBuPhS | Me | H | 4-FBz | 1 | 1 |
| 1-161 | O | NHPh | S | 4-HO-3,5-di-tBuPhS | Me | H | 4-FBz | 1 | 1 |
| 1-162 | O | NHBz | S | 4-HO-3,5-di-tBuPhS | Me | H | 4-FBz | 1 | 1 |
| 1-163 | O | NMeEt | S | 4-HO-3,5-di-tBuPhS | Me | H | 4-FBz | 1 | 1 |
| 1-164 | O | NEtPh | S | 4-HO-3,5-di-tBuPhS | Me | H | 4-FBz | 1 | 1 |
| 1-165 | O | NPhBz | S | 4-HO-3,5-di-tBuPhS | Me | H | 4-FBz | 1 | 1 |

TABLE 1-continued

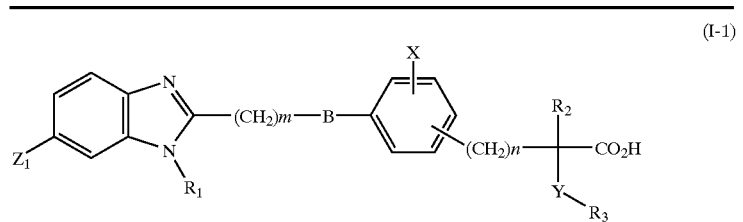

(I-1)

| E.C.No. | B | X | Y | $Z_1$ | $R_1$ | $R_2$ | $R_3$ | m | n |
|---|---|---|---|---|---|---|---|---|---|
| 1-166 | O | Ph | S | 4-HO-3,5-di-tBuPhS | Me | H | 4-FBz | 1 | 1 |
| 1-167 | O | Np | S | 4-HO-3,5-di-tBuPhS | Me | H | 4-FBz | 1 | 1 |
| 1-168 | O | CN | S | 4-HO-3,5-di-tBuPhS | Me | H | 4-FBz | 1 | 1 |
| 1-169 | O | $NO_2$ | S | 4-HO-3,5-di-tBuPhS | Me | H | 4-FBz | 1 | 1 |
| 1-170 | O | H | O | 4-HO-2,3,5-triMePhO | Me | H | H | 1 | 1 |
| 1-171 | O | H | O | 4-HO-2,3,5-triMePhO | Me | H | Me | 1 | 1 |
| 1-172 | O | H | O | 4-HO-2,3,5-triMePhO | Me | H | Et | 1 | 1 |
| 1-173 | O | H | O | 4-HO-2,3,5-triMePhO | Me | H | Bu | 1 | 1 |
| 1-174 | O | H | O | 4-HO-2,3,5-triMePhO | Me | H | Ph | 1 | 1 |
| 1-175 | O | H | O | 4-HO-2,3,5-triMePhO | Me | H | Bz | 1 | 1 |
| 1-176 | O | H | S | 4-HO-2,3,5-triMePhO | Me | H | Bz | 1 | 1 |
| 1-177 | O | H | O | MeO | Me | H | H | 1 | 1 |
| 1-178 | O | H | O | MeO | Me | H | Me | 1 | 1 |
| 1-179 | O | H | O | MeO | Me | H | Et | 1 | 1 |
| 1-180 | O | H | O | MeO | Me | H | Pr | 1 | 1 |
| 1-181 | O | H | O | MeO | Me | H | iPr | 1 | 1 |
| 1-182 | O | H | O | MeO | Me | H | Pn | 1 | 1 |
| 1-183 | O | H | O | MeO | Me | H | Hx | 1 | 1 |
| 1-184 | O | H | O | MeO | Me | H | Bz | 1 | 1 |
| 1-185 | O | H | O | MeO | Me | H | 4-FBz | 1 | 1 |
| 1-186 | O | H | O | MeO | Me | H | 3-ClBz | 1 | 1 |
| 1-187 | O | H | O | MeO | Me | H | Ph | 1 | 1 |
| 1-188 | O | H | O | EtO | Me | H | Bz | 1 | 1 |
| 1-189 | O | H | O | PrO | Me | H | Bz | 1 | 1 |
| 1-190 | O | H | O | iPrO | Me | H | Bz | 1 | 1 |
| 1-191 | O | H | O | BuO | Me | H | Bz | 1 | 1 |
| 1-192 | O | H | O | iBuO | Me | H | Bz | 1 | 1 |
| 1-193 | O | H | O | sBuO | Me | H | Bz | 1 | 1 |
| 1-194 | O | H | O | tBuO | Me | H | Bz | 1 | 1 |
| 1-195 | O | H | O | PnO | Me | H | Bz | 1 | 1 |
| 1-196 | O | H | O | HxG | Me | H | Bz | 1 | 1 |
| 1-197 | O | H | O | PhO | Me | H | Bz | 1 | 1 |
| 1-198 | O | H | O | 4-ClPhO | Me | H | Bz | 1 | 1 |
| 1-199 | O | H | O | 4-FPhG | Me | H | Bz | 1 | 1 |
| 1-200 | O | H | O | 2-FPhG | Me | H | Bz | 1 | 1 |
| 1-201 | O | H | O | 3-FPhO | Me | H | Bz | 1 | 1 |
| 1-202 | O | H | O | 4-$CF_3$PhO | Me | H | Bz | 1 | 1 |
| 1-203 | O | H | O | 3-$CF_3$PhO | Me | H | Bz | 1 | 1 |
| 1-204 | O | H | O | 4-MeOPhP | Me | H | Bz | 1 | 1 |
| 1-205 | O | H | O | 4-MePhP | Me | H | Bz | 1 | 1 |
| 1-206 | O | H | O | 4-PhPhO | Me | H | Bz | 1 | 1 |
| 1-207 | O | H | O | 3-HOPhO | Me | H | Bz | 1 | 1 |
| 1-208 | O | H | O | 3-AcPhO | Me | H | Bz | 1 | 1 |
| 1-209 | O | H | O | 4-cPrPhO | Me | H | Bz | 1 | 1 |
| 1-210 | O | H | O | 4-$Me_2$NPhO | Me | H | Bz | 1 | 1 |
| 1-211 | O | H | O | 4-CNPhO | Me | H | Bz | 1 | 1 |
| 1-212 | O | H | O | 4-$NO_2$PhO | Me | H | Bz | 1 | 1 |
| 1-213 | O | H | O | Me | Me | H | Bz | 1 | 1 |
| 1-214 | O | H | O | Et | Me | H | Bz | 1 | 1 |
| 1-215 | O | H | O | tBu | Me | H | Bz | 1 | 1 |
| 1-216 | O | H | O | Hx | Me | H | Bz | 1 | 1 |
| 1-217 | O | H | O | Ph | Me | H | Bz | 1 | 1 |
| 1-218 | O | H | O | Np | Me | H | Bz | 1 | 1 |
| 1-219 | O | H | O | 4-MeOPh | Me | H | Bz | 1 | 1 |
| 1-220 | O | H | O | Bz | Me | H | Bz | 1 | 1 |

TABLE 1-continued

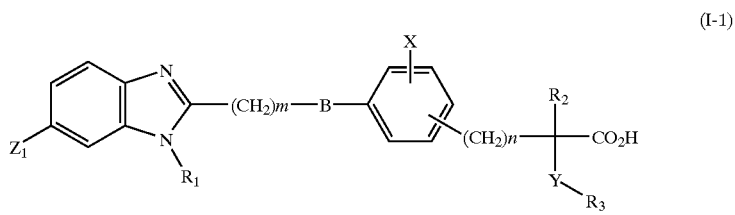

(I-1)

| E.C.No. | B | X | Y | Z₁ | R₁ | R₂ | R₃ | m | n |
|---|---|---|---|---|---|---|---|---|---|
| 1-221 | O | H | O | 4-CF₃Bz | Me | H | Bz | 1 | 1 |
| 1-122 | O | H | O | MeS | Me | H | Bz | 1 | 1 |
| 1-123 | O | H | O | PhS | Me | H | Bz | 1 | 1 |
| 1-124 | O | H | O | BzS | Me | H | Bz | 1 | 1 |
| 1-125 | O | H | O | 4-FPhS | Me | H | Bz | 1 | 1 |
| 1-226 | O | H | O | 4-CF₃PhS | Me | H | Bz | 1 | 1 |
| 1-227 | O | H | O | 4-FBzS | Me | H | Bz | 1 | 1 |
| 1-228 | O | H | O | F | Me | H | Bz | 1 | 1 |
| 1-229 | O | H | O | Cl | Me | H | Bz | 1 | 1 |
| 1-230 | O | H | O | Br | Me | H | Bz | 1 | 1 |
| 1-231 | O | H | O | 2-PyrS | Me | H | Bz | 1 | 1 |
| 1-232 | O | H | O | 3-PyrS | Me | H | 4-FBz | 1 | 1 |
| 1-233 | O | H | O | 4-PyrS | Me | H | 4-CF₃Bz | 1 | 1 |
| 1-234 | O | H | O | 2-PyrO | Me | H | 3-MeOBz | 1 | 1 |
| 1-235 | O | H | O | 3-PyrO | Me | H | Bz | 1 | 1 |
| 1-236 | O | H | O | 4-PyrO | Me | H | Bz | 1 | 1 |
| 1-237 | O | H | O | cPrS | Me | H | Bz | 1 | 1 |
| 1-238 | O | H | O | cHxS | Me | H | Bz | 1 | 1 |
| 1-239 | O | H | O | NH₂ | Me | H | Bz | 1 | 1 |
| 1-240 | O | H | O | NHMe | Me | H | Bz | 1 | 1 |
| 1-241 | O | H | O | NMeEt | Me | H | Bz | 1 | 1 |
| 1-242 | O | H | O | NHAc | Me | H | Bz | 1 | 1 |
| 1-243 | O | H | O | NHPh | Me | H | Bz | 1 | 1 |
| 1-244 | O | H | O | NHBz | Me | H | Bz | 1 | 1 |
| 1-245 | O | H | O | NHBoz | Me | H | Bz | 1 | 1 |
| 1-246 | O | H | O | NMeBoz | Me | H | Bz | 1 | 1 |
| 1-247 | O | H | O | NEtBz | Me | H | Bz | 1 | 1 |
| 1-248 | O | H | O | NPhBz | Me | H | Bz | 1 | 1 |
| 1-249 | O | H | O | NPhBoz | Me | H | Bz | 1 | 1 |
| 1-250 | O | H | O | NH(4-FBoz) | Me | H | Bz | 1 | 1 |
| 1-251 | O | H | O | NH(3-MeBoz) | Me | H | Bz | 1 | 1 |
| 1-252 | O | H | O | NHBoz | Me | Me | Bz | 1 | 1 |
| 1-253 | O | H | O | NHBoz | Me | Et | Bz | 1 | 1 |
| 1-254 | O | H | O | NHBoz | Me | Ph | Bz | 1 | 1 |
| 1-255 | O | H | O | NHBoz | Me | Bz | Bz | 1 | 1 |

(Wherein R₁, R₂, R₃, A, B, W₁, W₂, X, Y and Z₁ are as defined above and m and n are an integer from 1 to 8 inclusive.)

TABLE 2

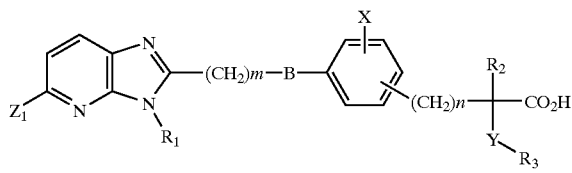

| E.C.No. | B | X | Y | Z₁ | R₁ | R₂ | R₃ | m | n |
|---|---|---|---|---|---|---|---|---|---|
| 2-1 | O | H | S | 4-AdaPhO | Me | H | 4-FBz | 1 | 1 |
| 2-2 | O | H | S | 4-AdaPhO | Me | H | 4-FBz | 1 | 0 |
| 2-3 | O | H | S | 4-AdaPhO | Me | H | 4-FBz | 1 | 2 |
| 2-4 | O | H | S | 4-AdaPhO | Me | H | 4-FBz | 1 | 3 |
| 2-5 | O | H | S | 4-AdaPhO | Me | H | 4-FBz | 1 | 4 |
| 2-6 | O | H | S | 4-AdaPhO | Me | H | 4-FBz | 1 | 5 |
| 2-7 | O | H | S | 4-AdaPhO | Me | H | 4-FBz | 1 | 6 |
| 2-8 | O | H | S | 4-AdaPhO | Me | H | 4-FBz | 1 | 7 |
| 2-9 | O | H | S | 4-AdaPhO | Me | H | 4-FBz | 1 | 8 |
| 2-10 | O | H | S | 4-AdaPhO | Me | H | 4-FBz | 2 | 1 |
| 2-11 | O | H | S | 4-AdaPhO | Me | H | 4-FBz | 3 | 1 |
| 2-12 | O | H | S | 4-AdaPhO | Me | H | 4-FBz | 4 | 1 |

TABLE 2-continued

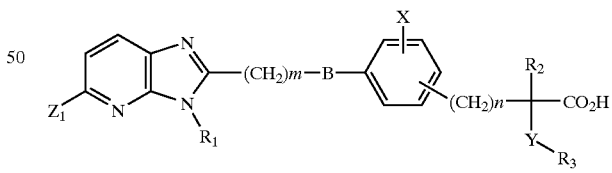

| E.C.No. | B | X | Y | Z₁ | R₁ | R₂ | R₃ | m | n |
|---|---|---|---|---|---|---|---|---|---|
| 2-13 | O | H | S | 4-AdaPhO | Me | H | 4-FBz | 5 | 1 |
| 2-14 | O | H | S | 4-AdaPhO | Me | H | 4-FBz | 6 | 1 |
| 2-15 | O | H | S | 4-AdaPhO | Me | H | 4-FBz | 7 | 1 |
| 2-16 | O | H | S | 4-AdaPhO | Me | H | 4-FBz | 8 | 1 |
| 2-17 | O | NPhBz | S | 4-AdaPhO | Me | H | 4-FBz | 1 | 1 |
| 2-18 | O | NPhBz | S | 4-AdaPhO | Me | H | 4-FBz | 1 | 0 |
| 2-19 | O | NPhBz | S | 4-AdaPhO | Me | H | 4-FBz | 1 | 2 |
| 2-20 | O | NPhBz | S | 4-AdaPhO | Me | H | 4-FBz | 1 | 3 |
| 2-21 | O | NPhBz | S | 4-AdaPhO | Me | H | 4-FBz | 1 | 4 |
| 2-22 | O | NPhBz | S | 4-AdaPhO | Me | H | 4-FBz | 1 | 5 |
| 2-23 | O | NPhBz | S | 4-AdaPhO | Me | H | 4-FBz | 1 | 6 |
| 2-24 | O | NPhBz | S | 4-AdaPhO | Me | H | 4-FBz | 1 | 7 |

TABLE 2-continued

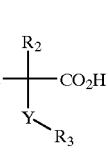

| E.C.No. | B | X | Y | Z₁ | R₁ | R₂ | R₃ | m | n |
|---|---|---|---|---|---|---|---|---|---|
| 2-25 | O | NPhBz | S | 4-AdaPhO | Me | H | 4-FBz | 1 | 8 |
| 2-26 | O | NPhBz | S | 4-AdaPhO | Me | H | 4-FBz | 2 | 1 |
| 2-27 | O | NPhBz | S | 4-AdaPhO | Me | H | 4-FBz | 3 | 1 |
| 2-28 | O | NPhBz | S | 4-AdaPhO | Me | H | 4-FBz | 4 | 1 |
| 2-29 | O | NPhBz | S | 4-AdaPhO | Me | H | 4-FBz | 5 | 1 |
| 2-30 | O | NPhBz | S | 4-AdaPhO | Me | H | 4-FBz | 6 | 1 |
| 2-31 | O | NPhBz | S | 4-AdaPhO | Me | H | 4-FBz | 7 | 1 |
| 2-32 | O | NPhBz | S | 4-AdaPhO | Me | H | 4-FBz | 8 | 1 |
| 2-33 | O | H | S | 4-HO-3,5-di-tBuPhS | Me | H | 4-FBz | 1 | 1 |
| 2-34 | O | H | S | 4-HO-3,5-di-tBuPhS | Me | H | 4-FBz | 1 | 0 |
| 2-35 | O | H | S | 4-HO-3,5-di-tBuPhS | Me | H | 4-FBz | 1 | 2 |
| 2-36 | O | H | S | 4-HO-3,5-di-tBuPhS | Me | H | 4-FBz | 1 | 3 |
| 2-37 | O | H | S | 4-HO-3,5-di-tBuPhS | Me | H | 4-FBz | 1 | 4 |
| 2-38 | O | H | S | 4-HO-3,5-di-tBuPhS | Me | H | 4-FBz | 1 | 5 |
| 2-39 | O | H | S | 4-HO-3,5-di-tBuPhS | Me | H | 4-FBz | 1 | 6 |
| 2-40 | O | H | S | 4-HO-3,5-di-tBuPhS | Me | H | 4-FBz | 1 | 7 |
| 2-41 | O | H | S | 4-HO-3,5-di-tBuPhS | Me | H | 4-FBz | 1 | 8 |
| 2-42 | O | H | S | 4-HO-3,5-di-tBuPhS | Me | H | 4-FBz | 2 | 1 |
| 2-43 | O | H | S | 4-HO-3,5-di-tBuPhS | Me | H | 4-FBz | 3 | 1 |
| 2-44 | O | H | S | 4-HO-3,5-di-tBuPhS | Me | H | 4-FBz | 4 | 1 |
| 2-45 | O | H | S | 4-HO-3,5-di-tBuPhS | Me | H | 4-FBz | 5 | 1 |
| 2-46 | O | H | S | 4-HO-3,5-di-tBuPhS | Me | H | 4-FBz | 6 | 1 |
| 2-47 | O | H | S | 4-HO-3,5-di-tBuPhS | Me | H | 4-FBz | 7 | 1 |
| 2-48 | O | H | S | 4-HO-3,5-di-tBuPhS | Me | H | 4-FBz | 8 | 1 |
| 2-49 | O | NPhBz | S | 4-HO-3,5-di-tBuPhS | Me | H | 4-FBz | 1 | 1 |
| 2-50 | O | NPhBz | S | 4-HO-3,5-di-tBuPhS | Me | H | 4-FBz | 1 | 0 |
| 2-51 | O | NPhBz | S | 4-HO-3,5-di-tBuPhS | Me | H | 4-FBz | 1 | 2 |
| 2-52 | O | NPhBz | S | 4-HO-3,5-di-tBuPhS | Me | H | 4-FBz | 1 | 3 |
| 2-53 | O | NPhBz | S | 4-HO-3,5-di-tBuPhS | Me | H | 4-FBz | 1 | 4 |
| 2-54 | O | NPhBz | S | 4-HO-3,5-di-tBuPhS | Me | H | 4-FBz | 1 | 5 |
| 2-55 | O | NPhBz | S | 4-HO-3,5-di-tBuPhS | Me | H | 4-FBz | 1 | 6 |
| 2-56 | O | NPhBz | S | 4-HO-3,5-di-tBuPhS | Me | H | 4-FBz | 1 | 7 |
| 2-57 | O | NPhBz | S | 4-HO-3,5-di-tBuPhS | Me | H | 4-FBz | 1 | 8 |
| 2-58 | O | NPhBz | S | 4-HO-3,5-di-tBuPhS | Me | H | 4-FBz | 2 | 1 |
| 2-59 | O | NPhBz | S | 4-HO-3,5-di-tBuPhS | Me | H | 4-FBz | 3 | 1 |
| 2-60 | O | NPhBz | S | 4-HO-3,5-di-tBuPhS | Me | H | 4-FBz | 4 | 1 |
| 2-61 | O | NPhBz | S | 4-HO-3,5-di-tBuPhS | Me | H | 4-FBz | 5 | 1 |
| 2-62 | O | NPhBz | S | 4-HO-3,5-di-tBuPhS | Me | H | 4-FBz | 6 | 1 |
| 2-63 | O | NPhBz | S | 4-HO-3,5-di-tBuPhS | Me | H | 4-FBz | 7 | 1 |
| 2-64 | O | NPhBz | S | 4-HO-3,5-di-tBuPhS | Me | H | 4-FBz | 8 | 1 |

(Wherein $R_1$, $R_2$, $R_3$, A, B, $W_1$, $W_2$, X, Y, $Z_1$, m and n are defined above.)

TABLE 3

(I-3)

| E.C.No. | B | X | R₄ | Z₄ | R₁ | R₂ | R₃ | m | n |
|---|---|---|---|---|---|---|---|---|---|
| 3-1 | O | H | Me | 4-AdaPhO | Me | H | 4-FBz | 1 | 1 |
| 3-2 | O | H | Me | 4-AdaPhO | Me | H | 4-FBz | 1 | 0 |
| 3-3 | O | H | Et | 4-AdaPhO | Me | H | 4-FBz | 1 | 2 |
| 3-4 | O | H | Pr | 4-AdaPhO | Me | H | 4-FBz | 1 | 3 |
| 3-5 | O | H | iPr | 4-AdaPhO | Me | H | 4-FBz | 1 | 4 |
| 3-6 | O | H | Bu | 4-AdaPhO | Me | H | 4-FBz | 1 | 5 |
| 3-7 | O | H | iBu | 4-AdaPhO | Me | H | 4-FBz | 1 | 6 |
| 3-8 | O | H | sBu | 4-AdaPhO | Me | H | 4-FBz | 1 | 7 |
| 3-9 | O | H | tBu | 4-AdaPhO | Me | H | 4-FBz | 1 | 8 |

TABLE 3-continued

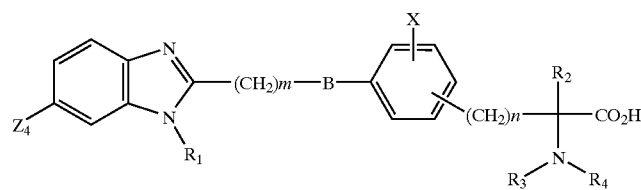

(I-3)

| E.C.No. | B | X | R₄ | Z₄ | R₁ | R₂ | R₃ | m | n |
|---|---|---|---|---|---|---|---|---|---|
| 3-10 | O | H | Pn | 4-AdaPhO | Me | H | 4-FBz | 2 | 1 |
| 3-11 | O | H | iPn | 4-AdaPhO | Me | H | 4-FBz | 3 | 1 |
| 3-12 | O | H | sPn | 4-AdaPhO | Me | H | 4-FBz | 4 | 1 |
| 3-13 | O | H | Hx | 4-AdaPhO | Me | H | 4-FBz | 5 | 1 |
| 3-14 | O | H | iHx | 4-AdaPhO | Me | H | 4-FBz | 6 | 1 |
| 3-15 | O | H | sHx | 4-AdaPhO | Me | H | 4-FBz | 7 | 1 |
| 3-16 | O | H | Ph | 4-AdaPhO | Me | H | 4-FBz | 8 | 1 |
| 3-17 | O | H | 4-FPh | 4-AdaPhO | Me | H | H | 1 | 1 |
| 3-18 | O | H | 4-ClPh | 4-AdaPhO | Me | H | Me | 1 | 1 |
| 3-19 | O | H | 3-CF₃Ph | 4-AdaPhO | Me | H | Et | 1 | 1 |
| 3-20 | O | H | 2-MePh | 4-AdaPhO | Me | H | Bu | 1 | 1 |
| 3-21 | O | H | 3-MeOPh | 4-AdaPhO | Me | H | Ph | 1 | 1 |
| 3-22 | O | H | 2-FPh | 4-AdaPhO | Me | H | Bz | 1 | 1 |
| 3-23 | O | H | Bz | 4-AdaPhO | Me | H | 4-ClBz | 1 | 1 |
| 3-24 | S | H | 2-ClBz | 4-AdaPhO | Me | H | 4-FBz | 1 | 1 |
| 3-25 | O | H | 4-ClBz | 4-AdaPhO | Me | H | 4-FBz | 1 | 1 |
| 3-26 | O | H | 2-FBz | 4-AdaPhO | 4-FBz | H | 4-FBz | 1 | 1 |
| 3-27 | O | H | 3-FBz | 4-AdaPhO | Et | H | 4-FBz | 1 | 1 |
| 3-28 | O | H | 4-FBz | 4-AdaPhO | Pr | H | 4-FBz | 1 | 1 |
| 3-29 | O | H | 2-CF₃Bz | 4-AdaPhO | iPr | H | 4-FBz | 1 | 1 |
| 3-30 | O | H | 3-CF₃Bz | 4-AdaPhO | Bu | H | 4-FBz | 1 | 1 |
| 3-31 | O | H | 4-CF₃Bz | 4-AdaPhO | iBu | H | 4-FBz | 1 | 1 |
| 3-32 | O | H | 2-MeBz | 4-AdaPhO | sBu | H | 4-FBz | 1 | 1 |
| 3-33 | O | H | 3-MeBz | 4-AdaPhO | Pn | H | 4-FBz | 1 | 1 |
| 3-34 | O | H | 4-MeBz | 4-AdaPhO | Hx | H | 4-FBz | 1 | 1 |
| 3-35 | O | H | 2-MeOBz | 4-AdaPhO | Ph | H | 4-FBz | 1 | 1 |
| 3-36 | O | H | 3-MeOBz | 4-AdaPhO | Bz | H | 4-FBz | 1 | 1 |
| 3-37 | O | H | 2-BozPh | 4-AdaPhO | Me | Me | 4-FBz | 1 | 1 |
| 3-38 | O | H | 2-BozPh | 4-AdaPhO | Me | Et | 4-FBz | 1 | 1 |
| 3-39 | O | H | 2-BozPh | 4-AdaPhO | Me | Pr | 4-FBz | 1 | 1 |
| 3-40 | O | H | 2-BozPh | 4-AdaPhO | Me | iPr | 4-FBz | 1 | 1 |
| 3-41 | O | H | 2-BozPh | 4-AdaPhO | Me | Bu | 4-FBz | 1 | 1 |
| 3-42 | O | H | 2-BozPh | 4-AdaPhO | Me | iBu | 4-FBz | 1 | 1 |
| 3-43 | O | H | 2-BozPh | 4-AdaPhO | Me | sBu | 4-FBz | 1 | 1 |
| 3-44 | O | H | 2-BozPh | 4-AdaPhO | Me | Pn | 4-FBz | 1 | 1 |
| 3-45 | O | H | 2-BozPh | 4-AdaPhO | Me | Hx | 4-FBz | 1 | 1 |
| 3-46 | O | H | 2-BozPh | 4-AdaPhO | Me | Ph | 4-FBz | 1 | 1 |
| 3-47 | O | H | 2-BozPh | 4-AdaPhO | Me | 4-FPh | 4-FBz | 1 | 1 |
| 3-48 | O | H | 2-BozPh | 4-AdaPhO | Me | 3-CF₃Ph | 4-FBz | 1 | 1 |
| 3-49 | O | H | 2-BozPh | 4-AdaPhO | Me | 3-MeOPh | 4-FBz | 1 | 1 |
| 3-50 | O | H | 2-BozPh | 4-AdaPhO | Me | 2-MePh | 4-FBz | 1 | 1 |
| 3-51 | O | H | 2-BozPh | 4-AdaPhO | Me | 4-CNPh | 4-FBz | 1 | 1 |
| 3-52 | O | H | 2-BozPh | 4-AdaPhO | Me | Bz | 4-FBz | 1 | 1 |
| 3-53 | O | H | 2-BozPh | 4-AdaPhO | Me | 3-FBz | 4-FBz | 1 | 1 |
| 3-54 | O | H | 2-BozPh | 4-AdaPhO | Me | 2-CF₃Bz | 4-FBz | 1 | 1 |
| 3-55 | O | H | 2-BozPh | 4-AdaPhO | Me | 3,5-diMeOBz | 4-FBz | 1 | 1 |
| 3-56 | O | H | 2-BozPh | 4-AdaPhO | Me | 4-ClBz | 4-FBz | 1 | 1 |
| 3-57 | O | Cl | 2-BozPh | 4-AdaPhO | Me | H | 4-FBz | 1 | 1 |
| 3-58 | O | F | 2-BozPh | 4-AdaPhO | Me | H | 4-FBz | 1 | 1 |
| 3-59 | O | Br | 2-BozPh | 4-AdaPhO | Me | H | 4-FBz | 1 | 1 |
| 3-60 | O | Me | 2-BozPh | 4-AdaPhO | Me | H | 4-FBz | 1 | 1 |
| 3-61 | O | MeO | 2-BozPh | 4-AdaPhO | Me | H | 4-FBz | 1 | 1 |
| 3-62 | O | EtO | 2-BozPh | 4-AdaPhO | Me | H | 4-FBz | 1 | 1 |
| 3-63 | O | iPr | 2-BozPh | 4-AdaPhO | Me | H | 4-FBz | 1 | 1 |
| 3-64 | O | CF₃ | 2-BozPh | 4-AdaPhO | Me | H | 4-FBz | 1 | 1 |
| 3-65 | O | HO | 2-BozPh | 4-AdaPhO | Me | H | 4-FBz | 1 | 1 |
| 3-66 | O | EtO | 2-BozPh | 4-AdaPhO | Me | H | 4-FBz | 1 | 1 |
| 3-67 | O | tBu | 2-BozPh | 4-AdaPhO | Me | H | 4-FBz | 1 | 1 |
| 3-68 | O | Ac | 2-BozPh | 4-AdaPhO | Me | H | 4-FBz | 1 | 1 |
| 3-69 | O | Boz | 2-BozPh | 4-AdaPhO | Me | H | 4-FBz | 1 | 1 |
| 3-70 | O | PhAc | 2-BozPh | 4-AdaPhO | Me | H | 4-FBz | 1 | 1 |
| 3-71 | O | cPnc | 2-BozPh | 4-AdaPhO | Me | H | 4-FBz | 1 | 1 |
| 3-72 | O | NH₂ | 2-BozPh | 4-AdaPhO | Me | H | 4-FBz | 1 | 1 |
| 3-73 | O | NHAc | 2-BozPh | 4-AdaPhO | Me | H | 4-FBz | 1 | 1 |
| 3-74 | O | NHBoz | 2-BozPh | 4-AdaPhO | Me | H | 4-FBz | 1 | 1 |
| 3-75 | O | NHMe | Me | 4-AdaPhO | Me | H | 4-FBz | 1 | 1 |

TABLE 3-continued (I-3)

| E.C.No. | B | X | R₄ | Z₄ | R₁ | R₂ | R₃ | m | n |
|---|---|---|---|---|---|---|---|---|---|
| 3-76 | O | NHiPr | Me | 4-AdaPhO | Me | H | 4-FBz | 1 | 1 |
| 3-77 | O | NHPh | Et | 4-AdaPhO | Me | H | 4-FBz | 1 | 1 |
| 3-78 | O | NHBz | Pr | 4-AdaPhO | Me | H | 4-FBz | 1 | 1 |
| 3-79 | O | NMeEt | iPr | 4-AdaPhO | Me | H | 4-FBz | 1 | 1 |
| 3-80 | O | NEtPh | Bu | 4-AdaPhO | Me | H | 4-FBz | 1 | 1 |
| 3-81 | O | NPhBz | iBu | 4-AdaPhO | Me | H | 4-FBz | 1 | 1 |
| 3-82 | O | Ph | sBu | 4-AdaPhO | Me | H | 4-FBz | 1 | 1 |
| 3-83 | O | Np | tBu | 4-AdaPhO | Me | H | 4-FBz | 1 | 1 |
| 3-84 | O | CN | Pn | 4-AdaPhO | Me | H | 4-FBz | 1 | 1 |
| 3-85 | O | NO₂ | iPn | 4-AdaPhO | Me | H | 4-FBz | 1 | 1 |
| 3-86 | O | H | Hx | 4-HO-3,5-di-tBuPhS | Me | H | 4-FBz | 1 | 1 |
| 3-87 | O | H | iHx | 4-HO-3,5-di-tBuPhS | Me | H | H | 1 | 1 |
| 3-88 | O | H | sHx | 4-HO-3,5-di-tBuPhS | Me | H | Me | 1 | 1 |
| 3-89 | O | H | Ph | 4-HO-3,5-di-tBuPhS | Me | H | Et | 1 | 1 |
| 3-90 | O | H | 4-FPh | 4-HO-3,5-di-tBuPhS | Me | H | Hx | 1 | 1 |
| 3-91 | O | H | 4-ClPh | 4-HO-3,5-di-tBuPhS | Me | H | Bz | 1 | 1 |
| 3-92 | O | H | 3-CF₃Ph | 4-HO-3,5-di-tBuPhS | Me | H | Ph | 1 | 1 |
| 3-93 | O | H | 2-MePh | 4-HO-3,5-di-tBuPhS | Me | H | 4-FBz | 1 | 0 |
| 3-94 | O | H | 3-MeOPh | 4-HO-3,5-di-tBuPhS | Me | H | 4-FBz | 1 | 2 |
| 3-95 | O | H | 2-FPh | 4-HO-3,5-di-tBuPhS | Me | H | 4-FBz | 1 | 3 |
| 3-96 | O | H | Bz | 4-HO-3,5-di-tBuPhS | Me | H | 4-FBz | 1 | 4 |
| 3-97 | O | H | 3-ClBz | 4-HO-3,5-di-tBuPhS | Me | H | 4-FBz | 1 | 5 |
| 3-98 | O | H | 2-ClBz | 4-HO-3,5-di-tBuPhS | Me | 4-FBz |  | 1 | 6 |
| 3-99 | O | H | 2-ClBz | 4-HO-3,5-di-tBuPhS | Me | 4-FBz |  | 1 | 7 |
| 3-100 | O | H | 2-FBz | 4-HO-3,5-di-tBuPhS | Me | 4-FBz |  | 1 | 8 |
| 3-101 | O | H | 3-FBz | 4-HO-3,5-di-tBuPhS | Me | 4-FBz |  | 2 | 1 |
| 3-102 | O | H | 4-FBz | 4-HO-3,5-di-tBuPhS | Me | 4-FBz |  | 3 | 1 |
| 3-103 | O | H | 2-CF₃Bz | 4-HO-3,5-di-tBuPhS | Me | 4-FBz |  | 4 | 1 |
| 3-104 | O | H | 3-CF₃Bz | 4-HO-3,5-di-tBuPhS | Me | 4-FBz |  | 5 | 1 |
| 3-105 | O | H | 4-CF₃Bz | 4-HO-3,5-di-tBuPhS | Me | 4-FBz |  | 6 | 1 |
| 3-106 | O | H | 2-MeBz | 4-HO-3,5-di-tBuPhS | Me | 4-FBz |  | 7 | 1 |
| 3-107 | O | H | 3-MeBz | 4-HO-3,5-di-tBuPhS | Me | H | 4-FBz | 8 | 1 |
| 3-108 | S | H | 2-MeOBz | 4-HO-3,5-di-BuPhS | Me | H | 4-FBz | 1 | 1 |
| 3-108 | S | H | 2-MeOBz | 4-HO-3,5-di-tBuPhS | Me | H | 4-FBz | 1 | 1 |
| 3-109 | O | H | 3-MeOBz | 4-HO-3,5-di-BuPhS | Me | H | 4-FBz | 1 | 1 |
| 3-110 | O | H | 4-MeOBz | 4-HO-3,5-di-tBuPhO | Me | H | 4-FBz | 1 | 1 |
| 3-111 | O | H | 2-BozPh | 4-HO-3,5-di-tBuPhS | Et | H | 4-FBz | 1 | 1 |
| 3-112 | O | H | 2-BozPh | 4-HO-3,5-di-tBuPhS | Pr | H | 4-FBz | 1 | 1 |

TABLE 3-continued (I-3)

| E.C.No. | B | X | R$_4$ | Z$_4$ | R$_1$ | R$_2$ | R$_3$ | m | n |
|---|---|---|---|---|---|---|---|---|---|
| 3-113 | O | H | 2-BozPh | 4-HO-3,5-di-tBuPhS | iPr | H | 4-FBz | 1 | 1 |
| 3-114 | O | H | 2-BozPh | 4-HO-3,5-di-tBuPhS | Bu | H | 4-FBz | 1 | 1 |
| 3-115 | O | H | 2-BozPh | 4-HO-3,5-di-tBuPhS | iBu | H | 4-FBz | 1 | 1 |
| 3-116 | O | H | 2-BozPh | 4-HO-3,5-di-tBuPhS | sBu | H | 4-FBz | 1 | 1 |
| 3-117 | O | H | 2-BozPh | 4-HO-3,5-di-tBuPhS | Pn | H | 4-FBz | 1 | 1 |
| 3-118 | O | H | 2-BozPh | 4-HO-3,5-di-tBuPhS | Hx | H | 4-FBz | 1 | 1 |
| 3-119 | O | H | 2-BozPh | 4-HO-3,5-di-tBuPhS | Ph | H | 4-FBz | 1 | 1 |
| 3-120 | O | H | 2-BozPh | 4-HO-3,5-di-tBuPhS | Bz | H | 4-FBz | 1 | 1 |
| 3-121 | O | H | 2-BozPh | 4-HO-3,5-di-tBuPhS | Me | Me | 4-FBz | 1 | 1 |
| 3-122 | O | H | 2-BozPh | 4-HO-3,5-di-tBuPhS | Me | Et | 4-FBz | 1 | 1 |
| 3-123 | O | H | 2-BozPh | 4-HO-3,5-di-tBuPhS | Me | Pr | 4-FBz | 1 | 1 |
| 3-124 | O | H | 2-I3ozPh | 4-HO-3,5-di-tBuPhS | Me | iPr | 4-FBz | 1 | 1 |
| 3-125 | O | H | 2-BozPh | 4-HO-3,5-di-tBuPhS | Me | Bu | 4-FBz | 1 | 1 |
| 3-126 | O | H | 2-BozPh | 4-HO-3,5-di-tBuPhS | Me | iBu | 4-FBz | 1 | 1 |
| 3-127 | O | H | 2-BozPh | 4-HO-3,5-di-tBuPhS | Me | sBu | 4-FBz | 1 | 1 |
| 3-128 | O | H | 2-BozPh | 4-HO-3,5-di-tBuPhS | Me | Pn | 4-FBz | 1 | 1 |
| 3-129 | O | H | 2-BozPh | 4-HO-3,5-di-tBuPhS | Me | Hx | 4-FBz | 1 | 1 |
| 3-130 | O | H | 2-BozPh | 4-HO-3,5-di-tBuPhS | Me | Ph | 4-FBz | 1 | 1 |
| 3-131 | O | H | 2-BozPh | 4-HO-3,5-di-tBuPhS | Me | 4-FPh | 4-FBz | 1 | 1 |
| 3-132 | O | H | 2-BozPh | 4-HO-3,5-di-tBuPhS | Me | 3-CF$_3$Ph | 4-FBz | 1 | 1 |
| 3-133 | O | H | 2-BozPh | 4-HO-3,5-di-tBuPhS | Me | 3-MeOPh | 4-FBz | 1 | 1 |
| 3-134 | O | H | 2-BozPh | 4-HO-3,5-di-BuPhS | Me | 2-MePh | 4-FBz | 1 | 1 |
| 3-135 | O | H | 2-BozPh | 4-HO-3,5-di-tBuPbS | Me | 4-CNPh | 4-FBz | 1 | 1 |
| 3-136 | O | H | 2-BozPh | 4-HO-3,5-di-BuPhS | Me | Bz | 4-FBz | 1 | 1 |
| 3-137 | O | H | 2-BozPh | 4-HO-3,5-di-tBuPbS | Me | 3-FBz | 4-FBz | 1 | 1 |
| 3-138 | O | H | 2-BozPh | 4-HO-3,5-di-tBuPhS | Me | 2-CF$_3$Bz | 4-FBz | 1 | 1 |
| 3-139 | O | H | 2-BozPh | 4-HO-3,5-di-tBuPhS | Me | 3,5-diMeOBz | 4-FBz | 1 | 1 |
| 3-140 | O | H | 2-I3ozPh | 4-HO-3,5-di-tBuPhS | Me | 4-ClBz | 4-FBz | 1 | 1 |
| 3-141 | O | Cl | 2-BozPh | 4-HO-3,5-di-tBuPhS | Me | H | 4-FBz | 1 | 1 |
| 3-142 | O | F | 2-BozPh | 4-HO-3,5-di-tBuPhS | Me | H | 4-FBz | 1 | 1 |
| 3-143 | O | Br | 2-BozPh | 4-HO-3,5-di-tBuPhS | Me | 4-FBz | | 1 | 1 |
| 3-144 | O | Me | 2-BoZPh | 4-HO-3,5-di-tBuPhS | Me | 4-FBz | | 1 | 1 |
| 3-145 | O | MeO | 2-BozPh | 4-HO-3,5-di-tBuPhS | Me | 4-FBz | | 1 | 1 |

TABLE 3-continued (I-3)

| E.C.No. | B | X | R$_4$ | Z$_4$ | R$_1$ | R$_2$ | R$_3$ | m | n |
|---|---|---|---|---|---|---|---|---|---|
| 3-146 | O | EtO | 2-BozPh | 4-HO-3,5-di-tBuPhS | Me | 4-FBz | 1 | 1 | |
| 3-147 | O | iPr | 2-BozPh | 4-HO-3,5-di-tBuPhS | Me | 4-FBz | 1 | 1 | |
| 3-148 | O | CF$_3$ | Me | 4-HO-3,5-di-tBuPhS | Me | 4-FBz | 1 | 1 | |
| 3-149 | O | HO | Me | 4-HO-3,5-di-tBuPhS | Me | 4-FBz | 1 | 1 | |
| 3-150 | O | EtO | Et | 4-HO-3,5-di-tBuPhS | Me | 4-FBz | 1 | 1 | |
| 3-151 | O | tBu | Pr | 4-HO-3,5-di-tBuPhS | Me | 4-FBz | 1 | 1 | |
| 3-152 | O | Ac | iPr | 4-HO-3,5-di-tBuPhS | Me | H | 4-FBz | 1 | 1 |
| 3-153 | O | Boz | Bu | 4-HO-3,5-di-tBuPhS | Me | H | 4-FBz | 1 | 1 |
| 3-154 | O | PhAc | iBu | 4-HO-3,5-di-tBuPhS | Me | H | 4-FBz | 1 | 1 |
| 3-155 | O | cPnc | sBu | 4-HO-3,5-di-tBuPhS | Me | H | 4-FBz | 1 | 1 |
| 3-156 | O | NH$_2$ | tBu | 4-HO-3,5-di-tBuPhS | Me | H | 4-FBz | 1 | 1 |
| 3-157 | O | NHAc | Pn | 4-HO-3,5-di-tBuPhS | Me | H | 4-FBz | 1 | 1 |
| 3-158 | O | NHBoz | iPn | 4-HO-3,5-di-tBuPhS | Me | H | 4-FBz | 1 | 1 |
| 3-159 | O | NHMe | sPn | 4-HO-3,5-di-tBuPhS | Me | H | 4-FBz | 1 | 1 |
| 3-160 | O | NHiPr | Hx | 4-HO-3,5-di-tBuPhS | Me | H | 4-FBz | 1 | 1 |
| 3-161 | O | NHPh | iHx | 4-HO-3,5-di-tBuPhS | Me | H | 4-FBz | 1 | 1 |
| 3-162 | O | NHBz | sHx | 4-HO-3,5-di-tBuPhS | Me | H | 4-FBz | 1 | 1 |
| 3-163 | O | NMeEt | Ph | 4-HO-3,5-di-tBuPhS | Me | H | 4-FBz | 1 | 1 |
| 3-164 | O | NEtPh | 4-FPh | 4-HO-3,5-di-tBuPbS | Me | H | 4-FBz | 1 | 1 |
| 3-165 | O | NPhBz | 4-ClPh | 4-HO-3,5-di-tBuPhS | Me | H | 4-FBz | 1 | 1 |
| 3-166 | O | Ph | 3-CF$_3$Ph | 4-HO-3,5-di-tBuPhS | Me | H | 4-FBz | 1 | 1 |
| 3-167 | O | Np | 2-MePh | 4-HO-3,5-di-tBuPhS | Me | H | 4-FBz | 1 | 1 |
| 3-168 | O | CN | 3-MeOPh | 4-HO-3,5-di-tBuPhS | Me | H | 4-FBz | 1 | 1 |
| 3-169 | O | NO$_2$ | 2-FPh | 4-HO-3,5-di-tBuPhS | Me | H | 4-FBz | 1 | 1 |
| 3-170 | O | H | 3-ClBz | 4-HO-2,3,5-triMePhO | Me | H | H | 1 | 1 |
| 3-171 | O | H | 4-ClBz | 4-HO-2,3,5-triMePhO | Me | H | Me | 1 | 1 |
| 3-172 | O | H | 2-FBz | 4-HO-2,3,5-triMePhO | Me | H | Et | 1 | 1 |
| 3-173 | O | H | 3-FBz | 4-HO-2,3,5-triMePhO | Me | H | Bu | 1 | 1 |
| 3-174 | O | H | 4-FBz | 4-HO-2,3,5-triMePhO | Me | H | Ph | 1 | 1 |
| 3-175 | O | H | 2-CF$_3$Bz | 4-HO-2,3,5-triMePhO | Me | H | Bz | 1 | 1 |
| 3-176 | O | H | 3-CF$_3$Bz | 4-HO-2,3,5-triMePhO | Me | H | Bz | 1 | 1 |
| 3-177 | O | H | Me | MeO | Me | H | H | 1 | 1 |
| 3-178 | O | H | 3-MeBz | MeO | Me | H | Me | 1 | 1 |
| 3-179 | O | H | 4-MeBz | MeO | Me | H | Et | 1 | 1 |
| 3-180 | O | H | 2-MeOBz | MeO | Me | H | Pr | 1 | 1 |

TABLE 3-continued (I-3)

| E.C.No. | B | X | R₄ | Z₄ | R₁ | R₂ | R₃ | m | n |
|---|---|---|---|---|---|---|---|---|---|
| 3-181 | O | H | 3-MeOBz | MeO | Me | H | iPr | 1 | 1 |
| 3-182 | O | H | 4-MeOBz | MeO | Me | H | Pn | 1 | 1 |
| 3-183 | O | H | 4-BrBz | MeO | Me | H | Hx | 1 | 1 |
| 3-184 | O | H | 2-BozPh | MeO | Me | H | Bz | 1 | 1 |
| 3-185 | O | H | 2-BozPh | MeO | Me | H | 4-FBz | 1 | 1 |
| 3-186 | O | H | 2-BozPh | MeO | Me | H | 3-ClBz | 1 | 1 |
| 3-187 | O | H | 2-BozPh | MeO | Me | H | Ph | 1 | 1 |
| 3-188 | O | H | 2-BozPh | MeO | Me | H | H | 1 | 1 |
| 3-189 | O | H | 2-BozPh | MeO | Me | H | H | 1 | 1 |
| 3-190 | O | H | 2-Bozph | MeO | Me | H | H | 1 | 1 |
| 3-191 | O | H | 2-BozPh | EtO | Me | H | Bz | 1 | 1 |
| 3-192 | O | H | 2-BozPh | PrO | Me | H | Bz | 1 | 1 |
| 3-193 | O | H | 2-BozPh | iPrO | Me | H | Bz | 1 | 1 |
| 3-194 | O | H | 2-BozPh | BuO | Me | H | Bz | 1 | 1 |
| 3-195 | O | H | 2-BozPh | iBuO | Me | H | Bz | 1 | 1 |
| 3-196 | O | H | 2-BozPh | sBuO | Me | H | Bz | 1 | 1 |
| 3-197 | O | H | 2-BozPh | tBuO | Me | H | Bz | 1 | 1 |
| 3-198 | O | H | 2-BozPh | PnO | Me | H | Bz | 1 | 1 |
| 3-199 | O | H | 2-BozPh | HxO | Me | H | Bz | 1 | 1 |
| 3-200 | O | H | 2-BozPh | PhO | Me | H | Bz | 1 | 1 |
| 3-201 | O | H | 2-BozPh | 4-ClPhO | Me | H | Bz | 1 | 1 |
| 3-202 | O | H | 2-BozPh | 4-FPhO | Me | H | Bz | 1 | 1 |
| 3-203 | O | H | 2-BozPh | 2-FPhO | Me | H | Bz | 1 | 1 |
| 3-204 | O | H | 2-BozPh | 3-FPhO | Me | H | Bz | 1 | 1 |
| 3-205 | O | H | 2-BozPh | 4-CF₃PhO | Me | H | Bz | 1 | 1 |
| 3-206 | O | H | 2-BozPh | 3-CF₃PhO | Me | H | Bz | 1 | 1 |
| 3-207 | O | H | 2-BozPh | 4-MeOPhO | Me | H | Bz | 1 | 1 |
| 3-208 | O | H | 2-BozPh | 4-MePhO | Me | H | Bz | 1 | 1 |
| 3-209 | O | H | 2-BozPh | 4-PhPhO | Me | H | Bz | 1 | 1 |
| 3-210 | O | H | 2-BozPh | 3-HOPhO | Me | H | Bz | 1 | 1 |
| 3-211 | O | H | 2-BozPh | 3-AcPhO | Me | H | Bz | 1 | 1 |
| 3-212 | O | H | 2-BozPh | 4-cPrPhO | Me | H | Bz | 1 | 1 |
| 3-213 | O | H | 2-BozPh | 4-Me₂NPhO | Me | H | Bz | 1 | 1 |
| 3-214 | O | H | 2-BozPh | 4-CNPhO | Me | H | Bz | 1 | 1 |
| 3-215 | O | H | 2-BozPh | 4-NO₂PhO | Me | H | Bz | 1 | 1 |
| 3-220 | O | H | 2-BozPh | Ph | Me | H | Bz | 1 | 1 |
| 3-221 | O | H | 2-BozPh | Np | Me | H | Bz | 1 | 1 |
| 3-222 | O | H | 2-BozPh | 4-MeOPh | Me | H | Bz | 1 | 1 |
| 3-223 | O | H | 2-BozPh | Bz | Me | H | Bz | 1 | 1 |
| 3-224 | O | H | 2-BozPh | 4-CF₃Bz | Me | H | Bz | 1 | 1 |
| 3-225 | O | H | 2-BozPh | MeS | Me | H | Bz | 1 | 1 |
| 3-226 | O | H | 2-BozPh | PbS | Me | H | Bz | 1 | 1 |
| 3-227 | O | H | 2-BozPh | BzS | Me | H | Bz | 1 | 1 |
| 3-228 | O | H | Me | 4-FPhS | Me | H | Bz | 1 | 1 |
| 3-229 | O | H | Me | 4-CF₃PhS | Me | H | Bz | 1 | 1 |
| 3-230 | O | H | Et | 4-FBzS | Me | H | Bz | 1 | 1 |
| 3-231 | O | H | Pr | F | Me | H | Bz | 1 | 1 |
| 3-232 | O | H | iPr | Cl | Me | H | Bz | 1 | 1 |
| 3-233 | O | H | Bu | Br | Me | H | Bz | 1 | 1 |
| 3-234 | O | H | iBu | 2-PyrS | Me | H | Bz | 1 | 1 |
| 3-235 | O | H | sBu | 3-PyrS | Me | H | 4-FBz | 1 | 1 |
| 3-236 | O | H | tBu | 4-PyrS | Me | H | 4-CF₃Bz | 1 | 1 |
| 3-237 | O | H | Pn | 2-PyrO | Me | H | 3-MeOBz | 1 | 1 |
| 3-238 | O | H | iPn | 3-PyrO | Me | H | Bz | 1 | 1 |
| 3-239 | O | H | sPn | 4-PyrO | Me | H | Bz | 1 | 1 |
| 3-240 | O | H | Hx | cPrS | Me | H | Bz | 1 | 1 |
| 3-241 | O | H | iHx | cHxS | H | Bz | 1 | 1 | |
| 3-242 | O | H | sHx | NH₂ | H | Bz | 1 | 1 | |
| 3-243 | O | H | Ph | NHMe | H | Bz | 1 | 1 | |
| 3-244 | O | H | 4-FPh | NMeEt | H | Bz | 1 | 1 | |
| 3-245 | O | H | 4-ClPh | NHAc | H | Bz | 1 | 1 | |
| 3-246 | O | H | 3-CF₃Ph | NHPh | H | Bz | 1 | 1 | |
| 3-247 | O | H | 2-MePh | NHBz | H | Bz | 1 | 1 | |
| 3-248 | O | H | 3-MeOPh | NHBoz | H | Bz | 1 | 1 | |
| 3-249 | O | H | 2-FPh | NMeBoz | H | Bz | 1 | 1 | |
| 3-250 | O | H | Bz | NEtBz | H | Bz | 1 | 1 | |

TABLE 3-continued (I-3)

| E.C.No. | B | X | R$_4$ | Z$_4$ | R$_1$ | R$_2$ | R$_3$ | m | n |
|---|---|---|---|---|---|---|---|---|---|
| 3-251 | O | H | 3-ClBz | NPhBz | H | Bz | 1 | 1 | |
| 3-252 | O | H | 2-ClBz | NPhBoz | H | Bz | 1 | 1 | |
| 3-253 | O | H | 4-ClBz | NH(4-FBoz) | H | Bz | 1 | 1 | |
| 3-254 | O | H | 2-FBz | NH(3-MeOBoz) | H | Bz | 1 | 1 | |
| 3-255 | O | H | 3-FBz | NHBoz | Me | Bz | 1 | 1 | |
| 3-256 | O | H | 4-FBz | NHBoz | Et | Bz | 1 | 1 | |
| 3-257 | O | H | 2-CF$_3$Bz | NHBoz | Ph | Bz | 1 | 1 | |
| 3-258 | O | H | 3-CF$_3$Bz | NHBoz | Bz | Bz | 1 | 1 | |
| 3-259 | O | H | Me | 4-AdaPhO | H | MeSO$_2$ | 1 | 1 | |
| 3-260 | O | H | Me | 4-HO-3,5-di-tBuPhS | Me | H | MeSO$_2$ | 1 | 1 |
| 3-261 | O | H | Me | MeO | Me | H | MeSO$_2$ | 1 | 1 |
| 3-262 | O | H | Me | 4-AdaPhO | Me | H | Tos | 1 | 1 |
| 3-263 | O | H | Me | 4-HO-3,5-di-tBuPhS | Me | H | Tos | 1 | 1 |
| 3-264 | O | H | Me | MeO | Me | H | Tos | 1 | 1 |
| 3-265 | O | H | Me | 4-AdaPhO | Me | H | CF$_3$SO$_2$ | 1 | 1 |
| 3-266 | O | H | Me | 4-HO-3,5-di-tBuPhS | Me | H | CF$_3$SO$_2$ | 1 | 1 |
| 3-267 | O | H | Me | MeO | Me | H | CF$_3$SO$_2$ | 1 | 1 |
| 3-268 | O | H | Me | 4-AdaPhO | Me | H | Bz | 1 | 1 |
| 3-269 | O | H | Me | 4-HO-3,5-di-tBuPhS | Me | H | Bz | 1 | 1 |
| 3-270 | O | H | Me | MeO | Me | H | Bz | 1 | 1 |
| 3-271 | O | H | Me | 4-AdaPhO | Me | H | CF$_3$SO$_2$ | 1 | 1 |
| 3-272 | O | H | Me | 4-HO-3,5-di-tBuPhS | Me | H | CF$_3$SO$_2$ | 1 | 1 |
| 3-273 | O | H | Me | MeO | Me | H | CF$_3$SO$_2$ | 1 | 1 |
| 3-274 | O | H | 4-CF$_3$Bz | 4-H$_2$N-3,5-di-MePhO | Me | H | H | 1 | 1 |
| 3-275 | O | H | 3-MeBz | 4-H$_2$N-3,5-di-MePhO | Me | H | Me | 1 | 1 |
| 3-276 | O | H | 4-MeBz | 4-H$_2$N-3,5-di-MePhO | Me | H | Et | 1 | 1 |
| 3-277 | O | H | 2-MeOBz | 4-H$_2$N-3,5-di-MePhO | Me | H | Pr | 1 | 1 |
| 3-278 | O | H | 3-MeOBz | 4-H$_2$N-3,5-di-MePhO | Me | H | iPr | 1 | 1 |
| 3-279 | O | H | 4-MeOBz | 4-H$_2$N-3,5-di-MePhO | Me | H | Pn | 1 | 1 |
| 3-280 | O | H | 4-BrBz | 4-H$_2$N-3,5-di-MePhO | Me | H | Hx | 1 | 1 |
| 3-281 | O | H | 2-BozPh | 4-H$_2$N-3,5-di-MePhO | Me | H | Bz | 1 | 1 |
| 3-282 | O | H | 2-BozPh | 4-H$_2$N-3,5-di-MePhO | Me | H | 4-FBz | 1 | 1 |
| 3-283 | O | H | 2-BozPh | 4-H$_2$N-3,5-di-MePhO | Me | H | 3-ClBz | 1 | 1 |
| 3-284 | O | H | 2-BozPh | 4-H$_2$N-3,5-di-MePhO | Me | H | Ph | 1 | 1 |
| 3-285 | O | H | 2-BozPh | 4-H$_2$N-3,5-di-MePhO | Me | H | H | 1 | 1 |
| 3-286 | O | H | 2-BozPh | 4-H$_2$N-3,5-di-MePhO | Me | H | H | 1 | 1 |
| 3-287 | O | H | 2-BozPh | 4-H$_2$N-3,5-di-MePhO | Me | H | H | 1 | 1 |
| 3-288 | O | H | 4-CF$_3$Bz | 4-(4-CF$_3$PhCarNH)-3,5-di-MePhO | Me | H | H | 1 | 1 |
| 3-289 | O | H | 3-MeBz | 4-(4-CF$_3$PhCarNH)-3,5-di-MePhO | Me | H | Me | 1 | 1 |
| 3-290 | O | H | 4-MeBz | 4-(4-CF$_3$PhCarNH)-3,5-di-MePhO | Me | H | Et | 1 | 1 |

TABLE 3-continued

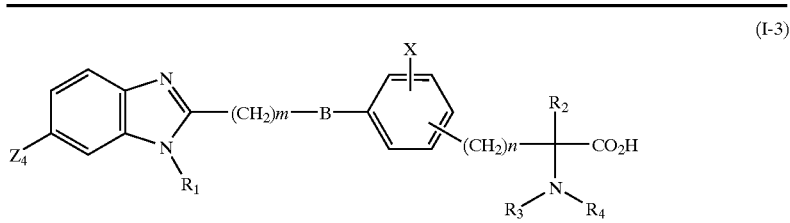

(I-3)

| E.C.No. | B | X | R$_4$ | Z$_4$ | R$_1$ | R$_2$ | R$_3$ | m | n |
|---|---|---|---|---|---|---|---|---|---|
| 3-291 | O | H | 2-MeOBz | 4-(4-CF$_3$PhCarNH)-3,5-di-MePhO | Me | H | Pr | 1 | 1 |
| 3-292 | O | H | 3-MeOBz | 4-(4-CF$_3$PhCarNH)-3,5-di-MePhO | Me | H | iPr | 1 | 1 |
| 3-293 | O | H | 4-MeOBz | 4-(4-CF$_3$PhCarNH)-3,5-di-MePhO | Me | H | Pn | 1 | 1 |
| 3-294 | O | H | 2-BrBz | 4-(4-CF$_3$PhCarNH)-3,5-di-MePhO | Me | H | Hx | 1 | 1 |
| 3-295 | O | H | 2-BozPh | 4-(4-CF$_3$PhCarNH)-3,5-di-MePhO | Me | H | Bz | 1 | 1 |
| 3-296 | O | H | 2-BozPh | 4-(4-CF$_3$PhCarNH)-3,5-di-MePhO | Me | H | 4-FBz | 1 | 1 |
| 3-297 | O | H | 2-BozPh | 4-(4-CF$_3$PhCarNH)-3,5-di-MePhO | Me | H | 3-ClBz | 1 | 1 |
| 3-298 | O | H | 2-BozPh | 4-(4-CF$_3$PhCarNH)-3,5-di-MePhO | Me | H | Ph | 1 | 1 |
| 3-299 | O | H | 2-BozPh | 4-(4-CF$_3$PhCarNH)-3,5-di-MePhO | Me | H | H | 1 | 1 |
| 3-300 | O | H | 3-BozPh | 4-(4-CF$_3$PhCarNH)-3,5-di-MePhO | Me | H | H | 1 | 1 |
| 3-301 | O | H | 4-BozPh | 4-(4-CF$_3$PhCarNH)-3,5-di-MePhO | Me | H | H | 1 | 1 |

(Wherein R$_1$, R$_2$, R$_3$, R$_4$, A, B, W$_1$, W$_2$, X, Y, Z$_4$, m and n are as defined above.)

TABLE 4

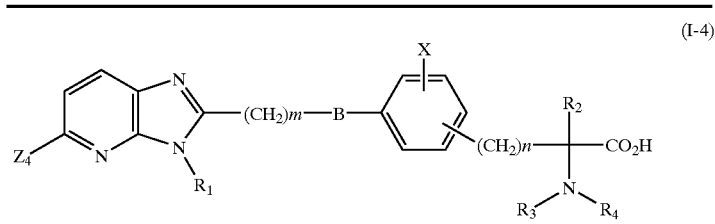

(I-4)

| E.C. No. | B | X | R$_4$ | Z$_4$ | R$_1$ | R$_2$ | R$_3$ | m | n |
|---|---|---|---|---|---|---|---|---|---|
| 4-1 | O | H | 3-ClBz | 4-AdaPhO | Me | H | 4-FBz | 1 | 1 |
| 4-2 | O | H | 3-ClBz | 4-AdaPhO | Me | H | 4-FBz | 1 | 0 |
| 4-3 | O | H | 3-ClBz | 4-AdaPhO | Me | H | 4-FBz | 1 | 2 |
| 4-4 | O | H | 3-ClBz | 4-AdaPhO | Me | H | 4-FBz | 1 | 3 |
| 4-5 | O | H | 3-ClBz | 4-AdaPhO | Me | H | 4-FBz | 1 | 4 |
| 4-6 | O | H | 3-ClBz | 4-AdaPhO | Me | H | 4-FBz | 1 | 5 |
| 4-7 | O | H | 3-ClBz | 4-AdaPhO | Me | H | 4-FBz | 1 | 6 |
| 4-8 | O | H | 3-ClBz | 4-AdaPhO | Me | H | 4-FBz | 1 | 7 |
| 4-9 | O | H | 3-ClBz | 4-AdaPhO | Me | H | 4-FBz | 1 | 8 |

TABLE 4-continued (I-4)

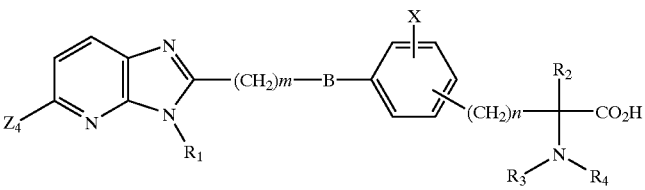

| E.C. No. | B | X | R$_4$ | Z$_4$ | R$_1$ | R$_2$ | R$_3$ | m | n |
|---|---|---|---|---|---|---|---|---|---|
| 4-10 | O | H | 3-ClBz | 4-AdaPhO | Me | H | 4-FBz | 2 | 1 |
| 4-11 | O | H | 3-ClBz | 4-AdaPhO | Me | H | 4-FBz | 3 | 1 |
| 4-12 | O | H | 3-ClBz | 4-AdaPhO | Me | H | 4-FBz | 4 | 1 |
| 4-13 | O | H | 3-ClBz | 4-AdaPhO | Me | H | 4-FBz | 5 | 1 |
| 4-14 | O | H | 3-ClBz | 4-AdaPhO | Me | H | 4-FBz | 6 | 1 |
| 4-15 | O | H | 3-ClBz | 4-AdaPhO | Me | H | 4-FBz | 7 | 1 |
| 4-16 | O | H | 3-ClBz | 4-AdaPhO | Me | H | 4-FBz | 8 | 1 |
| 4-17 | O | NPhBz | sPn | 4-AdaPhO | Me | H | 4-FBz | 1 | 1 |
| 4-18 | O | NPhBz | sPn | 4-AdaPhO | Me | H | 4-FBz | 1 | 0 |
| 4-19 | O | NPhBz | sPn | 4-AdaPhO | Me | H | 4-FBz | 1 | 2 |
| 4-20 | O | NPhBz | sPn | 4-AdaPhO | Me | H | 4-FBz | 1 | 3 |
| 4-21 | O | NPhBz | sPn | 4-AdaPhO | Me | H | 4-FBz | 1 | 4 |
| 4-22 | O | NPhBz | sPn | 4-AdaPhO | Me | H | 4-FBz | 1 | 5 |
| 4-23 | O | NPhBz | sPn | 4-AdaPhO | Me | H | 4-FBz | 1 | 6 |
| 4-24 | O | NPhBz | sPn | 4-AdaPhO | Me | H | 4-FBz | 1 | 7 |
| 4-25 | O | NPhBz | sPn | 4-AdaPhO | Me | H | 4-FBz | 1 | 8 |
| 4-26 | O | NPhBz | sPn | 4-AdaPhO | Me | H | 4-FBz | 2 | 1 |
| 4-27 | O | NPhBz | sPn | 4-AdaPhO | Me | H | 4-FBz | 3 | 1 |
| 4-28 | O | NPhBz | sPn | 4-AdaPhO | Me | H | 4-FBz | 4 | 1 |
| 4-29 | O | NPhBz | sPn | 4-AdaPhO | Me | H | 4-FBz | 5 | 1 |
| 4-30 | O | NPhBz | sPn | 4-AdaPhO | Me | H | 4-FBz | 6 | 1 |
| 4-31 | O | NPhBz | sPn | 4-AdaPhO | Me | H | 4-FBz | 7 | 1 |
| 4-32 | O | NPhBz | sPn | 4-AdaPhO | Me | H | 4-FBz | 8 | 1 |
| 4-33 | O | H | 4-MeBz | 4-HO-3,5-di-tBuPhS | Me | H | 4-FBz | 1 | 1 |
| 4-34 | O | H | 4-MeBz | 4-HO-3,5-di-tBuPhS | Me | H | 4-FBz | 1 | 0 |
| 4-35 | O | H | 4-MeBz | 4-HO-3,5-di-tBuPhS | Me | H | 4-FBz | 1 | 2 |
| 4-36 | O | H | 4-MeBz | 4-HO-3,5-di-tBuPhS | Me | H | 4-FBz | 1 | 3 |
| 4-37 | O | H | 4-MeBz | 4-HO-3,5-di-tBuPhS | Me | H | 4-FBz | 1 | 4 |
| 4-38 | O | H | 4-MeBz | 4-HO-3,5-di-tBuPhS | Me | H | 4-FBz | 1 | 5 |
| 4-39 | O | H | 4-MeBz | 4-HO-3,5-di-tBuPhS | Me | H | 4-FBz | 1 | 6 |
| 4-40 | O | H | 4-MeBz | 4-HO-3,5-di-tBuPhS | Me | H | 4-FBz | 1 | 7 |
| 4-41 | O | H | 4-MeBz | 4-HO-3,5-di-tBuPhS | Me | H | 4-FBz | 1 | 8 |
| 4-42 | O | H | 4-MeBz | 4-HO-3,5-di-tBuPhS | Me | H | 4-FBz | 2 | 1 |
| 4-43 | O | H | 4-MeBz | 4-HO-3,5-di-tBuPhS | Me | H | 4-FBz | 3 | 1 |
| 4-44 | O | H | 4-MeBz | 4-HO-3,5-di-tBuPhS | Me | H | 4-FBz | 4 | 1 |
| 4-45 | O | H | 4-MeBz | 4-HO-3,5-di-tBuPhS | Me | H | 4-FBz | 5 | 1 |
| 4-46 | O | H | 4-MeBz | 4-HO-3,5-di-tBuPhS | Me | H | 4-FBz | 6 | 1 |
| 4-47 | O | H | 4-MeBz | 4-HO-3,5-di-tBuPhS | Me | H | 4-FBz | 7 | 1 |
| 4-48 | O | H | 4-MeBz | 4-HO-3,5-di-tBuPhS | Me | H | 4-FBz | 8 | 1 |
| 4-49 | O | NPhBz | Bz | 4-HO-3,5-di-tBuPhS | Me | H | 4-FBz | 1 | 1 |
| 4-50 | O | NPhBz | Bz | 4-HO-3,5-di-tBuPhS | Me | H | 4-FBz | 1 | 0 |
| 4-51 | O | NPhBz | Bz | 4-HO-3,5-di-tBuPhS | Me | H | 4-FBz | 1 | 2 |
| 4-52 | O | NPhBz | Bz | 4-HO-3,5-di-tBuPhS | Me | H | 4-FBz | 1 | 3 |
| 4-53 | O | NPhBz | Bz | 4-HO-3,5-di-tBuPhS | Me | H | 4-FBz | 1 | 4 |
| 4-54 | O | NPhBz | Bz | 4-HO-3,5-di-tBuPhS | Me | H | 4-FBz | 1 | 5 |
| 4-55 | O | NPhBz | Bz | 4-HO-3,5-di-tBuPhS | Me | H | 4-FBz | 1 | 6 |
| 4-56 | O | NPhBz | Bz | 4-HO-3,5-di-tBuPhS | Me | H | 4-FBz | 1 | 7 |
| 4-57 | O | NPhBz | Bz | 4-HO-3,5-di-tBuPhS | Me | H | 4-FBz | 1 | 8 |
| 4-58 | O | NPhBz | Bz | 4-HO-3,5-di-tBuPhS | Me | H | 4-FBz | 2 | 1 |
| 4-59 | O | NPhBz | Bz | 4-HO-3,5-di-tBuPhS | Me | H | 4-FBz | 3 | 1 |
| 4-60 | O | NPhBz | Bz | 4-HO-3,5-di-tBuPhS | Me | H | 4-FBz | 4 | 1 |
| 4-61 | O | NPhBz | Bz | 4-HO-3,5-di-tBuPhS | Me | H | 4-FBz | 5 | 1 |
| 4-62 | O | NPhBz | Bz | 4-HO-3,5-di-tBuPhS | Me | H | 4-FBz | 6 | 1 |
| 4-63 | O | NPhBz | Bz | 4-HO-3,5-di-tBuPhS | Me | H | 4-FBz | 7 | 1 |
| 4-64 | O | NPhBz | Bz | 4-HO-3,5-di-tBuPhS | Me | H | 4-FBz | 8 | 1 |

(Wherein R$_1$, R$_2$, R$_3$, R$_4$, A, B, W$_1$, W$_2$, X, Y, Z$_4$, m and n are as defined above.)

TABLE 5

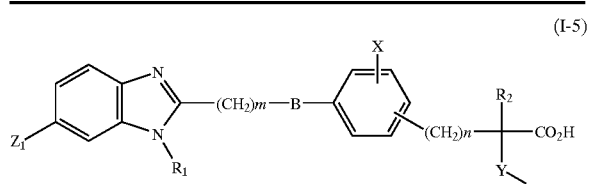

(I-5)

| E.C. No. | B | X | Y | $Z_1$ | $R_1$ | $R_2$ | $R_3$ | m | n |
|---|---|---|---|---|---|---|---|---|---|
| 5-1 | O | H | S | MeO | Me | H | H | 1 | 1 |
| 5-2 | O | H | SO | MeO | Me | H | H | 1 | 1 |
| 5-3 | O | H | $SO_2$ | MeO | Me | H | H | 1 | 1 |
| 5-4 | O | H | S | MeO | Me | H | Me | 1 | 1 |
| 5-5 | O | H | S | MeO | Me | H | Me | 1 | 0 |
| 5-6 | O | H | S | MeO | Me | H | Me | 1 | 2 |
| 5-7 | O | H | S | MeO | Me | H | Me | 1 | 3 |
| 5-8 | O | H | S | MeO | Me | H | Me | 1 | 4 |
| 5-9 | O | H | S | MeO | Me | H | Me | 1 | 5 |
| 5-10 | O | H | S | MeO | Me | H | Me | 1 | 6 |
| 5-11 | O | H | S | MeO | Me | H | Me | 1 | 7 |
| 5-12 | O | H | S | MeO | Me | H | Me | 1 | 8 |
| 5-13 | O | H | S | MeO | Me | H | Me | 2 | 1 |
| 5-14 | O | H | S | MeO | Me | H | Me | 3 | 1 |
| 5-15 | O | H | S | MeO | Me | H | Me | 4 | 1 |
| 5-16 | O | H | S | MeO | Me | H | Me | 5 | 1 |
| 5-17 | O | H | S | MeO | Me | H | Me | 6 | 1 |
| 5-18 | O | H | S | MeO | Me | H | Me | 7 | 1 |
| 5-19 | O | H | S | MeO | Me | H | Me | 8 | 1 |
| 5-20 | O | H | S | MeO | Me | H | Me | 2 | 2 |
| 5-21 | O | H | SO | MeO | Me | H | Me | 1 | 1 |
| 5-22 | O | H | $SO_2$ | MeO | Me | H | Me | 1 | 1 |
| 5-23 | O | H | S | HO | Me | H | H | 1 | 1 |
| 5-24 | O | H | SO | HO | Me | H | H | 1 | 1 |
| 5-25 | O | H | $SO_2$ | HO | Me | H | H | 1 | 1 |
| 5-26 | O | H | S | HO | Me | H | Me | 1 | 1 |
| 5-27 | O | H | S | HO | Me | H | Me | 1 | 0 |
| 5-28 | O | H | S | HO | Me | H | Me | 1 | 2 |
| 5-29 | O | H | S | HO | Me | H | Me | 1 | 3 |
| 5-30 | O | H | S | HO | Me | H | Me | 1 | 4 |
| 5-31 | O | H | S | HO | Me | H | Me | 1 | 5 |
| 5-32 | O | H | S | HO | Me | H | Me | 1 | 6 |
| 5-33 | O | H | S | HO | Me | H | Me | 1 | 7 |
| 5-34 | O | H | S | HO | Me | H | Me | 1 | 8 |
| 5-35 | O | H | S | HO | Me | H | Me | 2 | 1 |
| 5-36 | O | H | S | HO | Me | H | Me | 3 | 1 |
| 5-37 | O | H | S | HO | Me | H | Me | 4 | 1 |
| 5-38 | O | H | S | HO | Me | H | Me | 5 | 1 |
| 5-39 | O | H | S | HO | Me | H | Me | 6 | 1 |
| 5-40 | O | H | S | HO | Me | H | Me | 7 | 1 |
| 5-41 | O | H | S | HO | Me | H | Me | 8 | 1 |
| 5-42 | O | H | S | HO | Me | H | Me | 2 | 2 |
| 5-43 | O | H | SO | HO | Me | H | Me | 1 | 1 |
| 5-44 | O | H | $SO_2$ | HO | Me | H | Me | 1 | 1 |
| 5-45 | O | H | S | GlcA | Me | H | H | 1 | 1 |
| 5-46 | O | H | SO | GlcA | Me | H | H | 1 | 1 |
| 5-47 | O | H | $SO_2$ | GlcA | Me | H | H | 1 | 1 |
| 5-48 | O | H | S | GlcA | Me | H | Me | 1 | 1 |
| 5-49 | O | H | S | GlcA | Me | H | Me | 1 | 0 |
| 5-50 | O | H | S | GlcA | Me | H | Me | 1 | 2 |
| 5-51 | O | H | S | GlcA | Me | H | Me | 1 | 3 |
| 5-52 | O | H | S | GlcA | Me | H | Me | 1 | 4 |
| 5-53 | O | H | S | GlcA | Me | H | Me | 1 | 5 |
| 5-54 | O | H | S | GlcA | Me | H | Me | 1 | 6 |
| 5-55 | O | H | S | GlcA | Me | H | Me | 1 | 7 |
| 5-56 | O | H | S | GlcA | Me | H | Me | 1 | 8 |
| 5-57 | O | H | S | GlcA | Me | H | Me | 2 | 1 |
| 5-58 | O | H | S | GlcA | Me | H | Me | 3 | 1 |
| 5-59 | O | H | S | GlcA | Me | H | Me | 4 | 1 |
| 5-60 | O | H | S | GlcA | Me | H | Me | 5 | 1 |
| 5-61 | O | H | S | GlcA | Me | H | Me | 6 | 1 |
| 5-62 | O | H | S | GlcA | Me | H | Me | 7 | 1 |
| 5-63 | O | H | S | GlcA | Me | H | Me | 8 | 1 |
| 5-64 | O | H | S | GlcA | Me | H | Me | 2 | 2 |
| 5-65 | O | H | SO | GlcA | Me | H | Me | 1 | 1 |
| 5-66 | O | H | $SO_2$ | GlcA | Me | H | Me | 1 | 1 |
| 5-67 | O | H | S | MeS | Me | H | Me | 1 | 1 |
| 5-68 | O | H | S | MeS | Me | H | H | 1 | 1 |

(Wherein $R_1$, $R_2$, $R_3$, A, B, $W_1$, $W_2$, X, Y, $Z_1$, m and n are as defined above.)

The table above may preferably include the following exemplification compound Nos.:

1-1) 3-[4-[6-(4-adamantan-1-ylphenoxy)-1-methyl-1H-benzimidazol-2-ylmethoxy]phenyl]-2-(4-fluorobenzyloxy)propionic acid, 1-86) 3-[4-[6-(3,5-di-t-butyl-4-hydroxyphenylthio)-1-methyl-1H-benzimidazol-2-ylmethoxy]phenyl]-2-(4-fluorobenzyloxy)propionic acid, 1-87) 4-[6-(3,5-di-t-butyl-4-hydroxyphenylthio)-1-methyl-1H-benzimidazol-2-ylmethoxy]phenyllactic acid, 1-170) 4-[6-(4-hydroxy-2,3,5-trimethylphenoxy)-1-methyl-1H-benzimidazol-2-ylmethoxy]phenyllactic acid, 1-177) 4-(1-methyl-6-methoxy-1H-benzimidazol-2-ylmethoxy)phenyllactic acid, 1-179) 2-ethoxy-3-[4-(1-methyl-6-methoxy-1H-benzimidazol-2-ylmethoxy)phenyl]propionic acid, 3-188) N-(2-benzoylphenyl)-4-(6-methoxy-1-methyl-1H-benzimidazol-2-ylmethoxy)phenylalanine, 3-285) 4-[6-(4-amino-3,5-dimethylphenoxy)-1-methyl-1H-benzimidazol-2-ylmethoxy]-N-(2-benzoylphenyl)phenylalanine, 3-299) 4-[6-[4-(4-trifluoromethylphenylureide)-3,5-dimethylphenoxy]-1-methyl-1H-benzimidazol-2-ylmethoxy]-N-(2-benzoylphenyl)phenylalanine, 5-1) 3-[4-(6-methoxy-1-methyl-1H-benzimidazol-2-ylmethoxy)phenyl]-2-mercaptopropionic acid, 5-4) 3-[4-(6-methoxy-1-methyl-1H-benzimidazol-2-ylmethoxy)phenyl]-2-methylthiopropionic acid, 5-21) 3-[4-(6-methoxy-1-methyl-1H-benzimidazol-2-ylmethoxy)phenyl]-2-methylsulfenylpropionic acid, 5-22) 3-[4-(6-methoxy-1-methyl-1H-benzimidazol-2-ylmethoxy)phenyl]-2-methylsulfonylpropionic acid, 5-23) 3-[4-(6-hydroxy-1-methyl-1H-benzimidazol-2-ylmethoxy)phenyl]-2-mercaptopropionic acid, 5-26) 3-[4-(6-hydroxy-1-methyl-1H-benzimidazol-2-ylmethoxy)phenyl]-2-methylthiopropionic acid, 5-43) 3-[4-(6-hydroxy-1-methyl-1H-benzimidazol-2-ylmethoxy)phenyl]-2-methylsulfenylpropionic acid, 5-45) 3-[4-[6-(β-D-glucopyranosyloxyuronic acid)-1-methyl-1H-benzimidazol-2-ylmethoxy]phenyl]-2-mercaptopropionic acid, 5-48) 3-[4-[6-(β-D-glucopyranosyloxyuronic acid)-1-methyl-1H-benzimidazol-2-ylmethoxy]phenyl]-2-methylthiopropionic acid, 5-65) 3-[4-[6-(β-D-glucopyranosyloxyuronic acid)-1-methyl-1H-benzimidazol-2-ylmethoxy]phenyl]-2-methylsulfenylpropionic acid, 5-67) 3-[4-(1-methyl-6-methylthio-1H-benzimidazol-2-ylmethoxy)phenyl]-2-methylthiopropionic acid, 5-68) 3-[4-(1-methyl-6-methylthio-1H-benzimidazol-2-ylmethoxy)phenyl]-2-mercaptopropionic acid, pharmacologically acceptable esters or amides thereof, or pharmacologically acceptable salts thereof.

More preferable are:

1-1) 3-[4-[6-(4-adamantan-1-ylphenoxy)-1-methyl-1H-benzimidazol-2-ylmethoxy]phenyl]-2-(4-fluorobenzyloxy)propionic acid,
1-86) 3-[4-[6-(3,5-di-t-butyl-4-hydroxyphenylthio)-1-methyl-1H-benzimidazol-2-ylmethoxy]phenyl]-2-(4-fluorobenzyloxy)propionic acid,
1-87) 4-[6-(3,5-di-t-butyl-4-hydroxyphenylthio)-1-methyl-1H-benzimidazol-2-ylmethoxy]phenyllactic acid,
1-170) 4-[6-(4-hydroxy-2,3,5-trimethylphenoxy)-1-methyl-1H-benzimidazol-2-ylmethoxy]phenyllactic acid,
1-177) 4-(1-methyl-6-methoxy-1H-benzimidazol-2-ylmethoxy)phenyllactic acid,
1-179) 2-ethoxy-3-[4-(1-methyl-6-methoxy-1H-benzimidazol-2-ylmethoxy)phenyl]propionic acid,
3-188) N-(2-benzoylphenyl)-4(6-methoxy-1-methyl-1H-benzimidazol-2-ylmethoxy)phenylalanine,
3-285) 4-[6-(4-amino-3,5-dimethylphenoxy)-1-methyl-1H-benzimidazol-2-ylmethoxy]-N-(2-benzoylphenyl)phenylalanine,
3-299) 4-[6-[4-(4trifluoromethylphenylureide)-3,5-dimethylphenoxy]-1-methyl-1H-benzimidazol-2-ylmethoxy]-N-(2-benzoylphenyl)phenylalanine,
5-1) 3-[4-(6-methoxy-1-methyl-1H-benzimidazol-2-ylmethoxy)phenyl]-2-mercaptopropionic acid,
5-4) 3-[4-(6-methoxy-1-methyl-1H-benzimidazol-2-ylmethoxy)phenyl]-2methylthiopropionic acid,
5-21) 3-[4-(6-methoxy-1-methyl-1H-benzimidazol-2-ylmethoxy)phenyl]-2-methylsulfenylpropionic acid,
5-22) 3-[4-(6-methoxy-1-methyl-1H-benzimidazol-2-ylmethoxy)phenyl]-2-methylsulfonylpropionic acid,
5-26) 3-[4-(6-hydroxy-1-methyl-1H-benzimidazol-2-ylmethoxy)phenyl]-2-methylthiopropionic acid,
5-48) 3-[4-[6-(β-D-glucopyranosyloxyuronic acid)-1-methyl-1H-benzimidazol-2-ylmethoxy]phenyl]-2-methylthiopropionic acid,
5-67) 3-[4-(1-methyl-6-methylthio-1H-benzimidazol-2-ylmethoxy)phenyl]-2-methylthiopropionic acid,
5-68) 3-[4-(1-methyl-6-methylthio-1H-benzimidazol-2-ylmethoxy)phenyl]-2-mercaptopropionic acid, pharmacologically acceptable esters or amides thereof, or pharmacologically acceptable salts thereof.

Most preferable are:

1-1) 3-[4-[6-(4-adamantan-1-ylphenoxy)-1-methyl-1H-benzimidazol-2-ylmethoxy]phenyl]-2-(4-fluorobenzyloxy)propionic acid,
1-86) 3-[4-[6-(3,5-di-t-butyl-4-hydroxyphenylthio)-1-methyl-1H-benzimidazol-2-ylmethoxy]phenyl]-2-(4-fluorobenzyloxy)propionic acid,
1-179) 2-ethoxy-3-[4-(1-methyl-6-methoxy-1H-benzimidazol-2-ylmethoxy)phenyl]propionic acid,
3-188) N-(2-benzoylphenyl)-4-(6-methoxy-1-methyl-1H-benzimidazol-2-ylmethoxy)phenylalanine,
3-285) 4-[6-(4-amino-3,5-dimethylphenoxy)-1-methyl-1H-benzimidazol-2-ylmethoxy]-N-(2-benzoylphenyl)phenylalanine,
5-21) 3-[4-(6-methoxy-1-methyl-1H-benzimidazol-2-ylmethoxy)phenyl]-2-methylsulfenylpropionic acid,
5-67) 3-[4-(1-methyl-6-methylthio-1H-benzimidazol-2-ylmethoxy)phenyl]-2-methylthiopropionic acid, pharmacologically acceptable esters or amides thereof, or pharmacologically acceptable salts thereof.

Compounds having formula (I) of the present invention can be prepared according to the following processes A–S:

Process A

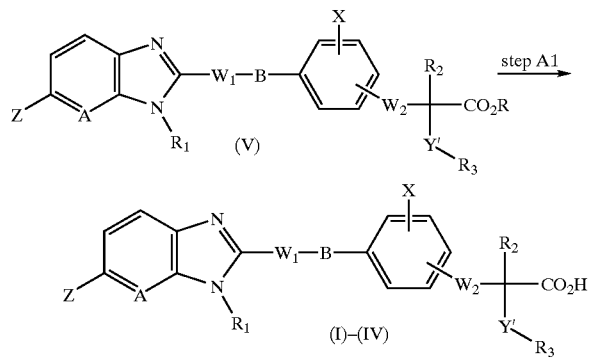

wherein $R_1$, $R_2$, $R_3$, $W_1$, $W_2$, X, Y, A and B independently represent as defined above, Z represents $Z_1$, $Z_2$O-group, $Z_3$S-group or $Z_4$ as described above, Y' represents Y or N—$R_4$-group as described above (where $R_4$ represents as defined above), and R represents an ester residue as described above.

In Process A, compound (V) can be allowed to react with water in an inert solvent in the presence of an acid or base to prepare compounds having general formulae (I)–(IV).

Any inert solvent can be used in the reaction above as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; ethers such as diethyl ether, diisopropyl ether, tetrahydrofuran, dioxane, dimethoxyethane or di(ethylene glycol) dimethyl ether; amides such as dimethylformamide, dimethylacetamide or hexamethylphosphoric triamide; alcohols such as methanol, ethanol or propanol; water; and mixtures thereof. Ethers, alcohols, amides, water and mixtures thereof are preferable, and alcohols and ethers are more preferable. Particularly, toluene and tetrahydrofuran are preferable.

Any acid which can be used as an acid catalyst in conventional reactions may be used in the above-described reaction. Such acids include, but are not limited to, for example: inorganic acids such as hydrochloric acid, hydrobromic acid, sulfuric acid, perchloric acid or phosphoric acid; Bronsted acids including organic acids such as acetic acid, formic acid, oxalic acid, methanesulfonic acid, p-toluenesulfonic acid, camphorsulfonic acid, trifluoroacetic acid or trifluoromethanesulfonic acid; Lewis acids such as zinc chloride, tin tetrachloride, boron trichloride, boron trifluoride or boron tribromide; and acidic ion-exchange resins. Inorganic and organic acids (particularly hydrochloric acid, acetic acid or trifluoroacetic acid) are preferable.

Any base which will not have any effect on any other moieties than the target moiety in the compound may be used in the above-described reaction. Such bases include, but are not limited to, for example: alkali metal carbonates such as lithium carbonate, sodium carbonate or potassium carbonate; alkali metal bicarbonates such as lithium bicarbonate, sodium bicarbonate or potassium bicarbonate; alkali metal hydroxides such as lithium hydroxide, sodium hydroxide or potassium hydroxide; metal alkoxides such as lithium methoxide, sodium methoxide, sodium ethoxide or potassium-t-butoxide; and ammonia such as aqueous ammonia solution or concentrated ammonia-methanol. Alkali metal hydroxides and metal alkoxides (particularly, alkali metal hydroxides and metal alkoxides) are preferable.

The reaction may typically be performed at from −20° C. to 150° C., and preferably at from 0° C. to 60° C. though the temperature may depend on the starting material compounds, solvents and/or other conditions to be used.

The reaction may typically be carried out for from 30 minutes to 5 days, and preferably from 5 to 72 hours though the reaction time may depend on the starting material compounds, solvents, reaction temperature and/or other conditions to be used.

In this process, when R represents a benzyl group which may be substituted, then compound (V) can be subjected to a catalytic reduction process in inert solvent under atmospheric or higher pressure (preferably under pressure higher than atmospheric) to produce target compounds (I)–(IV).

Any catalyst which can be used in conventional catalytic reduction processes may be used in the above-described catalytic reduction process. Such catalysts include, but are not limited to, for example, palladium-carbon, Raney Nickel, rhodium-aluminum oxide, triphenylphosphine-rhodium oxide, palladium-barium sulfate, palladium black, platinum oxide and platinum black. Palladium-carbon is preferable.

Any inert solvent can be used in the catalytic reduction process above as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, di(ethylene glycol), glycerin, octanol, cyclohexanol or methyl cellosolve; amides such as formamide, dimethylformamide, dimethylacetamide or hexamethylphosphoric triamide; organic acids such as acetic acid or trifluoroacetic acid; and mixtures thereof. Ethers, alcohols and organic acids are preferable, and alcohols are more preferable.

The reaction may typically be performed at from 0° C. to 100° C., and preferably at from 10° C. to 50° C. though the temperature may depend on the starting material compounds, catalysts, solvents and/or other conditions to be used.

The reaction may typically be carried out for from 30 minutes to 48 hours though the reaction time may depend on the starting material compounds, catalysts, solvents, reaction temperature and/or other conditions to be used.

Process B

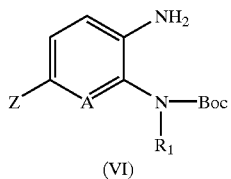

(VI)

+

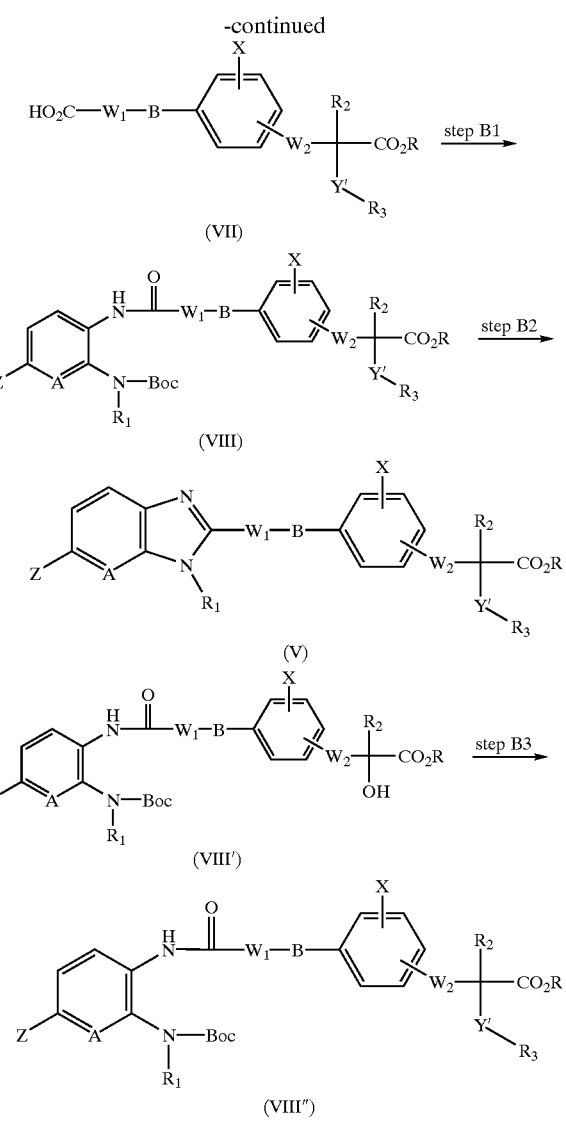

wherein

R$_1$, R$_2$, R$_3$, W$_1$, W$_2$, X, Y', Z, A, B and R independently represent as defined above, and Boc group represents t-butoxycarbonyl group.

Process B, which is a process for preparing compounds of general formula (V), can be carried out by allowing compound (VI) to react with compound (VII) and then treating the reaction product with an acid. In other words, in this process, the t-butoxycarbonyl group (the amino protecting group) may be removed by treatment with an acid as in the above-described reaction without purifying the amide compound (the intermediate product), and a ring is then formed.

Alternatively, the present process can also be performed by purifying the intermediate product (VIII) obtained by reaction of compound (VI) with compound (VII) (step B1), and then allowing the intermediate product (VIII) to be contacted with an acid (step B2).

Step B1 can be performed according to any of the following processes (a)–(c).

(a) Acid Halide Process

An acid halide process may be performed by allowing compound (VII) to react with a halogenation agent (e.g., thionyl chloride, thionyl bromide, oxalic chloride, oxalic dichloride, phosphorus oxychloride, phosphorus trichloride or phosphorus pentachloride) in an inert solvent to obtain an acid halide, and allowing the acid halide to react with compound (VI) or an acidified salt thereof in an inert solvent in the presence or absence (preferably in the presence) of a base(s).

Bases which may be used in the above-described reaction include, for example: alkali metal carbonates such as lithium carbonate, sodium carbonate or potassium carbonate; alkali metal bicarbonates such as lithium bicarbonate, sodium bicarbonate or potassium bicarbonate; alkali metal hydrides such as lithium hydride, sodium hydride or potassium hydride; alkali metal hydroxides such as lithium hydroxide, sodium hydroxide or potassium hydroxide; alkali metal alkoxides such as lithium methoxide, sodium methoxide, sodium ethoxide or potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicyclo [5.4.0]-7-undecene (DBU). Organic amines (particularly, triethylamine) are preferable.

Any inert solvent can be used in the above-described reaction as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as dichloromethane, chloroform, 1,2-dichloroethane or carbon tetrachloride; ethers such as diethyl ether, diisopropyl ether, tetrahydrofuran, dioxane, dimethoxyethane or di(ethylene glycol) dimethyl ether; ketones such as acetone; amides such as formamide, dimethylformamide, dimethylacetamide or hexamethylphosphoric triamide; sulfoxides such as dimethyl sulfoxide; and sulfolane. Halogenated hydrocarbons, ethers and amides particularly dichloromethane, chloroform, tetrahydrofuran and dimethylformamide) are preferable.

The reaction temperature may depend on the starting material compounds, agents and/or other conditions to be used though the reaction of the halogenation agent with compound (VII) as well as the reaction of the acid halide with compound (VI) or acidified salt thereof may typically be performed at from −20° C. to 150° C. Preferably, the reaction of the halogenation agent with compound (VII) may be performed at from −10° C. to 100° C. while the reaction of the acid halide with compound (VI) or an acidified salt thereof may be performed at from −20° C. to 100° C.

The reaction time may depend on the starting material compounds, agents, reaction temperature and/or other conditions to be used though the reaction of halogenation agent with compound (VII) as well as the reaction of the acid halide with compound (VI) or an acidified salt thereof may typically be performed for from 30 minutes to 80 hours, and preferably from 1 to 48 hours.

(b) Active Ester Process

An active ester process may be performed by allowing compound (VII) to react with an active esterification agent to prepare an active ester which is then allowed to react with compound (VI) or an acidified salt thereof in an inert solvent in the presence or absence (preferably in the presence) of a base.

The active ester process can be preferably performed in the presence of a condensation agent including, for example: N-hydroxy compounds such as N-hydroxysuccinimide, 1-hydroxybenzotriazole or N-hydroxy-5-norbornene-2,3-dicarboxyimide; disulfide compounds such as dipyridyldisulfide; carbodiimide compounds such as dicyclohexylcarbodiimide; carbonyldiimidazole; and triphenylphosphine.

Any inert solvent can be used in the above-described reaction as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as dichloromethane, 1,2-dichloroethane or carbon tetrachloride; ethers such as diethyl ether, diisopropyl ether, tetrahydrofuran, dioxane, dimethoxyethane or di(ethylene glycol) dimethyl ether; ketones such as acetone; amides such as formamide, dimethylformamide, dimethylacetamide or hexamethylphosphoric triamide; sulfoxides such as dimethyl sulfoxide; and sulfolane. Ethers and amides (particularly dioxane, tetrahydrofuran and dimethylformamide) are preferable.

Bases which can be used in the above-described reaction include, for example, those which can be used for the acid halide process described above.

The reaction temperature may depend on the starting material compounds, agents and/or other conditions to be used though the active esterification process may be performed at from −70° C. to 150° C., and preferably at from −10° C. to 100° C. while the reaction of the active ester with compound (VI) or an acidified salt thereof may be performed at from −20° C. to 100° C., and preferably at from 0° C. to 50° C.

The reaction time may depend on the starting material compounds, agents, reaction temperature and/or other conditions to be used though the active esterification reaction as well as the reaction of the active ester with compound (VI) or acidified salt thereof may typically be performed for from 30 minutes to 80 hours, and preferably from 1 to 48 hours.

(c) Mixed Acid Anhydride Process

A mixed acid anhydride process may be performed by allowing compound (VII) to react with a mixed acid anhydration agent in an inert solvent in the presence or absence (preferably in the presence) of a base to prepare a mixed acid anhydride which is then allowed to react with compound (VI) or an acidified salt thereof in an inert solvent.

Bases which may be used in the above-described reaction include, for example: alkali metal carbonates such as lithium carbonate, sodium carbonate or potassium carbonate; alkali metal bicarbonates such as lithium bicarbonate, sodium bicarbonate or potassium bicarbonate; alkali metal hydrides such as lithium hydride, sodium hydride or potassium hydride; alkali metal hydroxides such as lithium hydroxide, sodium hydroxide or potassium hydroxide; alkali metal alkoxides such as lithium methoxide, sodium methoxide, sodium ethoxide or potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]-octane (DABCO) or 1,8-diazabicyclo [5.4.0]-7-undecene (DBU). Organic amines (particularly, triethylamine) are preferable.

Mixed acid anhydration agents which can be used in the above-described reaction include, for example: $C_1$–$C_4$ alkyl halide carbonates such as chloroethyl carbonate or chloroisobutyl carbonate; $C_1$–$C_5$ alkanoyl halides such as pivaloyl chloride; and di-$C_1$–$C_4$ alkyl or di-$C_6$–$C_{14}$ aryl cyanophosphates such as cyanodiethyl phosphonate or cyanodiphenyl phosphonate. Di-$C_1$–$C_4$ alkyl and di-$C_6$–$C_{14}$ aryl cyanophosphates (particularly cyanodiethyl phosphonate) are preferable.

Any inert solvent can be used in the above-described reaction for preparing the mixed acid anhydride as long as it will not inhibit the reaction and may dissolve the starting materials to some extent. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as dichloromethane, 1,2-dichloroethane or carbon tetrachloride; ethers such as diethyl ether, diisopropyl ether, tetrahydrofuran, dioxane, dimethoxyethane or di(ethylene glycol) dimethyl ether; ketones such as acetone; amides such as formamide, dimethylformamide, dimethylacetamide or hexamethylphosphoric triamide; sulfoxides such as dimethyl sulfoxide; and sulfolane. Ethers and amides (particularly tetrahydrofuran and dimethylformamide) are preferable.

The reaction temperature for preparing mixed acid anhydrides may depend on the starting material compounds, agents and/or other conditions to be used though the reaction may typically be performed at from $-50°$ C. to $100°$ C., and preferably from $0°$ C. to $60°$ C.

The reaction time for preparing the mixed acid anhydride may depend on the starting material compounds, agents, reaction temperature and/or other conditions to be used though it may typically be from 30 minutes to 72 hours, and preferably from 1 to 24 hours.

The reaction of the mixed acid anhydride with compound (VI) or an acidified salt thereof may be performed in an inert solvent in the presence or absence (preferably in the presence) of a base. The same bases and inert solvents as those which can be used in the above-described process for preparing the mixed acid anhydride may also be used in this reaction.

The temperature for reaction of the mixed acid anhydride with compound (VI) or acidified salt thereof may depend on the starting material compounds, agents and/or other conditions to be used though it may typically be from $-30°$ C. to $100°$ C., and preferably from $0°$ C. to $80°$ C.

The reaction of the mixed acid anhydride with compound (VI) or an acidified salt thereof may typically be performed for from 5 minutes to 24 hours, and preferably from 30 minutes to 16 hours, though the time may depend on the starting material compounds, agents, reaction temperature and/or other conditions to be used.

In this reaction, compound (VI) can be reacted directly with compound (VII) in the presence of a base when a di-$C_1$–$C_4$ alkyl cyanophosphate or a di-$C_6$–$C_{14}$ aryl cyanophosphate is used.

After reaction is completed, the target compound (VIII) obtained in this step may be isolated from the reaction mixture according to any conventional method. For example, the reaction product may appropriately be neutralized; impurities, if any, may be removed by filtration; then an organic solvent comprising two or more liquids which are not miscible with each other (such as water and ethyl acetate) may be added; the organic phase containing the target compound may be separated, washed with, for example, water, and dried on, for example, magnesium sulfate anhydride, sodium sulfate anhydride, or sodium hydrogen carbonate anhydride; and the solvent may be then removed by distillation.

Step B2 (ring closure using an acid) may be performed by allowing compound (VIII) to react in an inert solvent in the presence of an acid.

Any acid which can be used as an acid catalyst in conventional reactions may be used in this step. Such acids include, but are not limited to, for example: inorganic acids such as hydrochloric acid, hydrobromic acid, sulfuric acid, perchloric acid or phosphoric acid; Bronsted acids including organic acids such as acetic acid, formic acid, oxalic acid, methanesulfonic acid, p-toluenesulfonic acid, camphorsulfonic acid, trifluoroacetic acid or trifluoromethanesulfonic acid; Lewis acids such as zinc chloride, tin tetrachloride, boron trichloride, boron trifluoride or boron tribromide; and acidic ion-exchange resins. Inorganic and organic acids (particularly hydrochloric acid, acetic acid and trifluoroacetic acid) are preferable.

Any inert solvent can be used in this step as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; esters such as methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, di(ethylene glycol), glycerin, octanol, cyclohexanol or methyl cellosolve; amides such as formamide, dimethylformamide, dimethylacetamide or hexamethylphosphoric triamide; water; and mixtures thereof. Ethers and amides (particularly dioxane, tetrahydrofuran and dimethylformamide) are preferable.

The reaction temperature may depend on the starting material compounds, acids, solvents and/or other conditions to be used though the reaction may typically be performed at from $-20°$ C. to the boiling point, and preferably from $0°$ C. to $100°$ C.

The reaction time may depend on the starting material compounds, acids, solvents, reaction temperature and/or other conditions to be used though the reaction may typically be performed for from 15 minutes to 48 hours, and preferably from 30 minutes to 20 hours.

Step B3 is the substitution of a functional group by —$YR_3$ in compound (VIII). In this step, compound (VIII″), which corresponds to compound (VIII) where the —$YR_3$ group comprises an alkoxyl, alkylthio or amino group, can be obtained by subjecting compound (VIII'), which corresponds to compound (VIII) where —$YR_3$ group comprises an —OH group, to any one of the following reactions (i)–(iv): (i) Mitsunobu reaction; (ii) etherification; (iii) alkane (or aryl) sulfonylation followed by thioetherification; or (iv) alkane (or aryl) sulfonylation followed by azidocomplexing and then reductive reaction.

In step B3,
(i) Mitsunobu reaction for preparing compound (VIII') may be performed in an inert solvent in the presence of a phosphine (preferably tributylphosphine or triphenylphosphine) and an azodicarboxylate compound (preferably diethyl azodicarboxylate or 1,1-dipiperidine azodicarboxylate);
(ii) etherification can be performed in the same manner as in step D1 described below;
(iii) alkane (or aryl) sulfonylation followed by thioetherification can be performed in the same manner as in step F1 described below; and
(iv) alkane (or aryl) sulfonylation followed by azidocomplexing and then reductive reaction can be performed in the same manner as in step G1 described below.

Further, the amino compound can be subjected to alkylation using an alkyl halide substantially according to step H1 described later, or to any conventional reductive alkylation using an aldehyde or a ketone, to obtain an alkylamide.

Process C

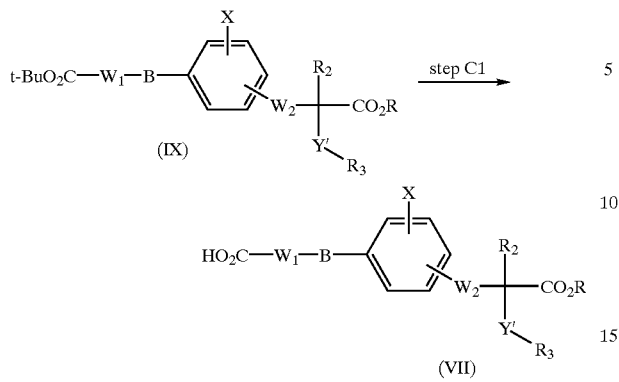

Process D

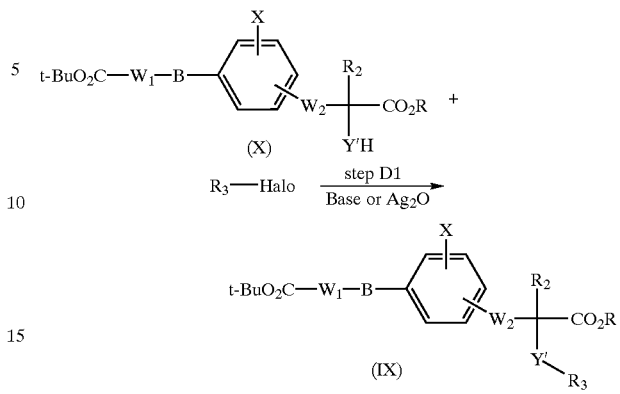

wherein $R_2$, $R_3$, $W_1$, $W_2$, X, Y', B and R independently represent as defined above.

In Process C, compound (IX) can be allowed to react in an inert solvent in the presence of an acid to prepare compound (VII).

Any acid which can be used as an acid catalyst in conventional reactions may be used in this process. Such acids include, but are not limited to, for example: inorganic acids such as hydrochloric acid, hydrobromic acid, sulfuric acid, perchloric acid or phosphoric acid; Bronsted acids including organic acids such as acetic acid, formic acid, oxalic acid, methanesulfonic acid, p-toluenesulfonic acid, camphorsulfonic acid, trifluoroacetic acid or trifluoromethanesulfonic acid; Lewis acids such as zinc chloride, tin tetrachloride, boron trichloride, boron trifluoride or boron tribromide; and acidic ion-exchange resins. Inorganic and organic acids (particularly hydrochloric acid, acetic acid and trifluoroacetic acid) are preferable.

Any inert solvent can be used in this process as long as it is inert in the reaction. Such inert solvents include, but are not limited to, for example: aliphatic hydrocarbons such as hexane, heptane, ligroin or petroleum ether, aromatic hydrocarbons such as benzene, toluene or xylene; halogenated hydrocarbons such as chloroform, dichloromethane, 1,2-dichloroethane or carbon tetrachloride; esters such as methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; alcohols such as methanol, ethanol, n-propanol, isopropanol, n-butanol, isobutanol, t-butanol, isoamyl alcohol, di(ethylene glycol), glycerine, octanol, cyclohexanol or methyl cellosolve; amides such as formamide, dimethylformamide, dimethylacetamide or hexamethylphosphoric triamide; water; and mixtures thereof. Ethers and amides (particularly dioxane, tetrahydrofuran and dimethylformamide) are preferable.

The reaction may typically be performed at from −20° C. to the boiling point, and preferably from 0° C. to 80° C. though the reaction temperature may depend on the starting material compounds, acids, solvents and/or other conditions to be used.

The reaction may typically be performed for from 15 minutes to 48 hours, and preferably from 30 minutes to 20 hours though the reaction time may depend on the starting material compounds, acids, solvents, reaction temperature and/or other conditions to be used.

wherein $R_2$, $R_3$, $W_1$, $W_2$, X, Y', B and R independently represent as defined above, and Halo group represents any one of the halogen atoms described above.

In Process D, compound (X) can be allowed to react with a halide compound having general formula of $R_3$-Halo in an inert solvent in the presence of a base or silver oxide to prepare compound (IX).

Bases which may be used in this process include, for example: alkali metal carbonates such as lithium carbonate, sodium carbonate, potassium carbonate or cesium carbonate; alkali metal bicarbonates such as lithium bicarbonate, sodium bicarbonate or potassium bicarbonate; alkali metal hydrides such as lithium hydride, sodium hydride or potassium hydride; alkali metal hydroxides such as lithium hydroxide, sodium hydroxide or potassium hydroxide; alkali metal alkoxides such as lithium methoxide, sodium methoxide, sodium ethoxide or potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicyclo[5.4.0]-7-undecene (DBU). Alkali metal hydrides (particularly, sodium hydride) are preferable.

Any inert solvent can be used in this process as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; esters such as methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; amides such as formamide, dimethylformamide, dimethylacetamide or hexamethylphosphoric triamide; and mixtures thereof. Ethers and amides (particularly dioxane, tetrahydrofuran and dimethylformamide) are preferable.

The reaction may typically be performed at from −20° C. to the boiling point, and preferably from 0° C. to 100° C. though the reaction temperature may depend on the starting material compounds, acids, solvents and/or other conditions to be used.

The reaction may typically be performed for from 15 minutes to 48 hours, and preferably from 30 minutes to 20 hours though the reaction time may depend on the starting material compounds, bases, solvents, reaction temperature and/or other conditions to be used.

Process E

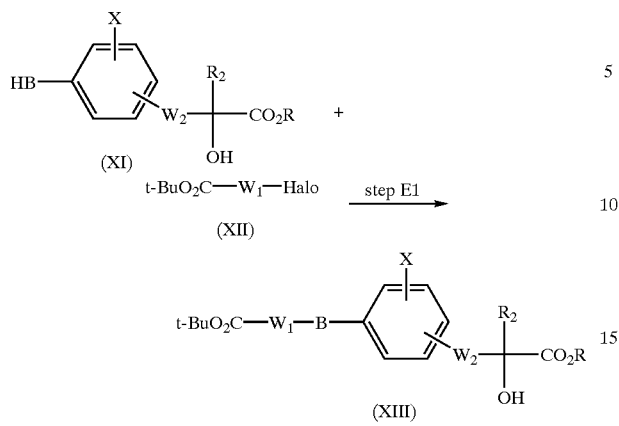

wherein

R$_2$, W$_1$, W$_2$, X, B, R and Halo group independently represent as defined above.

In Process E, compound (XI) can be allowed to react with a halide having general formula (XII) in an inert solvent in the presence of a base or silver oxide to prepare compound (XIII).

Bases which may be used in the above-described reaction include, for example: alkali metal carbonates such as lithium carbonate, sodium carbonate, potassium carbonate or cesium carbonate; alkali metal bicarbonates such as lithium bicarbonate, sodium bicarbonate or potassium bicarbonate; alkali metal hydrides such as lithium hydride, sodium hydride or potassium hydride; alkali metal hydroxides such as lithium hydroxide, sodium hydroxide or potassium hydroxide; alkali metal alkoxides such as lithium methoxide, sodium methoxide, sodium ethoxide or potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU). Alkali metal hydrides and alkali metal carbonates (particularly, sodium hydride, potassium carbonate or cesium carbonate) are preferable.

Any inert solvent can be used in this process as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; esters such as methyl acetate, ethyl acetate, propyl acetate, butyl acetate or diethyl carbonate; ketones such as acetone or methyl ethyl ketone; ethers such as diethyl ether, diisopropyl ether, tetrahydrofuran, dioxane, dimethoxyethane or di(ethylene glycol) dimethyl ether; amides such as formamide, dimethylformamide, dimethylacetamide or hexamethylphosphoric triamide; and mixtures thereof. Ketones, ethers and amides (particularly, acetone, dioxane, tetrahydrofuran and dimethylformamide) are preferable.

The reaction may typically be performed at from −20° C. to the boiling point, and preferably from 0° C. to 100° C. though the reaction temperature may depend on the starting material compounds, acids, solvents and/or other conditions to be used.

The reaction may typically be performed for from 15 minutes to 48 hours, and preferably from 30 minutes to 20 hours though the reaction time may depend on the starting material compounds, acids, solvents, reaction temperature and/or other conditions to be used.

Process F

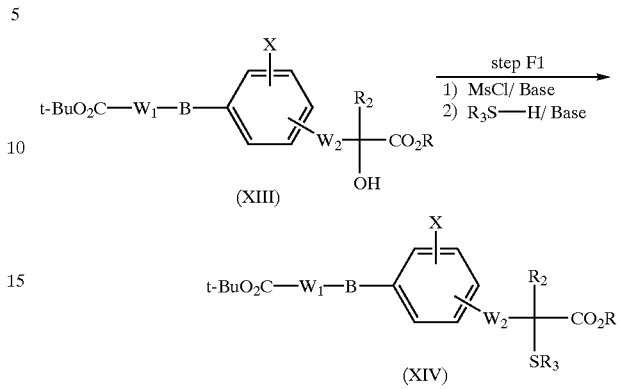

wherein

R$_2$, R$_3$, W$_1$, W$_2$, X, B and R independently represent as defined above.

Process F, which is a process for preparing compound (XIV), can be performed by, in an inert solvent, allowing compound (XII) to react with methanesulfonyl chloride in the presence of a base followed by reaction with a mercaptan having general formula R$_3$SH in the presence of a base.

Bases which may be used in step F1 include, for example: alkali metal carbonates such as lithium carbonate, sodium carbonate or potassium carbonate; alkali metal bicarbonates such as lithium bicarbonate, sodium bicarbonate or potassium bicarbonate; alkali metal hydrides such as lithium hydride, sodium hydride or potassium hydride; alkali metal hydroxides such as lithium hydroxide, sodium hydroxide or potassium hydroxide; alkali metal alkoxides such as lithium methoxide, sodium methoxide, sodium ethoxide or potassium t-butoxide; and organic amines such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicyclo[5.4.0]-7-undecene (DBU). Organic amines (particularly, triethylamine) are preferable. Bases which can be used in the first step can also be used in the second step of the above-described reaction. Alkali metal hydrides (particularly, sodium hydride) are preferable.

Any inert solvent can be used in the above-described reaction as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; esters such as methyl acetate, ethyl acetate, propyl acetate, butyl acetate or diethyl carbonate; ethers such as diethyl ether, diisopropyl ether, tetrahydrofuran, dioxane, dimethoxyethane or di(ethylene glycol) dimethyl ether; amides such as formamide, dimethylformamide, dimethylacetamide or hexamethylphosphoric triamide; and mixtures thereof. Ethers and amides (particularly, dioxane, tetrahydrofuran and dimethylformamide) are preferable.

The reaction may typically be performed at from −20° C. to the boiling point, and preferably at from 0° C. to 100° C. though the reaction temperature may depend on the starting material compounds, acids, solvents and/or other conditions to be used.

The reaction may typically be performed for from 15 minutes to 48 hours, and preferably from 30 minutes to 20 hours though the reaction time may depend on the starting material compounds, acids, solvents, reaction temperature and/or other conditions to be used Process G

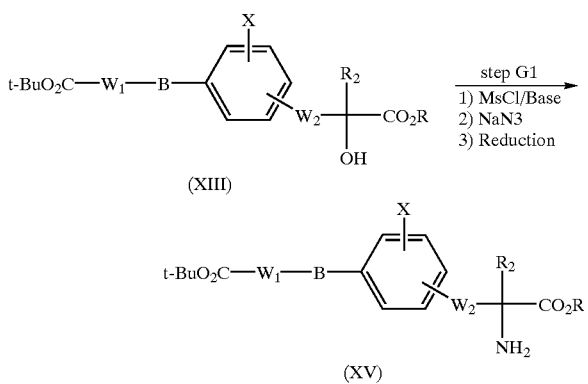

wherein $R_2, R_3, W_1, W_2, X, Y, B$ and $R$ independently represent as defined above.

In Process G, compound (XIII) can be allowed to react with methanesulfonyl chloride in the presence of a base in an inert solvent, and then with sodium azide to form azide compound which is then reduced to obtain compound (XV).

The same conditions as those used in step F1 may be used for the reaction with methanesulfonyl chloride and the following reaction with sodium azide as well except that base is not required in the second step. Further, the reductive reaction may be performed according to azide-to-amino conversion (i.e., the above described catalytic reduction and reaction with phosphine).

Process H

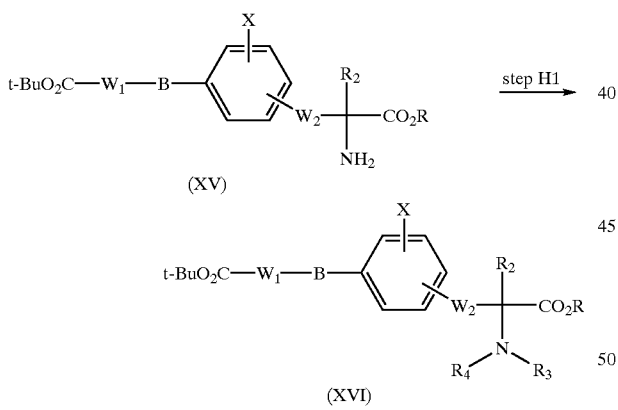

wherein $R_2, R_3, R_4, W_1, W_2, X, B$ and $R$ independently represent as defined above.

In Process I, compound (XV) is subjected to alkylation, aralkylation or arylation of the amino group to prepare compound (XVI).

Step H1 may be performed substantially according to any known synthesis process. For example, alkylation or aralkylation of the amino group may be performed by allowing the amino group to react with an alkyl halide or aralkyl halide, while arylation may be performed by allowing the amino group to react with an aryl halide in the presence of a base.

Bases which can be used in step H1 of Process H include, for example: alkali metal carbonates such as lithium carbonate, sodium carbonate or potassium carbonate; alkali metal bicarbonates such as lithium bicarbonate, sodium bicarbonate or potassium bicarbonate; alkali metal hydrides such as lithium hydride, sodium hydride or potassium hydride; alkali metal hydroxides such as lithium hydroxide, sodium hydroxide or potassium hydroxide; alkali metal alkoxides such as lithium methoxide, sodium methoxide, sodium ethoxide or potassium t-butoxide; and organic amines such as triethylamine, tributylamine, diisopropyl ethylamine, N-methyl morpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) or 1,8-diazabicyclo [5.4.0]-7-undecene (DBU). Alkali metal bicarbonates are preferable.

Process I

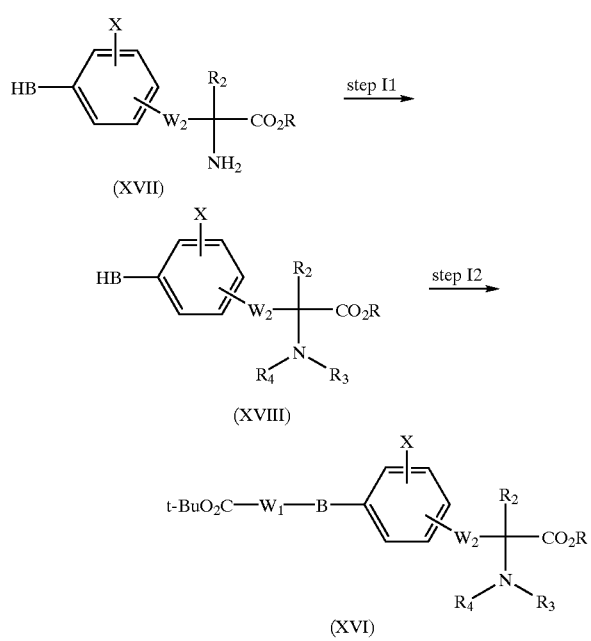

wherein $R_2, R_3, R_4, W_1, W_2, X, B$ and $R$ independently represent as defined above.

Process I, which is a process for preparing compound (XVI), can be performed by subjecting compound (XVII) to alkylation, aralkylation or arylation of the amino group as in Process H (step I1) and then to the same reaction as step E1 (step I2). This step may be performed after the amino group is protected by any conventional protecting group.

Process J

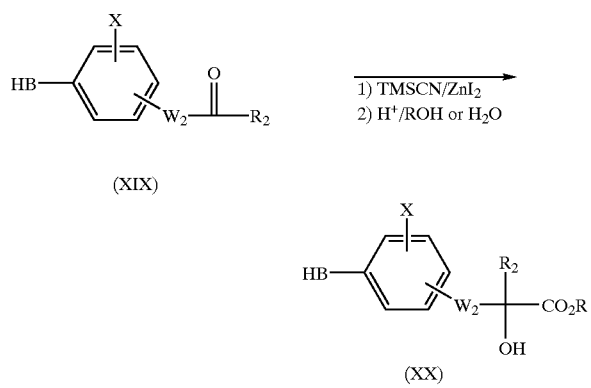

wherein

R$_2$, W$_2$, X, B and R independently represent as defined above.

In Process J, a ketone or aldehyde having general formula (XIX) is converted to a cyanohydrin which is then subjected to hydrolysis or alcoholysis in the presence of acid to obtain compound (XX).

This process may be performed by using zinc iodide as a catalyst in the presence or absence of an inert solvent.

Compound (XVII) may also be prepared by subjecting a ketone or aldehyde of general formula (XIX) to one of the conventional processes for synthesizing amino acids, e.g. Strecker amino acid synthesis in which a ketone or aldehyde is reacted with hydrogen cyanide and ammonia.

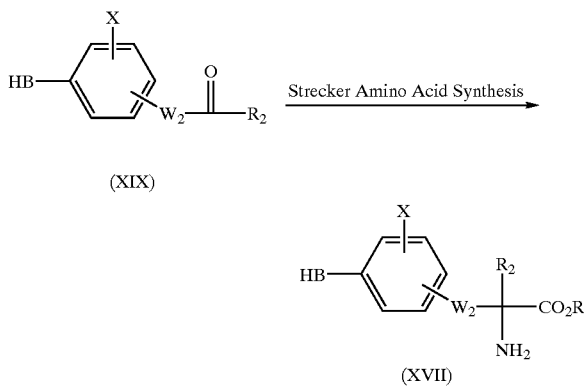

Process K

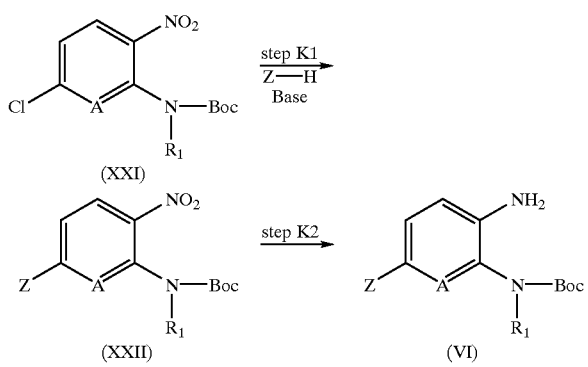

wherein

R$_1$, Z, A and Boc group independently represent as defined above.

Process K, which is a process for preparing compound (VI), can be performed by allowing compound (XXI) to react with a compound having general formula Z—H in an inert solvent in the presence of a base (step K1) and then reducing the reaction product obtained (step K2).

Bases which may be used in step D1 described above can also be used in step K1 as well. Among all, alkali metal hydrides particularly, sodium hydride) are preferable. The same conditions as those for step D1 described above may also be used in step K1.

Step K2, which is a process for the reduction of a nitro group in an aromatic compound, may be performed according to any conventional process such as catalytic reduction, reduction using a combination of a metal and an acid (e.g., zinc-acetic acid, tin-alcohol or tin-hydrochloric acid) or reaction with sodium hydrosulfite.

Process L

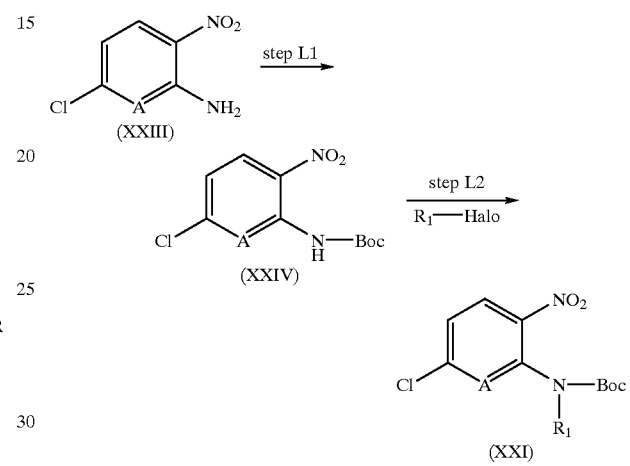

wherein

R$_1$, A and Boc group independently represent as defined above.

Process L, which is a process for preparing compound (XXI), can be performed by protecting the amino group in compound (XXIII) by using a protecting group therefor, t-butoxycarbonyl group in an inert solvent in the presence or absence of a base (step L1) and then subjecting the protected compound to alkylation, arylation or aralkylation (step L2).

Step L1 is a process for introduction of a protecting group into the amino group (Boc-lation) in which compound (XXIII) is allowed to react with di-t-butyl dicarbonate in an inert solvent in the presence of a base.

Step L2 is alkylation, arylation or aralkylation of the Boc-protected-amino group which can be performed according to any conventionally known process.

Further, when an amino group is present in Z of the above-described compounds (I)–(IV) and intermediate compound (VI), acylation, sulfonylation, or carbamoylation may be obtained by alkylation, arylation or aralkylation of the amino group or by any other conventionally known process.

Process M

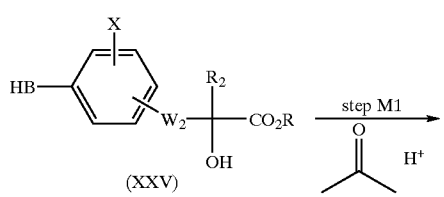

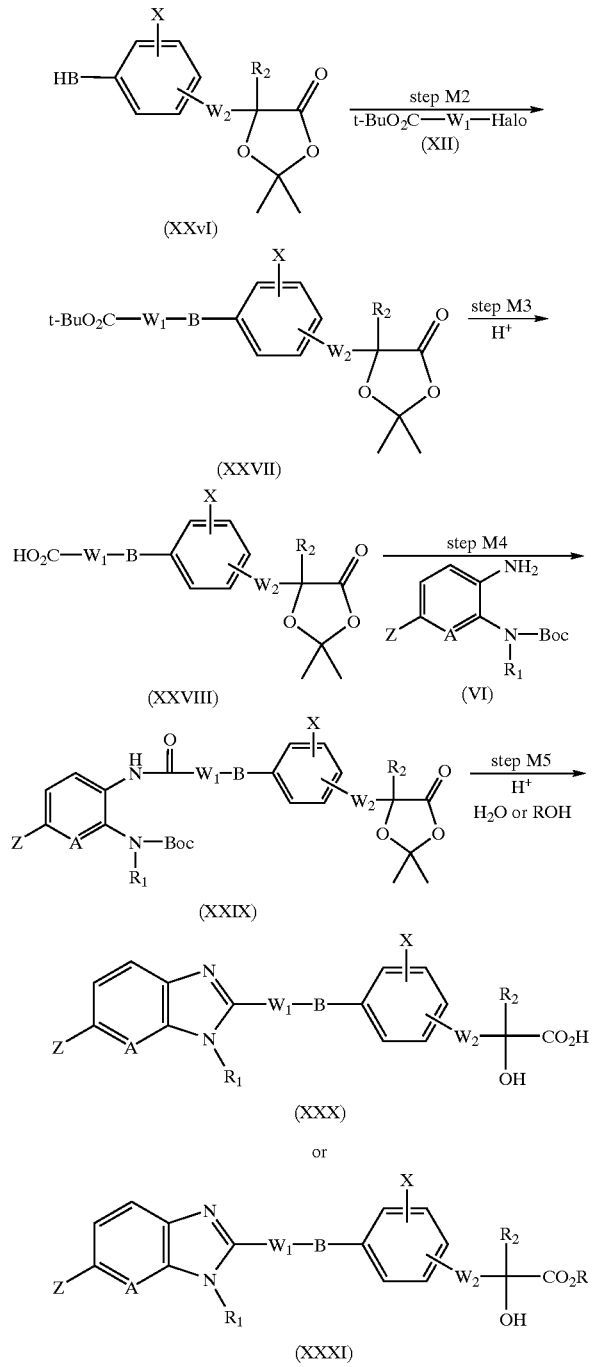

wherein

R₁, R₂, W₁, W₂, X, Z, A, B, R, Boc and Halo groups independently represent as defined above.

Process M is an alternative process for synthesizing compounds (I)–(III) in which —Y—R₃ group is a hydroxy group.

In Step M1, compound (XXV) is allowed to form an acetonide between the hydroxy group and carboxyl group in the molecule to prepare compound (XXVI). Step M1 may be performed by allowing compound (XXV) to react with acetone or 2,2-dimethoxypropane in or without (preferably without) inert solvent in the presence of an acid.

Any acid may be used in the above-described reaction, which can be used as an acid catalyst in conventional reactions. Such acids include, but are not limited to, for example: inorganic acids such as hydrochloric acid, hydrobromic acid, sulfuric acid, perchloric acid or phosphoric acid; Bronsted acids including organic acids such as acetic acid, formic acid, oxalic acid, methanesulfonic acid, p-toluenesulfonic acid, camphorsulfonic acid, trifluoroacetic acid or trifluoromethanesulfonic acid; Lewis acids such as zinc chloride, tin tetrachloride, boron trichloride, boron trifluoride or boron tribromide; and acidic ion-exchange resins. Inorganic and organic acids (particularly hydrochloric acid, acetic acid and trifluoroacetic acid) are preferable.

The reaction may typically be performed at from −20° C. to the boiling point, and preferably from 0° C. to 80° C. though the reaction temperature may depend on the starting material compounds, acids and/or other conditions to be used.

The reaction may typically be performed for from 15 minutes to 48 hours, and preferably from 30 minutes to 20 hours though the reaction time may depend on the starting material compounds, acids, reaction temperature and/or other conditions to be used.

In Step M2, compound (XXVI) may be allowed to react with compound (XII) in an inert solvent in the presence of a base substantially according to Process E to prepare compound (XXVII).

In Step M3, compound (XXVII) may be allowed to react in an inert solvent in the presence of an acid substantially according to Process C to prepare compound (XXVIII).

In Step M4, compound (XXVIII) may be allowed to react with compound (VI) in an inert solvent in the presence of a condensation agent substantially according to Step B1 to prepare compound (XXIX).

In Step M5, compound (XXIX) may be allowed to react with water or an alcohol in an inert solvent (or the inert solvent may be the water or alcohol) in the presence of an acid substantially according to Step B2 to prepare a compound having general formula (XXX) or (XXXI).

Compounds (I)–(IV) in which Y represents S(O)p group where p represents an integer selected from 0–2 may be synthesized according to the following process.

Process N

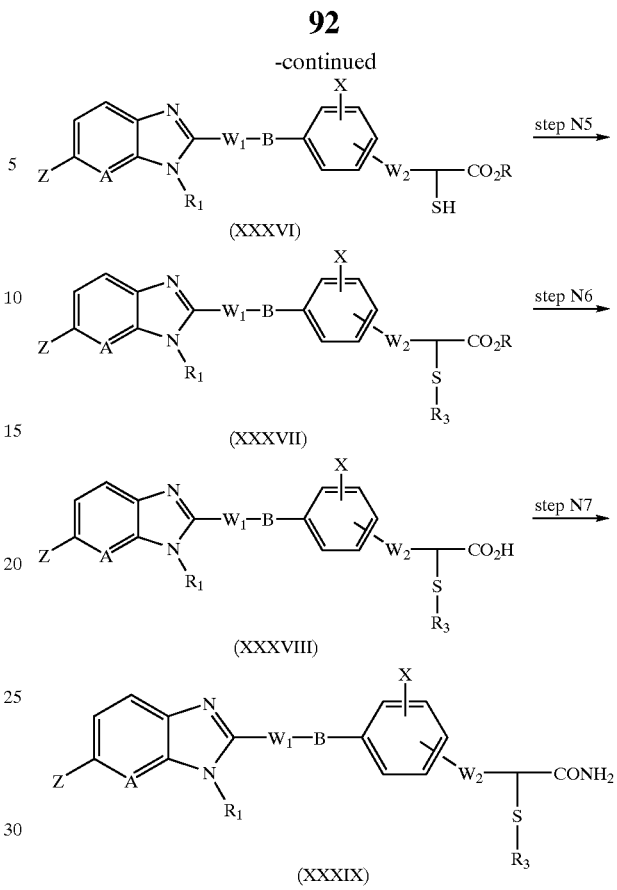

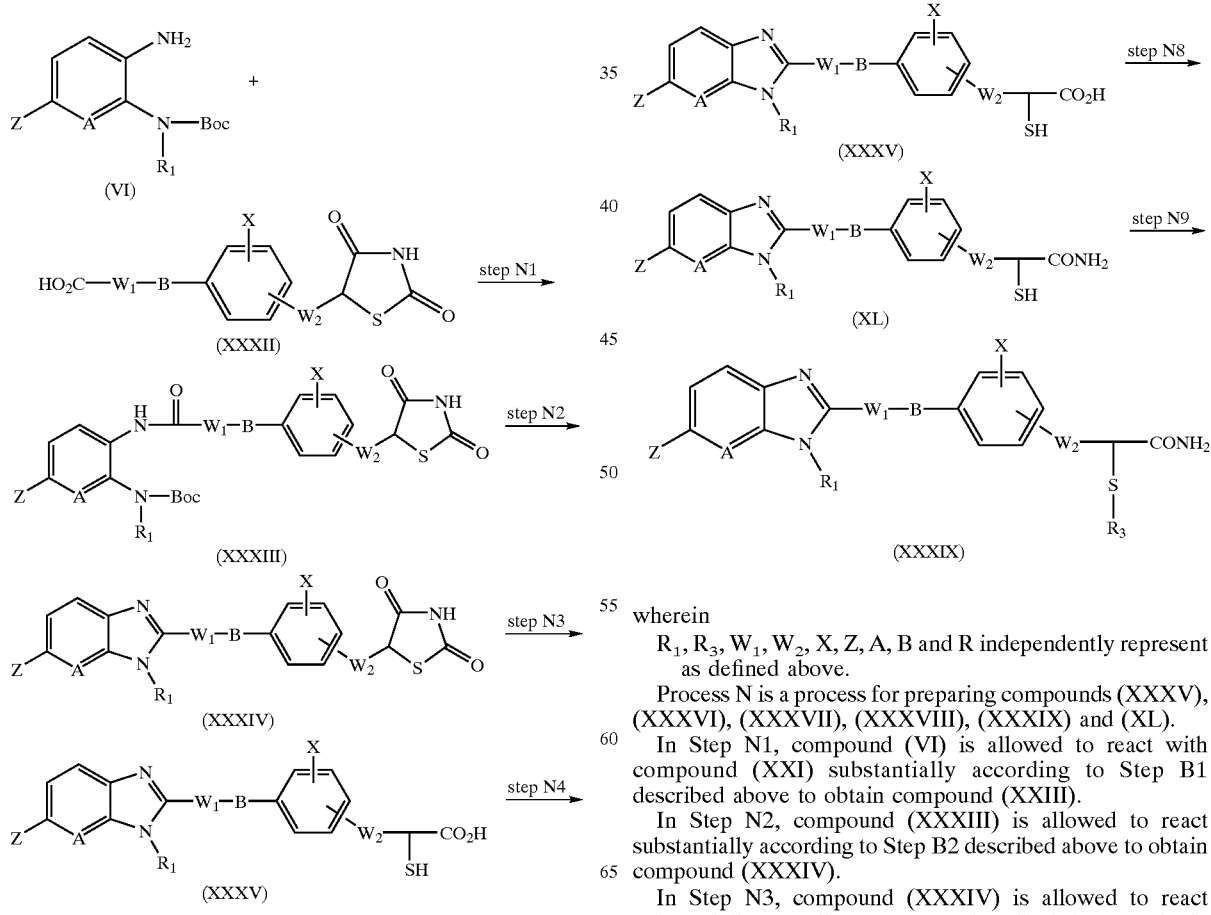

wherein

R$_1$, R$_3$, W$_1$, W$_2$, X, Z, A, B and R independently represent as defined above.

Process N is a process for preparing compounds (XXXV), (XXXVI), (XXXVII), (XXXVIII), (XXXIX) and (XL).

In Step N1, compound (VI) is allowed to react with compound (XXI) substantially according to Step B1 described above to obtain compound (XXIII).

In Step N2, compound (XXXIII) is allowed to react substantially according to Step B2 described above to obtain compound (XXXIV).

In Step N3, compound (XXXIV) is allowed to react substantially according to Step A1 described above to obtain compound (XXXV). Step N3 may be performed by allowing compound (XXXIV) to react with water in an inert solvent in the presence of a base.

Any inert solvent can be used in the above-described reaction as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; ethers such as diethyl ether, diisopropyl ether, tetrahydrofuran, dioxane, dimethoxyethane or di(ethylene glycol) dimethyl ether; amides such as dimethylformamide, dimethylacetamide or hexamethylphosphoric triamide; alcohols such as methanol, ethanol or propanol; water; and mixtures thereof. Ethers, alcohols, amides, water and mixtures thereof are preferable, alcohols and ethers are more preferable, and alcohols and tetrahydrofuran are most preferable.

Any bases which may not affect any other moieties than the target moiety in the compound can be used in the above-described reaction, including, for example: alkali metal carbonates such as lithium carbonate, sodium carbonate or potassium carbonate; alkali metal bicarbonates such as lithium bicarbonate, sodium bicarbonate or potassium bicarbonate; alkali metal hydroxides such as lithium hydroxide, sodium hydroxide or potassium hydroxide; metal alkoxides such as lithium methoxide, sodium methoxide, sodium ethoxide or potassium t-butoxide; and ammonia such as aqueous ammonia solution or concentrated ammonia-methanol. Alkali metal hydroxides and metal alkoxides (particularly, alkali metal hydroxides and metal alkoxides) are preferable.

The reaction may typically be performed at from −20° C. to 150° C., and preferably from 0° C. to 100° C. though the reaction temperature may depend on the starting material compounds, solvents and/or other conditions to be used.

The reaction may typically be performed for from 30 minutes to 5 days, and preferably from 2 to 72 hours though the reaction time may depend on the starting material compounds, solvents, reaction temperature and/or other conditions to be used.

Step N4, where compound (XXXV) is subjected to esterification to prepare compound (XXXVI), is performed substantially according to step B1 described above except for using an alcohol having the general formula ROH instead of compound (IV) and adapting any one of the following processes(a)–(c): (a) acid halide process; (b) active ester process; or (c) mixed acid anhydration process.

Alternatively, Step N4 may also be performed by allowing compound (XXXV) to react with the alcohol of general formula ROH in an inert solvent or in the alcohol in the presence of an acid. Any inert solvent can be used in the above-described reaction as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; ethers such as diethyl ether, diisopropyl ether, tetrahydrofuran, dioxane, dimethoxyethane or di(ethylene glycol) dimethyl ether; amides such as dimethylformamide, dimethylacetamide or hexamethylphosphoric triamide; alcohols such as methanol, ethanol or propanol; water; and mixtures thereof. Ethers, alcohols, amides and mixtures thereof are preferable, alcohols and ethers are more preferable, and alcohol and tetrahydrofuran are most preferable.

Any acid may be used in the above-described reaction, which can be used as acid catalyst in conventional reactions. Such acids include, but are not limited to, for example: inorganic acids such as hydrochloric acid, hydrobromic acid, sulfuric acid, perchloric acid or phosphoric acid; Bronsted acids including organic acids such as acetic acid, formic acid, oxalic acid, methanesulfonic acid, p-toluenesulfonic acid, camphorsulfonic acid, trifluoroacetic acid or trifluoromethanesulfonic acid; Lewis acids such as zinc chloride, tin tetrachloride, boron trichloride, boron trifluoride or boron tribromide; and acidic ion-exchange resins. Inorganic and organic acids (particularly hydrochloric acid, acetic acid or trifluoroacetic acid) are preferable.

The reaction may typically be performed at from −20° C. to 150° C., and preferably from 0° C. to 60° C. though the reaction temperature may depend on the starting material compounds, solvents and/or other conditions to be used.

The reaction may typically be performed for from 30 minutes to 5 days, and preferably from 5 to 72 hours though the reaction time may depend on the starting material compounds, solvents, reaction temperature and/or other conditions to be used.

In step N5, compound (XXVI) may be allowed to react with a compound having general formula $R_3$-Halo (where $R_3$ is not hydrogen) substantially according to Step D1 described above to obtain compound (XXXVII).

In step N6, compound (XXXVII) may be subjected to ester hydrolysis substantially according to Step A1 described above to obtain compound (XXXVI).

In step N7, compound (XXXVIII) may be allowed to react with ammonia substantially according to Step B1 described above to obtain compound (XXXIX).

In step N8, compound (XXXV) may be allowed to react with ammonia substantially according to Step B1 described above to obtain compound (XL).

In step N9, compound (XL) may be allowed to react with a compound having general formula $R_3$-Halo (where $R_3$ is not hydrogen) substantially according to Step D1 described above to obtain compound (XXXIX).

Process O

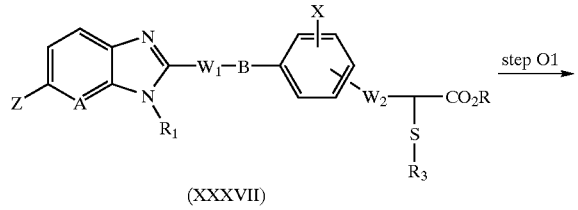

(XXXVII)

-continued
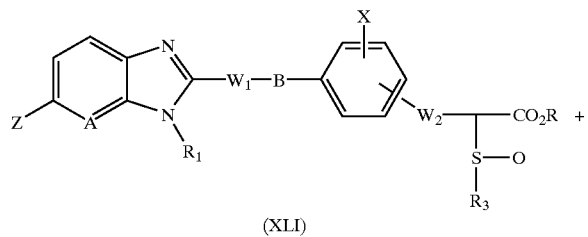
(XLI)
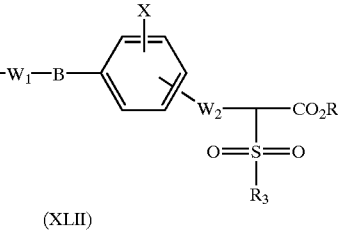
(XLII)
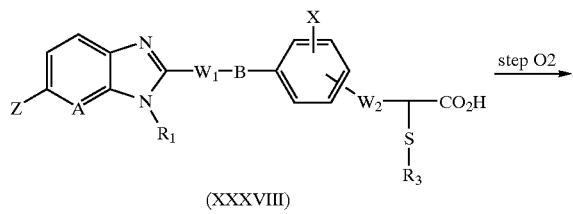
(XXXVIII)
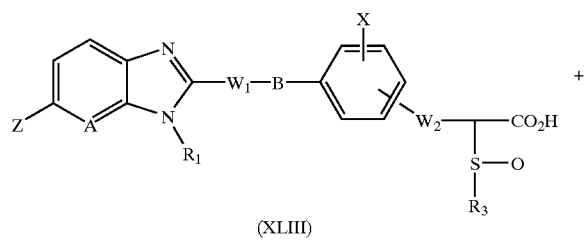
(XLIII)
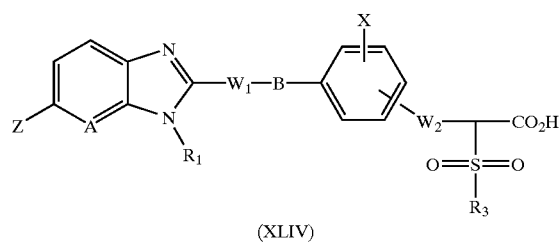
(XLIV)
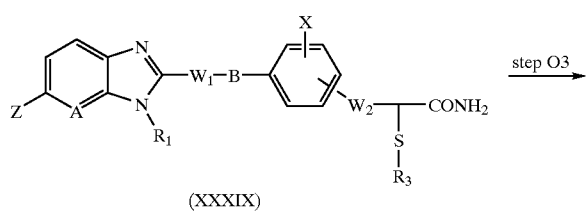
(XXXIX)
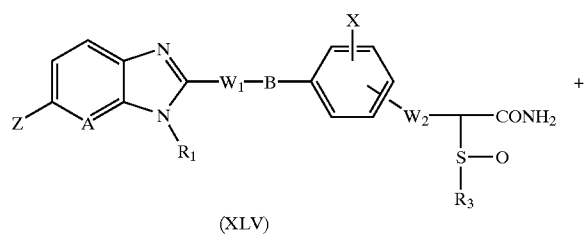
(XLV)

-continued

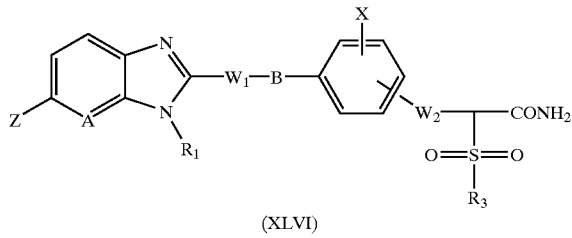

(XLVI)

wherein

R$_1$, R$_3$, W$_1$, W$_2$, X, Z, A, B and R independently represent as defined above.

Process O is a method for preparing compounds (XLI), (XLII), (XLIII), (XLIV), (XLV) and (XLVI) by oxidization of a sulfide.

In Step O1, compound (XXXVII) is allowed to react with a peroxide such as m-chloroperoxybenzoic acid, hydrogen peroxide or t-butylhydroperoxide in an inert solvent in the presence or absence of a base to obtain compounds (XLI) and (XLII). Any inert solvent can be used in the above-described reaction as long as it is inert in the reaction. Such inert solvents include, but are not limited to, for example: aliphatic hydrocarbons such as hexane, heptane, ligroin or petroleum ether; aromatic hydrocarbons such as benzene, toluene or xylene; halogenated hydrocarbons such as chloroform, dichloromethane, 1,2-dichloroethane or carbon tetrachloride; ethers such as diethyl ether, diisopropyl ether, tetrahydrofuran, dioxane, dimethoxyethane or di(ethylene glycol) dimethyl ether; amides such as dimethylformamide, dimethylacetamide or hexamethylphosphoric triamide; alcohols such as methanol, ethanol or propanol; water; and mixtures thereof. Halogenated hydrocarbons, alcohols, amides, and mixtures thereof are preferable, alcohols and halogenated hydrocarbons are more preferable, and alcohols and dichloromethane are most preferable.

Any bases which may not affect any other moieties than the target moiety in the compound can be used in the above-described reaction, including, for example: alkali metal carbonates such as lithium carbonate, sodium carbonate or potassium carbonate; alkali metal bicarbonates such as lithium bicarbonate, sodium bicarbonate or potassium bicarbonate; alkali metal hydroxides such as lithium hydroxide, sodium hydroxide or potassium hydroxide; metal alkoxides such as lithium methoxide, sodium methoxide, sodium ethoxide or potassium t-butoxide; and ammonia such as aqueous ammonia solution or concentrated ammonia-methanol. Alkali metal carbonates and alkali metal bicarbonates are preferable, and alkali metal bicarbonates are more preferable.

The reaction may typically be performed at from −20° C. to 150° C., and preferably from 0° C. to 60° C. though the reaction temperature may depend on the starting material compounds, solvents and/or other conditions to be used.

The reaction may typically be performed for from 1 minute to 1 day, and preferably from 5 minutes to 2 hours though the reaction time may depend on the starting material compounds, solvents, reaction temperature and/or other conditions to be used.

Step O2, which is a process for preparing compounds (XLIII) and (XLIV), can be performed by allowing compound (XXXVIII) to react with a peroxide such as m-chloroperoxybenzoic acid, hydrogen peroxide or t-butyl hydroperoxide in an inert solvent in the presence or absence of a base substantially according to Step O1 above.

Step O3, which is a process for preparing compounds (XLV) and (XLVI), can be performed by allowing compound (XXXIX) to react with a peroxide such as m-chloroperoxybenzoic acid, hydrogen peroxide or t-butyl hydroperoxide in an inert solvent in the presence or absence of a base substantially according to Step O1 above.

Process P

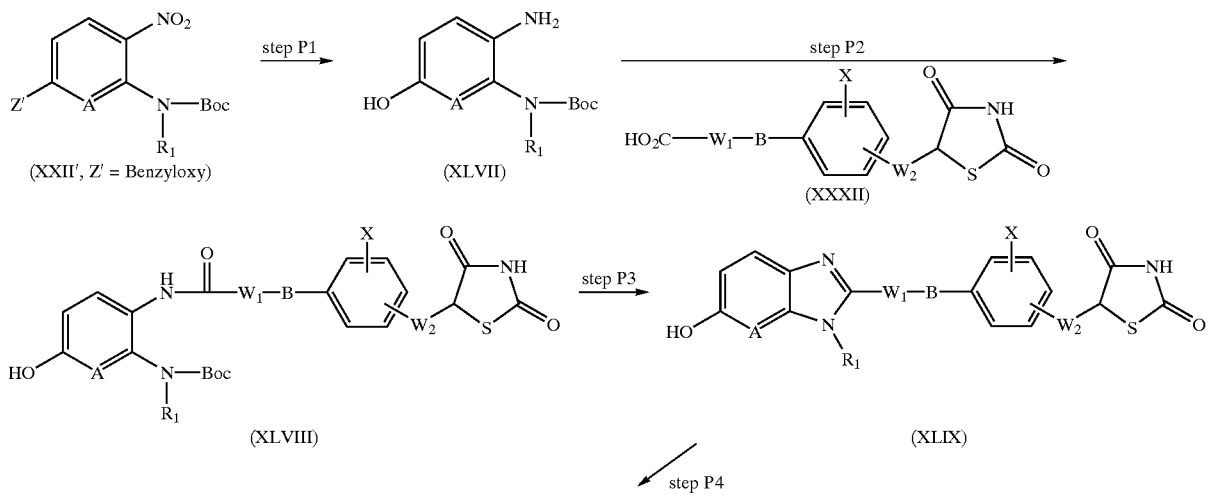

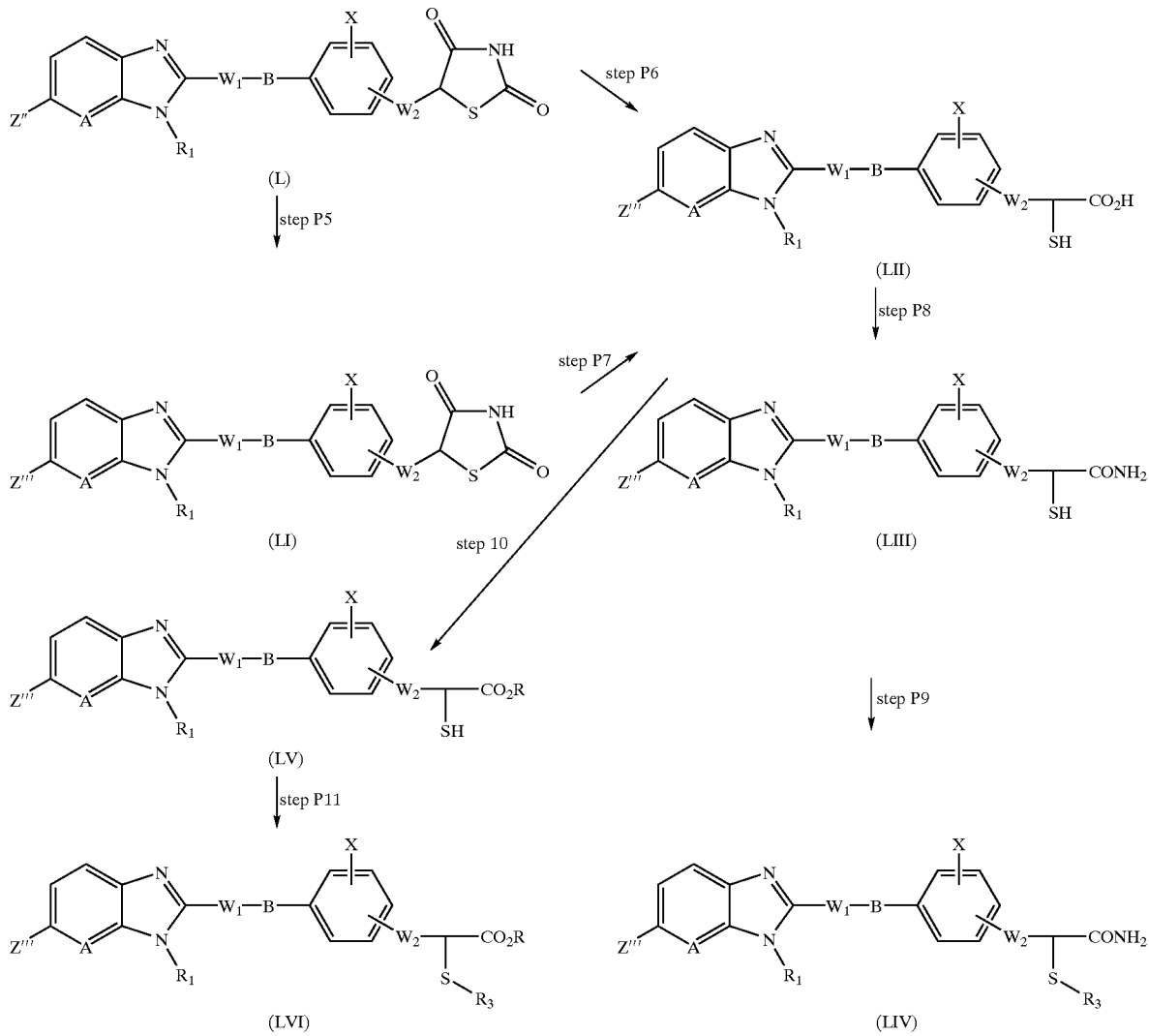

wherein $R_1$, $R_3$, $W_1$, $W_2$, X, Z, A, B and R independently represent as defined above, Z' represents a benzyloxy group within the definition of Z, Z" represents a saturated heterocyclic oxy group (which may have 1–5 substitution moieties $\alpha_1$) within the definition of Z where the substitution moiety or moieties $\alpha_1$ are protected, and Z''' represents a saturated heterocyclic oxy group (which may have 1–5 substitution moieties $\alpha_1$) within the definition of Z.

Process P is a process for preparing compounds having general formula (I) according to the present invention where Z represents a saturated heterocyclic oxy group (which may have 1–5 substitution moieties $\alpha_1$), i.e., compounds (LI), (LII), (LIII), (LIV), (LV) and (LVI).

In Step P1, compound (XXII') where Z' represents a benzyloxy group is allowed to react in an inert solvent substantially according to Step K2 described above to obtain compound (XLVII).

In Step P2, compound (XLVII) is allowed to react with compound (XXXII) in an inert solvent substantially according to Step B1 described above to obtain compound (XLVIII).

In Step P3, compound (XLVIII) is allowed to react in an inert solvent substantially according to Step B2 described above to obtain compound (XLIX).

In Step P4, compound (XLIX) is allowed to react with a compound having a Z group protected by substitution moiety or moieties $\alpha_1$ (e.g., methyl 1,2,3,4-tetra-O-acetyl-β-D-glucopyranuronate) in an inert solvent substantially according to J. Am. Chem. Soc., 77, 3310 (1955) or Chem. Pharm. Bull. 39(8), 2124–2125 (1991) to obtain compound (L).

In Step P5, compound (L) is subjected to hydrolysis in an inert solvent substantially according to J. Am. Chem. Soc., 77, 3310 (1955) or Chem. Pharm. Bull. 39(8), 2124–2125 (1991) to obtain compound (LI).

In Step P6, compound (L) is subjected to hydrolysis in an inert solvent substantially according to Step A1 described above to obtain compound (LII).

In Step P7, compound (LI) is subjected to hydrolysis in an inert solvent substantially according to Step A1 described above to obtain compound (LII).

In Step P8, compound (LII) is allowed to react with ammonia in an inert solvent substantially according to Step B1 described above to obtain compound (LIII).

In Step P9, compound (LIII) is allowed to react with a compound having general formula $R_3$-Halo (where $R_3$ is not hydrogen) in an inert solvent substantially according to Step D1 described above to obtain compound (LIV).

In Step P10, compound (LII) is subjected to esterification substantially according to Step N4 described above to obtain compound (LV).

In Step P11, compound (LV) is allowed to react with a compound having general formula $R_3$-Halo (where $R_3$ is not hydrogen) in an inert solvent substantially according to Step D1 described above to obtain compound (LVI).

In Step Q2, compound (LVII) is allowed to react with ammonia in an inert solvent substantially according to Step B1 described above to obtain compound (LVIII).

Step Q3, which is a process for preparing compounds (LIX) and (LX), can be performed by allowing compound (LVI) to react with a peroxide such as m-chloroperoxybenzoic acid, hydrogen peroxide or t-butyl hydroperoxide in an inert solvent in the presence or absence of a base substantially according to Step O1 above.

Step Q4, which is a process for preparing compounds (LXI) and (LXII), can be performed by allowing compound Process Q

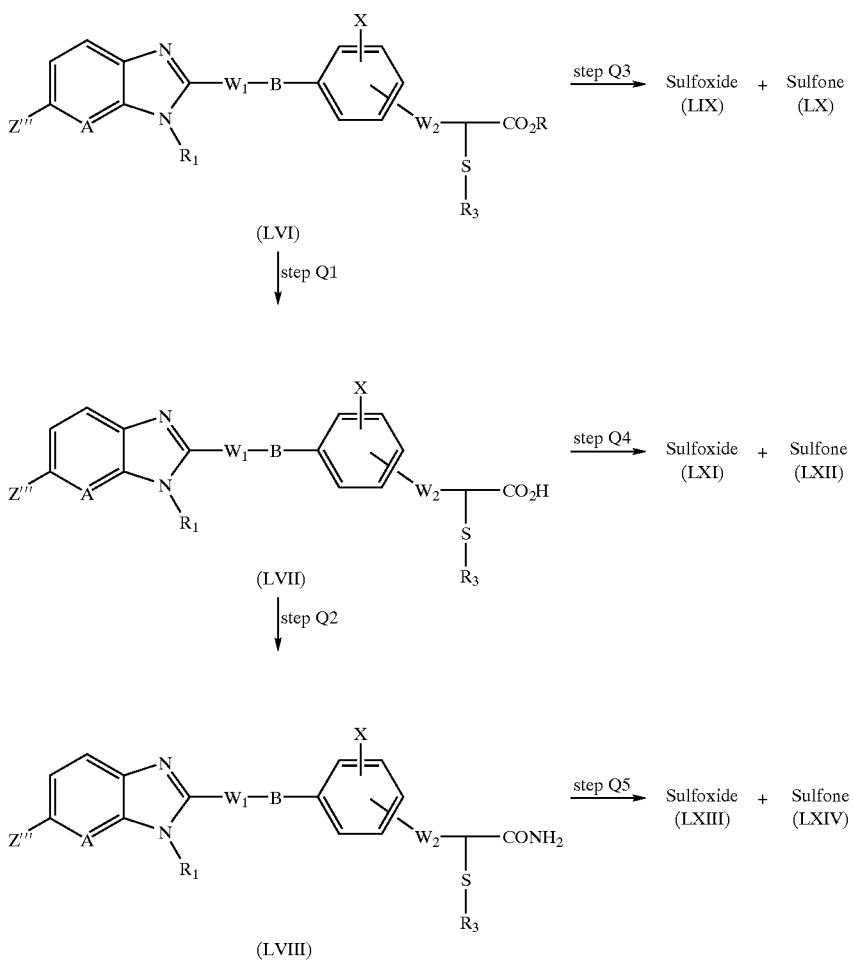

wherein $R_1$, $R_3$, $W_1$, $W_2$, X, Z''', A, B and R independently represent as defined above except that $R_3$ is not hydrogen.

In Process Q, sulfide compounds (LVII) and (LVIII) are prepared, and then compounds (LIX), (LX), (LXI), (LXII), (LXIII) and (LXIV) are prepared therefrom as well as from the sulfide compound (LVI) by oxidizing the sulfide compounds (LVI)–(LVIII) in the same manner as described in Process O.

In Step Q1, compound (LVI) is subjected to hydrolysis in an inert solvent substantially according to Step A1 described above to obtain compound (LVII).

(LVII) to react with a peroxide such as m-chloroperoxybenzoic acid, hydrogen peroxide or t-butyl hydroperoxide in inert solvent in the presence or absence of a base substantially according to Step O1 above.

Step Q5, which is a process for preparing compounds (LXIII) and (LXIV), can be performed by allowing compound (LVIII) to react with a peroxide such as m-chloroperoxybenzoic acid, hydrogen peroxide or t-butyl hydroperoxide in an inert solvent in the presence or absence of a base substantially according to Step O1 above.

Alternatively, compounds (I)–(IV) according to the present invention where Z represents a saturated heterocyclic oxy group (which may have 1–5 substitution moieties $α_1$) can also be synthesized according to the following process.

Process R

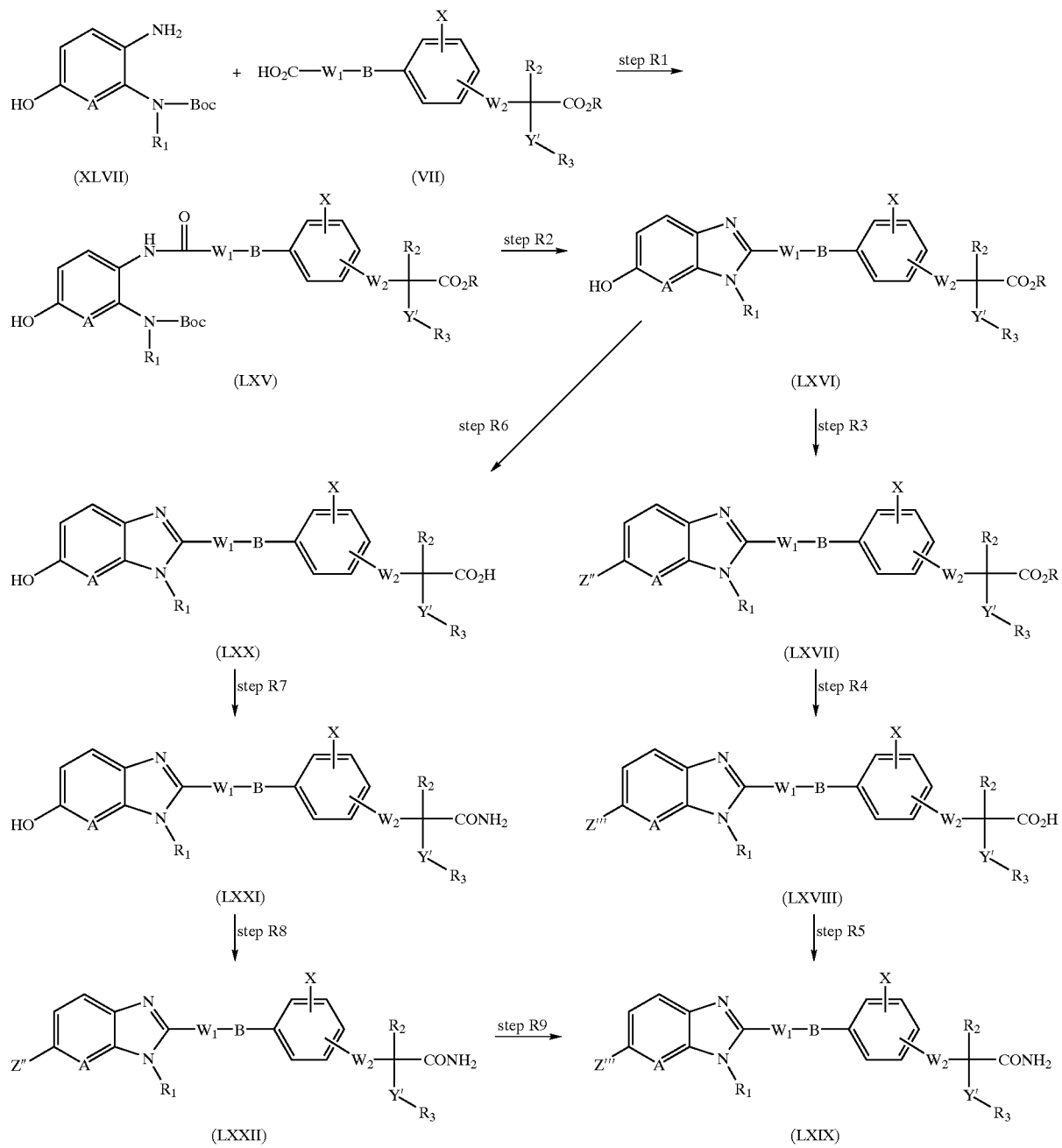

wherein $R_1$, $R_2$, $R_3$, $W_1$, $W_2$, X, Y', Z'', Z''', A, B and R independently represent as defined above.

Process R is a process for preparing compounds having general formula (I) or (IV) according to the present invention where Z represents a saturated heterocyclic oxy group (which may have 1–5 substitution moieties $\alpha_1$) which may be protected, i.e., compounds (LXVII), (LXVIII), (LXIX) or (LXXII).

In Step R1, compound (XLVII) is allowed to react with compound (VII) in an inert solvent substantially according to Step B1 described above to obtain compound (LXV).

In Step R2, compound (LXV) is allowed to react in an inert solvent substantially according to Step B2 described above to obtain compound (LXVI).

In Step R3, compound (LXVI) is allowed to react with a compound having a Z group protected by substitution moiety or moieties $\alpha_1$ (e.g., methyl 1,2,3,4-tetra-O-acetyl-β-D-glucopyranuronate) in an inert solvent substantially according to J. Am. Chem. Soc., 77, 3310 (1955) or Chem. Pharm. Bull. 39 (8), 2124–2125 (1991) to obtain compound (LXVII).

In Step R4, compound (LXVII) is subjected to hydrolysis in an inert solvent substantially according to J. Am. Chem. Soc., 77, 3310 (1955) or Chem. Pharm. Bull. 39 (8), 2124–2125 (1991) to obtain compound (LXVIII).

In Step R5, compound (LXVIII) is allowed to react with ammonia in an inert solvent substantially according to Step B1 described above to obtain compound (LXIX).

In Step R6, compound (LXVI) is subjected to hydrolysis in an inert solvent substantially according to Step A1 described above to obtain compound (LXX).

In Step R7, compound (LXX) is allowed to react with ammonia in an inert solvent substantially according to Step B1 described above to obtain compound (LXXI).

In Step R8, compound (LXXI) is allowed to react with a compound having a Z group protected by substitution moiety or moieties $\alpha_1$ (e.g., methyl 1,2,3,4-tetra-O-acetyl-β-D-glucopyranuronate) in an inert solvent substantially according to J. Am. Chem. Soc., 77, 3310 (1955) or Chem. Pharm. Bull. 39 (8), 2124–2125 (1991) to obtain compound (LXXII).

In Step R9, compound (LXXII) is subjected to hydrolysis in an inert solvent substantially according to J. Am. Chem. Soc., 77, 3310 (1955) or Chem. Pharm. Bull. 39 (8), 2124–2125 (1991) to obtain compound (LXIX).

Compounds (I)–(IV) where Z represents a hydroxy group can be synthesized according to the following process.

Process S

Process S is a process for preparing compounds (XXXV)–(XL) obtained in Process N and compounds (XXXVI)–(XLVI) obtained in Process O where Z represents a hydroxy group.

Compounds (VI) and (XXVII), which are starting materials in Processes N and O, where Z represents a hydroxy group can be subjected to reactions according to Processes N and O to obtain compounds (XXXV)–(XL) and (XLI)–(XLVI) where Z represents a hydroxy group.

Compound (VI) where Z represents a hydroxy group (i.e., compound (XLVI)) can be prepared according to step P1 described above.

Alternatively, starting material compounds having a substitution moiety or moieties protected may be used instead of those shown in the above-described chemical synthesis pathways and after reactions the protecting group or groups can be removed to obtain the target compounds shown in the pathways.

For example, when substitution moiety γ represents a hydroxy group, compounds which have protected hydroxy group(s) can be subjected to the above-described chemical reactions and then the protecting group(s) can be removed to obtain the target compounds shown in the above-described chemical synthesis pathways.

After completion of the reactions, the target compounds obtained in the respective steps may be collected from the reaction mixtures according to any conventional method. For example, the target compound can be collected by: appropriately neutralizing the reaction products; removing, if any, insoluble materials by filtration; then adding organic solvents which are not miscible with water (e.g. ethyl acetate); separating the organic phase containing the target compound which is then washed with, for example, water, and dried on anhydrous magnesium sulfate, anhydrous sodium sulfate, anhydrous sodium bicarbonate or the like; and removing solvent by distillation. The target compounds can be separated and purified by a suitable combination of any conventional methods for separation/purification of organic compounds such as recrystallization and reprecipitation, chromatography using appropriate eluant(s).

Further, the compounds according to the present invention can be obtained according, for example, to the conventional method described below.

Physiologically active compounds (e.g. compounds disclosed in Japanese Patent Application Laid-Open H9 (1997)-295970) may be administered to homeotherm and biological samples may be collected from the animal after a predetermined time. Next, target compound(s) in the biological sample may be isolated and purified by any separation method such as column chromatography to obtain the compound(s) according to the present invention.

The term "homeotherm" refers to an animal which is capable of thermoregulation to maintain its constant body temperature regardless of atmospheric temperature, including: warm blooded animals, e.g. mammals such as a human, dog, monkey, rabbit, guinea pig, rat or mouse; and birds such as a chicken.

The term "biological sample" includes, for example, plasma, urine, feces (bile), liver and kidney.

The above-described compounds (I)–(IV) according to the present invention and pharmacologically acceptable salts, esters or amides thereof have the following activities: PPARγ activation activity; insulin resistance improving activity; hypoglycemic activity; anti-inflammatory activity; immunoregulatory activity; aldose reductase inhibiting activity; 5-lipoxygenase inhibiting activity; inhibition of lipid peroxide expression; PPAR activation activity; anti-osteoporotic activity; leukotriene antagonistic activity; enhancement of adipose cell formation; inhibition of carcinoma cell proliferation; and calcium antagonistic activity.

The present invention provides treatment and/or prevention of, for example: diabetes mellitus; hyperlipidemia; obesity; impaired glucose tolerance; hypertension; fatty liver; diabetic complications such as retinopathy, nephrosis, neuropathy, cataract or coronary artery disease; arteriosclerosis; gestational diabetes mellitus; polycystic ovary syndrome; cardiovascular diseases such as ischemic heart disease; cell injury lesions including those caused by non-atherosclerosis or ischemic heat disease such as cerebral injury caused by stroke; gout; inflammatory diseases such as arthrosteitis, pain, fervesence, rheumatic arthritis, inflammatory enteritis, acne, sunburn, psoriasis, eczema, allergic disease, asthma, GI ulcer, cachexia, autoimmune disease and pancreatitis; cancer; osteoporosis; and cataract by administering to an animal (including a human) in need thereof, an effective amount of a compound of the formula (I)–(IV).

Further, pharmaceutical compositions which comprise at least one compound selected from the group consisting of the above-described compounds (I)–(IV) according to the present invention and pharmacologically acceptable salts, esters or amides thereof and at least one compound selected from the group consisting of RXR activators (RXR agonists), α-glucosidase inhibitors, aldose reductase inhibitors, biguanides, statine type compounds, squalene synthesis inhibitors, fibrate type compounds, LDL disassimilation promotors and angiotensin-converting enzyme-inhibitors (particularly preferable are compositions for prevention and/or treatment of diabetes or diabetic complication) are also useful.

The above-described compounds (I)–(IV) according to the present invention or pharmacologically acceptable salts, esters or amides thereof can be used for treatment or prevention of the above-described diseases by administering the compound alone or in combination with a suitable pharmacologically acceptable carrier in a suitable dosage form, such as tablets, capsules, granules, powders or syrups for oral administration, or injections or suppositories for parenteral administration. Other usual dosage forms, e.g., ointments and sprays, may be used for alternate administration routes.

Such formulations may be prepared according to any well known technique, and may also include carrier(s) such as excipients, lubricants, binders, disintegrators, stabilizers, corrigents and/or diluents. Excipients include both organic and inorganic excipients. Examples of organic excipients are, for example: glucose derivatives such as lactose, sucrose, glucose, mannitol and sorbitol; starch derivatives such as corn starch, potato starch, α starch and dextrin; cellulose derivatives such as crystalline cellulose; gum Arabic; dextran; and Pullulan. Examples of inorganic excipients are, for example: silicate derivatives such as light anhydrous silicic acid, synthetic aluminium silicate, calcium silicate and magnesium metaaluminosilicate; phosphates such as calcium hydrogen phosphate; carbonates such as calcium carbonate; and sulfates such as calcium sulfate. Lubricants include, for example: stearic acid and metal stearates such as calcium stearate and magnesium stearate; talc; colloidal silica; waxes such as bee gum or spermaceti; boric acid; adipic acid; sulfates such as sodium sulfate; glycol; fumaric acid; sodium benzoate; DL leucine; sodium fatty acid salt; lauryl sulfates such as lauryl sodium sulfate or lauryl magnesium sulfate; silicates such as silicic anhydride or silicic hydrate; and the above-described starch derivatives. Binders include, for example, hydroxypropyl cellulose, hydroxypropyl methylcellulose, polyvinylpyrrolidone, Macrogol and the above-described excipient compounds. Disintegrators include, for example: cellulose derivatives such as low substituted hydroxypropylcellulose, carboxymethyl cellulose, calcium carboxymethyl cellulose, internal-crosslinked sodium carboxymethyl cellulose; chemically modified starch-cellulose compounds such as carboxymethyl starch, sodium carboxymethyl starch or cross-linked polyvinylpyrrolidone. Stabilizers include, for example: p-hydroxybenzoic esters such as methylparaben or propylparaben; alcohols such as chlorobutanol, benzyl alcohol or phenylethyl alcohol; benzalkonium chloride; phenols such as phenol or cresol; thimerosal; dehydroacetic acid; and sorbic acid. Corrigents include sweeteners, souring agents and flavors which are commonly used in the art.

The dose will vary depending on the disease state, age of the patient, e.g. human, the chosen route of administration, etc. In the case of oral administration, a desirable single unit dose contains the compound of the present invention in an amount of 0.001 to 500 mg/kg of body weight and preferably from 0.01 to 50 mg/kg of body weight. In the case of intravenous administration, a desirable single unit dose contains the compound of the present invention in an amount of 0.005 to 50 mg/kg of body weight and preferably 0.05 to 5 mg/kg of body weight. It is desirable to administer the single unit dose one time or several times throughout the day depending on the conditions of the patient. Other dosage forms for other administration routes will also be within the aforesaid ranges and preferably in an amount of 0.01 to 50 mg/kg of body weight. Dosage for treatment or prevention of a specific patient in need thereof is determined by those skilled in the art by applying usual techniques.

The following examples, preparation examples and test examples are intended to further illustrate the present invention and are not intended to limit the scope of this invention.

EXAMPLE 1

Methyl 3-[4-[6-(4-adamantan-1-ylphenoxy)-1-methyl-1H-benzimidazol-2-ylmethoxy]phenyl]-2-(4-fluorobenzyloxy)propionate (methyl ester of exemplification compound number 1-1)

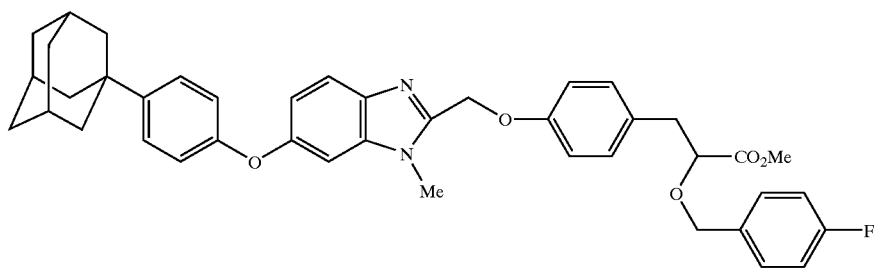

A mixture of methyl 3-[4-[4-(4-adamantan-1-yl)phenoxy)-2-(N-t-butoxycarbonyl-N-methylamino)phenylaminocarbonylmethoxy]phenyl-2-(4-fluorobenzyloxy)-propionate (0.8 g) and 4N hydrogen chloride/dioxane (20 ml) was stirred at room temperature for 1 hour. The solvent of the reaction mixture was evaporated under reduced pressure. The residue was neutralized with sodium hydrogencarbonate and extracted with ethyl acetate. The extract was washed with saturated aqueous sodium chloride solution and dried over anhydrous sodium sulfate. The ethyl acetate was evaporated under reduced pressure. The residue crystallized in hexane: ethyl acetate=4:1 solution and the crystals were isolated by filtration to afford the title compound (0.43 g, mp 118–120° C.).

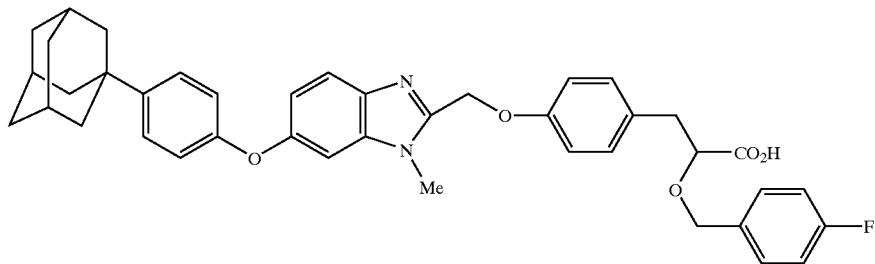

A mixture of methyl 3-[4-[6-(4-adamantan-1-ylphenoxy)-1-methyl-1H-benzimidazol-2-ylmethoxy]phenyl]-2-(4-fluorobenzyloxy)propionate (0.25 g), aqueous 2N sodium hydroxide solution (2 ml) and methanol (5 ml) was stirred at room temperature for 2 hours. To the reaction mixture was added tetrahydrofuran (5 ml) and the mixture was stirred for 4 hours. The reaction mixture was poured into water and neutralized with hydrochloric acid and sodium hydrogencarbonate and extracted with ethyl acetate. The extract was washed with saturated aqueous sodium chloride solution and dried over anhydrous sodium sulfate. The ethyl acetate was evaporated under reduced pressure. The residue crystallized in ethyl acetate and the crystals were isolated by filtration to afford the title compound (0.23 g, mp 148–149° C.).

EXAMPLE 3

Methyl 3-[4-[6-(3,5-di-t-butyl-4-hydroxyphenylthio)-1-methyl-1H-benzimidazol-2-ylmethoxy]phenyl]-2-(4-fluorobenzyloxy)propionate (methyl ester of exemplification compound number 1-86)

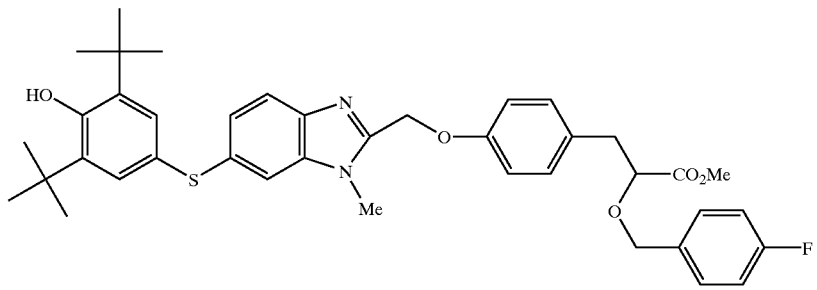

A mixture of methyl 3-[4-[4-(3,5-di-t-butyl-4-hydroxyphenylthio)-2-(N-t-butoxycarbonyl-N-methylamino)phenylaminocarbonylmethoxy]phenyl]-2-(4-fluorobenzyloxy)propionate (0.5 g) and 4N hydrogen chloride/dioxane was treated in a similar procedure to that described in Example 1 to afford the title compound (0.24 g, Rf=0.15 (thin layer chromatography on silica gel using hexane: ethyl acetate=3:1 as the eluant)).

EXAMPLE 4

3-[4-[6-(3,5-Di-t-butyl-4-hydroxyphenylthio)-1-methyl-1H-benzimidazol-2-ylmethoxy]phenyl]-2-(4-fluorobenzyloxy)propionic acid (exemplification compound number 1-86)

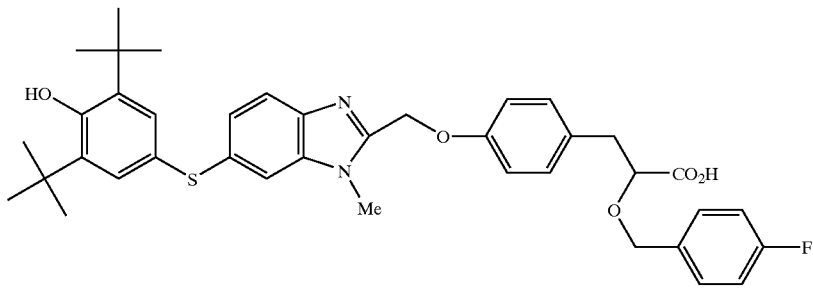

Reaction and isolation were conducted in a similar procedure to that described in Example 2 using methyl 3-[4-[6-(3,5-di-t-butyl4-hydroxyphenylthio)-1-methyl-1H-benzimidazol-2-ylmethoxy]phenyl]-2-(4-fluorobenzyloxy) propionate (0.22 g), aqueous 2N sodium hydroxide solution (2 ml) and methanol (5 ml) to afford the title compound (0.13 g, mp 40–46° C.).

EXAMPLE 5

Methyl 4-(1-methyl-6-methoxy-1H-benzimidazol-2-ylmethoxy)phenyllactate (methyl ester of exemplification compound number 1-177)

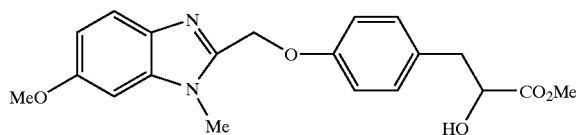

A mixture of 4-(5,5-dimethyl-2-oxodioxolan-3-ylmethyl)phenoxyaceto-N-[2-(N-t-butoxycarbonyl-N-methylamino)4-methoxyphenyl]amide (4.5 g), methanol (40 ml) and 4N hydrogen chloride/dioxane (40 ml) was treated in a similar procedure to that described in Example 1 and the residue was recrystallized from dimethylformamide/ethyl acetate to afford the title compound (1.84 g, mp 169–170° C.).

EXAMPLE 6

4-(1-Methyl-6-methoxy-1H-benzimidazol-2-ylmethoxy)phenyllactic acid hydrochloride (hydrochloride of exemplification compound number 1-177)

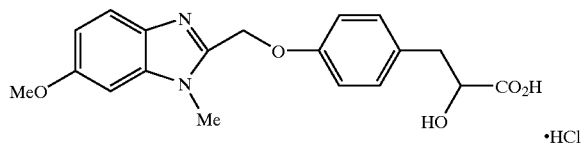

A mixture of methyl 4-(1-methyl-6-methoxy-1H-benzimidazol-2-ylmethoxy)phenyllactate (0.2 g), methanol (5 ml) and 4N hydrogen chloride/dioxane (10 ml) was stirred at room temperature for 2 hours. The reaction mixture was concentrated to give crystals. The crystals were washed with a mixture of methanol and ether to afford the title compound (0.2 g, mp 193–195° C.).

EXAMPLE 7

4-(1-Methyl-6-methoxy-1H-benzimidazole-2-ylmethoxy)phenyllactic acid (exemplification compound number 1-177)

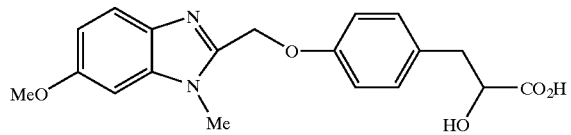

A mixture of methyl 4-(1-methyl-6-methoxy-1H-benzimidazol-2-ylmethoxy)phenyllactate (0.15 g), concentrated hydrochloric acid (2 ml) and dioxane (2 ml) was heated at reflux for 3 hours. The reaction mixture was concentrated and the water of the residue was removed by azeotropic distillation in dioxane and the crystals were isolated by filtration to afford the title compound (0.15 g, mp 216–218° C.).

EXAMPLE 8

Methyl 2-ethoxy-3-[4-(1-methyl-6-methoxy-1H-benzimidazol-2-ylmethoxy)phenyl]propionate (methyl ester of exemplification compound number 1-179)

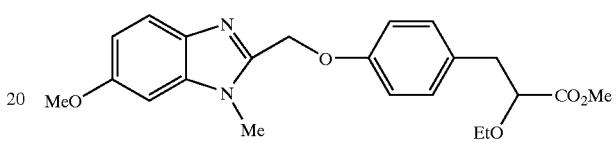

A mixture of methyl 4-(1-methyl-6-methoxy-1H-benzimidazol-2-ylmethoxy)phenyl]propionate (0.6 g), methyl iodide (0.52 ml), silver oxide (0.88 g) and dimethylformamide (15 ml) was heated for 4.5 hours and then stirred at room temperature overnight. The insoluble material in the reaction mixture was removed by filtration and the filtrate was concentrated. The residue was partitioned between ethyl acetate and water and the extract was washed with saturated aqueous sodium chloride solution and dried over anhydrous sodium sulfate. The ethyl acetate was evaporated under reduced pressure. The residue was chromatographed on a silica gel column using hexane:ethyl acetate=2:3 as the eluant to afford the title compound (0.15 g, mp 88–92° C.).

EXAMPLE 9

2-Ethoxy-3-[4-(1-methyl-6-methoxy-1H-benzimidazol-2-ylmethoxy)phenyl]propionic acid hydrochloride (hydrochloride of exemplification compound number 1-179)

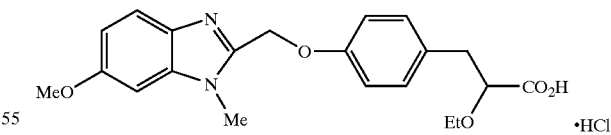

A mixture of methyl 2-ethoxy-3-[4-(1-methyl-6-methoxy-1H-benzimidazol-2-ylmethoxy)phenyl]propionate (0.17 g), concentrated hydrochloric acid (2 ml) and dioxane (2 ml) was heated at reflux for 1.5 hours. The reaction mixture was concentrated and the water of the residue was removed by azeotropic distillation in dioxane and the crystals were isolated by filtration to afford the title compound (0.16 g, mp 143–146° C.).

EXAMPLE 10

Methyl 4-[6-(4hydroxy-2,3,5-trimethylphenoxy)-1-methyl-1H-benzimidazol-2-ylmethoxy]phenyllactate (methyl ester of exemplification compound number 1-170)

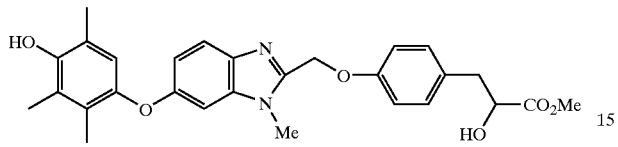

The reaction was conducted in a similar procedure in that of Example 1 using 4-(5,5-dimethyl-2-oxodioxolan-3-ylmethyl)phenoxyaceto-N-[2-(N-t-butoxycarbonyl-N-methylamino)-4-(4-methoxymethoxy-2,3,5-trimethylphenoxy)phenyl]amide (5.98 g), methanol (50 ml) and 4N hydrogen chloride/dioxane (50 ml). The solvent of the reaction mixture was evaporated under reduced pressure and the residue was neutralized with sodium hydrogencarbonate and extracted with ethyl acetate. The extract was washed with saturated aqueous sodium chloride solution and dried over anhydrous sodium sulfate. The ethyl acetate was evaporated under reduced pressure. The residue was chromatographed on a silica gel column using hexane: ethyl acetate=1:2–1:3 as the eluant to afford the title compound (3.15 g, mp 172–173° C.).

EXAMPLE 11

Methyl 4-[6-(4-hydroxy-2,3,5-trimethylphenoxy)-1-methyl-1H-benzimidazol-2-ylmethoxy]phenyllactate hydrochloride (methyl ester hydrochloride of exemplification compound number 1-170)

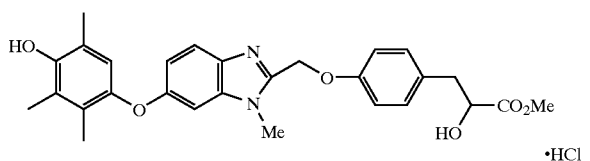

The title compound (0.195 g, mp 113–119° C.) was obtained by a similar procedure to that described in Example 6 using methyl 4-[6-(4-hydroxy-2,3,5-trimethylphenoxy)-1-methyl-1H-benzimidazol-2-ylmethoxy]phenyllactate (0.2 g), methanol (2 ml) and 4N hydrogen chloride/dioxane (5 ml).

EXAMPLE 12

Methyl 4-[6-(3,5-di-t-butyl-4-hydroxyphenylthio)-1-methyl-1H-benzimidazol-2-ylmethoxy]phenyllactate (methyl ester of exemplification compound number 1-87)

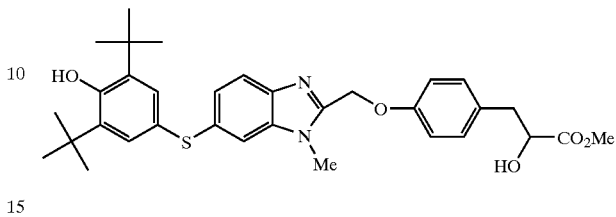

The title compound (2.6 g, mp 155–156° C.) was obtained by a similar procedure to that described in Example 1 using 4-(5,5-dimethyl-2-oxodioxolan-3-ylmethyl)phenoxyaceto-N-[2-(N-t-butoxycarbonyl-N-methylamino)-4-(3,5-di-t-butyl-4-hydroxyphenylthio)phenyl]amide (5.1 g), methanol (40 ml) and 4N hydrogen chloride/dioxane (40 ml).

EXAMPLE 13

Methyl 4-[6-(3,5-di-t-butyl-4-hydroxyphenylthio)-1-methyl-1H-benzimidazol-2-ylmethoxy]phenyllactate hydrochloride (methyl ester Hydrochoride of exemplification compound number 1-87)

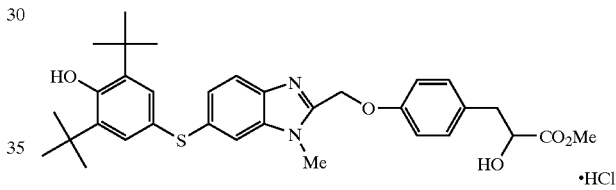

The title compound (0.19 g, mp 135–139° C.) was obtained by a similar reaction and purification to those in Example 6 using methyl 4-[6-(3,5-di-t-butyl-4-hydroxyphenylthio)-1-methyl-1H-benzimidazol-2-ylmethoxy]phenyllactate (0.2 g) and 4N hydrogen chloride/dioxane (10 ml)

EXAMPLE 14

4(6-Methoxy-1-methyl-1H-benzimidazol-2-ylmethoxy)phenylalanine methyl ester (methyl ester of exemplification compound number 3-177)

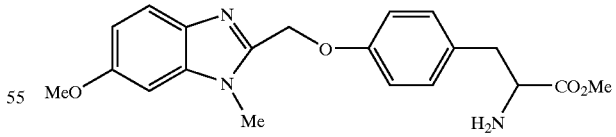

A mixture of methyl 2-azido-3[4-(6-methoxy-1-methyl-1H-benzimidazol-2-yl)phenyl]propionate (2.42 g) in tetrahydrofuran (20 ml) and triphenylphosphine (1.6 g) was stirred at room temperature for 1.5 hours. To the reaction mixture was added water (5 ml) and the mixture was stirred at 60° C. for 1 hour. The reaction mixture was partitioned between ethyl acetate and water. The extract was washed with saturated aqueous sodium chloride solution and dried over anhydrous magnesium sulfate. The ethyl acetate was evaporated under reduced pressure. The residue was chromatographed on a silica gel column using ethyl acetate-tetrahydrofuran as the eluant to afford the title compound (1.63 g, mp 108–111° C.).

EXAMPLE 15

N-(2-Benzoylphenyl)-4-(6-methoxy-1-methyl-1H-benzimidazol-2-ylmethoxy)phenylalanine methyl ester (methyl ester of exemplification compound number 3-188)

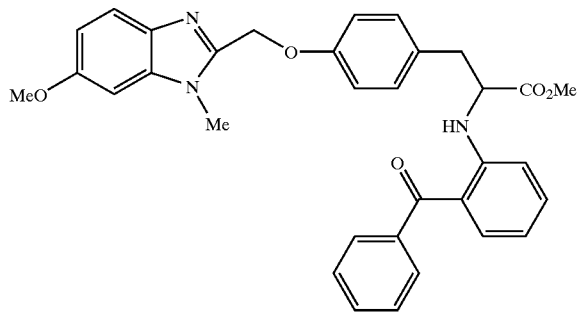

A mixture of 4-(6-methoxy-1-methyl-1H-benzimidazol-2-ylmethoxy)phenylalanine methyl ester (1.1 g), 2-benzoylcyclohexanone (0.7 g), palladium on carbon (10%, 0.2 g) and anisole (15 ml) was heated at reflux for 21 hours. Insoluble material of the reaction mixture was removed by filtration and the anisole of the filtrate was evaporated under reduced pressure. The residue was chromatographed on a silica gel column using hexane:ethyl acetate=1:2 as the eluant to afford the title compound (0.95 g, Rf=0.51 (thin layer chromatography on silica gel using hexane:ethyl acetate=1:3 as the eluant)).

EXAMPLE 16

N-(2-Benzoylphenyl)-4-(6-methoxy-1-methyl-1H-benzimidazol-2-ylmethoxy)phenylalanine methyl ester hydrochloride (methyl ester hydrochloride of exemplification compound number 3-188)

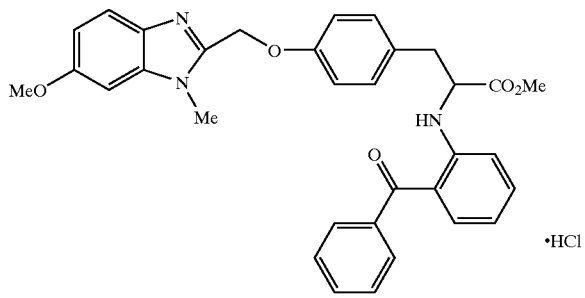

The title compound (0.195 g, mp 132–136° C.) was obtained by a similar procedure to that described in Example 6 using N-(2-benzoylphenyl)-4-(6-methoxy-1-methyl-1H-benzimidazol-2-ylmethoxy)phenylalanine methyl ester (0.45 g), methanol (2 ml) and 4N hydrogen chloride/dioxane (10 ml).

EXAMPLE 17

N-(2-Benzoylphenyl)-4-(6-methoxy-1-methyl-1H-benzimidazol-2-ylmethoxy)phenylalanine (exemplification compound number 3-188)

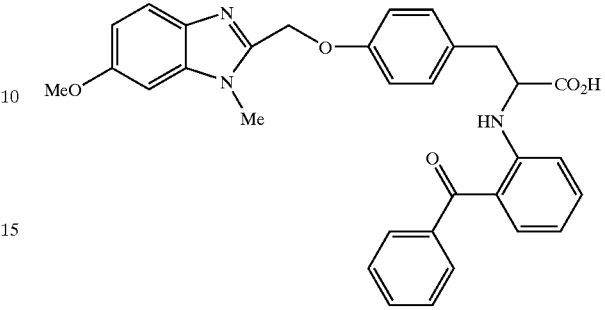

The title compound (0.44 g, mp 140–146° C.) was obtained by a similar procedure to that described in Example 6 using N-(2-benzoylphenyl)-4-(6-methoxy-1-methyl-1H-benzimidazol-2-ylmethoxy)phenylalanine methyl ester (0.45 g), concentrated hydrochloric acid (5 ml) and dioxane (5 ml).

EXAMPLE 18

4-(6-Methoxy-1-methyl-1H-benzimidazol-2-ylmethoxy)phenylalanine dihydrochloride (dihydrochloride of exemplification compound number 3-177)

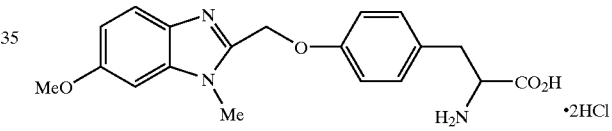

The title compound (0.11 g, mp 235–237° C. (dec)) was obtained by a similar procedure to that described in Example 6 using 4-(6-methoxy-1-methyl-1H-benzimidazol-2-ylmethoxy)phenylalanine methyl ester (0.12 g), concentrated hydrocloric acid (2 ml) and dioxane (2 ml).

EXAMPLE 19

4-[6-(4-Amino-3,5-dimethylphenoxy)-1-methyl-1H-benzimidazol-2-ylmethoxy]-N-(2-benzoylphenyl) phenylalanine methyl ester (methyl ester of exemplification compound number 3-285)

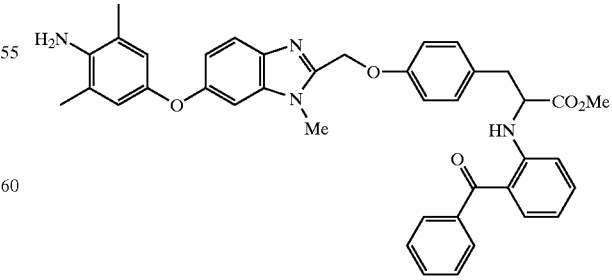

The title compound (0.62 g, Rf=0.39: thin layer chromatography on silica gel (LiChroprep NH2 (Merck)) using hexane:ethyl acetate=1:2 as the eluant) was obtained by a similar procedure to that described in Example 6 using 4-[2-(N-t-butoxycarbonyl-N-methylamino)-4-(4-t-butoxycarbonylamino-3,5-dimethylphenoxy)phenylaminocarbonylmethoxy]-N-(2-benzoylphenyl)phenylalanine methyl ester (1.05 g), methanol (5 ml) and 4N hydrogen chloride/dioxane (10 ml) and then by liquid chromatography (LiChroprep NH2 (Merck)) using hexane:ethyl acetate=1:2 as the eluant.

The reaction mixture was neutralized with 1N hydrochloric acid and partitioned between ethyl acetate and water. The extract was washed with saturated aqueous sodium chloride solution and dried over anhydrous sodium sulfate and then concentrated under reduced pressure. The residue was chromatographed on LiChroprepDIOL (Merck) using ethyl acetate as the eluant to give a yellow material. To a solution of the material in tetrahydrofuran (3 ml) was added 4N hydrogen chloride/dioxane (1 ml) to give crystals. The crystals were isolated by filtration to afford the title compound (0.11 g, mp 148–155° C.).

EXAMPLE 21

4-[6-[4-(4-Trifluoromethylphenylureido)-3,5-dimethylphenoxy]-1-methyl-1H-benzimidazol-2-ylmethoxy]-N-(2-benzoylphenyl)phenylalanine methyl ester (methyl ester of exemplification compound number 3-299)

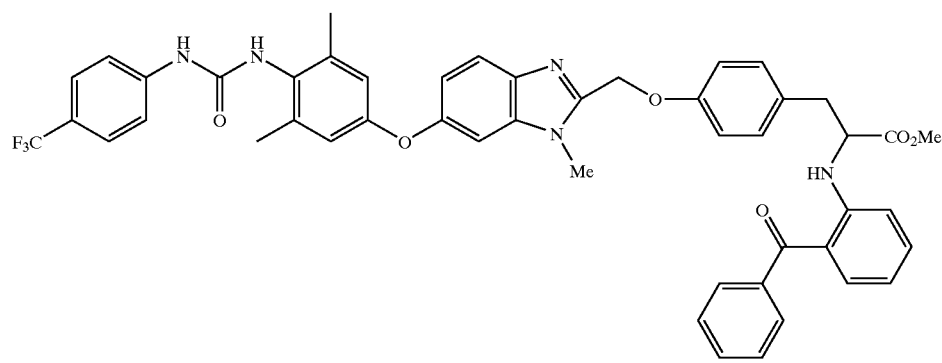

EXAMPLE 20

4-[6-(4Amino-3,5dimethylphenoxy)-1-methyl-1H-benzimidazol-2-ylmethoxy]-N-(2-benzoylphenyl)phenylalanine dihydrochloride (dihydrochloride of exemplification compound number 3-285)

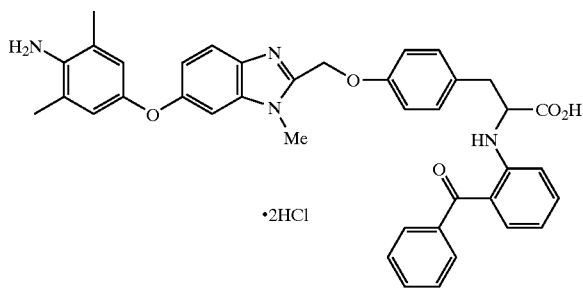

A mixture of 4-[6-(4-amino-3,5-dimethylphenoxy)-1-methyl-1H-benzimidazol-2-ylmethoxy]-N-(2-benzoylphenyl)phenylalanine methyl ester (0.25 g), lithium hydroxide monohydrate (0.04 g), tetrahydrofuran (5 ml) and water (2 ml) was stirred at room temperature for 3 hours.

To a solution of 4-[6-(4-amino-3,5-dimethylphenoxy)-1-methyl-1H-benzimidazol-2-ylmethoxy]-N-(2-benzoylphenyl)phenylalanine methyl ester (0.35 g) in tetrahydrofuran (5 ml) was added 4-trifluorophenylisocyanate (0.1 ml). The mixture was stirred at room temperature for 20 hours and then was concentrated under reduced pressure. The residue was chromatographed on LiChroprepDIOL (Merck) using hexane:ethyl acetate=1:3 as the eluant to afford the title compound (0.43 g, Rf=0.59: thin layer chromatography on silica gel (LiChroprepDIOL (Merck)) using ethyl acetate as the eluant).

EXAMPLE 22

4-[6-[4-(4-Trifluoromethylphenylureido)-3,5-dimethylphenoxy]-1-methyl-1H-benzimidazol-2-ylmethoxy]-N-(2-benzoylphenyl)phenylalanine (exemplification compound number 3-299)

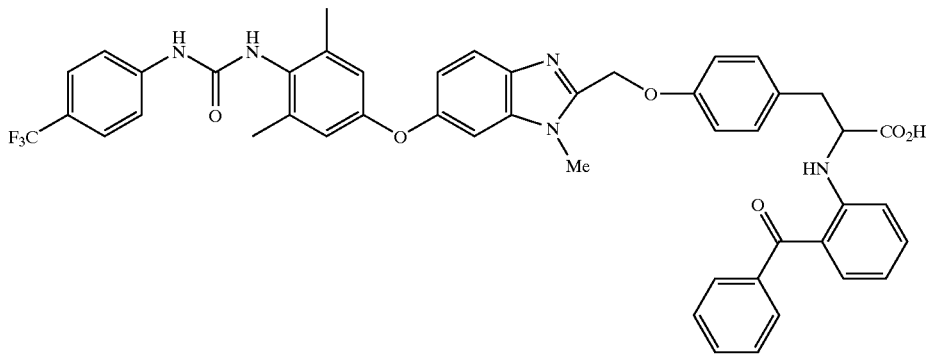

A mixture of 4-[6-[4—4-trifluoromethylphenylureido)-3,5-dimethylphenoxy]-1-methyl-1H-benzimidazol-2-ylmethoxy]-N-(2-benzoylphenyl)phenylalanine methyl ester (0.4 g), lithium hydroxide monohydrate (0.042 g), tetrahydrofuran (5 ml) and water (2 ml) was sired at room temperature for 4 hours and then allowed to stand for 2 days. The reaction mixture was neutralized with 1N hydrochloric acid and partitioned between ethyl acetate and water. The extract was washed with saturated aqueous sodium chloride solution and dried over anhydrous sodium sulfate and then concentrated under reduced pressure. To a solution of the residual yellow material in tetrahydrofuran (10 ml) was added 4N hydrogen chloride/dioxane (4 ml) and then the solvent was evaporated under reduced pressure. To the residue was added ether to give crystals. The crystals were isolated by filtration to afford the title compound (0.38 g, mp 165–172° C.).

EXAMPLE 23

N-Methanesulfonyl-4-(6-methoxy-1-methyl-1H-benzimidazol-2-ylmethoxy)phenylalanine methyl ester (methyl ester of exemplification compound number 3-261)

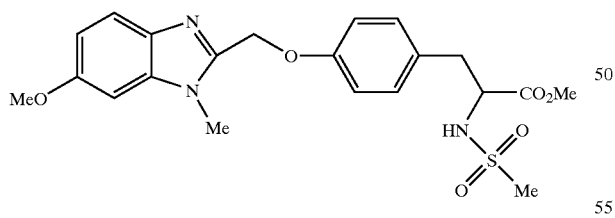

To a solution of 4-(6-methoxy-1-methyl-1H-benzimidazol-2-ylmethoxy)phenylalanine methyl ester (0.2 g) in tetrahydrofuran (6 ml) and dimethylformamide (3 ml) were added successively pyridine (0.09 ml) and methanesulfonic anhydride (0.14 g). The mixture was stirred at room temperature for 3 hours and was partitioned between ethyl acetate and water. The extract was washed with saturated aqueous sodium chloride solution, dried over anhydrous magnesium sulfate and concentrated under reduced pressure to give crystals. The crystals were isolated by filtration to afford the title compound (0.12 g, mp 168–171° C.).

EXAMPLE 24

N-Methanesulfonyl-4-(6-methoxy-1-methyl-1H-benzimidazol-2-ylmethoxy)phenylalanine hydrochloride (hydrochloride of exemplification compound number 3-261)

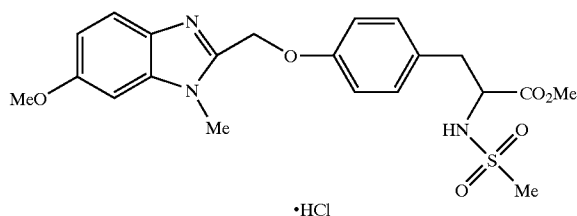

The title compound (0.11 g, mp 211–217 (dec)) was obtained by a similar procedure to that described in Example 6 using N-methanesulfonyl-4-(6-methoxy-1-methyl-1H-benzimidazol-2-ylmethoxy)phenylalanine methyl ester (0.11 g), concentrated hydrochloric acid (1 ml) and dioxane (4 ml).

EXAMPLE 25

Ethyl 3-[4-(6-methoxy-1-methyl-1H-benzimidazol-2-ylmethoxy)phenyl]-2-mercaptopropionate (ethyl ester of exemplification compound number 5-1)

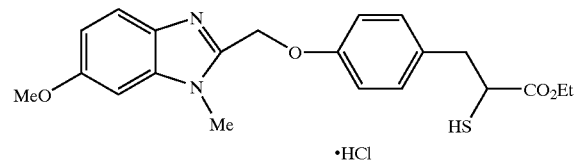

A solution of potassium hydroxide (30 g) in water (150 ml) was added to a suspension of 5-[4-(6-methoxy-1-methyl-1H-benzimidazol-2-ylmethoxy)benzyl]thiazolidin-2,4-done hydrochloride (8.0 g) in ethanol (150 ml). The mixture was stirred at 75° C. for 4 hours and poured into ice-water and acidified with hydrochloric acid and stirred for 30 minutes to give crystals. The crystals were isolated by filtration and washed with water and dried under reduced pressure.

A solution of the crystals in anhydrous ethanol (100 ml) and 4N hydrogen chloride/dioxane (200 ml) was allowed to stand at room temperature for 2 days. The solvent was evaporated under reduced pressure. To the residue was added water and the mixture was neutralized with aqueous sodium hydrogencarbonate solution and then partitioned between ethyl acetate and water. The extract was washed with saturated aqueous sodium chloride solution and dried over anhydrous sodium sulfate and then concentrated under reduced pressure. The residue was chromatographed on a LiChroprepNH2 (Merck) column using hexane:ethyl acetate=4:1 as the eluant to afford the title compound (3.93 g, Rf=0.45: thin layer chromatography on silica gel (LiChroprepNH2 (Merck)) using hexane:ethyl acetate=1:5 as the eluant).

EXAMPLE 26

Ethyl 3-[4-(6-methoxy-1-methyl-1H-benzimidazol-2-ylmethoxy)phenyl]-2-methylthiopropionate (ethyl ester of exemplification compound number 5-4)

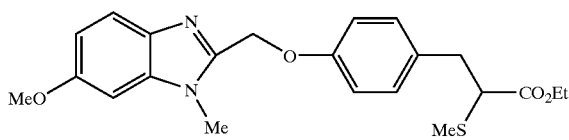

To a solution of ethyl 3-[4-(6-methoxy-1-methyl-1H-benzimidazol-2-ylmethoxy)phenyl]-2-mercaptopropionate (3.9 g) in tetrahydrofuran (80 ml) were added successively methyl iodide (0.87 ml) and triethylamine (1.94 ml). The mixture was allowed to stand overnight. To the mixture was further added methyl iodide (0.6 ml) and triethylamine (1.3 ml) and then the mixture was stirred for 70 minutes. The solvent of the reaction mixture was evaporated under reduced pressure. The residue was partitioned between ethyl acetate and water. The extract was washed with saturated aqueous sodium chloride solution and dried over anhydrous magnesium sulfate and then concentrated under reduced pressure. The residue was chromatographed on a silica gel column using hexane:ethyl acetate=1:1 as the eluant to afford the title compound (3.58 g, Rf=0.45: thin layer chromatography on silica gel using hexane:ethyl acetate=1:1 as the eluant) which was allowed to stand at room temperature to give a solid (mp 74–76° C.).

EXAMPLE 27

3-[4-(6-Methoxy-1-methyl-1H-benzimidazol-2-ylmethoxy)phenyl]-2-methylthiopropionic acid hydrochloride (hydrochloride of exemplification compound number 5-4)

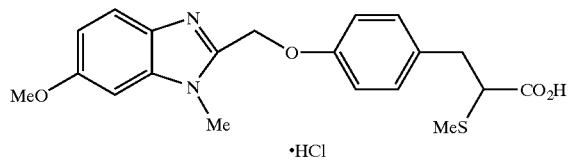

To a solution of ethyl 3-[4-(6-methoxy-1-methyl-1H-benzimidazol-2-ylmethoxy)phenyl]-2-methylthiopropionate (2.0 g) in tetrahydrofuran (25 ml) were added successively potassium hydroxide monohydrate (0.42g), and dimethylformamide (5 ml). The mixture was stirred at room temperature for 2 hours. After addition of potassium hydroxide (0.42 g) and water (5 ml) the mixture was stirred at room temperature for 20 minutes. And then after addition of dimethylformamide (5 ml) the mixture was further stirred at room temperature for 1 hour and allowed to stand over night. To the reaction mixture was further added potassium hydroxide (0.42 g), water (5 ml) and dimethylformamide (5 ml) and the the mixture was stirred at 75° C. for 8 hours. The reaction mixture was poured into 1N hydrochloric acid (800 ml), stirred for 30 minutes and filtrated to give crystals. The crystals were washed successively with water, acetone and ethyl acetate and dried under reduced pressure to afford the title compound (1.27 g, mp 201–206° C.).

EXAMPLE 28

3-[4-(6-Methoxy-1-methyl-1H-benzimidazol-2-ylmethoxy)phenyl]-2-methylthiopropionic amide (amide of exemplification compound number 5-4)

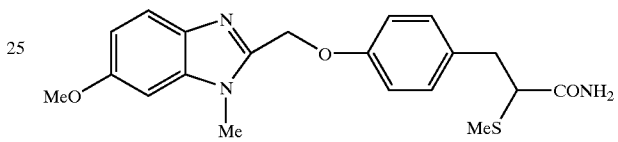

To a mixture of 3-[4-(6-methoxy-1-methyl-1H-benzimidazol-2-ylmethoxy)phenyl]-2-methylthiopropionic acid (1.1 g), tetrahydrofuran (15 ml) and dimethylformamide (15 ml) were added successively triethylamine (0.82 ml) and ethyl chloroformate (0.28 ml). The mixture was stirred at room temperature for 30 minutes. After addition of aqueous ammonia solution (5 ml, 28%) the mixture was stirred at room temperature for 15 minutes and allowed to stand overnight. The solvent of the reaction mixture was evaporated under reduced pressure. The residue was partitioned between ethyl acetate and water. The extract was washed with saturated aqueous sodium chloride solution and dried over anhydrous magnesium sulfate and concentrated under reduced pressure. The residue was washed with ethyl acetate and then recrystallized from a mixture of ethanol and ethyl acetate to afford the title compound (0.45 g, mp 204–206° C.).

EXAMPLE 29

3-[4-(6-Methoxy-1-methyl-1H-benzimidazol-2-ylmethoxy)phenyl]-2-methylsulfenylpropionic amide (amide of exemplification compound number 5-21) and 3-[4-(6-methoxy-1-methyl-1H-benzimidazol-2-ylmethoxy)phenyl]-2-methylsulfonylpropionic amide (amide of exemplification compound number 5-22)

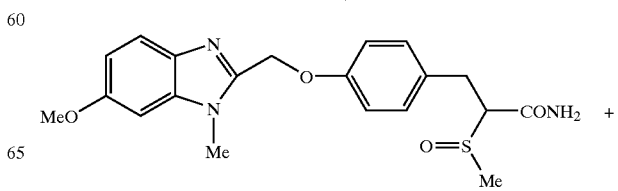

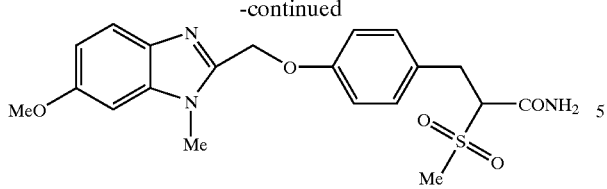

3-[4-(6-Methoxy-1-methyl-1H-benzimidazol-2-ylmethoxy)phenyl]-2-methylthiopropionic amide (0.35 g) was added to sulfolane (8 ml) and methylene chloride (15 ml). To the mixture was added successively sodium hydrogencarbonate (84 mg) and m-chloroperoxybenzoic acid (0.22 g). This mixture was stirred at room temperature for 1.5 hours. Aqueous sodium sulfate solution (5 ml, 2%) was added to the reaction mixture and the mixture was stirred at room temperature for 10 minutes. The mixture was partitioned between ethyl acetate and water. The extract was washed with saturated aqueous sodium chloride solution, dried over anhydrous magnesium sulfate and concentrated under reduced pressure. The residue was chromatographed on a LiChroprepNH2 (Merck) column using ethanol:ethyl acetate=1:15 as the eluant to give the title compounds (3.93 g, Rf=0.45: thin layer chromatography on a silica gel plate (LiChroprepNH2 (Merck)) using hexane:ethyl acetate=1:5 as the eluant) as crystals. The crystals were recrystallized from a mixture of ethanol and ethyl acetate to afford 3-[4-(6-methoxy-1-methyl-1H-benzimidazol-2-ylmethoxy)phenyl]-2-methylsulfenylpropionic amide (0.14 g, mp 188–190° C.) and 3-[4-(6-methoxy-1-methyl-1H-benzimidazol-2-ylmethoxy)phenyl]-2-methylsulfonylpropionic amide (0.12 g, mp 233–236° C.).

EXAMPLE 30

3-[4-[6-(β-D-Glucopyranosyloxyuronic acid)-1-methyl-1H-benzimidazol-2-ylmethoxy]phenyl]-2-methylthiopropionic amide (amide of exemplification compound number 5-48)

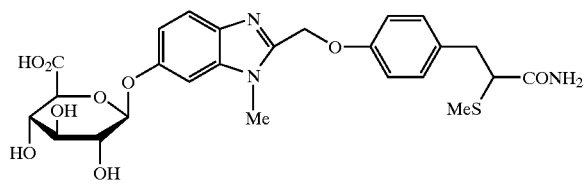

5-[4-[6-Methoxy-1-methyl-1H-benzimidazol-2-ylmethoxy]benzyl]thiazolidine-2,4-dione hydrochloride (5 mg/kg) was orally administered to a rat and bile obtained from the rat was collected from 0 through 24 hours. The bile was lyophylized and the residue was chromatographed on an ODS column (packing agent: ODS-A 120-S-75 a product of YMS Co., Ltd.) using a gradient elution of water (pH 4 prepared with 1 mol/ml hydrochloric acid):acetonitrile= 100:0 to 60:40 as the eluant to give a crude metabolite. The crude metabolite was further purified by HPLC to afford the title compound (m/z 548 [M+H]$^+$ EIS-MS; Q-TOF hybrid-type MS/MS spectrometer (a product of Micromass UK Co.)).

The HPLC Conditions (Gradient Method)

HPLC devices: Hitachi HPLC gradient system (L-6200 Intelligent Pump, D-2500 Chromato-Integrator, L-4000 UV-detector)

column: YMC-Pack ODS-A A-312 (length 150 mm, internal diameter 6.0 mm, particle diameter 5 μm, a product of YMC Co., Ltd.)

flow rate: 1.0 ml/min temperature: room temperature retention time: 13.9 minutes mobile phase: mobile phase A: water (0.01% trifluoroacetic acid solution) mobile phase B: acetonitrile (0.01% trifluoroacetic acid solution)

gradient elution conditions:
  0 min mobile phase A 88%, mobile phase B 12%
  30 min mobile phase A 40%, mobile phase B 60%
  35 min mobile phase A 10%, mobile phase B 90%
  40 min mobile phase A 10%, mobile phase B 90% detection: UV detection: detection wave length 220 nm
  RI detection: $^{14}$C detection
  detector: Flow-one/beta-Radiomatic525TR (a product of Packard Co., Ltd.)
  liquid scintillator: ULTIMA-FLO M (a product of Packard Co., Ltd.)
  flow rate: 3.0 ml/min

EXAMPLE 31

3-[4-(6-Methoxy-1-methyl-1H-benzimidazol-2-ylmethoxy)phenyl]-2-methylsulfenylpropionic amide (amide of exemplification compound number 5-21)

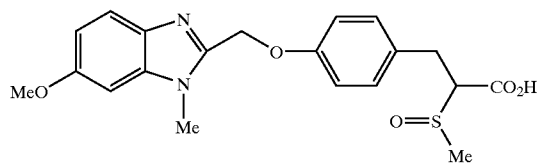

The title compound (m/z 403 [M+H] (EIS-MS; Q-TOF hybrid-type MS/MS spectrometer (a product of Micromass UK Co.)), retention time 18.2 minutes) was obtained by a similar procedure to that described in Example 30.

EXAMPLE 32

3-[4-(6-Hydroxy-1-methyl-1H-benzimidazol-2-ylmethoxy)phenyl]-2-methylthiopropionic amide (amide of exemplification compound number 5-26)

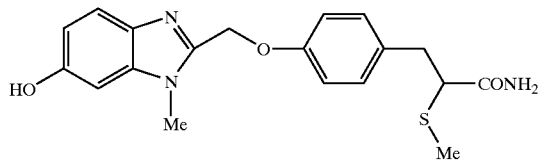

The title compound (m/z 372 [M+H]$^+$ (EIS-MS; Q-TOF hybrid-type MS/MS spectrometer (a product of Micromass UK Co.)), retention time 18.2 minutes) was obtained by a similar procedure to that described in Example 30.

Example 33

3-[4-[6-Methoxy-1-methyl-1H-benzimidazol-2-ylmethoxy]phenyl]-2-methylsulphenylpropionic amide (amide of exemplification compound number 5-21)

5-[4-[6-Methoxy-1-methyl-1H-benzimidazol-2-ylmethoxy]benzyl]thiazolidine-2,4-dione hydrochloride (5 mg/kg) was orally administered to a rat and urine obtained from the rat was collected from 0 through 24 hours. The urine was lyophilized and the residue was chromatographed on an ODS column (packing agent: ODS-A 120-S-75 a product of YMS Co., Ltd.) using a gradient elution of water (pH 4 prepared with 1 mol/ml hydrochloric acid) :acetonitrile=100:0 to 60:40 as the eluant to give a crude metabolite. The crude metabolite was further purified by HPLC to afford the title compound (m/z 402 [M+H]$^+$ (EIS-MS; Q-TOF hybrid-type MS/MS spectrometer (a product of Micromass UK Co.))).

The HPLC Conditions (Gradient Method)

HPLC devices: Hitachi HPLC gradient system (L-6200 Intelligent Pump, D-2500 Chromato-Integrator, L-4000 UV-detector)

column: YMC-Pack ODS-A A-312 (length 150 mm, internal diameter 6.0 mm, diameter of particle 5 µm, a product of YMC Co., Ltd.)

flow rate: 1.0 ml/min temperature: room temperature retention time: 17.2 minutes mobile phase: mobile phase A: water (0.01% trifluoroacetic acid solution) mobile phase B: acetonitrile (0.01% trifluoroacetic acid solution)

gradient elution conditions:
  0 min mobile phase A 88%, mobile phase B 12%
  30 min mobile phase A 40%, mobile phase B 60%
  35 min mobile phase A 10%, mobile phase B 90%
  40 min mobile phase A 10%, mobile phase B 90% detection: UV detection: detection wave length 220 nm
  RI detection: $^{14}$C detection
  detector: Flow-one/beta-Radiomatic525TR (a product of Packard Co., Ltd.)
  liquid scintillator: ULTIMA-FLO M (a product of Packard Co., Ltd.)
  flow rate: 3.0 ml/min

EXAMPLE 34

3-[4-(6-Methoxy-1-methyl-1H-benzimidazol-2-ylmethoxy)phenyl]-2-methylsulphenylpropionic amide (exemplification compound number 5-21)

The title compound (m/z 403 [M+H]$^+$ (EIS-MS; Q-TOF hybrid-type MS/MS spectrometer (a product of Micromass UK Co.)), retention time 18.3 minutes) was obtained by a similar procedure to that described in Example 33.

EXAMPLE 35

3-[4-[6-(β-D-Glucopyranosyloxyuronic acid)-1-methyl-1H-benzimidazol-2-ylmethoxy]phenyl]-2-mercaptopropionic acid hydrochloride (hydrochloride of exemplification compound number 5-45)

An aqueous solution of potassium hydroxide is added to a suspension of 1-O-[1-methyl-2-[4-(2,4-thiazolidinedione-5-ylmethyl)phenoxymethyl]-1H-benzimidazol-2yl]-β-D-glucopyranosyloxyuronic acid in ethanol and the mixture is stirred. The reaction mixture is poured into ice-water and acidified with hydrochloric acid. This mixture is stirred and the precipitate is filtered and dried under reduced pressure to afford the title compound.

EXAMPLE 36

Ethyl 3-[4-(6-hydroxy-1-methyl-1H-benzimidazol-2-ylmethoxy)phenyl]-2-methylthiopropionate hydrochloride (Ethyl ester hydrochloride of exemplification compound number 5-26)

A mixture of t-butyl N-{2-[4(2-methylthio-2-ethoxycarbonylethyl)phenoxyacetylamino]-5-hydroxyphenyl}-N-methylcarbamate (11 g), ethanol (50 ml) and 4N-hydrogen chloride/dioxane (200 ml) was allowed to stand at room temperature. The solvent of the reaction mixture was evaporated and the residue was filtered to give a precipitate which was washed with ethyl acetate to afford the title compound (6.12 g, mp 149–152° C.) as a grayish white powder.

EXAMPLE 37

3-[4-(6-Hydroxy-1-methyl-1H-benzimidazol-2-ylmethoxy)phenyl]-2-methylthiopropionic acid hydrochloride (hydrochloride of exemplification compound number 5-26)

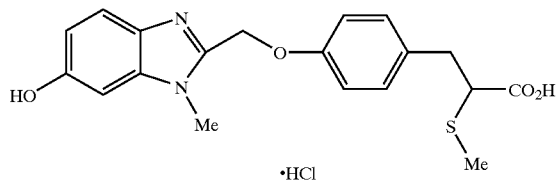

The title compound (2.7 g, mp 195–198° C., pale red powder) was obtained by a similar procedure to that described in Example 27 using ethyl 3-[4-(6hydroxy-1-methyl-1H-benzimidazol-2-ylmethoxy)phenyl]-2-methylthiopropionate hydrochloride (6 g), potassium hydroxide (6 g), N,N-dimethylformamide (50 ml) and distilled water (50 ml).

EXAMPLE 38

2-Mercapto-3-[4-(6-methoxy-1-methyl-1H-benzimidazol-2-ylmethoxy)phenyl]propionic amide (amide of exemplification compound number 5-1)

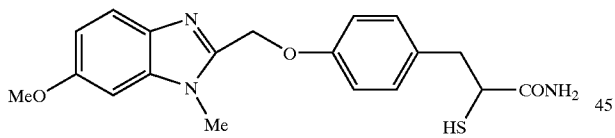

A mixture of 2-acetylthio-3-[4-(6-methoxy-1-methyl-1H-benzimidazol-2-ylmethoxy)phenyl]propionic acid (1.53 g), anhydrous triethylamine (0.4 g), chloroethylformate (0.65 g), anhydrous tetrahydrofuran (10 ml) and anhydrous N,N-dimethylformamide (10 ml) was stirred at room temperature for 1 hour. An aqueous solution of ammonia (20 ml, 28%) was added to the reaction mixture and this mixture was stirred for 2 hours and then allowed to stand overnight. The reaction mixture was partitioned between ethyl acetate and water. The extract was washed with saturated aqueous sodium chloride solution and dried over anhydrous magnesium sulfate and then concentrated. The residue was purified by liquid chromatography (LiChroprepNH2 (Merck)) using ethanol:ethyl acetate=1:12 as the eluant to afford the title compound (0.21 g, mp 204–208° C.) as a pale yellow powder.

EXAMPLE 39

Methyl 3-[4-(1methyl-6-methylthio-1H-benzimidazol-2-ylmethoxy)phenyl]-2-methylthiopropionate hydrochloride (methyl ester hydrochloride of exemplification compound number 5-67)

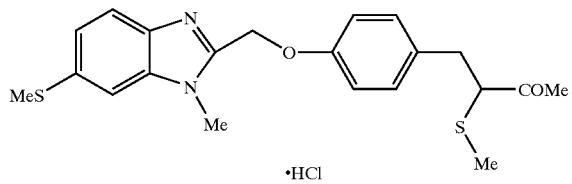

A mixture of methyl 3-[4-(1-methyl-6methylthio-1H-benzimidazol-2-ylmethoxy)phenyl]-2-mercaptopropionate (7.14 g), methyl iodide (3.78 g), triethylamine (2.69 g), and anhydrous tetrahydrofuran (200 ml) was stirred at room temperature for 23 hours. The reaction mixture was concentrated and partitioned between ethyl acetate and water. The extract was dried over anhydrous sodium sulfate and then concentrated. The residue was chromatographed on a silica gel column using hexane:ethyl acetate=1:2 as the eluant and the product was treated with 4N hydrogen chloride/ethyl acetate to afford the title compound (5.75 g, mp 163–166° C.).

EXAMPLE 40

3-[4-(1-methyl-6-methylthio-1H-benzimidazol-2-ylmethoxy)phenyl]-2-methylthiopropionic acid hydrochloride (hydrochloride of exemplification compound number 5-67)

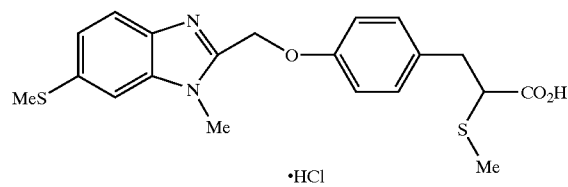

A mixture of methyl 3-[4-(1-methyl-6-methylthio-1H-benzimidazol-2-ylmethoxy)phenyl]-2-methylthiopropionate hydrochloride (5.75 g), concentrated hydrochloric acid (100 ml) and 1,4-dioxane (100 ml) was heated at reflux for 90 minutes. The reaction mixture was concentrated to dryness. To the residue was added tetrahydrofuran and the mixture was irradiated with ultrasonic waves. The insoluble material was isolated by filtration, washed with ethyl acetate, dissolved in N,N-dimethylformamide and reprecipitated with ether to afford the title compound (5.02 g, mp 193–196° C.).

EXAMPLE 41

Methyl 3-[4-(1-methyl-6-methylthio-1H-benzimidazol-2-ylmethoxy)phenyl]-2-methylthiopropionate (methyl ester of exemplification compound number 5-67)

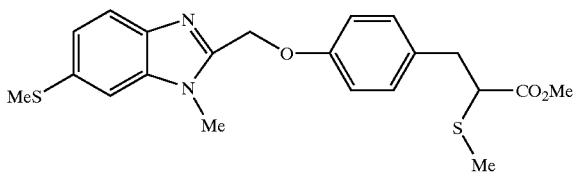

Crude 2-(N-t-butoxycarbonyl-N-methylamino)-4-methylthioaniline (54.8 g, Rf=0.16: thin layer chromatography on a silica gel plate using hexane:ethyl acetate=3:1 as the eluant) was obtained by a similar procedure to that described in Reference example 5 using 2-(N-t-butoxycarbonyl-N-methylamino)-4-methylthionitrobenzene (55.9 g), palladium on carbon (7.25 g, 10%) and a mixture of methanol:1,4-dioxane=1:1 (600 ml).

A mixture of 2-(N-t-butoxycarbonyl-N-methylamino)-4-methylthioaniline (54.8 g), 4-(2,4-dioxothiazolidin-5-ylmethyl)phenoxyacetic acid (64.0 g), diethyl cyanophosphonate (36.8 g), triethylamine (22.8 g) and anhydrous tetrahydrofuran (300 ml) was stirred for 67 hours at room temperature. The reaction mixture was concentrated and water was added to the residue. The mixture was neutralized with 3N hydrochloric acid and sodium bicarbonate and extracted with ethyl acetate. The extract was dried over anhydrous sodium sulfate and concentrated. The residue was dissolved in 4N hydrogen chloride/dioxane (150 ml) and the solution was stirred at room temperature for 15 hours and then at 80° C. for 5 hours. The reaction mixture was concentrated, neutralized with sodium bicarbonate and extracted with a mixture of tetrahydrofuran and ethyl acetate. The extract was dried over anhydrous sodium sulfate. The solvent of the extract was evaporated and the residue was reprecipitated using N,N-dimethylformamide and ethyl acetate to give a precipitate. The precipitate was suspended in 4N hydrogen chloride/ethyl acetate and insoluble material was obtained by filtration which was washed with ethyl acetate and dried in the air to give the desired intermediate.

A solution of the intermediate (35.2 g) in water (200 ml) and a methanolic solution of sodium methoxide (300 ml, 28%) was stirred at 80° C. for 90 minutes. The reaction mixture was concentrated and acidified with 6N hydrochloric acid to give a precipitate. The precipitate was collected by filtration, successively washed with water and ethyl acetate and then dried under reduced pressure to afford the desired product.

A mixture of the product (22.4 g), 4N hydrogen chloride/dioxane (150 ml) and methanol (150 ml) was stirred at room temperature for 65 hours. The reaction mixture was concentrated, neutralized with aqueous sodium bicarbonate solution (5%) and extracted with ethyl acetate. The extract was dried over anhydrous sodium sulfate and then concentrated. The residue was chromatographed on a silica gel column using hexane:ethyl acetate=1:3 as the eluant to afford the title compound (7.49 g, mp 97–100° C.).

Reference Example 1

Methyl 4-(t-butoxycarbonylmethoxy)phenyllactate

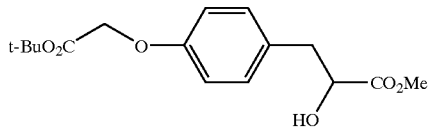

A mixture of methyl 4-hydroxyphenyllactate (18.5 g), t-butyl bromoacetate (14 ml), anhydrous potassium carbonate (26.0 g) and anhydrous dimethylformamide (300 ml) was stirred at 60° C. for 10 hours and then allowed to stand at room temperature overnight The reaction mixture was partitioned between ethyl acetate and water. The extract was washed with saturated aqueous sodium chloride solution, dried over anhydrous sodium sulfate and concentrated under reduced pressure. The residue was chromatographed on a silica gel column using hexane:ethyl acetate=2:1–1:1 as the eluant to afford the title compound (17.5 g, Rf=0.62: thin layer chromatography on a silica gel plate using hexane:ethyl acetate=1:1 as the eluant).

Reference Example 2

Methyl 3-[4-(t-butoxycarbonylmethoxy)phenyl]-2-(4-fluorobenzyloxy)propionate

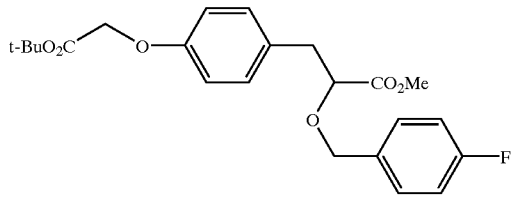

A mixture of methyl 4-(t-butoxycarbonylmethoxy)phenyllactate (3.0 g), 4-fluorobenzylbromide (2.4 ml), silver oxide (9.0 g) and toluene (60 ml) was stirred at 80° C. under a nitrogen atmosphere for 3 hours. The reaction mixture was filtered and the filtrate was concentrated under reduced pressure. The residue was chromatographed on a silica gel column using hexane:ethyl acetate=5:1 as the eluant to afford the title compound (2.9 g, Rf=0.39: thin layer chromatography on a silica gel plate using hexane:ethyl acetate=3:1 as the eluant).

Reference Example 3

Methyl 3-[4-(carboxymethoxy)phenyl]-2-(4-fluorobenzyloxy)propionate

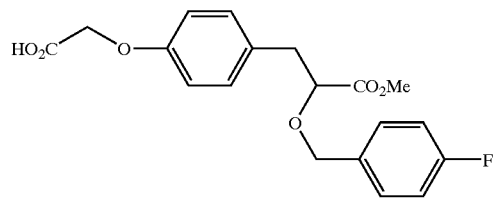

A solution of methyl 3-[4-(t-butoxycarbonylmethoxy)phenyl]-2-(4-fluorobenzyloxy)propionate (2.8 g) in 4N hydrogen chloride/dioxane (50 ml) was stirred at room temperature for 3 hours. The reaction mixture was concen-

Reference Example 4

4-(4-(Adamantan-1-ylphenoxy)-2-(N-t-butoxycarbonyl-N-methylamino)nitrobenzene

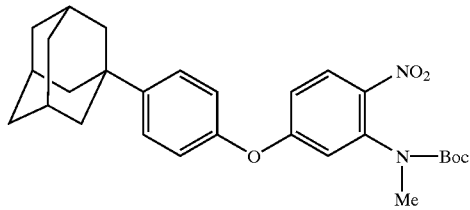

After washing sodium hydride (2.1 g) with hexane, dimethylformamide (200 ml) was added it. In an ice bath 4-(1-adamantyl)phenol (10 g) was added and this mixture was stirred at room temperature for 1 hour. To this reaction mixture was added 4-chloro-2-(N-t-butoxycarbonyl-N-methylamino)nitrobenzene (15.1 g) in an ice bath. The mixture was stirred at room temperature for 2 hours and then allowed to stand at room temperature 2 days. The dimethylformamide was evaporated under reduced pressure. The residue was partitioned between ethyl acetate and water. The extract was washed with saturated aqueous sodium chloride solution, dried over anhydrous sodium sulfate and concentrated under reduced pressure. The residue was chromatographed on a silica gel column using hexane:ethyl acetate=10:1 as the eluant to afford the title compound (23.0 g, Rf=0.63: thin layer chromatography on a silica gel plate using hexane:ethyl acetate=3:1 as the eluant).

Reference Example 5

4-(4-Adamantan-1-ylphenoxy)-2-(N-t-butoxycarbonyl-N-methylamino)aniline

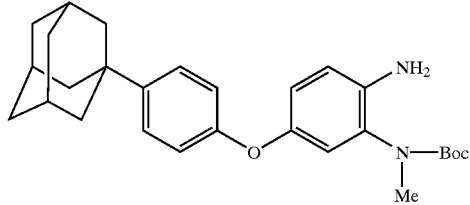

A mixture of 4-(4-adamantan-1-ylphenoxy)-2-(N-t-butoxycarbonyl-N-methylamino)nitrobenzene (14 g), palladium on carbon (1.50 g, 10%) and methanol (300 ml) was stirred at room temperature under a hydrogen atmosphere for 2 hours and then 50° C. for 2 hours, allowed to stand at room temperature overnight and then stirred at 50° C. for 2 hours. The insoluble material of the reaction mixture was filtered and the filtrate was concentrated under reduced pressure. The residue was chromatographed on a silica gel column using hexane:ethyl acetate=3:1 as the eluant to afford the title compound (6.70 g, mp 85–90° C.).

Reference Example 6

Methyl 3-{4-[4-(4-adamantan-1-ylphenoxy)-2-(N-t-butoxycarbonyl-N-methylamino)phenylaminocarbonylmethoxy]phenyl}-2-4-fluorobenzyloxy)propionate

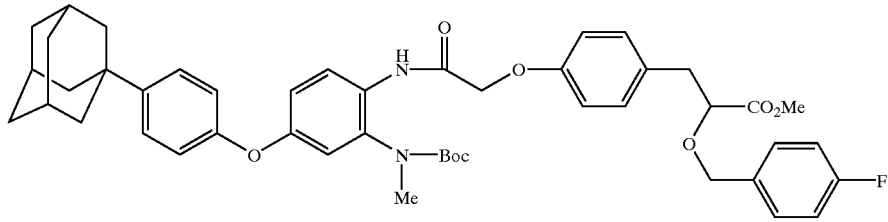

Diethyl cyanophosphonate (0.30 ml) was added to a solution of methyl 3-[4-(carboxymethoxy)phenyl]-2-(4-fluorobenzyloxy)propionate (0.6 g), 4-(4-adamantan-1-ylphenoxy)-2-(N-t-butoxycarbonyl-N-methylamino)aniline (0.75 g) and triethylamine (0.28 ml) in tetrahydrofuran (15 ml). The mixture was stirred at room temperature for 5 hours. The reaction mixture was partitioned between ethyl acetate and water. The extract was washed with saturated aqueous sodium chloride solution, dried over anhydrous sodium sulfate and concentrated under reduced pressure. The residue was chromatographed on a silica gel column using hexane:ethyl acetate=3:1 as the eluant to afford the title compound (1.08 g, mp 52–56° C.).

Reference Example 7

4-(3,5-Di-t-butyl-4-hydroxyphenylthio-2-(N-t-butoxycarbonyl-N-methylamino)nitrobenzene

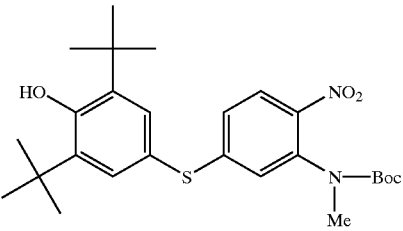

A mixture of 3,5-di-t-butyl-4-hydroxyphenylmercaptane (8.0 g), 4-chloro-2-(N-t-butoxycarbonyl-N-methylamino) nitrobenzene (9.62 g), potassium carbonate (23.2 g) and dimethylformamide (150 ml) was stirred at 80° C. for 1 hour. The dimethylformamide was evaporated under reduced pressure. The residue was partitioned between ethyl acetate and water. The extract was washed with saturated aqueous sodium chloride solution, dried over anhydrous sodium sulfate and concentrated under reduced pressure. The residue was chromatographed on a silica gel column using hexane:ethyl acetate=20:1–10:1 as the eluant to afford the title compound (12.1 g, mp 140–141° C.).

Reference Example 8

4-(3,5-Di-t-butyl-4-hydroxyphenylthio)-2-(N-t-butoxycarbonyl-N-methylamino)aniline

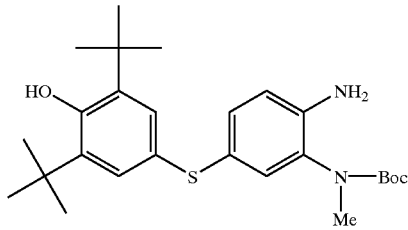

The title compound (8.82 g, mp 95–96° C.) was obtained by a similar procedure to that described in Reference example 5 using 4-(3,5-di-t-butyl-4-hydroxyphenylthio)-2-(N-t-butoxycarbonyl-N-methylamino)nitrobenzene (9.4 g), palladium on carbon (9.4 g, 10%) and methanol (100 ml).

Reference Example 9

Methyl 3-{4-[4-(3,5-di-t-butyl-4-hydroxyphenylthio)-2-(N-t-butoxycarbonyl-N-methylamino)phenylaminocarbonylmethoxy]phenyl}-2-(4-fluorobenzyloxy)-propionate

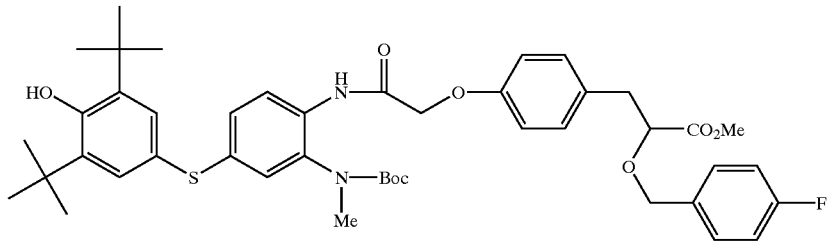

The title compound (0.60 g, Rf=0.48: thin layer chromatography on a silica gel plate using hexane:ethyl acetate=3:1 as the eluant) was obtained by a similar procedure to that described in Reference example 6 using 4-(3,5-di-t-butyl-4-hydroxyphenylthio)-2-(N-t-butoxycarbonyl-N-methylamino)aniline (2.28 g), methyl 3-[4-(carboxymethoxy)phenyl]-2-(4-fluorobenzyloxy)propionate (1.75 g), triethylamine(0.83 ml), tetrahydrofuran (50 ml) and diethyl cyanophosphonate (0.90 ml).

Reference Example 10

4-(5,5-Dimethyl-2-oxodioxolan-3-ylmethyl)phenol

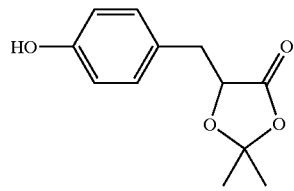

Concentrated sulfuric acid (10 ml) was added dropwise to a solution of 4-hydroxyphenyllactic acid (30 g) in acetone (30 ml) at −50° C. and the mixture was stirred at room temperature for 4 hours. The reaction mixture was poured into ice-water and neutralized with aqueous sodium hydroxide solution and aqueous sodium hydrogencarbonate solution and extracted with ethyl acetate. The extract was washed with saturated aqueous sodium chloride solution, dried over anhydrous sodium sulfate and concentrated to afford the title compound (21.6 g, Rf=0.34: thin layer chromatography on a silica gel plate using hexane:ethyl acetate=4:1 as the eluant).

Reference Example 11

Benzyl 4-(5,5-dimethyl-2-oxodioxolan-3-ylmethyl)phenoxyacetate

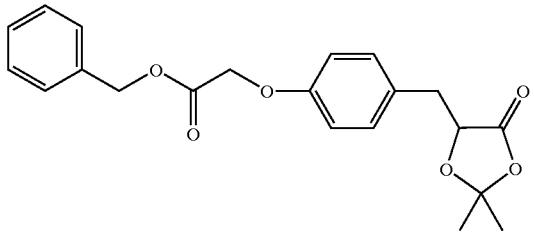

A mixture of 4-(5,5-dimethyl-2-oxodioxolan-3-ylmethyl)phenol (21.5 g), benzyl bromoacetate (44 g), cesium carbonate (63 g) and acetone (500 ml) was stirred at room temperature for 1.5 hours. The solvent of the reaction mixture was evaporated under reduced pressure. The residue was partitioned between ethyl acetate and water. The extract was washed with saturated aqueous sodium chloride solution, dried over anhydrous sodium sulfate and concentrated under reduced pressure. The residue was chromatographed on a silica gel column using hexane:ethyl acetate= 5:1–3:1 as the eluant to afford the title compound (32.9 g, Rf=0.51: thin layer chromatography on a silica gel plate using hexane:ethyl acetate=4:1 as the eluant).

Reference Example 12

4-(5,5-Dimethyl-2-oxodioxolan-3-ylmethyl) phenoxyacetic acid

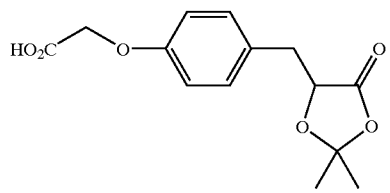

A mixture of benzyl 4-(5,5-dimethyl-2-oxodioxolan-3-ylmethyl)phenoxyacetate (15 g), palladium on carbon (2 g, 5%) and dioxane (150 ml) was stirred at room temperature under a hydrogen atmosphere for 1.5 hours. The insoluble material of the reaction mixture was filtered and the filtrate was concentrated under reduced pressure. The residue was filtered and washed with diisopropyl ether and dried to afford the title compound (9.42 g, mp 138–139° C.).

Reference Example 13

4-(5,5-Dimethyl-2-oxodioxolan-3-ylmethyl) phenoxyacetyl-N-[2-(N-t-butoxycarbonyl-N-methylamino)-4-methoxyphenyl]amide

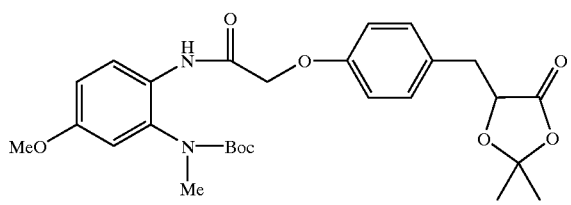

The title compound (4.56 g, Rf=0.17: thin layer chromatography on a silica gel plate using hexane:ethyl acetate=3:1 as the eluant) was obtained by a similar procedure to that described in Reference example 6 using 2-(N-t-butoxycarbonyl-N-methylamino)-4-methoxyaniline (2.5 g), 4-(5,5-dimethyl-2-oxodioxolan-3-ylmethyl)phenoxyacetic acid (3.0 g), triethylamine (1.66 ml), tetrahydrofuran (100 ml) and diethyl cyanophosphonate (1.82 ml).

Reference Example 14

4-Methoxymethoxy-2,3,5-trimethylphenol

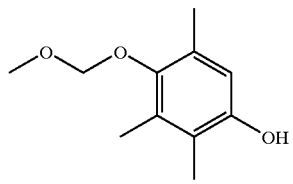

Sodium hydride (8.51 g, 55% suspension in mineral oil) was added to a solution of 4-hydroxy-2,3,5-trimethylphenol pivalate (35.4 g) in tetrahydrofuran (300 ml) at room temperature. The mixture was stirred for 30 minutes. To the reaction mixture was added dropwise methoxymethyl chloride (15.7 g). This mixture was stirred at room temperature for 1 hour. The solvent of the reaction mixture was evaporated under reduced pressure. The residue was partitioned between ethyl acetate and water. The organic extract was dried over anhydrous sodium sulfate and concentrated under reduced pressure. The residue was dissolved in methanol (100 ml) and to this solution was added dropwise a solution of potassium hydroxide (16.8 g) in methanol (100 ml). The mixture was stirred at room temperature and concentrated under reduced pressure. The residue was neutralized with 3N hydrochloric acid and extracted with ethyl acetate. The extract was dried over anhydrous sodium sulfate and concentrated under reduced pressure. The residue was chromatographed on a silica gel column using hexane:ethyl acetate=5:1 as the eluant to afford the title compound (27.5 g, Rf=0.16: thin layer chromatography on a silica gel plate using hexane:ethyl acetate=4:1 as the eluant).

Reference Example 15

2-(N-t-Butoxycarbonyl-N-methylamino)-4-(methoxymethoxy-2,3,6-trimethylphenoxy) nitrobenzene

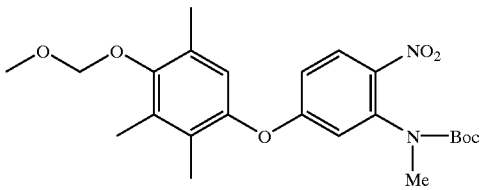

Sodium hydride (6.11 g, 55% suspension in mineral oil) was added to a solution of 4-methoxymethoxy-2,3,5-trimethylphenol (27.5 g) in dimethylformamide (300 ml). After stirring the mixture for 1 hour 4chloro-2-(N-t-butoxycarbonyl-N-methylamino)nitrobenzene (40.1 g) was added in small portions to the mixture and stirred at 120° C. for 2 hours. The solvent of the reaction mixture was evaporated under reduced pressure. The residue was partitioned between ethyl acetate and water. The extract was dried over anhydrous sodium sulfate and concentrated under reduced pressure. The residue was chromatographed on a silica gel column using hexane: ethyl acetate=5:1 as the eluant to afford the title compound (57.0 g, Rf=0.55: thin layer chromatography on a silica gel plate using hexane: ethyl acetate=4:1 as the eluant).

Reference Example 16

2-(N-t-Butoxycarbonyl-N-methylamino)-4-(4-methoxymethoxy-2,3,6-trimethylphenoxy)aniline

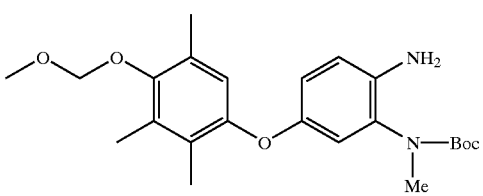

The title compound (52.5 g, Rf=0.31: thin layer chromatography on a silica gel plate using hexane: ethyl acetate=3:1 as the eluant) was obtained by a similar procedure to that described in Reference example 5 using 2-(N-t-butoxycarbonyl-N-methylamino)-4-(4-methoxymethoxy-2,3,6-trimethylphenoxy)nitrobenzene (57.0 g), palladium on carbon (3 g, 10%) and methanol (500 ml).

Reference Example 17

4-(5,5-Dimethyl-2-oxodioxolan-3-ylmethyl)phenoxyacetyl-N-[2-(N-t-butoxycarbonyl-N-methylamino)-4-(4-methoxymethoxy-2,3,5-trimethylphenoxy)phenyl]amide

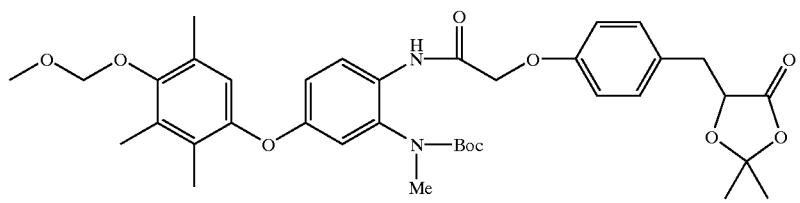

The title compound (6 g, Rf=0.25: thin layer chromatography on a silica gel plate using hexane: ethyl acetate=3:1 as the eluant) was obtained by a similar procedure to that described in Reference example 6 using 2-(N-t-butoxycarbonyl-N-methylamino) -4-methoxymethoxy-2,3,6-trimethylphenoxy)aniline (4.0 g), 4-(5,5-dimethyl-2-oxodioxolan-3-ylmethyl)phenoxyacetic acid (3.23 g), triethylamine (1.73 ml), tetrahydrofuran (150 ml) and diethyl cyanophosphonate (1.9 ml).

Reference Example 18

4-(5,5-Dimethyl-2-oxodioxolan-3-ylmethyl)phenoxyacetyl-N-[2-(N-t-butoxycarbonyl-N-methylamino)-4-(3,5-di-t-butyl-4-hydroxyphenylthio)phenyl]amide

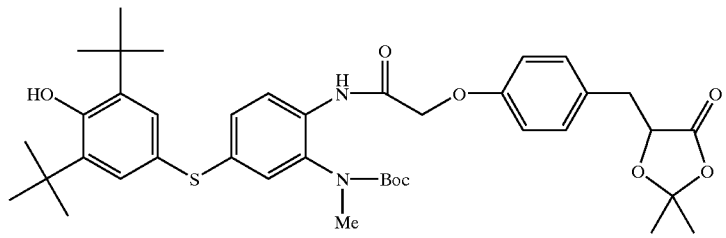

The title compound (5.15 g, Rf=0.38: thin layer chromatography on a silica gel plate using hexane: ethyl acetate=2:1 as the eluant) was obtained by a similar procedure to that described in Reference example 6 using 4-(3,5-di-t-butyl-4-hydroxyphenylthio)-2-(N-t-butoxycarbonyl-N-methylamino)aniline (4.5 g), 4-(5,5-dimethyl-2-oxodioxolan-3-ylmethyl)phenoxyacetic acid (3.0 g), triethylamine (1.66 ml), tetrahydrofuran (100 ml) and diethyl cyanophosphonate (1.82 ml).

Reference Example 19

Methyl 2-axido-3-[4-(6-methoxy-1-methyl-1H-benzimidazole-2-yl)phenyl]propionate

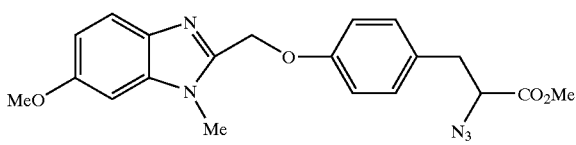

A mixture of methyl 4-(1-methyl-6-methoxy-1H-benzimidazole-2-yl-methoxy)phenyllactate (2.5 g), diphenylphosphoryl azide (2.3 ml), diethyl azodicarboxylate (4.8 ml), triphenylphosphine (2.8 g) and tetrahydrofuran (100 ml) was stirred at room temperature for 1 hour and then allowed to stand overnight. The solvent of the reaction mixture was evaporated under reduced pressure. The residue was chromatographed on a silica gel column using hexane: ethyl acetate=2:1 as the eluant to afford the title compound (2.1 g, mp 105–107° C.).

Reference Example 20

N-(2-Benzoylphenyl)tyrosine methyl ester

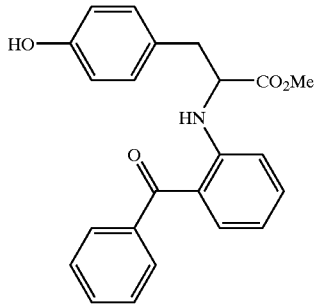

A mixture of tyrosine methyl ester hydrochloride (4.8 g), 2-benzoylcyclohexanone (5.0 g), palladium on carbon (1.0 g, 10%), triethylamine (2.9 ml) and anisole (70 ml) was heated at reflux for 20 hours. The reaction mixture was filtered and the filtrate was partitioned between ethyl acetate and water. The extract was washed with saturated aqueous sodium chloride solution, dried over anhydrous magnesium sulfate and concentrated under reduced pressure. The residue was chromatographed on a silica gel column using hexane: ethyl acetate=3:1 as the eluant to afford the title compound (1.83 g, Rf=0.39: thin layer chromatography on a silica gel plate using hexane: ethyl acetate=3:1 as the eluant).

Reference Example 21

4-t-Butoxycarbonylmethoxy-N-(2-benzoylphenyl)alanine methyl ester

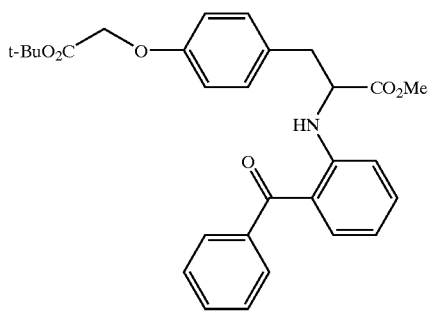

A mixture of N-(2-benzoylphenyl)tyrosine methyl ester (0.97 g), t-butyl bromoacetate (0.55 ml), cesium carbonate (1.14 g), and acetone (15 ml) was stirred at room temperature for 1.5 hours and allowed to stand overnight. The reaction mixture was partitioned between ethyl acetate and water. The extract was washed with saturated aqueous chloride solution, dried over anhydrous magnesium sulfate and concentrated under reduced pressure to afford the title compound (1.42 g, Rf=0.65: thin layer chromatography on a silica gel plate using hexane: ethyl acetate=3:1 as the eluant).

Reference Example 22

4-Carboxymethoxy-N-(2-benzoylphenyl)alanine methyl ester

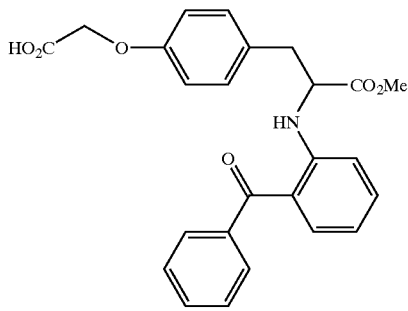

A mixture of 4-t-butoxycarbonylmethoxy-N-(2-benzoylphenyl)alanine methyl ester (1.4 g), 4N hydrogen chloride/dioxane (10 ml) and dioxane (10 ml) was stirred at room temperature for 3 hours and allowed to stand overnight. The reaction mixture was concentrated under reduced pressure. To the residue was added toluene and the mixture was concentrated under reduced pressure. The residue was chromatographed on a silica gel column (LiChroprepDIOL (Merck)) using hexane: ethyl acetate=2:1–1:1 as the eluant to afford the title compound (0.87 g, Rf=0.53: thin layer chromatography on a silica gel plate using hexane: ethyl acetate=3:2 as the eluant).

Reference Example 23

2-(N-t-Butoxycarbonyl-N-methylamino)-4-(4-amino-3,5-dimethylphenoxy)nitrobenzene

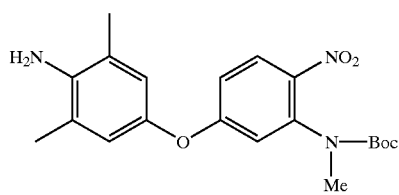

4-Amino-3,5-dimethylphenol (1.10 g) was added to a suspension of sodium hydride (0.35 g, 55% (w/w) dispersion in mineral oil) in anhydrous N,N-dimethylformamide and the mixture was stirred at room temperature for 15 minutes. To the mixture was added in small portions 4-chloro-2-(N-t-butoxycarbonyl-N-methylamino)-nitrobenzene and the mixture was stirred at 120° C. for 1 hour. The reaction mixture was concentrated and the residue was partitioned between ethyl acetate and water The extract was dried over anhydrous sodium sulfate and concentrated under reduced pressure. The residue was chromatographed on a silica gel column using hexane: ethyl acetate=3:1 the eluant to afford the title compound (2.27 g, Rf=0.24: thin layer chromatography on a silica gel plate using hexane: ethyl acetate=3:1 as the eluant).

Reference Example 24

2-(N-t-Butoxycarbonyl-N-methylamino)-4-(4-t-butoxycarbonylamino-3,5-dimethylphenoxy)nitrobenzene

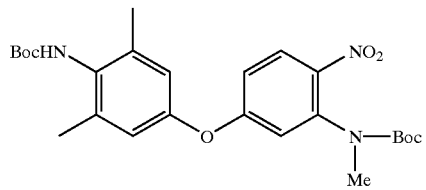

A mixture of 2-(N-t-butoxycarbonyl-N-methylamino)-4-(4-amino-3,5-dimethylphenoxy)nitrobenzene (2.27 g), di-t-butylcarbonate (1.28 g), triethylamine (0.59 g) and anhydrous tetrahydrofuran (20 ml) was heated at reflux for 6 hours. The reaction mixture was concentrated and the residue was partitioned between ethyl acetate and water. The extract was dried over anhydrous sodium sulfate and concentrated under reduced pressure. The residue was chromatographed on a silica gel column using hexane: ethyl acetate=10:1 as the eluant to afford the title compound (1.74 g, mp 154–156° C.).

Reference Example 25

2-(N-t-Butoxycarbonyl-N-methylamino)-4-(4-t-butoxycarbonylamino-3,5-dimethylphenoxy)aniline

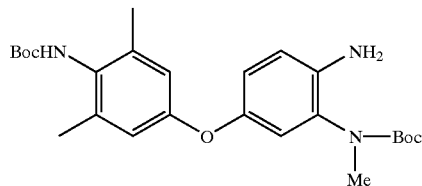

The title compound (1.56 g, Rf=0.14: thin layer chromatography on a silica gel plate using hexane: ethyl acetate=3:1 as the eluant) was obtained by a similar procedure to that described in Reference example 5 using 2-(N-t-butoxycarbonyl-N-methylamino)-4-(4-t-butoxycarbonylamino-3,5-dimethylphenoxy)nitrobenzene (1.71 g), palladium on carbon (0.2 g, 10%) and methanol (100 ml).

Reference Example 26

4-[N-t-Butoxycarbonyl-N-methylamino)-4-(4-t-butoxycarbonylamino-3,5-dimethylphenoxy)phenylaminocarbonylmethoxy]-N-(2-benzoylphenyl)phenylalanine methyl ester

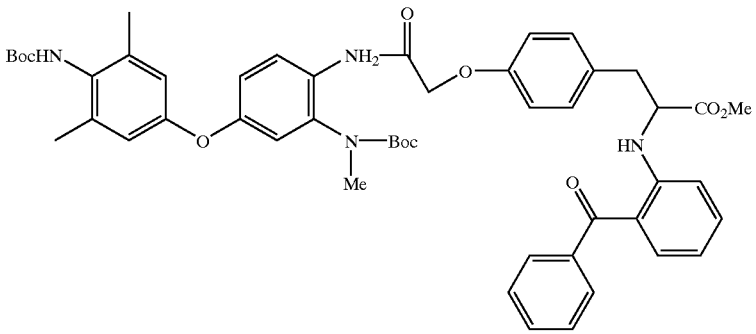

The title compound (1.06 g, Rf=0.93: thin layer chromatography on a silica gel plate using ethyl acetate as the eluant) was obtained by a similar procedure to that described in Reference example 6 using 2-(N-t-butoxycarbonyl-N-methylamino)-4-(4-t-butoxycarbonylamino-3,5-dimethylphenoxy)aniline (0.69 g), 4-carboxymethoxy-N-(2-benzoylphenyl)alanine methyl ester (0.85 g), triethylamine (0.3 ml), tetrahydrofuran (20 ml) and diethyl cyanophosphonate (0.33 ml).

Reference Example 27

1-O-[1-methyl-2-[4-(2,4-thiazolidinedione-5-ylmethyl)phenoxymethyl]-1H-benzimidazol-2-yl]-β-D-glucopyranosyloxyuronic acid

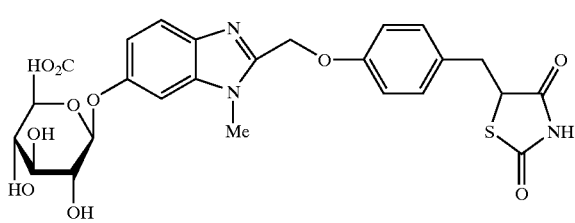

A mixture of 5-[4-(6-hydroxy-1-methyl-1H-benzimidazol-2-ylmethoxy)benzyl]thizolidin-2,4-dione hydrochloride, 1,2,3,4-tetra-O-acetyl-β-D-pyranuronic acid methyl ester, toluenesulfonic acid and nitrobenzene was stirred under reduced pressure in a heating bath. The solvent of the reaction mixture was evaporated under reduced pressure. The residue was chromatographed on a column to give the desired compound having protecting groups. An aqueous solution of sodium hydroxide was added dropwise to solution of the product in methanol in an ice bath and the mixture was stirred. The reaction mixture was saturated with sodium chloride, acidified with hydrochloric acid and extracted with ethyl acetate. The ethyl acetate was evaporated and the residue was purified by chromatography on a column to afford the title compound.

Example 28

5-[4-(6-Hydroxy-1-methyl-1H-benzimidazol-2-ylmethoxy)benzyl]thiazolidine-2,4-dione hydrochloride

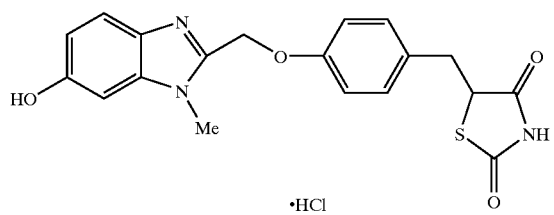

A mixture of t-butyl N-(2-amino-5-hydroxyphenyl)-N-methylcarbamate (0.43 g), 5-(4-carboxymethoxybenzyl) thiazolidine-2,4-dione (0.51 g), diethyl cyanophosphonate (0.29 g) triethylamine (0.18 g) and tetrahydrofuran (20 ml) was stirred at room temperature for 8 hours. The reaction mixture was concentrated and the residue was partitioned between ethyl acetate and water. The extract was dried over anhydrous sodium sulfate and concentrated under reduced pressure. The residue was chromatographed on a silica gel column using hexane: ethyl acetate=2:3 as the eluant to afford t-butyl N-{5-hydroxy-2-[4-(2,4-dioxothiazolidin-5-ylmethyl) phenoxymethylcarbonylamino]phenyl}-N-methylcarbamate (0.75 g).

A suspension of this carbamate (0.75 g) in 4N hydrogen chloride/dioxane (10 ml) was allowed to stand at room temperature for 19 hours. The solvent of the reaction mixture was evaporated under reduced pressure. Ethyl acetate was added to the residue and the mixture was treated with ultrasonic waves, filtered and then dried to afford the title compound (0.52 g, mp 217–220° C.).

Reference Example 29 t-Butyl N-(5-benzyloxy-2-nitrophenyl)-N-methylcarbamate

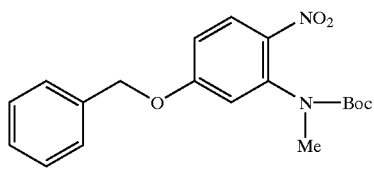

A mixture of sodium hydride (5.24 g, 55% dispersion in mineral oil), benzyl alcohol (13 g) and anhydrous N,N-dimethylformamide (150 ml) was stirred at room temperature for 30 minutes. To this mixture was added t-butyl N-(5-chloro-2-nitrophenyl)-N-methylcarbamate (8.7 g) at room temperature and this mixture was stirred for 18 hours. The reaction mixture was concentrated and the residue was partitioned between ethyl acetate and water. The extract was washed with saturated aqueous sodium chloride solution, dried over anhydrous sodium sulfate and concentrated. The residue was chromatographed on a silica gel column using hexane: ethyl acetate=10:1 as the eluant to afford the title compound (29.2 g, yellow crystals, mp 108–110° C.).

Reference Example 30 t-Butyl N-(2-amino-5-hydroxyphenyl)-N-methylcarbamate

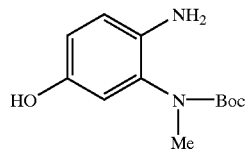

A mixture of t-butyl N-(5-benzyloxy-2-nitrophenyl)-N-methylcarbamate (15 g), palladium on carbon (3 g, 10%), toluene (150 ml) and methanol (150 ml) was stirred under a hydrogen atmosphere at room temperature for 12.5 hours. The palladium on carbon was filtered and the filtrate was concentrated to afford the title compound (12.3 g, brown oil, Rf=0.15: thin layer chromatography on a silica gel plate using hexane: ethyl acetate=4 : 1 as the eluant).

Reference Example 31

Ethyl 3-(4-hydroxyphenyl)-2-mercaptopropionate

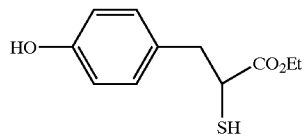

A mixture of 5-(4-acetoxybenzyl)thiazolidine-2,4-dione (100 g), potassium hydroxide (150 g), distilled water (500 ml) and ethanol (500 ml) was stirred at 75° C. for 2.5 hours and potassium hydroxide (250 g) was further added to the reaction mixture. This mixture was stirred at 75° C. for 2 hours, allowed to stand overnight and then concentrated to 300 ml. The mixture was poured into ice-water, adjusting to pH 3 with concentrated hydrochloric acid and extracted with ethyl acetate. The extract was washed with saturated aqueous sodium chloride solution, dried over anhydrous magnesium sulfate and concentrated. To a solution of the residual oil in anhydrous ethanol (500 ml) was added 4N hydrogen chloride/dioxane (500 ml) at room temperature and the mixture was allowed to stand for 2 days. The reaction mixture was concentrated and the residue was purified by liquid chromatography on silica gel using hexane: ethyl acetate=3:1 as the eluant to afford the title compound (50.1 g, pale yellow oil, Rf=0.87: thin layer chromatography on a silica gel plate using hexane: ethyl acetate=1:1 as the eluant).

Reference Example 32

Ethyl 3-(4-hydroxyphenyl)-2-methylthiopropionate

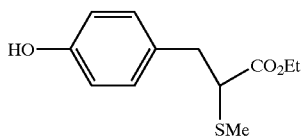

A mixture of Ethyl 3-(4-hydroxyphenyl)-2-mercaptopropionate (30 g), methyl iodide (28.4 g), triethylamine (20.2 g) and tetrahydrofuran (150 ml) was stirred at room temperature for 7 hours. The reaction mixture was concentrated and the residue was partitioned between toluene and water. The extract was washed with saturated aqueous sodium chloride solution, dried over anhydrous magnesium sulfate and concentrated to afford the title compound (30.3 g, pale yellow oil, Rf=0.37: thin layer chromatography on a silica gel plate using hexane: ethyl acetate=4:1 as the eluant).

Reference Example 33

Ethyl 3-(4-t-butoxycarbonylmethoxyphenyl)-2-methylthiopropionate

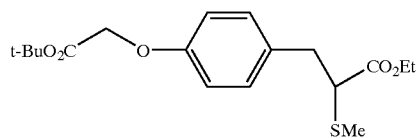

The title compound (24.3 g, pale yellow oil, Rf=0.46: thin layer chromatography on a silica gel plate using hexane: acetate=7:1 as the eluant) was obtained by a similar procedure to that described in Reference example 21 using ethyl 3-(4-hydroxyphenyl)-2-methylthiopropionate (14 g), cesium carbonate (28.5 g), t-butyl bromoacetate (20 g) and acetonitrile (200 ml).

Reference Example 34

Ethyl 3-(4-carboxymethoxyphenyl)-2-methylthiopropionate

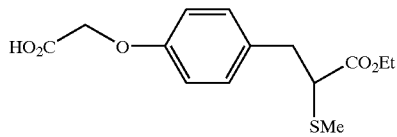

The title compound (11.9 g, mp 77–78° C., milk white powder) was obtained by a similar procedure to that described in Reference example 3 using ethyl 3-(4-t-butoxycarbonylmethoxyphenyl)-2-methylthiopropionate (24 g) and 4N hydrogen chloride/dioxane (150 ml).

Reference Example 35 t-Butyl N-[2-[4-(2-methylthio-2-ethoxycarbonylethyl)phenoxyacetylamino]-5-hydroxyphenyl]-N-methylcarbamate

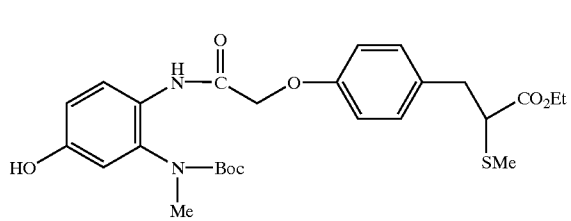

The title compound (11.1 g, Rf=0.14: thin layer chromatography on a silica gel plate using hexane: ethyl acetate=2:1 as the eluant) was obtained by a similar procedure to that described in Reference example 6 using t-butyl N-(2-amino-5-hydroxyphenyl)-N-methylcarbamate (2.2 g), 3-(4-carboxymethoxyphenyl)-2-methylthiopropionate (12.2 g), triethylamine (6.1 g), anhydrous tetrahydrofuran (250 ml) and diethyl cyanophosphonate (9.79 g).

Reference Example 36

2-(N-t-butoxycarbonyl-N-methylamino)-4-methylthionitrobenzene

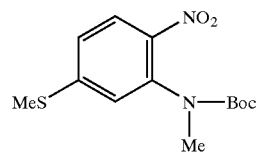

A mixture of 4-chloro-2-(N-t-butoxycarbonyl-N-methylamino)nitrobenzene (57.3 g), sodium thiomethoxide (21.0 g) and anhydrous N,N-dimethylformamide (400 ml) was stirred at room temperature for 23 hours. The reaction mixture was partitioned between ethyl acetate and water. The extract was dried over anhydrous sodium sulfate and concentrated. The residue was irradiated with ultarsonic waves in n-hexane. The insoluble product was collected by filtration and washed with n-hexane to afford the title compound (55.9 g, mp 114–117° C.).

Reference Example 37

2-Acetylthio-3-[4-(6-methoxy-1-methyl-1H-benzimidazol-2-ylmethoxy)phenyl]propionic acid

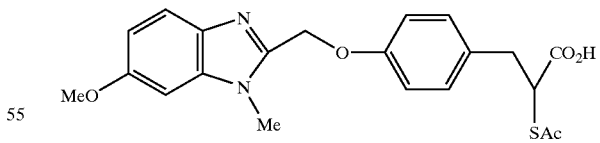

To a mixture of 2-mercapto-3-[4-(6-methoxy-1-methyl-1H-benzimidazol-2-ylmethoxy)phenyl]propionic acid hydrochloride (1.5 g), pyridine (0.87 g), tetrahydrofuran (30 ml) and N,N-dimethylformamide (30 ml) was added acetic anhydride (0.56 g). The mixture was stirred at room temperature for 5 hours and allowed to stand for 36 hours and then concentrated. The residual insoluble material was collected by filtration and washed with ethyl acetate to afford the title compound (1.55 g, mp 209–214° C., pale yellow powder).

Experiment

Hypoglycemic Activity

Blood was collected from the tail veins of KK mice (4–5 months old) suffering from diabetes mellitus, and it was subjected to an assay of the blood sugar level. The mice were divided in groups (4 mice per group) as to have equal blood sugar levels on average in each group. Powdered mouse feed (F-1, Funabashi Farm) containing 0.01% of a test compound was given the mice for 3 days. Those mice groups fed with the test compound were referred to as "drug treated group". Further, those groups fed with powdered feed free of the test compound were referred to as "control group". Blood was collected from the tail veins of the mice 3 days later and was subjected to a centrifuge, and the glucose concentration in the resultant plasma was assayed with a glucose analyzer (Glucoloader, A&T Company). The average blood sugar lowering rate was calculated from the following formula:

Blood sugar lowering rate (%)=(Average blood sugar level in control group−Average blood sugar level in drug treated group)×100/Blood sugar level in control group

TABLE 6

| Test Compound | Blood sugar lowering rate (%) |
|---|---|
| Compound in Example 2 | 58.5 |
| 4 | 40.8 |
| 9 | 48.4 |
| 16 | 32.1 |
| 20 | 40.0 |

Formulation Examples

(1) Capsules

| | |
|---|---|
| Compound of Example 2 | 10 mg |
| Lactose | 110 mg |
| Corn starch | 58 mg |
| Magnesium stearate | 2 mg |
| | 180 mg |

Each ingredient powder as shown above was admixed well and passed through a sieve of 60 mesh (mesh standard: Tyler standard). The resultant powder (180 mg) was used to fill a gelatin capsule (No. 3).

(2) Tablets:

| | |
|---|---|
| Compound of Example 2 | 10 mg |
| Lactose | 85 mg |
| Corn starch | 34 mg |
| Finely crystalline cellulose | 20 mg |
| Magnesium stearate | 1 mg |
| | 150 mg |

Each ingredient powder as shown above was admixed well and then charged to a tableting compression mold (150 mg). If needed, the tablet may be coated with sugar or a film.

(3) Granules:

| | |
|---|---|
| Compound of Example 2 | 10 mg |
| Lactose | 839 mg |
| Corn starch | 150 mg |
| Hydroxypropyl cellulose | 1 mg |
| | 1000 mg |

Each ingredient powder as shown above was admixed well, moistened with purified water and charged to a basket type granulating machine for granulation. The resultant granules were dried.

The compound having the general formula (I) to (IV) above, pharmacologically acceptable salts thereof, pharmacologically acceptable esters thereof, or pharmacologically acceptable amides thereof, showing excellent insulin resistance improving activity, hypoglycemic activity, anti-inflammatory activity, immunoregulatory activity, aldose reductase inhibiting activity, 5-lipoxygenase inhibiting activity, peroxidized lipid production suppressing activity, PPAR activating activity, anti-osteoporosis activity, leukotrienes antagonistic activity, adipose cell formation promoting activity, cancer cell proliferation suppressing activity or calcium antagonism, are useful for treatment and prophylaxis of such diseases as diabetes mellitus, hyperlipemia, obesity, impaired glucose tolerance, hypertension, fatty liver, diabetic complications (e.g. retinopathy, nephropathy, neurosis, cataract, coronary artery diseases, etc.), arteriosclerosis, gestational diabetes mellitus, polycystic ovary syndrome, cardiovascular diseases (e.g. ischemic heart disease, etc.), cell injury lesion (e.g. cerebral injury induced by stroke, etc.) caused by atherosclerosis or ischemic heart disease, gout, inflammatory diseases (e.g. arthrostesis, pain, fervescence, rheumatic arthritis, inflammatory enteritis, acne, sunburn, psoriasis, eczema, allergic diseases, asthma, GI ulcer, cachexia, autoimmune disease, pancreatitis, etc.), cancer, osteoporosis, cataract, etc. Further the use of (i) at least one selected from α-glucosidase inhibitors, aldose reductase inhibitors, biguanides, statin type compounds, squalene synthesis inhibitors, fibrate type compounds, LDL dissimilation promotors, angiotensin converting enzyme inhibitors, and RXR activators together with (ii) at least one compound having the general formula (I) to (IV) above, pharmacologically acceptable salts thereof, pharmacologically acceptable esters thereof or pharmacologically acceptable amides thereof are also useful for treatment and/or prevention of said diseases, and particularly for the treatment and/or prevention of diabetes mellitus and diabetic complications.

What is claimed is:

1. An α-substituted carboxylic acid derivative having the general formula (IV):

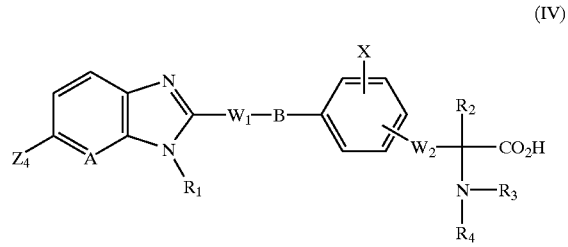

(IV)

wherein:

$R_1$, $R_2$ and $R_3$ are the same or different, and each is a
(i) hydrogen atom, (ii) $C_1$–$C_6$ alkyl group, (iii)

$C_6$–$C_{10}$ aryl group (optionally having 1–5 substituents $\alpha_1$ hereafter defined), (iv) $C_7$–$C_{16}$ aralkyl group (optionally having 1–5 substituents $\alpha_1$ hereafter defined on the aryl moiety thereof), (v) $C_1$–$C_6$ alkylsulfonyl group, (Vi) $C_1$–$C_6$ halogenoalkylsulfonyl group, (vii) $C_6$–$C_{10}$ arylsulfonyl group (optionally having 1–5 substituents $\alpha_1$ hereafter defined) or (viii) $C_7$–$C_{16}$ aralkylsulfonyl group (optionally having 1–5 substituents $\alpha_1$ hereafter defined on the aryl moiety thereat);

$R_4$ is a (i) $C_1$–$C_6$ alkyl group, (ii) $C_6$–$C_{10}$ aryl group (optionally having 1–5 substituents $\alpha_1$ hereafter defined) or (iii) $C_7$–$C_{16}$ aralkyl group (optionally having 1–5 substituents $\alpha_1$ hereafter defined on the aryl moiety thereof);

A is a =CH-group;

B is an oxygen atom or a sulfur atom;

$W_1$ is a $C_1$–$C_8$ alkylene group;

$W_2$ is a single bond or a $C_1$–$C_6$ alkylene group;

X is a (i) hydrogen atom, (ii) $C_1$–$C_6$ alkyl group, (iii) $C_1$–$C_6$ halogenoalkyl group, (iv) $C_1$–$C_6$ alkoxy group, (v) halogen atom, (vi) hydroxy group, (vii) cyano group, (viii) nitro group, (ix) $C_3$–$C_{10}$ cycloalkyl group, (x) $C_6$–$C_{10}$ aryl group (optionally having 1–5 substituents $\beta$ hereafter defined), (xi) $C_7$–$C_{16}$ aralkyl group (optionally having 1–5 substituents $\beta$ hereafter defined on the aryl moiety thereof), (xii) $C_1$–$C_7$ aliphatic acyl group, (xiii) $C_4$–$C_{11}$ cycloalkylcarbonyl group, (xiv) $C_7$–$C_{11}$ arylcarbonyl group (optionally having 1–5 substituents $\beta$ hereafter defined), (xv) $C_8$–$C_{17}$ aralkylcarbonyl group (optionally having 1–5 substituents $\beta$ hereafter defined on the aryl moiety thereof), (xvi) monocyclic type heteroaromatic ring-carbonyl group (optionally having 1–5 substituents $\beta$ hereafter defined), (xvii) carbamoyl group, (xviii) $C_7$–$C_{11}$ arylaminocarbonyl group (optionally having 1–5 substituents $\beta$ hereafter defined on the aryl moiety thereof) or (xix) amino group (optionally having 1 to 2 substituents $\beta$ defined hereafter);

Y is an oxygen atom or an S(O)p group (wherein p is an integer from 0 to 2);

$Z_4$ is a (i) $C_1$–$C_6$ alkoxy group, (ii) $C_1$–$C_6$ alkylthio group, (iii) halogen atom, (iv) $C_6$–$C_{10}$ aryl group (optionally having 1–5 substituents $\alpha_1$ hereafter defined), (v) $C_2$–$C_{16}$ aralkyl group (optionally having 1–5 substituents $\alpha_1$ hereafter defined on the aryl moiety thereof), (vi) $C_6$–$C_{10}$ aryloxy group (optionally having 1–5 substituents $\alpha_1$ hereafter defined), (vii) $C_{7-C16}$ aralkyloxy group (optionally having 1–5 substituents $\alpha_1$ hereafter defined on the aryl moiety thereof), (viii) $C_3$–$C_{10}$ cycloalkyloxy group, (ix) $C_3$–$C_{10}$ cycloalkylthio group, (x) saturated heterocyclic ring-oxy group (optionally having 1–5 substituents $\alpha_1$ hereafter defined), (xi) monocyclic type heteroaromatic ring-oxy group (optionally having 1–5 substituents $\alpha_1$ hereafter defined), (xii) $C_6$–$C_{10}$ arylthio group (optionally having 1–5 substituents $\alpha_1$ hereafter defined), (xiii) $C_7$–$C_{16}$ aralkylthio group (optionally having 1–5 substituents $\alpha_1$ hereafter defined on the aryl moiety thereof), (xiv) saturated heterocyclic ring-thio group (optionally having 1–5 substituents $\alpha_1$ hereafter defined), (xv) monocyclic type heteroaromatic ring-thio group (optionally having 1–5 substituents $\alpha_1$ hereafter defined), (xvi) amino group (optionally having 1–2 substituents $\alpha_1$ hereafter defined) or (xvii) hydroxy group; said substituent $\alpha_1$ is a (i) $C_1$–$C_6$ alkyl group, (ii) $C_1$–$C_6$ halogenoalkyl group, (iii) $C_1$–$C_6$ alkoxy group, (iv) halogen atom, (v) hydroxy group, (vi) cyano group, (vii) nitro group, (viii) $C_3$–$C_{10}$ cycloalkyl group, (ix) $C_6$–$C_{10}$ aryl group (optionally having 1–5 substituents $\beta$ hereafter defined), (x) $C_7$–$C_{16}$ aralkyl group (optionally having 1–5 substituents $\beta$ hereafter defined on the aryl moiety thereof), (xi) $C_1$–$C_7$aliphatic acyl group, (xii) $C_4$–$C_{11}$cycloalkylcarbonyl group, (xiii) $C_7$–$C_{11}$ arylcarbonyl group (optionally having 1–5 substituents $\beta$ hereafter defined), (xiv) $C_8$–$C_{17}$ aralkylcarbonyl group (optionally having 1–5 substituents $\beta$ hereafter defined on the aryl moiety thereof), (xv) monocyclic type heteroaromatic ring-carbonyl group (optionally having 1–5 substituents $\beta$ hereafter defined), (xvi) carbamoyl group, (xvii) $C_7$–$C_{11}$ arylaminocarbonyl group (optionally having 1–5 substituents $\beta$ hereafter defined on the aryl moiety thereof), (xviii) amino group (optionally having 1 to 2 substituents $\beta$ defined hereafter) or (xix) carboxyl group;

said substituent $\beta$ is a (i) $C_1$–$C_{10}$ alkyl group, (ii) halogen atom, (iii) $C_6$–$C_{10}$ aryl group (optionally having 1–5 substituents $\gamma$ hereafter defined), (iv) $C_7$–$C_{16}$ aralkyl group (optionally having 1–5 substituents $\gamma$ hereafter defined on the aryl moiety thereof), (v) $C_1$–$C_7$aliphatic acyl group, (vi) $C_7$–$C_{11}$ arylcarbonyl group (optionally having 1–5 substituents $\gamma$ hereafter defined), (vii) $C_8$–$C_{17}$aralkylcarbonyl group (optionally having 1–5 substituents $\alpha_1$ hereafter defined on the aryl moiety thereof), (viii) $C_4$–$C_{11}$ cycloalkylcarbonyl group, (ix) monocyclic type heteroaromatic ring-carbonyl group (optionally having 1–5 substituents $\gamma$ hereafter defined), (x) carbamoyl group or (xi) $C_7$–$C_{11}$ arylaminocarbonyl group (optionally having 1–5 substituents $\gamma$ hereafter defined on the aryl moiety thereof; and said substituent $\gamma$ is a $C_1$–$C_6$ alkyl group, a $C_1$–$C_6$ halogenoalkyl group, a halogen atom or a hydroxy group;

or a pharmacologically acceptable ester thereof, a pharmacologically acceptable amide thereof or a pharmacologically acceptable salt thereof.

2. An α-substituted carboxylic acid derivative according to claim 1, wherein $R_4$ is a $C_1$–$C_4$ alkyl group or a phenyl group (optionally having 1–3 substituents $\alpha_1$), or a pharmacologically acceptable ester thereof, a pharmacologically acceptable amide thereof or a pharmacologically acceptable salt thereof.

3. An α-substituted carboxylic acid derivative according to claim 1, wherein $R_4$ is a phenyl group (optionally having one substituent $\alpha_1$)), or a pharmacologically acceptable ester thereof, a pharmacologically acceptable amide thereof or a pharmacologically acceptable salt thereof.

4. An α-substituted carboxylic acid derivative according to any one of claims 1 to 3, wherein $Z_4$ is a (i) $C_1$–$C_4$ alkoxy group, (ii) $C_1$–$C_2$ alkylthio group, (iii) phenoxy group (optionally having 1–3 substituents $\alpha_1$) or (iv) phenylthio group (optionally having 1–3 substituents $\alpha_1$), or a pharmacologically acceptable ester thereof, a pharmacologically acceptable amide thereof or a pharmacologically acceptable salt thereof.

5. An α-substituted carboxylic acid derivative according to any one of claims 1 to 3, wherein $Z_4$ is a $C_1$–$C_2$ alkoxy group, or a pharmacologically acceptable ester thereof, a pharmacologically acceptable amide thereof or a pharmacologically acceptable salt thereof.

6. An α-substituted carboxylic acid derivative according to any one of claims 1 to 3, wherein $Z_4$ is a phenoxy group (optionally having 1–3 substituents $\alpha_1$), or a pharmacologically acceptable ester thereof, a pharmacologically acceptable amide thereof or a pharmacologically acceptable salt thereof.

7. An α-substituted carboxylic acid derivative according to claim 1, wherein:

$R_1$ is a $C_1$–$C_2$ alkyl group;

$R_2$ is a hydrogen atom;

$R_3$ is a hydrogen atom;

$R_4$ is a phenyl group (optionally having one substituent $\alpha_1$);

A is a =CH-group;

B is an oxygen atom;

W is a methylene group;

$W_2$ is a methylene group;

X is a hydrogen atom;

$Z_4$ is a $C_1$–$C_2$ alkoxy group; and said substituent $\alpha_1$ is a benzoyl group;

or a pharmacologically acceptable ester thereof, a pharmacologically acceptable amide thereof or a pharmacologically acceptable salt thereof.

8. An α-substituted carboxylic acid derivative according to claim 1, wherein:

$R_1$ is a $C_1$–$C_2$ alkyl group;

$R_2$ is a hydrogen atom;

$R_3$ is a hydrogen atom;

$R_4$ is a phenyl group (optionally having one substituent $\alpha_1$);

A is a =CH-group;

B is an oxygen atom;

W is a methylene group $W_2$ is a methylene group;

X is a hydrogen atom;

$Z_4$ is a phenoxy group (optionally having 1–3 substituents $\alpha_1$);

said substituent $\alpha_1$ is a $C_1$–$C_4$ alkyl group, a benzoyl group or an amino group (optionally having one substituent β);

said substituent β is a phenylaminocarbonyl group (optionally having one substituent γ on the phenyl moiety thereof); and said substituent γ is a trifluoromethyl group;

or a pharmacologically acceptable ester thereof, a pharmacologically acceptable amide thereof or a pharmacologically acceptable salt thereof.

9. An α-substituted carboxylic acid derivative which is N-(2-benzoylphenyl)-4-(6-methoxy-1-methyl-1H-benzimidazol-2-ylmethoxy)-phenylalanine.

10. An α-substituted carboxylic acid derivative which is 4-[6-amino-3,5-dimethylphenoxy)-1methyl-1H-benzimidazol-2-ylmethoxy]-N-(2-benzoylphenyl) phenylalanine.

11. An α-substituted carboxylic acid derivative which is 4-[6-[4-(4trifluoromethylphenylureido)-3,5-dimethyphenoxy]-1-methyl-1H-benzimidazol-2-ylmethoxy]-N-(2-benzoylphenyl)phenylalanine.

12. A pharmaceutical composition comprising an effective amount as an insulin resistance improving agent, hypoglycemic agent, immunoregulatory agent, aldose reductase inhibitor, 5-lipoxygenase inhibitor, peroxidized lipid production suppressor, PPAR activator, leukotriene antagonist, adipose cell formation promotor or calcium antagonist of a pharmacologically active compound together with a carrier therefor, wherein said pharmacologically active compound is a compound according to any one of claims 1–3, 7, 8, 9, 10 and 11 or a pharmacologically acceptable ester thereof, a pharmacologically acceptable amide thereof or a pharmacologically acceptable salt thereof.

13. A pharmaceutical composition comprising an effective amount as an insulin resistance improving agent, hypoglycemic agent, immunoregulatory agent, aldose reductase inhibitor, 5-lipoxygenase inhibitor, peroxidized lipid production suppressor, PPAR activator, leukotriene antagonist, adipose cell formation promotor or calcium antagonist of a pharmacologically active compound together with a carrier therefor, wherein said pharmacologically active compound is a compound according to claim 4 or a pharmacologically acceptable ester thereof, a pharmacologically acceptable amide thereof or a pharmacologically acceptable salt thereof.

14. A pharmaceutical composition comprising an effective amount as an insulin resistance improving agent, hypoglycemic agent, immunoregulatory agent, aldose reductase inhibitor, 5-lipoxygenase inhibitor, peroxidized lipid production suppressor, PPAR. activator, leukotriene antagonist, adipose cell formation promotor or calcium antagonist of a pharmacologically active compound together with a carrier therefor, wherein said pharmacologically active compound is a compound according to any one of claim 9, 10 or 11.

* * * * *

UNITED STATES PATENT AND TRADEMARK OFFICE
CERTIFICATE OF CORRECTION

PATENT NO.    : 6,596,751 B2
DATED         : July 22, 2003
INVENTOR(S)   : Fujita et al.

It is certified that error appears in the above-identified patent and that said Letters Patent is hereby corrected as shown below:

Column 109,
Line 1, above the structural formula, insert -- EXAMPLE 2 3- [4- [6- (4-Adamantan-1-ylphenoxy) -1-methyl-1H-benzimidazol-2-ylmethoxy]phenyl] -2- (4-fluorobenzyloxy) propionic acid (exemplification compound number 1-1) --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,596,751 B2  Page 1 of 1
APPLICATION NO. : 09/972206
DATED : July 22, 2003
INVENTOR(S) : Takashi Fujita et al.

It is certified that error appears in the above-identified patent and that said Letters Patent is hereby corrected as shown below:

Column 149, delete lines 41 and 42,
(which is a definition of "Y").

Signed and Sealed this

Twentieth Day of March, 2007

JON W. DUDAS
*Director of the United States Patent and Trademark Office*